(12) United States Patent
Levin et al.

(10) Patent No.: US 11,311,627 B1
(45) Date of Patent: *Apr. 26, 2022

(54) NUCLEIC ACID-POLYPEPTIDE COMPOSITIONS AND METHODS OF INDUCING EXON SKIPPING

(71) Applicant: Avidity Biosciences, Inc., La Jolla, CA (US)

(72) Inventors: Arthur A. Levin, Del Mar, CA (US); Andrew John Geall, Carlsbad, CA (US); Venkata Ramana Doppalapudi, San Diego, CA (US); Michael Caramian Cochran, La Jolla, CA (US); Hanhua Huang, San Diego, CA (US); Rob Burke, Encinitas, CA (US)

(73) Assignee: AVIDITY BIOSCIENCES LLC, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/463,473

(22) Filed: Aug. 31, 2021

Related U.S. Application Data

(63) Continuation of application No. 16/129,696, filed on Sep. 12, 2018, now Pat. No. 11,179,472, which is a continuation of application No. 16/128,450, filed on Sep. 11, 2018, now Pat. No. 10,994,020, which is a continuation of application No. PCT/US2018/012672, filed on Jan. 5, 2018.

(60) Provisional application No. 62/561,939, filed on Sep. 22, 2017, provisional application No. 62/443,514, filed on Jan. 6, 2017.

(51) Int. Cl.
| | |
|---|---|
| *C07H 21/04* | (2006.01) |
| *A61K 47/68* | (2017.01) |
| *C12N 15/113* | (2010.01) |
| *C07K 16/28* | (2006.01) |
| *C07K 14/00* | (2006.01) |
| *A61K 47/64* | (2017.01) |
| *A61K 47/60* | (2017.01) |
| *A61P 21/00* | (2006.01) |
| *A61K 31/713* | (2006.01) |
| *A61K 31/7088* | (2006.01) |
| *A61K 48/00* | (2006.01) |
| *C07K 16/40* | (2006.01) |
| *A61K 38/00* | (2006.01) |

(52) U.S. Cl.
CPC ...... *A61K 47/6803* (2017.08); *A61K 31/7088* (2013.01); *A61K 31/713* (2013.01); *A61K 47/60* (2017.08); *A61K 47/6455* (2017.08); *A61K 47/6807* (2017.08); *A61K 47/6849* (2017.08); *A61K 48/0058* (2013.01); *A61K 48/0066* (2013.01); *A61K 48/0083* (2013.01); *A61P 21/00* (2018.01); *C07K 14/003* (2013.01); *C07K 16/2881* (2013.01); *C07K 16/40* (2013.01); *C12N 15/113* (2013.01); *A61K 38/00* (2013.01); *C12N 2310/11* (2013.01); *C12N 2310/315* (2013.01); *C12N 2310/3233* (2013.01); *C12N 2310/3513* (2013.01); *C12N 2320/32* (2013.01); *C12N 2320/33* (2013.01)

(58) Field of Classification Search
None
See application file for complete search history.

(56) References Cited

U.S. PATENT DOCUMENTS

| | | |
|---|---|---|
| 4,694,778 A | 9/1987 | Learn et al. |
| 5,142,047 A | 8/1992 | Summerton et al. |
| 5,185,444 A | 2/1993 | Summerton et al. |
| 5,334,711 A | 8/1994 | Sproat et al. |
| 5,627,053 A | 5/1997 | Usman et al. |
| 5,716,824 A | 2/1998 | Beigelman et al. |
| 5,736,557 A | 4/1998 | Hofheinz et al. |
| 5,889,136 A | 3/1999 | Scaringe et al. |
| 6,008,400 A | 12/1999 | Scaringe et al. |
| 6,111,086 A | 8/2000 | Scaringe |
| 6,194,551 B1 | 2/2001 | Idusogie et al. |
| 6,528,624 B1 | 3/2003 | Idusogie et al. |
| 6,538,124 B1 | 3/2003 | Idusogie et al. |
| 6,821,783 B1 | 11/2004 | Comely et al. |
| 6,884,869 B2 | 4/2005 | Senter et al. |
| 7,364,731 B2 | 4/2008 | Idusogie et al. |
| 7,452,987 B2 | 11/2008 | Giese et al. |
| 7,498,298 B2 | 3/2009 | Doronina et al. |
| 7,833,992 B2 | 11/2010 | Vargeese et al. |

(Continued)

FOREIGN PATENT DOCUMENTS

| | | |
|---|---|---|
| EP | 0336675 A1 | 10/1989 |
| EP | 0334656 B1 | 3/1994 |

(Continued)

OTHER PUBLICATIONS

Aartsma-Rus et al. Guidelines for antisense oligonucleotide design and insight into splice-modulating mechanisms. Mol Ther 17(3):548-53 (2009).

(Continued)

*Primary Examiner* — Kimberly Chong
(74) *Attorney, Agent, or Firm* — Wilson Sonsini Goodrich & Rosati

(57) ABSTRACT

Disclosed herein are molecules and pharmaceutical compositions that induce an insertion, deletion, duplication, or alteration in an incorrectly spliced mRNA transcript to induce exon skipping or exon inclusion. Also described herein include methods for treating a disease or disorder that comprises a molecule or a pharmaceutical composition that induces an insertion, deletion, duplication, or alteration in an incorrectly spliced mRNA transcript to induce exon skipping or exon inclusion.

24 Claims, 45 Drawing Sheets
Specification includes a Sequence Listing.

(56) References Cited

U.S. PATENT DOCUMENTS

| | | |
|---|---|---|
| 7,850,975 B2 | 12/2010 | Mullis |
| 7,893,245 B2 | 2/2011 | Giese et al. |
| 7,923,547 B2 | 4/2011 | McSwiggen et al. |
| 7,943,762 B2 | 5/2011 | Weller et al. |
| 8,084,582 B2 | 12/2011 | Dahiyat et al. |
| 8,084,598 B1 | 12/2011 | Bentwich |
| 8,090,542 B2 | 1/2012 | Khvorova et al. |
| 8,202,979 B2 | 6/2012 | McSwiggen et al. |
| 8,273,866 B2 | 9/2012 | McSwiggen et al. |
| 8,288,352 B2 | 10/2012 | Doronina et al. |
| 8,324,370 B2 | 12/2012 | Giese et al. |
| 8,324,371 B2 | 12/2012 | Popplewell et al. |
| 8,361,979 B2 | 1/2013 | Aartsma-Rus et al. |
| 8,461,325 B2 | 6/2013 | Popplewell et al. |
| 8,501,703 B2 | 8/2013 | Bennett et al. |
| 8,501,930 B2 | 8/2013 | Rozema et al. |
| 8,591,910 B2 | 11/2013 | Mullis |
| 8,604,184 B2 | 12/2013 | Mullis et al. |
| 8,609,105 B2 | 12/2013 | Senter et al. |
| 8,618,277 B2 | 12/2013 | Beigelman et al. |
| 8,648,185 B2 | 2/2014 | McSwigen et al. |
| 8,697,688 B2 | 4/2014 | Howard et al. |
| 8,835,402 B2 | 9/2014 | Kole et al. |
| 8,895,722 B2 | 11/2014 | Iversen et al. |
| 8,933,215 B2 | 1/2015 | Giese et al. |
| 8,936,910 B2 | 1/2015 | Mitsch et al. |
| 8,969,526 B2 | 3/2015 | Baehner et al. |
| 9,078,911 B2 | 7/2015 | Lu |
| 9,089,614 B2 | 7/2015 | Lin et al. |
| 9,096,877 B2 | 8/2015 | Johnson et al. |
| 9,139,828 B2 | 9/2015 | Platenburg et al. |
| 9,175,286 B2 | 11/2015 | Wilton et al. |
| 9,181,551 B2 | 11/2015 | McSwiggen et al. |
| 9,222,092 B2 | 12/2015 | Giese et al. |
| 9,228,187 B2 | 1/2016 | Wilton et al. |
| 9,243,251 B2 | 1/2016 | Popplewell et al. |
| 9,243,252 B2 | 1/2016 | Popplewell et al. |
| 9,249,416 B2 | 2/2016 | Wilton et al. |
| 9,260,471 B2 | 2/2016 | Cancilla et al. |
| 9,416,361 B2 | 8/2016 | Iversen et al. |
| 9,434,948 B2 | 9/2016 | Sazani et al. |
| 9,441,229 B2 | 9/2016 | Wilton et al. |
| 9,447,415 B2 | 9/2016 | Wilton et al. |
| 9,447,417 B2 | 9/2016 | Sazani et al. |
| 9,481,905 B2 | 11/2016 | Chen et al. |
| 9,499,818 B2 | 11/2016 | Van Deutekom |
| 9,528,109 B2 | 12/2016 | De Kimpe et al. |
| 9,605,019 B2 | 3/2017 | Verdine et al. |
| 9,657,294 B2 | 5/2017 | Beigelman et al. |
| 9,695,211 B2 | 7/2017 | Wada et al. |
| 9,695,423 B2 | 7/2017 | Giese et al. |
| 9,732,344 B2 | 8/2017 | Beigelman et al. |
| 9,765,338 B2 | 9/2017 | Bennett et al. |
| 9,771,588 B2 | 9/2017 | McSwiggen et al. |
| 9,796,974 B2 | 10/2017 | Rajeev et al. |
| 9,890,379 B2 | 2/2018 | De Kimpe et al. |
| 9,926,557 B2 | 3/2018 | De Kimpe et al. |
| 9,982,257 B2 | 5/2018 | Butler et al. |
| 10,000,754 B2 | 6/2018 | Beigelman et al. |
| 2002/0142980 A1 | 10/2002 | Thompson et al. |
| 2009/0092985 A1 | 4/2009 | Cardozo et al. |
| 2011/0081362 A1 | 4/2011 | Elledge et al. |
| 2011/0263686 A1 | 10/2011 | Wilton et al. |
| 2011/0294753 A1 | 12/2011 | De Kimpe et al. |
| 2011/0301218 A1 | 12/2011 | Bozzoni et al. |
| 2012/0065169 A1 | 3/2012 | Hanson et al. |
| 2012/0094299 A1 | 4/2012 | Ranum et al. |
| 2012/0172415 A1 | 7/2012 | Voit et al. |
| 2012/0270925 A1 | 10/2012 | Wilton et al. |
| 2013/0028919 A1 | 1/2013 | Howard et al. |
| 2013/0172238 A1 | 7/2013 | Mitsch et al. |
| 2013/0309256 A1 | 11/2013 | Lyon et al. |
| 2014/0127239 A1 | 5/2014 | Howard |
| 2014/0194610 A1 | 7/2014 | Verdine et al. |
| 2014/0286970 A1 | 9/2014 | Jeffrey et al. |
| 2014/0294851 A1 | 10/2014 | Nguyen |
| 2014/0296321 A1 | 10/2014 | Iversen |
| 2014/0315862 A1 | 10/2014 | Kaye |
| 2015/0037360 A1 | 2/2015 | Smith |
| 2015/0105539 A1 | 4/2015 | Miao et al. |
| 2015/0105540 A1 | 4/2015 | Miao et al. |
| 2015/0110791 A1 | 4/2015 | Zhang et al. |
| 2015/0211006 A1 | 7/2015 | Butler et al. |
| 2016/0002637 A1 | 1/2016 | Sazani et al. |
| 2016/0053262 A1 | 2/2016 | Platenburg et al. |
| 2016/0102135 A1 | 4/2016 | Escobar-Cabrera |
| 2016/0298111 A1 | 10/2016 | Bestwick et al. |
| 2016/0304864 A1 | 10/2016 | De Kimpe et al. |
| 2016/0304877 A1 | 10/2016 | Swayze et al. |
| 2016/0367687 A1 | 12/2016 | Manoharan et al. |
| 2017/0107512 A1 | 4/2017 | De Kimpe et al. |
| 2017/0204410 A1 | 7/2017 | Watanabe et al. |
| 2017/0204414 A1 | 7/2017 | Van Deutekom et al. |
| 2017/0281795 A1 | 10/2017 | Geall et al. |
| 2017/0342416 A1 | 11/2017 | McSwiggen et al. |
| 2018/0016574 A1 | 1/2018 | Bestwick et al. |
| 2018/0044675 A1 | 2/2018 | Watanabe et al. |
| 2018/0112214 A1 | 4/2018 | De Kimpe et al. |
| 2018/0127758 A1 | 5/2018 | Bennett |
| 2018/0163209 A1 | 6/2018 | Bennett et al. |
| 2018/0305689 A1 | 10/2018 | Sætrom et al. |
| 2018/0369400 A1 | 12/2018 | Levin et al. |
| 2019/0000986 A1 | 1/2019 | Levin et al. |
| 2019/0240346 A1 | 8/2019 | Sugo et al. |
| 2020/0282074 A1 | 9/2020 | Levin et al. |

FOREIGN PATENT DOCUMENTS

| | | |
|---|---|---|
| EP | 1579015 A2 | 9/2005 |
| EP | 1068241 B1 | 10/2007 |
| EP | 2119783 A1 | 11/2009 |
| EP | 2049664 B1 | 9/2011 |
| EP | 2278004 B1 | 10/2012 |
| EP | 2344637 B1 | 12/2014 |
| EP | 1423406 B2 | 11/2015 |
| EP | 3031920 A1 | 6/2016 |
| EP | 2421971 B1 | 7/2016 |
| EP | 2287306 B2 | 10/2016 |
| EP | 3030658 A4 | 3/2017 |
| EP | 2287305 B2 | 11/2017 |
| EP | 2486141 B1 | 1/2018 |
| EP | 2902406 B1 | 1/2018 |
| EP | 2595664 B1 | 10/2018 |
| WO | WO-9104753 A1 | 4/1991 |
| WO | WO-9207065 A1 | 4/1992 |
| WO | WO-9315187 A1 | 8/1993 |
| WO | WO-9726270 A2 | 7/1997 |
| WO | WO-9734631 A1 | 9/1997 |
| WO | WO-9813526 A1 | 4/1998 |
| WO | WO-0149698 A1 | 7/2001 |
| WO | WO-2006000057 A1 | 1/2006 |
| WO | WO-2008036127 A2 | 3/2008 |
| WO | WO-2009099942 A2 | 8/2009 |
| WO | WO-2009099991 A2 | 8/2009 |
| WO | WO-2009144481 A2 | 12/2009 |
| WO | WO-2011150408 A2 | 12/2011 |
| WO | WO-2013166155 A1 | 11/2013 |
| WO | WO-2014080251 A1 | 5/2014 |
| WO | WO-2014140317 A2 | 9/2014 |
| WO | WO-2014145090 A1 | 9/2014 |
| WO | WO-2014177042 A1 | 11/2014 |
| WO | WO-2014197854 A1 | 12/2014 |
| WO | WO-2015021457 A2 | 2/2015 |
| WO | WO-2015038426 A1 | 3/2015 |
| WO | WO-2015057699 A2 | 4/2015 |
| WO | WO-2015069587 A2 | 5/2015 |
| WO | WO-2015107425 A2 | 7/2015 |
| WO | WO-2016187425 A1 | 11/2016 |
| WO | WO-2016207240 A1 | 12/2016 |
| WO | WO-2017148879 A1 | 9/2017 |
| WO | WO-2017173408 A1 | 10/2017 |
| WO | WO-2017192679 A1 | 11/2017 |
| WO | WO-2017221883 A1 | 12/2017 |

(56) References Cited

FOREIGN PATENT DOCUMENTS

| WO | WO-2018002812 A1 | 1/2018 |
|---|---|---|
| WO | WO-2018129384 A1 | 7/2018 |
| WO | WO-2019060775 A1 | 3/2019 |

OTHER PUBLICATIONS

Aartsma-Rus et al. Targeted exon skipping as a potential gene correction therapy for Duchenne muscular dystrophy. Neuromuscul Disord. 12 Suppl 1:S71-7 (2002).

Abramova et al. Novel oligonucleotide analogues based on morpholino nucleoside subunits-antisense technologies: new chemical possibilities. Indian Journal of Chemistry 48B:1721-1726 (2009).

Agarwal et al. A Pictet-Spengler ligation for protein chemical modification. PNAS 110(1):46-51 (2013).

Albarran et al. Efficient intracellular delivery of a pro-apoptotic peptide with a pH-responsive carrier. React Funct Polym 71:261-265 (2011).

Arechavala-Gomeza et al. Comparative analysis of antisense oligonucleotide sequences for targeted skipping of exon 51 during dystrophin pre-mRNA splicing in human muscle. Hum Gene Ther. 18(9):798-810 (2007).

Axup et al. Synthesis of site-specific antibody-drug conjugates using unnatural amino acids. PNAS 109(40):16101-16106 (2012).

Baumer et al. Antibody-mediated delivery of anti-KRAS-siRNA in vivo overcomes therapy resistance in colon cancer. Clin Can Res 21(6):1383-1394 (2015).

Beduneau et al. Design of targeted lipid nanocapsules by conjugation of whole antibodies and antibody Fab' fragments. Biomaterials 28(33):4978-4990 (2007).

Beigelman et al. Chemical modification of hammerhead ribozymes. Catalytic activity and nuclease resistance. J Biol Chem 270:25702-25708 (1995).

Bell et al. Epidermal Growth Factor Receptor Mutations and Gene Amplification in Non-Small-Cell Lung Cancer: Molecular Analysis of the IDEAL/INTACT Gefitinib Trials. J Clin Oncol 23(31):8081-8092 (2005).

Bird et al. Single-chain antigen-binding proteins. Science 242:423-442 (1988).

Blaney et al. Traceless solid-phase organic synthesis. Chem. Rev. 102:2607-2024 (2002.

Bulmus et al. A new pH-responsive and glutathione-reactive, endosomal membrane-disruptive polymeric carrier for intracellular delivery of biomolecular drugs. J Controlled Release 93:105-120 (2003).

Burke et al. siRNA-mediated knockdown of P450 oxidoreductase in rats: a tool to reduce metabolism by CYPs and increase exposure of high clearance compounds. Pharm. Res. 31(12):3445-3460 (2014).

Burlina et al. Chemical engineering of RNase resistant and catalytically active hammerhead ribozymes. Bioorg Med Chem 5:1999-2010 (1997).

Casi et al. Site-specific traceless coupling of potent cytotoxic drugs to recombinant antibodies for pharmacodelivery. J Am Chem Soc 134(13):5887-5892 (2012).

Castaneda et al. Acid-cleavable thiomaleamic acid linker for homogeneous antibody-drug conjugation, Chern. Commun. 49:8187-8189 (2013).

Chen et al. Strand-specific 5'-O-methylation of siRNA duplexes controls guide strand selection and targeting specificity. RNA 14:263-274 (2008).

Clackson et al. Making antibody fragments using phage display libraries. Nature 352(6336):624-628 (1991).

Colberre-Garapin et al. A new dominant hybrid selective marker for higher eukaryotic cells. J Mol Biol 150:1-14 (1981).

Cole et al. The EBV-hybridoma technique and its application to human lung cancer. In, Monoclonal Antibodies and Cancer Therapy (vol. 27, UCLA Symposia on Molecular and Cellular Biology, New Series) (eds. R.A. Reisfeld and S.Sell), New York: Alan R. Liss, Inc. pp. 77-96 (1985).

Co-pending U.S. Appl. No. 17/463,484, inventors Levin; Arthur A. et al., filed Aug. 31, 2021.

Crouse et al. Expression and amplification of engineered mouse dihydrofolate reductase minigenes. Mol Cell Biol 3(2):257-266 (1983).

Cuellar et al. Systematic evaluation of antibody-mediated siRNA delivery using an industrial platform of THIOMAB-siRNA conjugates. Nucleic Acids Res 43(2):1189-1203 (2015).

Dawson et al. Modulation of Reactivity in Native Chemical Ligation through the Use of Thiol Additives. J. Am. Chem. Soc. 119:4325-4329 (1997).

Dawson et al. Synthesis of proteins by native chemical ligation. Science 266(5186):776-779 (1994).

De Angelis et al. Chimeric snRNA molecules carrying antisense sequences against the splice junctions of exon 51 of the dystrophin pre-mRNA induce exon skipping and restoration of a dystrophin synthesis in Delta 48-50 DMD cells. PNAS USA 99:9456-9461 (2002).

Debinski et al. Monovalent immunotoxin containing truncated form of Pseudomonas exotoxin as potent antitumor agent. Cancer Research 52(19):5379-5385 (1992).

Deleavey et al. Designing chemically modified oligonucleotides for targeted gene silencing. Chem Biol. 19(8):937-954 (2012).

Dietel et al. A 2015 update on predictive molecular pathology and its role in targeted cancer therapy: a review focussing on clinical relevance. Cancer Gene Ther 22(9):417-430 (2015).

Dimasi et al. Development of a trispecific antibody designed to simultaneously and efficiently target three different antigens on tumor cells. Mol Pharm 12(9):3490-3501 (2015).

Domingo et al. Transferrin receptor as a target for antibody—drug conjugates. Methods in Enzymology 112:238-247 (1985).

Duncan et al. A polymer-Triton X-100 conjugate capable of pH-dependent red blood cell lysis: a model system illustrating the possibility of drug delivery within acidic intracellular compartments. J Drug Target 2:341-347 (1994).

Earnshaw et al. Modified oligoribonucleotides as site-specific probes of RNA structure and function. Biopolymers (Nucleic Acid Sciences) 48:39-55 (1998).

Echigoya et al. In Silico Screening Based on Predictive Algorithms as a Design Tool for Exon Skipping Oligonucleotides in Duchenne Muscular Dystrophy. PLoS One 10(3):e0120058 (2015).

El-Sayed et al. Rational design of composition and activity correlations for pH-responsive and glutathione-reactive polymer therapeutics. J Control Release 104:417-427 (2005).

Feener et al. Alternative splicing of human dystrophin mRNA generates isoforms at the carboxy terminus. Nature 338:509-511 (Apr. 6, 1989).

Flanary et al. Antigen delivery with poly(propylacrylic acid) conjugation enhanced MHC-1 presentation and T-cell activation. Bioconjugate Chern. 20:241-248 (2009).

Gaziova et al. Chemically defined polyethylene glycol siRNA conjugates with enhanced gene silencing effect. Bioorg Med Chem 22(7):2320-2326 (2014).

Goldspiel et al. Human gene therapy. Clin Pharm 12:488-505 (1993).

Griffey et al. 2'-0-aminopropyl ribonucleotides: a zwitterionic modification that enhances the exonuclease resistance and biological activity of antisense oligonucleotides, J. Med. Chem. 39(26):5100-5109 (1997).

Hackeng et al. Protein synthesis by native chemical ligation: Expanded scope by using straightforward methodology. PNAS USA 96:10068-10073 (1999).

Hanes et al. In vitro selection and evolution of functional proteins by using ribosome display. PNAS USA 94:4937-4942 (1997).

Hejesen et al. A traceless aryl-triazene linker for DNA-directed chemistry. Org Biomol Chem 11(15):2493-2497 (2013).

Henry et al. pH-responsive poly(styrene-alt-maleic anhydride) alkylamide copolymers for intracellular drug delivery. Biomacromolecules 7:2407-2414 (2006).

Hitachi et al. Role of microRNAs in skeletal muscle hypertrophy. Front Physiol 16(4):408 (2014).

(56) References Cited

OTHER PUBLICATIONS

Hoffman et al. Restoring Dystrophin Expression in Duchenne Muscular Dystrophy Muscle: Progress in Exon Skipping and Stop Codon Read Through. Am J Pathol 179(1):12-22 (2011).
Hu et al. Site-specific Antibody-polymer Conjugates for siRNA Delivery. J AM Chem Soc 135(37):13885-13891 (2013).
Huang et al. Mechanisms of resistance to EGFR tyrosine kinase inhibitors. Acta Pharma Sinica B 5(5):390-401 (2015).
Hudson et al. Cellular delivery of hammerhead ribozymes conjugated to a transferrin receptor antibody. Int J Pharmaceuticals 182(1):49-58 (1999).
Huse et al. Generation of a large combinatorial library of the immunoglobulin repertoire in phage lambda. Science 246(4935):1275-1281 (1989).
Huston et al. Protein engineering of antibody binding sites: recovery of specific activity in an anti-digoxin single-chain Fv analogue produced in *Escherichia coli*. PNAS USA 85(16):5879-5883 (1988).
Ishikawa et al. Preparation of monomeric Fab'-horseradish peroxidase conjugate using thiol groups in the hinge and its evaluation in enzyme immunoassay and immunohistochemical staining. Ann N Y Acad Sci. 420:74-89 (1983).
Iversen et al. Optimized siRNA-PEG conjugates for extended blood circulation and reduced urine excretion in mice. Theranostics 3(3):201-209 (2013).
Jancik et al. Clinical relevance of KRAS in human cancers. J Biomed Biotechnol 2010:150960 (13 pgs.) (2010).
Jearawiriyapaisarn et al. Sustained Dystrophin Expression Induced by Peptide-conjugated Morpholino Oligomers in the Muscles of mdx Mice. Mol Ther. 16(9): 1624-1629 (2008).
Jones et al. Poly(2-alkylacrylic acid) polymers deliver molecules to the cytosol by pH-sensitive disruption of endosomal vesicles. Biochem J 372:65-75 (2003).
Karpeisky et al. Highly efficient synthesis of 2'-O-amino nucleosides and their incorporation in hammerhead ribozymes. Tetrahedron Lett 39:1131-1134 (1998).
Khormaee et al. Endosomolyticanionic polymer for the cytoplasmic delivery of siRNAs in localized in vivo applications. Adv Funct Mater 23:565-574 (2013).
Kim et al. PEG conjugated VEGF siRNA for anti-angiogenic gene therapy. J Cont Rel 116:123-129 (2006).
Kohler et al. Continuous cultures of fused cells secreting antibody of predefined specificity. Nature 256:495-497 (1975).
Koizumi. ENA oligonucleotides as therapeutics. Curr Opin Mol Ther 8(2):144-149 (2006).
Kontermann et al. Bispecific antibodies. Drug Discov Today 20(7):838-847 (2015).
Kozbor et al. The production of monoclonal antibodies from human lymphocytes. Immunology Today 4:72-79 (1983).
Kutmeier et al. Assembly of humanized antibody genes from synthetic oligonucleotides using a single-round PCR. BioTechniques 17:242 (1994).
Lee et al. Antisense PMO cocktails effectively skip dystrophin exons 45-55 in myotubes transdifferentiated from DMD patient fibroblasts. PLoS One 13(5):e0197084 (2018).
Leigh et al. The Human Plasma Proteome: History, Character, and Diagnostic Prospects. Mol Cell Proteomics 1:845-867 (2002).
Levin. Targeting Therapeutic Oligonucleotides. N Engl J Med 376:86-88 (2017).
Loakes. Survey and summary: The applications of universal DNA base analogues. Nucleic Acids Research 29:2437-2447 (2001).
Loh et al. A Survey of siRNA Nanoscal Delivery Patents. 11 Nanotechnology Law & Bus. (pp. 29-37) (2014).
Lowy et al., Isolation of transforming DNA: Cloning the hamster aprt gene. Cell 22:817-823 (1980).
Lyon et al. Self-hydrolyzing maleimides improve the stability and pharmacological properties of antibody-drug conjugates. Nat. Biotechnol. 32(10):1059-1062 (2014).
Martinez et al. Single-stranded antisense siRNAs guide target RNA cleavage in RNAi. Cell 110(5):563-574 (2002).

McEnaney et al. Antibody-recruiting molecules: an emerging paradigm for engaging immune function in treating human disease. ACS Chem Biol. 7(7):1139-1151 (2012).
Mei et al. FBXO32 Targets c-Myc for Proteasomal Degradation and Inhibits c-Myc Activity. J Biol Chem 290:16202-16214 (2015).
Miyata et al. Polymer nanotechnology for nucleic acid delivery. Drug Delivery System 31(1):44-53 (2016) (English Abstract).
Morgan et al. Human gene therapy. Ann Rev Biochem 62:191-217 (1993).
Morrison et al. Chimeric human antibody molecules: mouse antigen-binding domains with human constant region domains. PNAS USA 81(21):6851-6855 (1984).
Mulligan et al. Selection for animal cells that express the *Escherichia coli* gene coding for xanthine-guanine phosphoribosyltransferase. PNAS USA 78(4):2072-2076 (1981).
Mulligan. The basic science of gene therapy. Science 260(5110):926-932 (1993).
Naisbitt et al. Disposition of amodiaquine and related antimalarial agents in human neutrophils: implications for drug design. J Pharmacol Exp Ther 280:884-893 (1997).
Neuberger et al. Recombinant antibodies possessing novel effector functions. Nature 312(5995):604-608 (1984).
Normand-Sdiqui et al. Oligonucleotide delivery: Uptake of rat transferrin receptor antibody (OX / 26) conjugates into an in vitro immortalised cell line model of the blood, brain barrier. Int J Pharmaceuticals 163:63-71 (1998).
Obika et al. Synthesis of 2'-0,4'-C-methyleneuridine and -cytidine. Novel bicyclic nucleosides having a fixed C3'-endo sugar puckering. Tetrahedron Lett. 38(50):8735-8738 (1997).
O'Hare et al. Transformation of mouse fibroblasts to methotrexate resistance by a recombinant plasmid expressing a prokaryotic dihydrofolate reductase. PNAS USA 78:1527-1531 (1981).
PCT/US2018/012672 International Search Report and Written Opinion dated May 24, 2018.
PCT/US2018/012672 Invitation to Pay Additional Fees dated Mar. 20, 2018.
PCT/US2018/052289 International Search Report and Written Opinion dated Jan. 11, 2019.
Perrault et al. Mixed deoxyribo- and ribo-oligonucleotides with catalytic activity. Nature 344:565-568 (1990).
Pieken et al. Kinetic characterization of ribonuclease-resistant 2'-modified hammerhead ribozymes. Science 253:314-317 (1991).
Rozema et al. Dynamic PolyConjugates for targeted in vivo delivery of siRNA to hepatocytes. PNAS USA 104(32):12982-12987 (2007).
Santerre et al. Expression of prokaryotic genes for hygromycin B and G418 resistance as dominant-selection markers in mouse L cells. Gene 30(1-3):147-156 (1984).
Schnyder et al. Targeting of skeletal muscle in vitro using biotinylated immunoliposomes. Biochem J 377(Pt.1):61-67 (2004).
Schwarz et al. Evidence that siRNAs function as guides, not primers, in the *Drosophila* and human RNAi pathways. Molecular Cell 10:537-548 (2002).
Sekyere et al. Examination of the distribution of the transferrin homologue, melanotransferrin (tumour antigen p97), in mouse and human. Biochimica et Biophysica Acta 1722(2):131-142 (2005).
Singh et al. Recent developments in oligonucleotide conjugation. Chem Soc Rev 39(6):2054-2070 (2010).
Skerra et al. Assembly of a functional Immunoglobulin Fv fragment in *Escherichia coli*. Science 240(4855):1038-1041 (1988).
Strop et al. Location matters: site of conjugation modulates stability and pharmacokinetics of antibody drug conjugates. Chem Biol 20(2):161-167 (2013).
Sugo et al. Development of antibody-siRNA conjugate targeted to cardiac and skeletal muscles. J Control release 237:1-13 (2016).
Summerton, et al. Morpholino antisense oligomers: design, preparation, and properties. Antisense Nucleic Acid Drug Dev. Jun. 1997;7(3):187-95.
Suñé-Pou et al. Targeting Splicing in the Treatment of Human Disease. Genes 8:E87 (2017).
Suriano et al. Beta-catenin (CTNNB1) gene amplification: a new mechanism of protein overexpression in cancer. Genes Chromosomes Cancer 42(3):238-246 (2005).

(56) References Cited

OTHER PUBLICATIONS

Szybalska et al. Genetics of human cell line. IV. DNA-mediated heritable transformation of a biochemical trait. PNAS USA 48:2026-2034 (1962).
Takeda et al. Construction of chimaeric processed immunoglobulin genes containing mouse variable and human constant region sequences. Nature 314(6010):452-454 (1985).
Talasila et al. EGFR Wild-type Amplification and Activation Promote Invasion and Development of Glioblastoma Independent of Angiogenesis. Acta Neuropathol. 125(5):683-698 (2013).
Tolstoshev. Gene Therapy, Concepts, Current Trials and Future Directions. Ann. Rev. Pharmacol. Toxicol. 32:573-596 (1993).
U.S. Appl. No. 16/128,450 Miscellaneous Communication re: Third Party Submission dated Jul. 1, 2019.
U.S. Appl. No. 16/128,450 Office Action dated Apr. 19, 2019.
U.S. Appl. No. 16/128,450 Office Action dated Apr. 30, 2020.
U.S. Appl. No. 16/128,450 Office Action dated Dec. 16, 2020.
U.S. Appl. No. 16/128,450 Office Action dated Sep. 19, 2019.
U.S. Appl. No. 16/129,696 Miscellaneous Communication re: Third Party Submission dated Jul. 3, 2019.
U.S. Appl. No. 16/129,696 Office Action dated Apr. 13, 2020.
U.S. Appl. No. 16/129,696 Office Action dated Apr. 17, 2019.
U.S. Appl. No. 16/129,696 Office Action dated Dec. 14, 2020.
U.S. Appl. No. 16/129,696 Office Action dated May 26, 2021.
U.S. Appl. No. 16/129,696 Office Action dated Sep. 19, 2019.
U.S. Appl. No. 16/649,572 Miscellaneous Communication re: Third Party Submission dated Mar. 19, 2021.
Usman et al. Exploiting the chemical synthesis of RNA. Trends Biochem Sci 17:334-339 (1992).
Valtorta et al. KRAS gene amplification in colorectal cancer and impact on response to EGFR-targeted therapy. Int J Cancer 133:1259-1266 (2013).
Van Deutekom et al. Antisense-induced exon skipping restores dystrophin expression in DMD patient derived muscle cells. Hum Mol Genet. 10(15):1547-54 (2001).
Van Vliet et al. Assessment of the feasibility of exon 45-55 multiexon skipping forduchenne muscular dystrophy. BMC Medical Genetics 9:105 (2008).
Verma et al. Modified oligonucleotides: synthesis and strategy for users. Annu Rev Biochem 67:99-134 (1998).
Walker et al. Improved cellular delivery of antisense oligonucleotides using transferrin receptor antibody-oligonucleotide conjugates. Pharmaceutical research 12(10):1548-1553 (1995).
Ward et al. Binding activities of a repertoire of single immunoglobulin variable domains secreted from *Escherichia coli*. Nature 341(6242):544-546 (1989).
Watts et al. Chemically modified siRNA: tools and applications. Drug Discov Today 13(19-20):842-855 (2008).
Wigler et al. Transfer of purified herpes virus thymidine kinase gene to cultured mouse cells. Cell 11:223-232 (1977).
Wigler et al. Transformation of mammalian cells with an amplifiable dominant-acting gene. PNAS USA 77:3567-3570 (1980).
Winkler. Oligonucleotide conjugates for therapeutic applications. Ther Del 4(7):791-809 (2013).
Wong et al. Co-injection of a targeted, reversibly masked endosomolytic polymer dramatically improves the efficacy of cholesterol-conjugated small interfering RNAs in vivo. Nucleic Acid Ther 22(6):380-390 (2012).
Wu et al. Building complex glycopeptides: Development of a cysteine-free native chemical ligation protocol. Angew. Chem. Int. Ed. 45:4116-4125 (2006).
Wu et al. Cell-penetrating peptides as transporters for morpholino oligomers: effects of amino acid composition on intracellular delivery and cytotoxicity. Nucleic Acids Res 35(15):5182-5191 (2007).
Wu et al. Delivery systems for gene therapy. Biotherapy 3:87-95 (1991).
Wu et al. Site-specific chemical modification of recombinant proteins produced in mammalian cells by using the genetically encoded aldehyde tag. PNAS USA 106(9):3000-3005 (2009).
Xia et al. Intravenous siRNA of brain cancer with receptor targeting and avidin-biotin technology. Pharm Res 24(12):2309-16 (2007).
Xu et al. Delivery systems for siRNA drug development in cancer therapy. Asian Journal of Pharmaceutical Sciences 10(1):1-12 (2015).
Yessine et al. Characterization of the membrane-destabilizing properties of different pH-sensitive methacrylic acid copolymers. Biochimica et Biophysica Acta 1613:28-38 (2003).
Yuan et al. Development of siRNA payloads to target KRAS-mutant cancer. Cancer Discov 4(10):1182-1197 (2014).
Zhang et al. A remote arene-binding site on prostate specific membrane antigen revealed by antibody-recruiting small molecules. J Am Chem Soc. 132(36):12711-12716 (2010).
Darimont et al. 8-05 Abstract: A novel Antibody-Oligonucleotide Conjugate (AOC) platform enables efficient regulation of muscle targets in mice. Journal Of Cachexia, Sarcopenia And Muscle 8:999-1080 (2017).
Gao et al. Effective Dystrophin Restoration by a Novel Muscle-Homing Peptide—Morpholino Conjugate in Dystrophin-Deficient mdx Mice. Mol Ther. 22(7):1333-1341 (2014).
Gooding et al. Oligonucleotide conjugates—Candidates for gene silencing therapeutics. Eur J Pharm Biopharm. 107:321-40 (2016).
U.S. Appl. No. 17/463,484 Office Action dated Jan. 4, 2022.

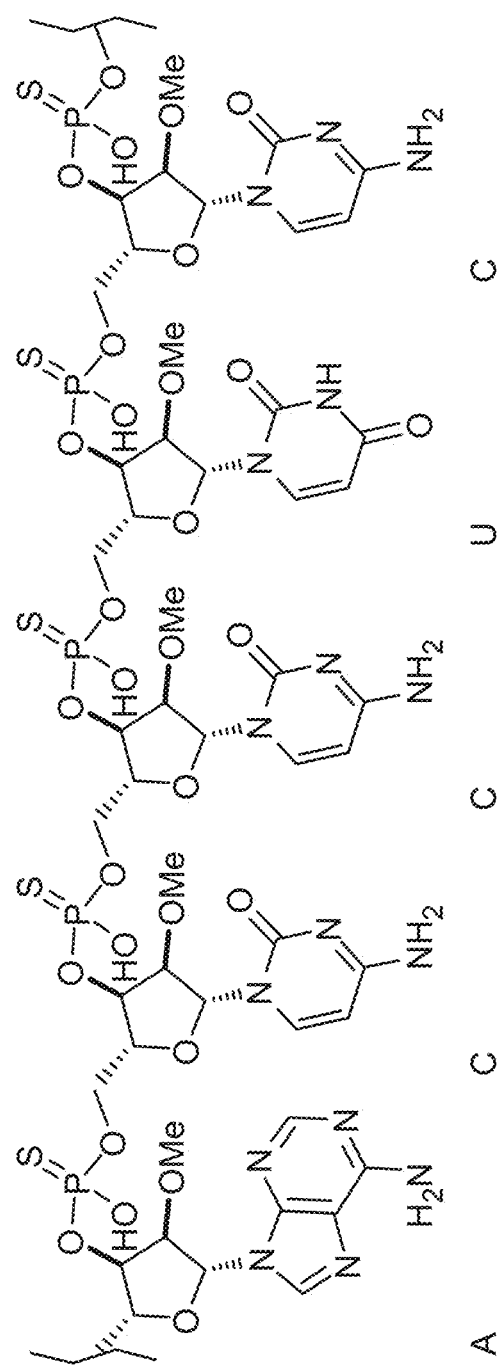
FIG. 2B (Cont.1)

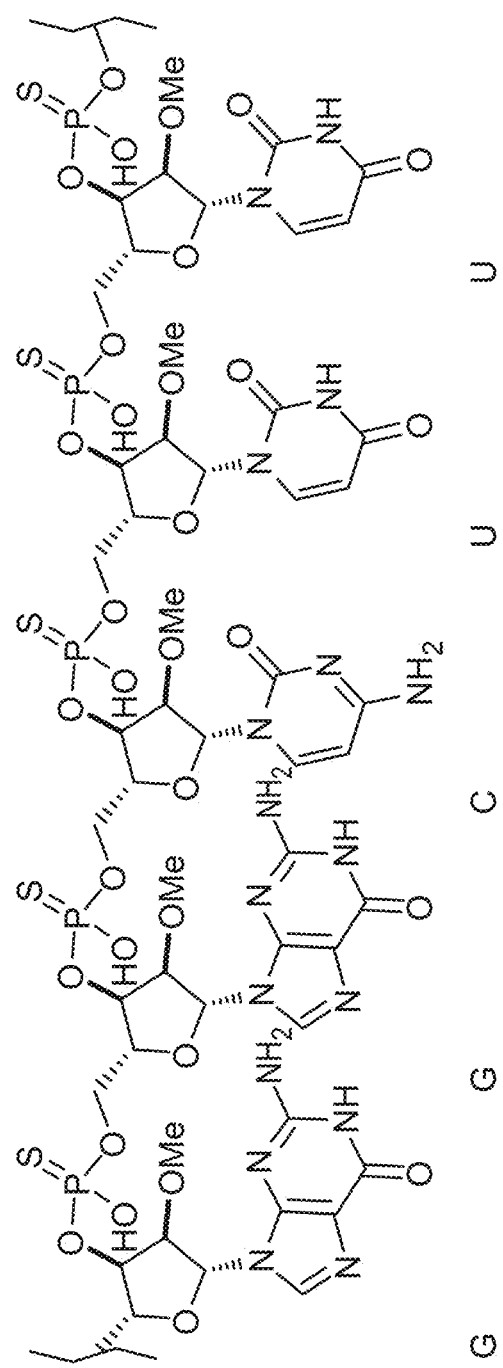
FIG. 2B (Cont.2)

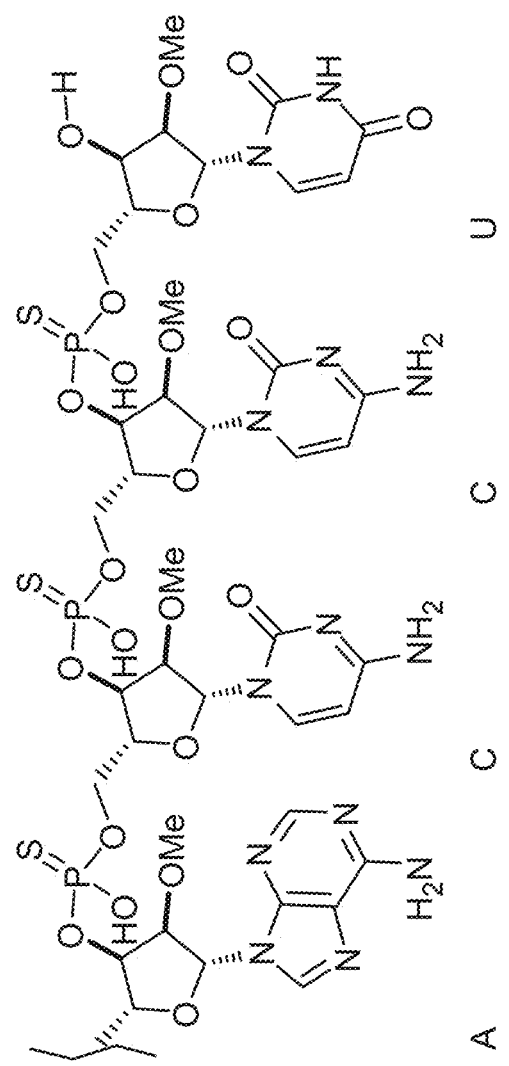
FIG. 2B (Cont.3)

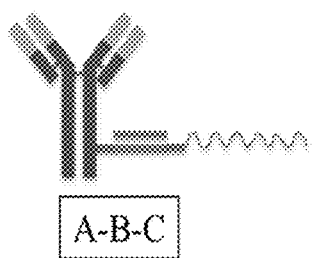
Fig. 19A
A-B-C
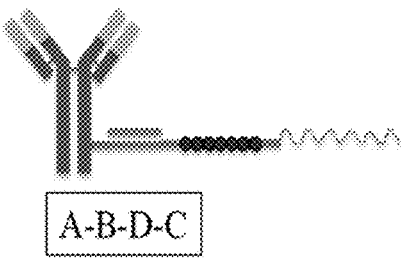
Fig. 19B
A-B-D-C
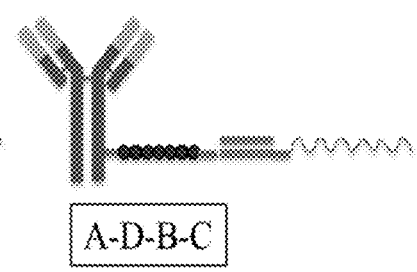
Fig. 19C
A-D-B-C
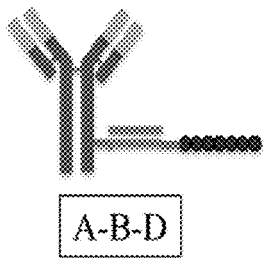
Fig. 19D
A-B-D
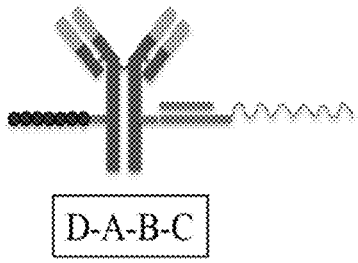
Fig. 19E
D-A-B-C
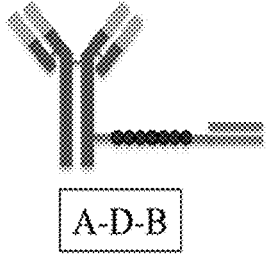
Fig. 19F
A-D-B
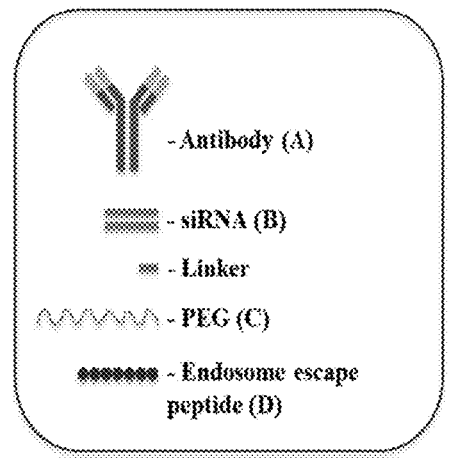
Legend
- Antibody (A)
- siRNA (B)
- Linker
- PEG (C)
- Endosome escape peptide (D)

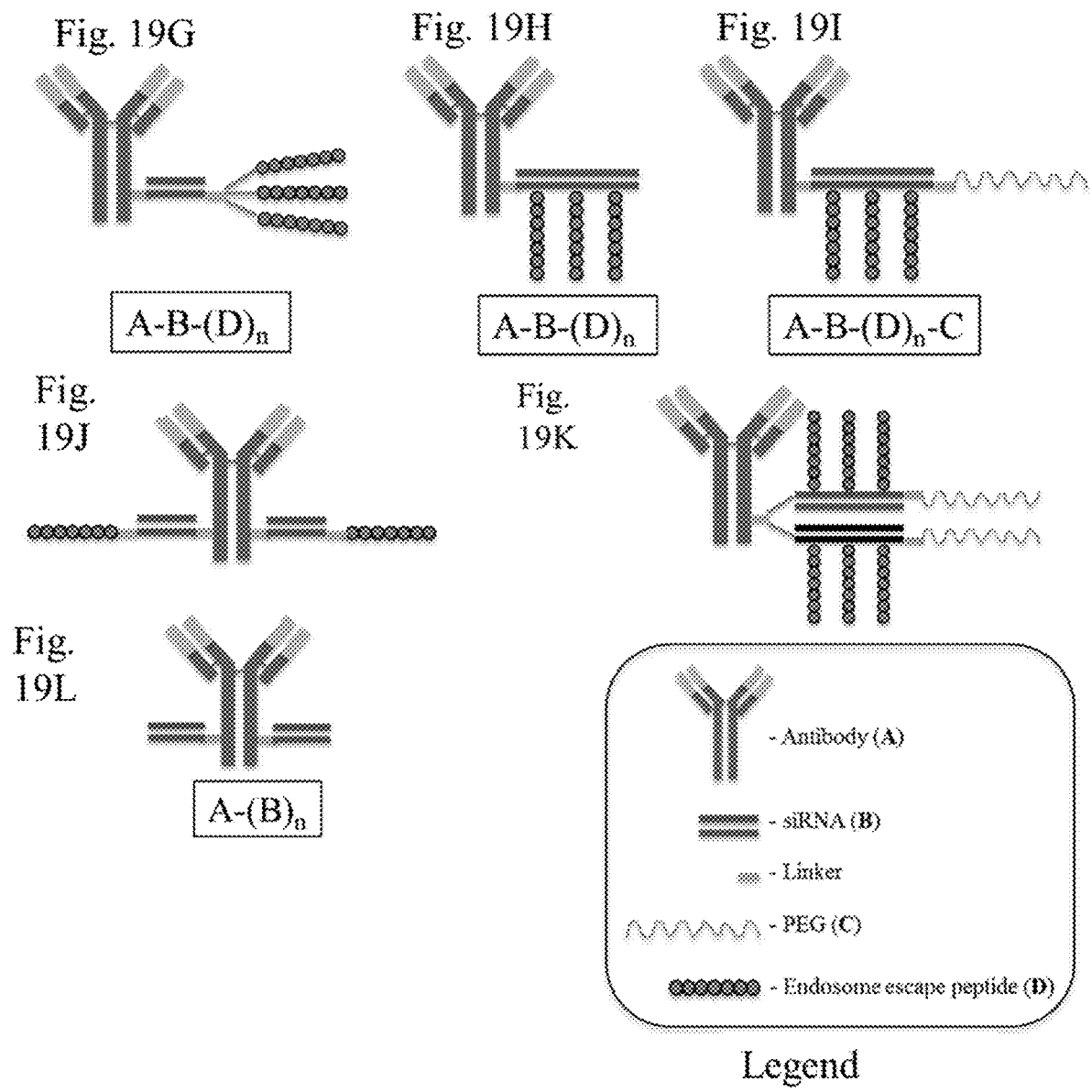

SEQUENCE LISTING

```
<160> NUMBER OF SEQ ID NOS: 977

<210> SEQ ID NO 1
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Gly Ile Phe Gly Glu Ile Glu Glu Leu Ile Glu Glu Gly Leu Glu
1               5                   10                  15

Asn Leu Ile Asp Trp Gly Asn Ala
            20

<210> SEQ ID NO 2
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Leu Phe Glu Ala Ile Glu Gly Phe Ile Glu Asn Gly Trp Glu Gly
1               5                   10                  15

Met Ile Asp Gly Trp Tyr Gly Cys
            20

<210> SEQ ID NO 3
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3
```

-continued

```
Gly Leu Phe Glu Ala Ile Glu Gly Phe Ile Glu Asn Gly Trp Glu Gly
1               5                   10                  15

Met Ile Trp Asp Tyr Gly Ser Gly Ser Cys Gly
            20                  25
```

<210> SEQ ID NO 4
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

```
Gly Leu Phe Glu Ala Ile Glu Gly Phe Ile Glu Asn Gly Trp Glu Gly
1               5                   10                  15

Met Ile Asp Gly Trp Tyr Gly
            20
```

<210> SEQ ID NO 5
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Gly Leu Phe Glu Ala Ile Glu Gly Phe Ile Glu Asn Gly Trp Glu Gly
1               5                   10                  15

Met Ile Trp Asp Tyr Gly Ser Gly Ser Cys Lys
            20                  25
```

<210> SEQ ID NO 6
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Cys Leu Ile Gly Ala Ile Leu Lys Val Leu Ala Thr Gly Leu Pro Thr
1               5                   10                  15

Leu Ile Ser Trp Ile Lys Asn Lys Arg Lys Gln
            20                  25
```

<210> SEQ ID NO 7
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```

<210> SEQ ID NO 8
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 8

Ile Phe Gly Ala Ile Ala Gly Leu Leu Lys Asn Ile Phe
1               5                   10

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Phe Phe Gly His Leu Phe Lys Leu Ala Thr Lys Ile Ile Pro Ser Leu
1               5                   10                  15

Phe Gln

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Leu Ile Ile Leu Arg Arg Arg Ile Arg Lys Gln Ala His Ala
1               5                   10                  15

His Ser Lys

<210> SEQ ID NO 12
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Pro Lys Gly Asp Pro Lys Gly Val Thr Val Thr Val Thr
1               5                   10                  15

Val Thr Gly Lys Gly Asp Pro Lys Pro Asp
            20                  25

<210> SEQ ID NO 13
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 13

Cys Ser Ile Pro Pro Glu Val Lys Phe Asn Lys Pro Phe Val Tyr Leu
1               5                   10                  15

Ile

<210> SEQ ID NO 14
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Ala Leu Phe Leu Gly Phe Leu Gly Ala Ala Gly Ser Thr Met Gly
1               5                   10                  15

Ala

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

His Gly Leu Ala Ser Thr Leu Thr Arg Trp Ala His Tyr Asn Ala Leu
1               5                   10                  15

Ile Arg Ala Phe
            20
```

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Leu Trp Arg Ala Leu Trp Arg Leu Leu Arg Ser Leu Trp Arg Leu
1               5                   10                  15

Leu Trp Arg Ala
            20

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 20
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Leu Phe Glu Ala Ile Glu Gly Phe Ile Glu Asn Gly Trp Glu Gly
1               5                   10                  15

Met Ile Asp Gly Trp Tyr Gly Cys
            20

<210> SEQ ID NO 21
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 22
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Gly Leu Phe Gly Ala Ile Ala Gly Phe Ile Glu Asn Gly Trp Glu Gly
1               5                   10                  15

Met Ile Asp Gly Arg Gln Ile Lys Ile Trp Phe Gln Asn Arg Arg Met
            20                  25                  30

Lys Trp Lys Lys
        35
```

<210> SEQ ID NO 23
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

```
Gly Leu Phe Gly Ala Ile Ala Gly Phe Ile Glu Asn Gly Trp Glu Gly
1               5                   10                  15

Met Ile Asp Gly Ser Ser Lys Lys Lys Lys
            20                  25
```

<210> SEQ ID NO 24
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Gly Leu Phe Glu Ala Ile Ala Gly Phe Ile Glu Asn Gly Trp Glu Gly
1               5                   10                  15

Met Ile Asp Gly Gly Gly Tyr Cys
            20
```

<210> SEQ ID NO 25
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Gly Leu Phe His Ala Ile Ala His Phe Ile His Gly Gly Trp His Gly
1               5                   10                  15

Leu Ile His Gly Trp Tyr Gly
            20
```

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Gly Leu Phe Glu Ala Ile Glu Gly Phe Ile Glu Asn Gly Trp Glu Gly
1               5                   10                  15

Leu Ala Glu Ala Leu Ala Glu Ala Leu Glu Ala Leu Ala Ala
            20                  25                  30
```

<210> SEQ ID NO 27

```
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Trp Lys Leu Phe Lys Lys Ile Gly Ala Val Leu Lys Val Leu Thr
1               5                   10                  15

Thr Gly Tyr Gly Arg Lys Lys Arg Arg Gln Arg Arg Arg
            20                  25

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggccaaacct cggcttacct gaaat                                           25

<210> SEQ ID NO 29
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ggccaaaccu cggcuuaccu                                                 20

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cagaattctg ccaattgctg ag                                              22

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttcttcagct tgtgtcatcc                                                 20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
acccagtcta ccaccctatc                                                 20
```

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctctttatct tctgcccacc tt                                              22

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gcgctatcag gagacaatga g                                               21

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gtttttatgt gattctgtaa tttccc                                          26

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
ctctctgtac cttatcttag tgtt                                            24

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tggaggagag actcgggaaa                                                 20

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ttgaagccat tttgttgctc ttt                                             23

<210> SEQ ID NO 39
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
acaggctctg caaagt                                                    16

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
aacagatgac aactactgcc gaaa                                           24

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ttggctctga tagggtggta gac                                            23

<210> SEQ ID NO 42
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
cttgttgaaa accc                                                      14

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tgagggtgtt aatgctgaaa gta                                            23

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
caccaactgg gaggaaagtt                                                20

```
<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ggccaaacct cggcttacct gaaat                                               25

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
agcccatctt ctcctggtcc tgggaagg                                            28

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
atcctctttg gtaacctcac ctcac                                               25

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tcgtccacaa aatgattctg aatta                                               25

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cggtgtgtgt atcattctct agtgt                                               25

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cctggaaaca gctcctaaca tc                                                  22

<210> SEQ ID NO 51
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cagtcaagcc caaagtctct c                                              21

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ctagtgccct tgttttcaga                                                20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
aggatctacc actgatgggt                                                20

<210> SEQ ID NO 54
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
gccugagcug aucugcuggc aucuugcagu u                                   31

<210> SEQ ID NO 55
<211> LENGTH: 57
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
gcagaauucg auccaccggc uguucaagcc ugagcugauc ugcucgcauc uugcagu       57

<210> SEQ ID NO 56
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
cagcaguagu ugucaucugc uc                                             22

<210> SEQ ID NO 57
<211> LENGTH: 29
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
cacaaagucu gcauccagga acauggguc                                           29

<210> SEQ ID NO 58
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
cugcaauucc ccgagucucu gc                                                  22

<210> SEQ ID NO 59
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
cucauaccuu cugcuugaug auc                                                 23

<210> SEQ ID NO 60
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
uccaacuggg gacgccucug uuccaaaucc                                          30

<210> SEQ ID NO 61
<211> LENGTH: 24
<212> TYPE: RNA
<213> ORGANISM: Homo sapiens

<400> SEQUENCE: 61
gauagguggu aucaacaucu guaa                                                24

<210> SEQ ID NO 62
<211> LENGTH: 21
<212> TYPE: RNA
<213> ORGANISM: Homo sapiens

<400> SEQUENCE: 62
gauagguggu aucaacaucu g                                                   21

<210> SEQ ID NO 63
<211> LENGTH: 25
<212> TYPE: RNA
<213> ORGANISM: Homo sapiens

<400> SEQUENCE: 63
gauagguggu aucaacaucu guaag                                               25
```

```
<210> SEQ ID NO 64
<211> LENGTH: 20
<212> TYPE: RNA
<213> ORGANISM: Homo sapiens

<400> SEQUENCE: 64
ggugguauca acaucuguaa                                                    20

<210> SEQ ID NO 65
<211> LENGTH: 20
<212> TYPE: RNA
<213> ORGANISM: Homo sapiens

<400> SEQUENCE: 65
guaucaacau cuguaagcac                                                    20

<210> SEQ ID NO 66
<211> LENGTH: 23
<212> TYPE: RNA
<213> ORGANISM: Homo sapiens

<400> SEQUENCE: 66
ugcauguucc agucguugug ugg                                                23

<210> SEQ ID NO 67
<211> LENGTH: 25
<212> TYPE: RNA
<213> ORGANISM: Homo sapiens

<400> SEQUENCE: 67
cacuauucca gucaaauagg ucugg                                              25

<210> SEQ ID NO 68
<211> LENGTH: 25
<212> TYPE: RNA
<213> ORGANISM: Homo sapiens

<400> SEQUENCE: 68
auuuaccaac cuucaggauc gagua                                              25

<210> SEQ ID NO 69
<211> LENGTH: 21
<212> TYPE: RNA
<213> ORGANISM: Homo sapiens

<400> SEQUENCE: 69
ggccuaaaac acauacacau a                                                  21

<210> SEQ ID NO 70
<211> LENGTH: 20
<212> TYPE: RNA
<213> ORGANISM: Canis sp.

<400> SEQUENCE: 70 cauuuugac cuacaugugg                                                     20

<210> SEQ ID NO 71
<211> LENGTH: 20
<212> TYPE: RNA
<213> ORGANISM: Canis sp.

<400> SEQUENCE: 71
uuugaccuac auguggaaag                                                    20
```

```
<210> SEQ ID NO 72
<211> LENGTH: 26
<212> TYPE: RNA
<213> ORGANISM: Canis sp.

<400> SEQUENCE: 72
uacauuuuug accuacaugu ggaaag                                          26

<210> SEQ ID NO 73
<211> LENGTH: 22
<212> TYPE: RNA
<213> ORGANISM: Canis sp.

<400> SEQUENCE: 73
auuuuugacc uacaugggaa ag                                              22

<210> SEQ ID NO 74
<211> LENGTH: 23
<212> TYPE: RNA
<213> ORGANISM: Canis sp.

<400> SEQUENCE: 74
uacgaguuga uugucggacc cag                                             23

<210> SEQ ID NO 75
<211> LENGTH: 25
<212> TYPE: RNA
<213> ORGANISM: Canis sp.

<400> SEQUENCE: 75
guggucuccu uaccuaugac ugugg                                           25

<210> SEQ ID NO 76
<211> LENGTH: 17
<212> TYPE: RNA
<213> ORGANISM: Canis sp.

<400> SEQUENCE: 76
ggucuccuua ccuauga                                                    17

<210> SEQ ID NO 77
<211> LENGTH: 24
<212> TYPE: RNA
<213> ORGANISM: Homo sapiens

<400> SEQUENCE: 77
ugucucagua aucuucuuac cuau                                            24

<210> SEQ ID NO 78
<211> LENGTH: 24
<212> TYPE: RNA
<213> ORGANISM: Homo sapiens

<400> SEQUENCE: 78
ucuuaccuau gacuauggau gaga                                            24

<210> SEQ ID NO 79
<211> LENGTH: 20
<212> TYPE: RNA
<213> ORGANISM: Homo sapiens

<400> SEQUENCE: 79
```
gcaugaacuc uuguggaucc                                              20

<210> SEQ ID NO 80
<211> LENGTH: 20
<212> TYPE: RNA
<213> ORGANISM: Homo sapiens

<400> SEQUENCE: 80
ccaggguacu acuuacauua                                              20

<210> SEQ ID NO 81
<211> LENGTH: 21
<212> TYPE: RNA
<213> ORGANISM: Homo sapiens

<400> SEQUENCE: 81
aucguguguc acagcaucca g                                            21

<210> SEQ ID NO 82
<211> LENGTH: 30
<212> TYPE: RNA
<213> ORGANISM: Homo sapiens

<400> SEQUENCE: 82
uguucagggc augaacucuu guggauccuu                                   30

<210> SEQ ID NO 83
<211> LENGTH: 31
<212> TYPE: RNA
<213> ORGANISM: Homo sapiens

<400> SEQUENCE: 83
uaggaggcgc cucccauccu guaggucacu g                                 31

<210> SEQ ID NO 84
<211> LENGTH: 31
<212> TYPE: RNA
<213> ORGANISM: Homo sapiens

<400> SEQUENCE: 84
aggucuagga ggcgccuccc auccuguagg u                                 31

<210> SEQ ID NO 85
<211> LENGTH: 25
<212> TYPE: RNA
<213> ORGANISM: Homo sapiens

<400> SEQUENCE: 85
gcgccuccca uccuguaggu cacug                                        25

<210> SEQ ID NO 86
<211> LENGTH: 26
<212> TYPE: RNA
<213> ORGANISM: Homo sapiens

<400> SEQUENCE: 86
cuucgaggag gucuaggagg cgccuc                                       26

<210> SEQ ID NO 87
<211> LENGTH: 21
<212> TYPE: RNA
<213> ORGANISM: Homo sapiens

<400> SEQUENCE: 87
cucccauccu guaggucacu g                                                    21

<210> SEQ ID NO 88
<211> LENGTH: 22
<212> TYPE: RNA
<213> ORGANISM: Homo sapiens

<400> SEQUENCE: 88
uaccaguuuu ugcccuguca gg                                                   22

<210> SEQ ID NO 89
<211> LENGTH: 26
<212> TYPE: RNA
<213> ORGANISM: Homo sapiens

<400> SEQUENCE: 89
ucaauaugcu gcuucccaaa cugaaa                                               26

<210> SEQ ID NO 90
<211> LENGTH: 25
<212> TYPE: RNA
<213> ORGANISM: Homo sapiens

<400> SEQUENCE: 90
cuaggaggcg ccucccaucc uguag                                                25

<210> SEQ ID NO 91
<211> LENGTH: 31
<212> TYPE: RNA
<213> ORGANISM: Homo sapiens

<400> SEQUENCE: 91
uuaugauuuc caucuacgau gucaguacuu c                                         31

<210> SEQ ID NO 92
<211> LENGTH: 31
<212> TYPE: RNA
<213> ORGANISM: Homo sapiens

<400> SEQUENCE: 92
cuuaccugcc aguggaggau uauauuccaa a                                         31

<210> SEQ ID NO 93
<211> LENGTH: 25
<212> TYPE: RNA
<213> ORGANISM: Homo sapiens

<400> SEQUENCE: 93
caucaggauu cuuaccugcc agugg                                                25

<210> SEQ ID NO 94
<211> LENGTH: 25
<212> TYPE: RNA
<213> ORGANISM: Homo sapiens

<400> SEQUENCE: 94
cgaugucagu acuuccaaua uucac                                                25

<210> SEQ ID NO 95
<211> LENGTH: 18
<212> TYPE: RNA
<213> ORGANISM: Homo sapiens

```
<400> SEQUENCE: 95
accauucauc aggauucu                                              18

<210> SEQ ID NO 96
<211> LENGTH: 18
<212> TYPE: RNA
<213> ORGANISM: Homo sapiens

<400> SEQUENCE: 96
accugccagu ggaggauu                                              18

<210> SEQ ID NO 97
<211> LENGTH: 27
<212> TYPE: RNA
<213> ORGANISM: Homo sapiens

<400> SEQUENCE: 97
ccaauauuca cuaaaucaac cuguuaa                                    27

<210> SEQ ID NO 98
<211> LENGTH: 30
<212> TYPE: RNA
<213> ORGANISM: Homo sapiens

<400> SEQUENCE: 98
caggauuguu accugccagu ggaggauuau                                 30

<210> SEQ ID NO 99
<211> LENGTH: 31
<212> TYPE: RNA
<213> ORGANISM: Homo sapiens

<400> SEQUENCE: 99
acgaugucag uacuuccaau auucacuaaa u                               31

<210> SEQ ID NO 100
<211> LENGTH: 31
<212> TYPE: RNA
<213> ORGANISM: Homo sapiens

<400> SEQUENCE: 100
auuuccaucu acgaugucag uacuuccaau a                               31

<210> SEQ ID NO 101
<211> LENGTH: 21
<212> TYPE: RNA
<213> ORGANISM: Homo sapiens

<400> SEQUENCE: 101
caggagcuuc caaaugcugc a                                          21

<210> SEQ ID NO 102
<211> LENGTH: 29
<212> TYPE: RNA
<213> ORGANISM: Homo sapiens

<400> SEQUENCE: 102
cuugucuuca ggagcuucca aaugcugca                                  29

<210> SEQ ID NO 103
<211> LENGTH: 22
<212> TYPE: RNA
<213> ORGANISM: Homo sapiens
```

```
<400> SEQUENCE: 103
uccucagcag aaagaagcca cg                                              22

<210> SEQ ID NO 104
<211> LENGTH: 20
<212> TYPE: RNA
<213> ORGANISM: Homo sapiens

<400> SEQUENCE: 104
uuagaaaucu cuccuugugc                                                 20

<210> SEQ ID NO 105
<211> LENGTH: 20
<212> TYPE: RNA
<213> ORGANISM: Homo sapiens

<400> SEQUENCE: 105
uaaauugggu guuacacaau                                                 20

<210> SEQ ID NO 106
<211> LENGTH: 24
<212> TYPE: RNA
<213> ORGANISM: Homo sapiens

<400> SEQUENCE: 106
cccugaggca uucccaucuu gaau                                            24

<210> SEQ ID NO 107
<211> LENGTH: 20
<212> TYPE: RNA
<213> ORGANISM: Homo sapiens

<400> SEQUENCE: 107
aggacuuacu ugcuuuguuu                                                 20

<210> SEQ ID NO 108
<211> LENGTH: 23
<212> TYPE: RNA
<213> ORGANISM: Homo sapiens

<400> SEQUENCE: 108
cuugaauuua ggagauucau cug                                             23

<210> SEQ ID NO 109
<211> LENGTH: 23
<212> TYPE: RNA
<213> ORGANISM: Homo sapiens

<400> SEQUENCE: 109
caucuucuga uaauuuccu guu                                              23

<210> SEQ ID NO 110
<211> LENGTH: 24
<212> TYPE: RNA
<213> ORGANISM: Homo sapiens

<400> SEQUENCE: 110
ucuucuguuu uuguuagcca guca                                            24

<210> SEQ ID NO 111
<211> LENGTH: 20
<212> TYPE: RNA
```

<213> ORGANISM: Homo sapiens

<400> SEQUENCE: 111
ucuauguaaa cugaaaauuu                                              20

<210> SEQ ID NO 112
<211> LENGTH: 20
<212> TYPE: RNA
<213> ORGANISM: Homo sapiens

<400> SEQUENCE: 112
uucuggagau ccauuaaaac                                              20

<210> SEQ ID NO 113
<211> LENGTH: 24
<212> TYPE: RNA
<213> ORGANISM: Homo sapiens

<400> SEQUENCE: 113
cagcaguugc gugaucucca cuag                                         24

<210> SEQ ID NO 114
<211> LENGTH: 21
<212> TYPE: RNA
<213> ORGANISM: Homo sapiens

<400> SEQUENCE: 114
uucaucaacu accaccacca u                                            21

<210> SEQ ID NO 115
<211> LENGTH: 25
<212> TYPE: RNA
<213> ORGANISM: Homo sapiens

<400> SEQUENCE: 115
cuaagcaaaa uaaucugacc uuaag                                        25

<210> SEQ ID NO 116
<211> LENGTH: 28
<212> TYPE: RNA
<213> ORGANISM: Homo sapiens

<400> SEQUENCE: 116
cuuguaaaag aacccagcgg ucuucugu                                     28

<210> SEQ ID NO 117
<211> LENGTH: 22
<212> TYPE: RNA
<213> ORGANISM: Homo sapiens

<400> SEQUENCE: 117
caucuacaga uguuugccca uc                                           22

<210> SEQ ID NO 118
<211> LENGTH: 23
<212> TYPE: RNA
<213> ORGANISM: Homo sapiens

<400> SEQUENCE: 118
gaaggauguc uuguaaaaga acc                                          23

<210> SEQ ID NO 119
<211> LENGTH: 20

```
<212> TYPE: RNA
<213> ORGANISM: Homo sapiens

<400> SEQUENCE: 119
accuguucuu caguaagacg                                           20

<210> SEQ ID NO 120
<211> LENGTH: 24
<212> TYPE: RNA
<213> ORGANISM: Homo sapiens

<400> SEQUENCE: 120
caugacacac cuguucuuca guaa                                      24

<210> SEQ ID NO 121
<211> LENGTH: 20
<212> TYPE: RNA
<213> ORGANISM: Homo sapiens

<400> SEQUENCE: 121
cauuugagaa ggaugucuug                                           20

<210> SEQ ID NO 122
<211> LENGTH: 24
<212> TYPE: RNA
<213> ORGANISM: Homo sapiens

<400> SEQUENCE: 122
aucucccaau accuggagaa gaga                                      24

<210> SEQ ID NO 123
<211> LENGTH: 31
<212> TYPE: RNA
<213> ORGANISM: Homo sapiens

<400> SEQUENCE: 123
gccaugcacu aaaaaggcac ugcaagacau u                              31

<210> SEQ ID NO 124
<211> LENGTH: 24
<212> TYPE: RNA
<213> ORGANISM: Homo sapiens

<400> SEQUENCE: 124
ucuuuaaagc caguugugug aauc                                      24

<210> SEQ ID NO 125
<211> LENGTH: 21
<212> TYPE: RNA
<213> ORGANISM: Homo sapiens

<400> SEQUENCE: 125
uuucugaaag ccaugcacua a                                         21

<210> SEQ ID NO 126
<211> LENGTH: 25
<212> TYPE: RNA
<213> ORGANISM: Homo sapiens

<400> SEQUENCE: 126
guacauacgg ccaguuuuug aagac                                     25

<210> SEQ ID NO 127
```

```
<211> LENGTH: 31
<212> TYPE: RNA
<213> ORGANISM: Homo sapiens

<400> SEQUENCE: 127
cuagauccgc uuuuaaaacc uguuaaaaca a                            31

<210> SEQ ID NO 128
<211> LENGTH: 31
<212> TYPE: RNA
<213> ORGANISM: Homo sapiens

<400> SEQUENCE: 128
ucuuuucuag auccgcuuuu aaaaccuguu a                            31

<210> SEQ ID NO 129
<211> LENGTH: 25
<212> TYPE: RNA
<213> ORGANISM: Homo sapiens

<400> SEQUENCE: 129
cuagauccgc uuuuaaaacc uguua                                   25

<210> SEQ ID NO 130
<211> LENGTH: 23
<212> TYPE: RNA
<213> ORGANISM: Homo sapiens

<400> SEQUENCE: 130
ccgucuucug ggucacugac uua                                     23

<210> SEQ ID NO 131
<211> LENGTH: 26
<212> TYPE: RNA
<213> ORGANISM: Homo sapiens

<400> SEQUENCE: 131
cuagauccgc uuuuaaaacc uguuaa                                  26

<210> SEQ ID NO 132
<211> LENGTH: 20
<212> TYPE: RNA
<213> ORGANISM: Homo sapiens

<400> SEQUENCE: 132
ccgcuuuuaa aaccuguuaa                                         20

<210> SEQ ID NO 133
<211> LENGTH: 26
<212> TYPE: RNA
<213> ORGANISM: Homo sapiens

<400> SEQUENCE: 133
uggauugcuu uucuuuucu agaucc                                   26

<210> SEQ ID NO 134
<211> LENGTH: 25
<212> TYPE: RNA
<213> ORGANISM: Homo sapiens

<400> SEQUENCE: 134
caugcuuccg ucuucggggu cacug                                   25
```

-continued

```
<210> SEQ ID NO 135
<211> LENGTH: 23
<212> TYPE: RNA
<213> ORGANISM: Homo sapiens

<400> SEQUENCE: 135
gaucuuguuu gagugaauac agu                                              23

<210> SEQ ID NO 136
<211> LENGTH: 22
<212> TYPE: RNA
<213> ORGANISM: Homo sapiens

<400> SEQUENCE: 136
guuauccagc caugcuuccg uc                                               22

<210> SEQ ID NO 137
<211> LENGTH: 25
<212> TYPE: RNA
<213> ORGANISM: Homo sapiens

<400> SEQUENCE: 137
ugauaauugg uaucacuaac cugug                                            25

<210> SEQ ID NO 138
<211> LENGTH: 22
<212> TYPE: RNA
<213> ORGANISM: Homo sapiens

<400> SEQUENCE: 138
guaucacuaa ccugugcugu ac                                               22

<210> SEQ ID NO 139
<211> LENGTH: 19
<212> TYPE: RNA
<213> ORGANISM: Homo sapiens

<400> SEQUENCE: 139
cugcuggcau cuugcaguu                                                   19

<210> SEQ ID NO 140
<211> LENGTH: 31
<212> TYPE: RNA
<213> ORGANISM: Homo sapiens

<400> SEQUENCE: 140
gccugagcug aucugcuggc aucuugcagu u                                     31

<210> SEQ ID NO 141
<211> LENGTH: 28
<212> TYPE: RNA
<213> ORGANISM: Homo sapiens

<400> SEQUENCE: 141
cuggcagaau ucgauccacc ggcuguuc                                         28

<210> SEQ ID NO 142
<211> LENGTH: 22
<212> TYPE: RNA
<213> ORGANISM: Homo sapiens

<400> SEQUENCE: 142
cagcaguagu ugucaucugc uc                                               22
```

```
<210> SEQ ID NO 143
<211> LENGTH: 19
<212> TYPE: RNA
<213> ORGANISM: Homo sapiens

<400> SEQUENCE: 143 ugaugggug guggguugg                                                  19

<210> SEQ ID NO 144
<211> LENGTH: 25
<212> TYPE: RNA
<213> ORGANISM: Homo sapiens

<400> SEQUENCE: 144
aucugcauua acacccucua gaaag                                          25

<210> SEQ ID NO 145
<211> LENGTH: 24
<212> TYPE: RNA
<213> ORGANISM: Homo sapiens

<400> SEQUENCE: 145
ccggcuguuc aguuguucug aggc                                           24

<210> SEQ ID NO 146
<211> LENGTH: 28
<212> TYPE: RNA
<213> ORGANISM: Homo sapiens

<400> SEQUENCE: 146
aucugcauua acacccucua gaaagaaa                                       28

<210> SEQ ID NO 147
<211> LENGTH: 28
<212> TYPE: RNA
<213> ORGANISM: Homo sapiens

<400> SEQUENCE: 147
gaaggagaag agauucuuac cuuacaaa                                       28

<210> SEQ ID NO 148
<211> LENGTH: 20
<212> TYPE: RNA
<213> ORGANISM: Homo sapiens

<400> SEQUENCE: 148
auucgaucca ccggcuguuc                                                20

<210> SEQ ID NO 149
<211> LENGTH: 20
<212> TYPE: RNA
<213> ORGANISM: Homo sapiens

<400> SEQUENCE: 149
cagcaguagu ugucaucugc                                                20

<210> SEQ ID NO 150
<211> LENGTH: 22
<212> TYPE: RNA
<213> ORGANISM: Homo sapiens

<400> SEQUENCE: 150
gccgguugac uucauccugu gc                                             22
```

<210> SEQ ID NO 151
<211> LENGTH: 22
<212> TYPE: RNA
<213> ORGANISM: Homo sapiens

<400> SEQUENCE: 151
cugcauccag gaacaugggu cc                                        22

<210> SEQ ID NO 152
<211> LENGTH: 23
<212> TYPE: RNA
<213> ORGANISM: Homo sapiens

<400> SEQUENCE: 152
gucugcaucc aggaacaugg guc                                       23

<210> SEQ ID NO 153
<211> LENGTH: 24
<212> TYPE: RNA
<213> ORGANISM: Homo sapiens

<400> SEQUENCE: 153
guugaagauc ugauagccgg uuga                                      24

<210> SEQ ID NO 154
<211> LENGTH: 24
<212> TYPE: RNA
<213> ORGANISM: Homo sapiens

<400> SEQUENCE: 154
uacuuacugu cuguagcucu uucu                                      24

<210> SEQ ID NO 155
<211> LENGTH: 24
<212> TYPE: RNA
<213> ORGANISM: Homo sapiens

<400> SEQUENCE: 155
cacucauggu cuccugauag cgca                                      24

<210> SEQ ID NO 156
<211> LENGTH: 22
<212> TYPE: RNA
<213> ORGANISM: Homo sapiens

<400> SEQUENCE: 156
cugcaauucc ccgagucucu gc                                        22

<210> SEQ ID NO 157
<211> LENGTH: 23
<212> TYPE: RNA
<213> ORGANISM: Homo sapiens

<400> SEQUENCE: 157
acugcuggac ccauguccug aug                                       23

<210> SEQ ID NO 158
<211> LENGTH: 21
<212> TYPE: RNA
<213> ORGANISM: Homo sapiens

<400> SEQUENCE: 158

-continued cuaaguugag guauggagag u                                         21

<210> SEQ ID NO 159
<211> LENGTH: 23
<212> TYPE: RNA
<213> ORGANISM: Homo sapiens

<400> SEQUENCE: 159
uauucacaga ccugcaauuc ccc                                       23

<210> SEQ ID NO 160
<211> LENGTH: 26
<212> TYPE: RNA
<213> ORGANISM: Homo sapiens

<400> SEQUENCE: 160
acaguggugc ugagauagua uaggcc                                    26

<210> SEQ ID NO 161
<211> LENGTH: 22
<212> TYPE: RNA
<213> ORGANISM: Homo sapiens

<400> SEQUENCE: 161
uaggccacuu uguugcucuu gc                                        22

<210> SEQ ID NO 162
<211> LENGTH: 19
<212> TYPE: RNA
<213> ORGANISM: Homo sapiens

<400> SEQUENCE: 162
uucagagggc gcuuucuuc                                            19

<210> SEQ ID NO 163
<211> LENGTH: 23
<212> TYPE: RNA
<213> ORGANISM: Homo sapiens

<400> SEQUENCE: 163
gggcaggcca uuccuccuuc aga                                       23

<210> SEQ ID NO 164
<211> LENGTH: 24
<212> TYPE: RNA
<213> ORGANISM: Homo sapiens

<400> SEQUENCE: 164
ucuucagggu uuguauguga uucu                                      24

<210> SEQ ID NO 165
<211> LENGTH: 27
<212> TYPE: RNA
<213> ORGANISM: Homo sapiens

<400> SEQUENCE: 165
cugggcugaa uugucugaau aucacug                                   27

<210> SEQ ID NO 166
<211> LENGTH: 26
<212> TYPE: RNA
<213> ORGANISM: Homo sapiens

<400> SEQUENCE: 166

```
cguuuggcac augugauccc acugag                                          26

<210> SEQ ID NO 167
<211> LENGTH: 24
<212> TYPE: RNA
<213> ORGANISM: Homo sapiens

<400> SEQUENCE: 167
gucuauaccu guuggcacau guga                                            24

<210> SEQ ID NO 168
<211> LENGTH: 25
<212> TYPE: RNA
<213> ORGANISM: Homo sapiens

<400> SEQUENCE: 168
ugcuuucugu aauucaucug gaguu                                           25

<210> SEQ ID NO 169
<211> LENGTH: 26
<212> TYPE: RNA
<213> ORGANISM: Homo sapiens

<400> SEQUENCE: 169
ccuccuuucu ggcauagacc uuccac                                          26

<210> SEQ ID NO 170
<211> LENGTH: 25
<212> TYPE: RNA
<213> ORGANISM: Homo sapiens

<400> SEQUENCE: 170
ugugucaucc auucgugcau cucug                                           25

<210> SEQ ID NO 171
<211> LENGTH: 25
<212> TYPE: RNA
<213> ORGANISM: Homo sapiens

<400> SEQUENCE: 171
uuaaggccuc uugugcuaca ggugg                                           25

<210> SEQ ID NO 172
<211> LENGTH: 23
<212> TYPE: RNA
<213> ORGANISM: Homo sapiens

<400> SEQUENCE: 172
ggggcucuuc uuuagcucuc uga                                             23

<210> SEQ ID NO 173
<211> LENGTH: 22
<212> TYPE: RNA
<213> ORGANISM: Homo sapiens

<400> SEQUENCE: 173
gacuuccaaa gucuugcauu uc                                              22

<210> SEQ ID NO 174
<211> LENGTH: 24
<212> TYPE: RNA
<213> ORGANISM: Homo sapiens
```

```
<400> SEQUENCE: 174
gccaacaugc ccaaacuucc uaag                                          24

<210> SEQ ID NO 175
<211> LENGTH: 26
<212> TYPE: RNA
<213> ORGANISM: Homo sapiens

<400> SEQUENCE: 175
cagagauuuc ucagcuccg ccagga                                         26

<210> SEQ ID NO 176
<211> LENGTH: 21
<212> TYPE: RNA
<213> ORGANISM: Homo sapiens

<400> SEQUENCE: 176
cuuacaucua gcaccucaga g                                             21

<210> SEQ ID NO 177
<211> LENGTH: 25
<212> TYPE: RNA
<213> ORGANISM: Homo sapiens

<400> SEQUENCE: 177
uccgccaucu guuagggucu gugcc                                         25

<210> SEQ ID NO 178
<211> LENGTH: 25
<212> TYPE: RNA
<213> ORGANISM: Homo sapiens

<400> SEQUENCE: 178
auuuggguua uccucugaau gucgc                                         25

<210> SEQ ID NO 179
<211> LENGTH: 22
<212> TYPE: RNA
<213> ORGANISM: Homo sapiens

<400> SEQUENCE: 179
cauaccucuu cauguaguuc cc                                            22

<210> SEQ ID NO 180
<211> LENGTH: 26
<212> TYPE: RNA
<213> ORGANISM: Homo sapiens

<400> SEQUENCE: 180
cauuugagcu gcguccaccu ugucug                                        26

<210> SEQ ID NO 181
<211> LENGTH: 26
<212> TYPE: RNA
<213> ORGANISM: Homo sapiens

<400> SEQUENCE: 181
uccugggcag acuggaugcu cuguuc                                        26

<210> SEQ ID NO 182
<211> LENGTH: 23
<212> TYPE: RNA
<213> ORGANISM: Homo sapiens
```

```
<400> SEQUENCE: 182
uugccugggc uuccugaggc auu                                              23

<210> SEQ ID NO 183
<211> LENGTH: 24
<212> TYPE: RNA
<213> ORGANISM: Homo sapiens

<400> SEQUENCE: 183
uucugaaaua acauauaccu gugc                                             24

<210> SEQ ID NO 184
<211> LENGTH: 25
<212> TYPE: RNA
<213> ORGANISM: Homo sapiens

<400> SEQUENCE: 184
uaguuucuga aauaacauau accug                                            25

<210> SEQ ID NO 185
<211> LENGTH: 21
<212> TYPE: RNA
<213> ORGANISM: Homo sapiens

<400> SEQUENCE: 185
gacuugucaa aucagauugg a                                                21

<210> SEQ ID NO 186
<211> LENGTH: 24
<212> TYPE: RNA
<213> ORGANISM: Homo sapiens

<400> SEQUENCE: 186
guuucugaaa uaacauauac cugu                                             24

<210> SEQ ID NO 187
<211> LENGTH: 20
<212> TYPE: RNA
<213> ORGANISM: Homo sapiens

<400> SEQUENCE: 187
caccagaaau acauaccaca                                                  20

<210> SEQ ID NO 188
<211> LENGTH: 20
<212> TYPE: RNA
<213> ORGANISM: Homo sapiens

<400> SEQUENCE: 188
caaugauuua gcugugacug                                                  20

<210> SEQ ID NO 189
<211> LENGTH: 23
<212> TYPE: RNA
<213> ORGANISM: Homo sapiens

<400> SEQUENCE: 189
cgaaacuuca uggagacauc uug                                              23

<210> SEQ ID NO 190
<211> LENGTH: 25
<212> TYPE: RNA
```

<213> ORGANISM: Homo sapiens

<400> SEQUENCE: 190
cuuguagacg cugcucaaaa uuggc    25

<210> SEQ ID NO 191
<211> LENGTH: 20
<212> TYPE: RNA
<213> ORGANISM: Homo sapiens

<400> SEQUENCE: 191
caugcacaca ccuuugcucc    20

<210> SEQ ID NO 192
<211> LENGTH: 24
<212> TYPE: RNA
<213> ORGANISM: Homo sapiens

<400> SEQUENCE: 192
ucuguacaau cugacgucca gucu    24

<210> SEQ ID NO 193
<211> LENGTH: 27
<212> TYPE: RNA
<213> ORGANISM: Homo sapiens

<400> SEQUENCE: 193
gucuuuauca ccauuccac uucagac    27

<210> SEQ ID NO 194
<211> LENGTH: 25
<212> TYPE: RNA
<213> ORGANISM: Homo sapiens

<400> SEQUENCE: 194
ccgucugcuu uuucuguaca aucug    25

<210> SEQ ID NO 195
<211> LENGTH: 22
<212> TYPE: RNA
<213> ORGANISM: Homo sapiens

<400> SEQUENCE: 195
uccauaucug uagcugccag cc    22

<210> SEQ ID NO 196
<211> LENGTH: 23
<212> TYPE: RNA
<213> ORGANISM: Homo sapiens

<400> SEQUENCE: 196
ccaggcaacu ucagaaucca aau    23

<210> SEQ ID NO 197
<211> LENGTH: 30
<212> TYPE: RNA
<213> ORGANISM: Homo sapiens

<400> SEQUENCE: 197
uuucuguuac cugaaaagaa uuauaaugaa    30

<210> SEQ ID NO 198
<211> LENGTH: 25

```
<212> TYPE: RNA
<213> ORGANISM: Homo sapiens

<400> SEQUENCE: 198
cauucauuuc cuuucgcauc uuacg                                         25

<210> SEQ ID NO 199
<211> LENGTH: 26
<212> TYPE: RNA
<213> ORGANISM: Homo sapiens

<400> SEQUENCE: 199
ugaucucuuu gucaauucca uaucug                                        26

<210> SEQ ID NO 200
<211> LENGTH: 30
<212> TYPE: RNA
<213> ORGANISM: Homo sapiens

<400> SEQUENCE: 200
uucagugaua uagguuuuac cuuuccccag                                    30

<210> SEQ ID NO 201
<211> LENGTH: 26
<212> TYPE: RNA
<213> ORGANISM: Homo sapiens

<400> SEQUENCE: 201
cuguagcugc cagccauucu gucaag                                        26

<210> SEQ ID NO 202
<211> LENGTH: 21
<212> TYPE: RNA
<213> ORGANISM: Homo sapiens

<400> SEQUENCE: 202
ucuucugcuc gggaggugac a                                             21

<210> SEQ ID NO 203
<211> LENGTH: 20
<212> TYPE: RNA
<213> ORGANISM: Homo sapiens

<400> SEQUENCE: 203
ccaguuacua uucagaagac                                               20

<210> SEQ ID NO 204
<211> LENGTH: 20
<212> TYPE: RNA
<213> ORGANISM: Homo sapiens

<400> SEQUENCE: 204
ucuucaggug caccuucugu                                               20

<210> SEQ ID NO 205
<211> LENGTH: 25
<212> TYPE: RNA
<213> ORGANISM: Homo sapiens

<400> SEQUENCE: 205
ugugaugugg uccacauucu gguca                                         25

<210> SEQ ID NO 206
```

```
<211> LENGTH: 20
<212> TYPE: RNA
<213> ORGANISM: Homo sapiens

<400> SEQUENCE: 206
ccauguguuu cugguauucc                                              20

<210> SEQ ID NO 207
<211> LENGTH: 25
<212> TYPE: RNA
<213> ORGANISM: Homo sapiens

<400> SEQUENCE: 207
cguguagagu ccaccuuugg gcgua                                        25

<210> SEQ ID NO 208
<211> LENGTH: 24
<212> TYPE: RNA
<213> ORGANISM: Homo sapiens

<400> SEQUENCE: 208
uacuaauuuc cugcaguggu cacc                                         24

<210> SEQ ID NO 209
<211> LENGTH: 24
<212> TYPE: RNA
<213> ORGANISM: Homo sapiens

<400> SEQUENCE: 209
uucuguguga aauggcugca aauc                                         24

<210> SEQ ID NO 210
<211> LENGTH: 20
<212> TYPE: RNA
<213> ORGANISM: Homo sapiens

<400> SEQUENCE: 210
ccuucaaagg aauggaggcc                                              20

<210> SEQ ID NO 211
<211> LENGTH: 25
<212> TYPE: RNA
<213> ORGANISM: Homo sapiens

<400> SEQUENCE: 211
ugcugaauuu cagccuccag ugguu                                        25

<210> SEQ ID NO 212
<211> LENGTH: 25
<212> TYPE: RNA
<213> ORGANISM: Homo sapiens

<400> SEQUENCE: 212
ugaagucuuc cucuuucaga uucac                                        25

<210> SEQ ID NO 213
<211> LENGTH: 24
<212> TYPE: RNA
<213> ORGANISM: Homo sapiens

<400> SEQUENCE: 213
cuggcuuucu cucaucugug auuc                                         24
```

```
<210> SEQ ID NO 214
<211> LENGTH: 20
<212> TYPE: RNA
<213> ORGANISM: Homo sapiens

<400> SEQUENCE: 214
guuguaaguu gucuccucuu                                               20

<210> SEQ ID NO 215
<211> LENGTH: 20
<212> TYPE: RNA
<213> ORGANISM: Homo sapiens

<400> SEQUENCE: 215
uugucuguaa cagcugcugu                                               20

<210> SEQ ID NO 216
<211> LENGTH: 20
<212> TYPE: RNA
<213> ORGANISM: Homo sapiens

<400> SEQUENCE: 216
gcucuaauac cuugagagca                                               20

<210> SEQ ID NO 217
<211> LENGTH: 22
<212> TYPE: RNA
<213> ORGANISM: Homo sapiens

<400> SEQUENCE: 217
cuuugagacc ucaaauccug uu                                            22

<210> SEQ ID NO 218
<211> LENGTH: 25
<212> TYPE: RNA
<213> ORGANISM: Homo sapiens

<400> SEQUENCE: 218
cuuuauuuuc cuuucaucuc ugggc                                         25

<210> SEQ ID NO 219
<211> LENGTH: 27
<212> TYPE: RNA
<213> ORGANISM: Homo sapiens

<400> SEQUENCE: 219
aucguuucuu cacggacagu gugcugg                                       27

<210> SEQ ID NO 220
<211> LENGTH: 24
<212> TYPE: RNA
<213> ORGANISM: Homo sapiens

<400> SEQUENCE: 220
gggcuuguga gacaugagug auuu                                          24

<210> SEQ ID NO 221
<211> LENGTH: 22
<212> TYPE: RNA
<213> ORGANISM: Homo sapiens

<400> SEQUENCE: 221
accuucagag gacuccucuu gc                                            22
```

```
<210> SEQ ID NO 222
<211> LENGTH: 25
<212> TYPE: RNA
<213> ORGANISM: Homo sapiens

<400> SEQUENCE: 222
uauguguuac cuacccuugu cgguc                                           25

<210> SEQ ID NO 223
<211> LENGTH: 20
<212> TYPE: RNA
<213> ORGANISM: Homo sapiens

<400> SEQUENCE: 223
ggagagagcu uccuguagcu                                                 20

<210> SEQ ID NO 224
<211> LENGTH: 23
<212> TYPE: RNA
<213> ORGANISM: Homo sapiens

<400> SEQUENCE: 224
ucacccuuuc cacaggcguu gca                                             23

<210> SEQ ID NO 225
<211> LENGTH: 20
<212> TYPE: RNA
<213> ORGANISM: Homo sapiens

<400> SEQUENCE: 225
uuugugucuu ucugagaaac                                                 20

<210> SEQ ID NO 226
<211> LENGTH: 20
<212> TYPE: RNA
<213> ORGANISM: Homo sapiens

<400> SEQUENCE: 226
aaagacuuac cuuaagauac                                                 20

<210> SEQ ID NO 227
<211> LENGTH: 20
<212> TYPE: RNA
<213> ORGANISM: Homo sapiens

<400> SEQUENCE: 227
aucugucaaa ucgccugcag                                                 20

<210> SEQ ID NO 228
<211> LENGTH: 20
<212> TYPE: RNA
<213> ORGANISM: Homo sapiens

<400> SEQUENCE: 228
uuaccuugac uugcucaagc                                                 20

<210> SEQ ID NO 229
<211> LENGTH: 20
<212> TYPE: RNA
<213> ORGANISM: Homo sapiens

<400> SEQUENCE: 229
uccagguuca aguggauac                                                  20
```

```
<210> SEQ ID NO 230
<211> LENGTH: 25
<212> TYPE: RNA
<213> ORGANISM: Homo sapiens

<400> SEQUENCE: 230
gcucuucugg gcuuauggga gcacu                                          25

<210> SEQ ID NO 231
<211> LENGTH: 27
<212> TYPE: RNA
<213> ORGANISM: Homo sapiens

<400> SEQUENCE: 231
accuuuaucc acuggagauu ugucugc                                        27

<210> SEQ ID NO 232
<211> LENGTH: 21
<212> TYPE: RNA
<213> ORGANISM: Homo sapiens

<400> SEQUENCE: 232
uuccaccagu aacugaaaca g                                              21

<210> SEQ ID NO 233
<211> LENGTH: 29
<212> TYPE: RNA
<213> ORGANISM: Homo sapiens

<400> SEQUENCE: 233
ccacucagag cucagaucuu cuaacuucc                                      29

<210> SEQ ID NO 234
<211> LENGTH: 27
<212> TYPE: RNA
<213> ORGANISM: Homo sapiens

<400> SEQUENCE: 234
cuuccacuca gagcucagau cuucuaa                                        27

<210> SEQ ID NO 235
<211> LENGTH: 25
<212> TYPE: RNA
<213> ORGANISM: Homo sapiens

<400> SEQUENCE: 235
gggauccagu auacuuacag gcucc                                          25

<210> SEQ ID NO 236
<211> LENGTH: 26
<212> TYPE: RNA
<213> ORGANISM: Homo sapiens

<400> SEQUENCE: 236
accagaguaa cagucugagu aggagc                                         26

<210> SEQ ID NO 237
<211> LENGTH: 23
<212> TYPE: RNA
<213> ORGANISM: Homo sapiens

<400> SEQUENCE: 237
```
cucauaccuu cugcuugaug auc                                               23

<210> SEQ ID NO 238
<211> LENGTH: 24
<212> TYPE: RNA
<213> ORGANISM: Homo sapiens

<400> SEQUENCE: 238
uucuguccaa gcccgguuga aauc                                              24

<210> SEQ ID NO 239
<211> LENGTH: 30
<212> TYPE: RNA
<213> ORGANISM: Homo sapiens

<400> SEQUENCE: 239
acaucaagga agauggcauu ucuaguuugg                                        30

<210> SEQ ID NO 240
<211> LENGTH: 25
<212> TYPE: RNA
<213> ORGANISM: Homo sapiens

<400> SEQUENCE: 240
acaucaagga agauggcauu ucuag                                             25

<210> SEQ ID NO 241
<211> LENGTH: 30
<212> TYPE: RNA
<213> ORGANISM: Homo sapiens

<400> SEQUENCE: 241
cuccaacauc aaggaagaug gcauuucuag                                        30

<210> SEQ ID NO 242
<211> LENGTH: 25
<212> TYPE: RNA
<213> ORGANISM: Homo sapiens

<400> SEQUENCE: 242
aucauuuuuu cucauaccuu cugcu                                             25

<210> SEQ ID NO 243
<211> LENGTH: 36
<212> TYPE: RNA
<213> ORGANISM: Homo sapiens

<400> SEQUENCE: 243
aucauuuuuu cucauaccuu cugcuaggag cuaaaa                                 36

<210> SEQ ID NO 244

<400> SEQUENCE: 244

000

<210> SEQ ID NO 245
<211> LENGTH: 21
<212> TYPE: RNA
<213> ORGANISM: Homo sapiens

<400> SEQUENCE: 245
cacccaccau cacccucugu g                                                 21

<210> SEQ ID NO 246
<211> LENGTH: 22
<212> TYPE: RNA
<213> ORGANISM: Homo sapiens

<400> SEQUENCE: 246
aucaucucgu ugauauccuc aa                                              22

<210> SEQ ID NO 247
<211> LENGTH: 21
<212> TYPE: RNA
<213> ORGANISM: Homo sapiens

<400> SEQUENCE: 247
uccugcauug uugccuguaa g                                               21

<210> SEQ ID NO 248
<211> LENGTH: 30
<212> TYPE: RNA
<213> ORGANISM: Homo sapiens

<400> SEQUENCE: 248
uccaacuggg gacgccucug uuccaaaucc                                      30

<210> SEQ ID NO 249
<211> LENGTH: 21
<212> TYPE: RNA
<213> ORGANISM: Homo sapiens

<400> SEQUENCE: 249 acugggacg ccucuguucc a                                                21

<210> SEQ ID NO 250
<211> LENGTH: 20
<212> TYPE: RNA
<213> ORGANISM: Homo sapiens

<400> SEQUENCE: 250
ccguaaugau uguucuagcc                                                 20

<210> SEQ ID NO 251
<211> LENGTH: 20
<212> TYPE: RNA
<213> ORGANISM: Homo sapiens

<400> SEQUENCE: 251
uguuaaaaaa cuuacuucga                                                 20

<210> SEQ ID NO 252
<211> LENGTH: 25
<212> TYPE: RNA
<213> ORGANISM: Homo sapiens

<400> SEQUENCE: 252
cauucaacug uugccuccgg uucug                                           25

<210> SEQ ID NO 253
<211> LENGTH: 24
<212> TYPE: RNA
<213> ORGANISM: Homo sapiens

<400> SEQUENCE: 253
cuguugccuc cgguucugaa ggug                                            24

```
<210> SEQ ID NO 254
<211> LENGTH: 31
<212> TYPE: RNA
<213> ORGANISM: Homo sapiens

<400> SEQUENCE: 254
cauucaacug uugccuccgg uucugaaggu g                              31

<210> SEQ ID NO 255
<211> LENGTH: 21
<212> TYPE: RNA
<213> ORGANISM: Homo sapiens

<400> SEQUENCE: 255
uacuaaccuu gguuucugug a                                         21

<210> SEQ ID NO 256
<211> LENGTH: 25
<212> TYPE: RNA
<213> ORGANISM: Homo sapiens

<400> SEQUENCE: 256
cugaaggugu ucuuguacuu caucc                                     25

<210> SEQ ID NO 257
<211> LENGTH: 27
<212> TYPE: RNA
<213> ORGANISM: Homo sapiens

<400> SEQUENCE: 257
uguauaggga cccuccuucc augacuc                                   27

<210> SEQ ID NO 258
<211> LENGTH: 25
<212> TYPE: RNA
<213> ORGANISM: Homo sapiens

<400> SEQUENCE: 258
cuaaccuugg uuucugugau uuucu                                     25

<210> SEQ ID NO 259
<211> LENGTH: 27
<212> TYPE: RNA
<213> ORGANISM: Homo sapiens

<400> SEQUENCE: 259
gguaucuuug auacuaaccu ugguuuc                                   27

<210> SEQ ID NO 260
<211> LENGTH: 22
<212> TYPE: RNA
<213> ORGANISM: Homo sapiens

<400> SEQUENCE: 260
auucuuucaa cuagaauaaa ag                                        22

<210> SEQ ID NO 261
<211> LENGTH: 25
<212> TYPE: RNA
<213> ORGANISM: Homo sapiens

<400> SEQUENCE: 261
```

```
gauucugaau ucuuucaacu agaau                                    25

<210> SEQ ID NO 262
<211> LENGTH: 20
<212> TYPE: RNA
<213> ORGANISM: Homo sapiens

<400> SEQUENCE: 262
aucccacuga uucugaauuc                                          20

<210> SEQ ID NO 263
<211> LENGTH: 22
<212> TYPE: RNA
<213> ORGANISM: Homo sapiens

<400> SEQUENCE: 263
uuggcucugg ccuguccuaa ga                                       22

<210> SEQ ID NO 264
<211> LENGTH: 30
<212> TYPE: RNA
<213> ORGANISM: Homo sapiens

<400> SEQUENCE: 264
cucuuuucca gguucaagug ggauacuagc                               30

<210> SEQ ID NO 265
<211> LENGTH: 31
<212> TYPE: RNA
<213> ORGANISM: Homo sapiens

<400> SEQUENCE: 265
caagcuuuuc uuuuaguugc ugcucuuuuc c                             31

<210> SEQ ID NO 266
<211> LENGTH: 30
<212> TYPE: RNA
<213> ORGANISM: Homo sapiens

<400> SEQUENCE: 266
uauucuuuug uucuucuagc cuggagaaag                               30

<210> SEQ ID NO 267
<211> LENGTH: 28
<212> TYPE: RNA
<213> ORGANISM: Homo sapiens

<400> SEQUENCE: 267
cugcuuccuc caaccauaaa acaaauuc                                 28

<210> SEQ ID NO 268
<211> LENGTH: 26
<212> TYPE: RNA
<213> ORGANISM: Homo sapiens

<400> SEQUENCE: 268
ccaaugccau ccuggaguuc cuguaa                                   26

<210> SEQ ID NO 269
<211> LENGTH: 20
<212> TYPE: RNA
<213> ORGANISM: Homo sapiens

<400> SEQUENCE: 269
```

```
uccuguagaa uacuggcauc                                              20

<210> SEQ ID NO 270
<211> LENGTH: 27
<212> TYPE: RNA
<213> ORGANISM: Homo sapiens

<400> SEQUENCE: 270
ugcagaccuc cugccaccgc agauuca                                      27

<210> SEQ ID NO 271
<211> LENGTH: 20
<212> TYPE: RNA
<213> ORGANISM: Homo sapiens

<400> SEQUENCE: 271
cuaccucuuu uuucugucug                                              20

<210> SEQ ID NO 272
<211> LENGTH: 20
<212> TYPE: RNA
<213> ORGANISM: Homo sapiens

<400> SEQUENCE: 272
uguuuuugag gauugcugaa                                              20

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
tggttcttac ccagccgccg                                              20

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
gttattcttt agaatggtgc                                              20

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
tgctattacc ttaacccaga                                              20

<210> SEQ ID NO 276
<211> LENGTH: 27
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 276
ctgtgcttac cgggtttttcc acctccc                                              27

<210> SEQ ID NO 277
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
atcgtcgtga ctgtctgttg gaggg                                                 25

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
gctcacgttg aggggcatcg                                                       20

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
acgttgaggg gcatcgtcgc                                                       20

<210> SEQ ID NO 280
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
ggggcaucgu cgugacuguc uguuggaggg                                            30

<210> SEQ ID NO 281
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
cgucgugacu gucuguugga gg                                                    22

<210> SEQ ID NO 282
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 282
cgtcgtgact gtctgttgga gg                                          22

<210> SEQ ID NO 283
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
ggcaucgucg cgggaggcug cuggagcg                                    28

<210> SEQ ID NO 284
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
ccgcgacaua ggacggagag cagagccc                                    28

<210> SEQ ID NO 285
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
actgtgaggg cgatcgctgc                                             20

<210> SEQ ID NO 286
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
acgatgagtg gcatagtcgc                                             20

<210> SEQ ID NO 287
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
ggcatcgtcg cgggaggctg                                             20

<210> SEQ ID NO 288
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 288
gggcatcgtc gcgggaggct					20

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
ggggcatcgt cgcgggaggc					20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
aggggcatcg tcgcgggagg					20

<210> SEQ ID NO 291
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
gaggggcatc gtcgcgggag					20

<210> SEQ ID NO 292
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292 tgagggcat cgtcgcggga					20

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
ttgaggggca tcgtcgcggg					20

<210> SEQ ID NO 294
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294

-continued gttgaggggc atcgtcgcgg				20

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
cgttgagggg catcgtcgcg				20

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
acgttgaggg gcatcgtcgc				20

<210> SEQ ID NO 297
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
aacgttgagg ggcatcgtcg				20

<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
taacgttgag gggcatcgtc				20

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
ctaacgttga ggggcatcgt				20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
gctaacgttg aggggcatcg                                          20

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
agctaacgtt gaggggcatc                                          20

<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
aagctaacgt tgaggggcat                                          20

<210> SEQ ID NO 303
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
gaagctaacg ttgaggggca                                          20

<210> SEQ ID NO 304
<211> LENGTH: 20
<212> TYPE: DNA
<213> ORGANISM: Rattus sp.

<400> SEQUENCE: 304
ctccgcaatg ctgaaaggtg                                          20

<210> SEQ ID NO 305
<211> LENGTH: 24
<212> TYPE: RNA
<213> ORGANISM: Rattus sp.

<400> SEQUENCE: 305
ggcgugccuc aaacauggug gcgg                                     24

<210> SEQ ID NO 306
<211> LENGTH: 27
<212> TYPE: DNA
<213> ORGANISM: Rattus sp.

<400> SEQUENCE: 306
ctgtgcttac cgggttttcc acctccc                                  27

<210> SEQ ID NO 307
<211> LENGTH: 25
<212> TYPE: DNA
<213> ORGANISM: Rattus sp.

<400> SEQUENCE: 307

```
atcgtcgtga ctgtctgttg gaggg                                        25

<210> SEQ ID NO 308
<211> LENGTH: 20
<212> TYPE: DNA
<213> ORGANISM: Rattus sp.

<400> SEQUENCE: 308
gctcacgttg aggggcatcg                                              20

<210> SEQ ID NO 309
<211> LENGTH: 20
<212> TYPE: DNA
<213> ORGANISM: Rattus sp.

<400> SEQUENCE: 309
ggtcactcac cggtagagaa                                              20

<210> SEQ ID NO 310
<211> LENGTH: 20
<212> TYPE: DNA
<213> ORGANISM: Rattus sp.

<400> SEQUENCE: 310
gggttccaag tctataaagg                                              20

<210> SEQ ID NO 311
<211> LENGTH: 14
<212> TYPE: DNA
<213> ORGANISM: Homo sapiens

<400> SEQUENCE: 311
tgtgtctttt ccag                                                    14

<210> SEQ ID NO 312
<211> LENGTH: 23
<212> TYPE: DNA
<213> ORGANISM: Homo sapiens

<400> SEQUENCE: 312
tttggagact gccagggacc atg                                          23

<210> SEQ ID NO 313
<211> LENGTH: 20
<212> TYPE: DNA
<213> ORGANISM: Homo sapiens

<400> SEQUENCE: 313
catggtccct ggcagtctcc                                              20

<210> SEQ ID NO 314
<211> LENGTH: 36
<212> TYPE: DNA
<213> ORGANISM: Homo sapiens

<400> SEQUENCE: 314
tcaatgggca aaacatggtc cctggcagtc tccaaa                            36

<210> SEQ ID NO 315
<211> LENGTH: 15
<212> TYPE: DNA
<213> ORGANISM: Homo sapiens

<400> SEQUENCE: 315
```

```
tttgtgttct cccag                                                15
```

<210> SEQ ID NO 316
<211> LENGTH: 23
<212> TYPE: DNA
<213> ORGANISM: Homo sapiens

<400> SEQUENCE: 316

```
ggaaacagaa gtacctgtgc gcc                                       23
```

<210> SEQ ID NO 317
<211> LENGTH: 18
<212> TYPE: DNA
<213> ORGANISM: Homo sapiens

<400> SEQUENCE: 317

```
ggcgcacagg tacttctg                                             18
```

<210> SEQ ID NO 318
<211> LENGTH: 36
<212> TYPE: DNA
<213> ORGANISM: Homo sapiens

<400> SEQUENCE: 318

```
aatcatttct gctggcgcac aggtacttct gtttcc                         36
```

<210> SEQ ID NO 319
<211> LENGTH: 18
<212> TYPE: DNA
<213> ORGANISM: Homo sapiens

<400> SEQUENCE: 319

```
cccctgcagc acgcgggt                                             18
```

<210> SEQ ID NO 320
<211> LENGTH: 37
<212> TYPE: DNA
<213> ORGANISM: Homo sapiens

<400> SEQUENCE: 320

```
gaggcagggc cggcaggacc ccctgcagca cgcgggt                        37
```

<210> SEQ ID NO 321
<211> LENGTH: 20
<212> TYPE: DNA
<213> ORGANISM: Homo sapiens

<400> SEQUENCE: 321

```
ggcatcgtcg cgggaggctg                                           20
```

<210> SEQ ID NO 322
<211> LENGTH: 20
<212> TYPE: DNA
<213> ORGANISM: Homo sapiens

<400> SEQUENCE: 322

```
gggcatcgtc gcgggaggct                                           20
```

<210> SEQ ID NO 323
<211> LENGTH: 20
<212> TYPE: DNA
<213> ORGANISM: Homo sapiens

```
<400> SEQUENCE: 323
ggggcatcgt cgcgggaggc                                            20

<210> SEQ ID NO 324
<211> LENGTH: 20
<212> TYPE: DNA
<213> ORGANISM: Homo sapiens

<400> SEQUENCE: 324
aggggcatcg tcgcgggagg                                            20

<210> SEQ ID NO 325
<211> LENGTH: 20
<212> TYPE: DNA
<213> ORGANISM: Homo sapiens

<400> SEQUENCE: 325
gaggggcatc gtcgcgggag                                            20

<210> SEQ ID NO 326
<211> LENGTH: 20
<212> TYPE: DNA
<213> ORGANISM: Homo sapiens

<400> SEQUENCE: 326
tgaggggcat cgtcgcggga                                            20

<210> SEQ ID NO 327
<211> LENGTH: 20
<212> TYPE: DNA
<213> ORGANISM: Homo sapiens

<400> SEQUENCE: 327
ttgaggggca tcgtcgcggg                                            20

<210> SEQ ID NO 328
<211> LENGTH: 20
<212> TYPE: DNA
<213> ORGANISM: Homo sapiens

<400> SEQUENCE: 328
gttgaggggc atcgtcgcgg                                            20

<210> SEQ ID NO 329
<211> LENGTH: 20
<212> TYPE: DNA
<213> ORGANISM: Homo sapiens

<400> SEQUENCE: 329
cgttgagggg catcgtcgcg                                            20

<210> SEQ ID NO 330
<211> LENGTH: 20
<212> TYPE: DNA
<213> ORGANISM: Homo sapiens

<400> SEQUENCE: 330
acgttgaggg gcatcgtcgc                                            20

<210> SEQ ID NO 331
<211> LENGTH: 20
<212> TYPE: DNA
<213> ORGANISM: Homo sapiens
```

```
<400> SEQUENCE: 331
aacgttgagg ggcatcgtcg                                              20

<210> SEQ ID NO 332
<211> LENGTH: 20
<212> TYPE: DNA
<213> ORGANISM: Homo sapiens

<400> SEQUENCE: 332
taacgttgag gggcatcgtc                                              20

<210> SEQ ID NO 333
<211> LENGTH: 20
<212> TYPE: DNA
<213> ORGANISM: Homo sapiens

<400> SEQUENCE: 333
ctaacgttga ggggcatcgt                                              20

<210> SEQ ID NO 334
<211> LENGTH: 20
<212> TYPE: DNA
<213> ORGANISM: Homo sapiens

<400> SEQUENCE: 334
gctaacgttg aggggcatcg                                              20

<210> SEQ ID NO 335
<211> LENGTH: 20
<212> TYPE: DNA
<213> ORGANISM: Homo sapiens

<400> SEQUENCE: 335
agctaacgtt gaggggcatc                                              20

<210> SEQ ID NO 336
<211> LENGTH: 20
<212> TYPE: DNA
<213> ORGANISM: Homo sapiens

<400> SEQUENCE: 336
aagctaacgt tgaggggcat                                              20

<210> SEQ ID NO 337
<211> LENGTH: 20
<212> TYPE: DNA
<213> ORGANISM: Homo sapiens

<400> SEQUENCE: 337
gaagctaacg ttgaggggca                                              20

<210> SEQ ID NO 338
<211> LENGTH: 20
<212> TYPE: DNA
<213> ORGANISM: Homo sapiens

<400> SEQUENCE: 338
tcctcatctt cttgttcctc                                              20

<210> SEQ ID NO 339
<211> LENGTH: 36
<212> TYPE: DNA
```

```
<213> ORGANISM: Homo sapiens

<400> SEQUENCE: 339
aacaacatcg atttcttcct catcttcttg ttcctc                              36

<210> SEQ ID NO 340
<211> LENGTH: 18
<212> TYPE: DNA
<213> ORGANISM: Homo sapiens

<400> SEQUENCE: 340
cccggaaggc agtctggc                                                  18

<210> SEQ ID NO 341
<211> LENGTH: 36
<212> TYPE: DNA
<213> ORGANISM: Homo sapiens

<400> SEQUENCE: 341
tcctccatgg cagtgacccg gaaggcagtc tggctg                              36

<210> SEQ ID NO 342
<211> LENGTH: 19
<212> TYPE: DNA
<213> ORGANISM: Homo sapiens

<400> SEQUENCE: 342
ctactggccg ctgaagggc                                                 19

<210> SEQ ID NO 343
<211> LENGTH: 36
<212> TYPE: DNA
<213> ORGANISM: Homo sapiens

<400> SEQUENCE: 343
gctcaaagtc agatgctact ggccgctgaa gggctt                              36

<210> SEQ ID NO 344
<211> LENGTH: 27
<212> TYPE: DNA
<213> ORGANISM: Human immunodeficiency virus 1

<400> SEQUENCE: 344
tcgtcggtct ctccgcttct tcttgcc                                        27

<210> SEQ ID NO 345
<211> LENGTH: 20
<212> TYPE: DNA
<213> ORGANISM: Human immunodeficiency virus 1

<400> SEQUENCE: 345
ctctggtggt gggtaagggt                                                20

<210> SEQ ID NO 346
<211> LENGTH: 37
<212> TYPE: DNA
<213> ORGANISM: Human immunodeficiency virus 1

<400> SEQUENCE: 346
cgggtctgtc gggttccctc tggtggtggg taagggt                             37

<210> SEQ ID NO 347
<211> LENGTH: 30
```

```
<212> TYPE: RNA
<213> ORGANISM: Rattus sp.

<400> SEQUENCE: 347
ggggcaucgu cgugacuguc uguuggaggg                                      30

<210> SEQ ID NO 348
<211> LENGTH: 22
<212> TYPE: RNA
<213> ORGANISM: Rattus sp.

<400> SEQUENCE: 348
cgucgugacu gucuguugga gg                                              22

<210> SEQ ID NO 349
<211> LENGTH: 22
<212> TYPE: DNA
<213> ORGANISM: Rattus sp.

<400> SEQUENCE: 349
cgtcgtgact gtctgttgga gg                                              22

<210> SEQ ID NO 350
<211> LENGTH: 28
<212> TYPE: RNA
<213> ORGANISM: Homo sapiens

<400> SEQUENCE: 350
ggcaucgucg cgggaggcug cuggagcg                                        28

<210> SEQ ID NO 351
<211> LENGTH: 28
<212> TYPE: RNA
<213> ORGANISM: Rattus sp.

<400> SEQUENCE: 351
ccgcgacaua ggacggagag cagagccc                                        28

<210> SEQ ID NO 352
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
ctgcaggtaa aagcatatgg atcaa                                           25

<210> SEQ ID NO 353
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
atcgcctgca ggtaaaagca tatgg                                           25

<210> SEQ ID NO 354
<211> LENGTH: 25
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 354
gtcaaatcgc ctgcaggtaa aagca                                              25

<210> SEQ ID NO 355
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
gatctgtcaa atcgcctgca ggtaa                                              25

<210> SEQ ID NO 356
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
caacagatct gtcaaatcgc ctgca                                              25

<210> SEQ ID NO 357
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
tttctcaaca gatctgtcaa atcgc                                              25

<210> SEQ ID NO 358
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
ccatttctca acagatctgt caaat                                              25

<210> SEQ ID NO 359
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
ataatgaaaa cgccgccatt tctca                                              25

<210> SEQ ID NO 360
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 360
aaatatcttt atatcataat gaaaa                                              25

<210> SEQ ID NO 361
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
tgttagccac tgattaaata tcttt                                              25

<210> SEQ ID NO 362
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
aaactgttca gcttctgtta gccac                                              25

<210> SEQ ID NO 363
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
ttgtgtcttt ctgagaaact gttca                                              25

<210> SEQ ID NO 364
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
ccaattctca ggaatttgtg tcttt                                              25

<210> SEQ ID NO 365
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
gtatttagca tgttcccaat tctca                                              25

<210> SEQ ID NO 366
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
cttaagatac catttgtatt tagca                                    25

<210> SEQ ID NO 367
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
cttaccttaa gataccattt gtatt                                    25

<210> SEQ ID NO 368
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
aaagacttac cttaagatac cattt                                    25

<210> SEQ ID NO 369
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
aaatcaaaga cttaccttaa gatac                                    25

<210> SEQ ID NO 370
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
aaaacaaatc aaagacttac cttaa                                    25

<210> SEQ ID NO 371
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
tcgaaaaaac aaatcaaaga cttac                                    25

<210> SEQ ID NO 372
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
ctgtaagata ccaaaaggc aaaac                                          25

<210> SEQ ID NO 373
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
cctgtaagat accaaaaagg caaaa                                         25

<210> SEQ ID NO 374
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
agttcctgta agataccaaa aaggc                                         25

<210> SEQ ID NO 375
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
gagttcctgt aagataccaa aaagg                                         25

<210> SEQ ID NO 376
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
cctggagttc ctgtaagata ccaaa                                         25

<210> SEQ ID NO 377
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
tcctggagtt cctgtaagat accaa                                         25

<210> SEQ ID NO 378
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
gccatcctgg agttcctgta agata                                    25

<210> SEQ ID NO 379
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
tgccatcctg gagttcctgt aagat                                    25

<210> SEQ ID NO 380
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
ccaatgccat cctggagttc ctgta                                    25

<210> SEQ ID NO 381
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
cccaatgcca tcctggagtt cctgt                                    25

<210> SEQ ID NO 382
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
gctgcccaat gccatcctgg agttc                                    25

<210> SEQ ID NO 383
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
cgctgcccaa tgccatcctg gagtt                                    25

<210> SEQ ID NO 384
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384

```
aacagtttgc cgctgcccaa tgcca                                              25
```

<210> SEQ ID NO 385
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385

```
ctgacaacag tttgccgctg cccaa                                              25
```

<210> SEQ ID NO 386
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386

```
gttgcattca atgttctgac aacag                                              25
```

<210> SEQ ID NO 387
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387

```
gctgaattat ttcttcccca gttgc                                              25
```

<210> SEQ ID NO 388
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388

```
attatttctt ccccagttgc attca                                              25
```

<210> SEQ ID NO 389
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389

```
ggcatctgtt tttgaggatt gctga                                              25
```

<210> SEQ ID NO 390
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390

```
tttgaggatt gctgaattat ttctt                                              25
```

<210> SEQ ID NO 391
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
aatttttcct gtagaatact ggcat                                          25

<210> SEQ ID NO 392
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
atactggcat ctgttttga ggatt                                           25

<210> SEQ ID NO 393
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
accgcagatt caggcttccc aattt                                          25

<210> SEQ ID NO 394
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
aatttttcct gtagaatact ggcat                                          25

<210> SEQ ID NO 395
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
ctgtttgcag acctcctgcc accgc                                          25

<210> SEQ ID NO 396
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
agattcaggc ttcccaattt ttcct                                          25

<210> SEQ ID NO 397
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
ctcttttttc tgtctgacag ctgtt                                          25

<210> SEQ ID NO 398
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
acctcctgcc accgcagatt caggc                                          25

<210> SEQ ID NO 399
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
cctacctctt ttttctgtct gacag                                          25

<210> SEQ ID NO 400
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
gacagctgtt tgcagacctc ctgcc                                          25

<210> SEQ ID NO 401
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
gtcgccctac ctcttttttc tgtct                                          25

<210> SEQ ID NO 402
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
gatctgtcgc cctacctctt ttttc                                          25

-continued

```
<210> SEQ ID NO 403
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
tattagatct gtcgccctac ctctt                                              25

<210> SEQ ID NO 404
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
attcctatta gatctgtcgc cctac                                              25

<210> SEQ ID NO 405
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
agataccaaa aaggcaaaac                                                    20

<210> SEQ ID NO 406
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
aagataccaa aaaggcaaaa                                                    20

<210> SEQ ID NO 407
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
cctgtaagat accaaaaagg                                                    20

<210> SEQ ID NO 408
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
gagttcctgt aagataccaa                                                    20

<210> SEQ ID NO 409
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
tcctggagtt cctgtaagat                                                   20

<210> SEQ ID NO 410
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
tgccatcctg gagttcctgt                                                   20

<210> SEQ ID NO 411
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
cccaatgcca tcctggagtt                                                   20

<210> SEQ ID NO 412
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
cgctgcccaa tgccatcctg                                                   20

<210> SEQ ID NO 413
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
ctgacaacag tttgccgctg                                                   20

<210> SEQ ID NO 414
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
gttgcattca atgttctgac                                                   20

<210> SEQ ID NO 415
<211> LENGTH: 20
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
attatttctt ccccagttgc                                              20

<210> SEQ ID NO 416
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
tttgaggatt gctgaattat                                              20

<210> SEQ ID NO 417
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
atactggcat ctgtttttga                                              20

<210> SEQ ID NO 418
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
aatttttcct gtagaatact                                              20

<210> SEQ ID NO 419
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
agattcaggc ttcccaattt                                              20

<210> SEQ ID NO 420
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
acctcctgcc accgcagatt                                              20

<210> SEQ ID NO 421
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 421
gacagctgtt tgcagacctc                                               20

<210> SEQ ID NO 422
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
ctcttttttc tgtctgacag                                               20

<210> SEQ ID NO 423
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
cctacctctt ttttctgtct                                               20

<210> SEQ ID NO 424
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
gtcgccctac ctcttttttc                                               20

<210> SEQ ID NO 425
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
gatctgtcgc cctacctctt                                               20

<210> SEQ ID NO 426
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
tattagatct gtcgccctac                                               20

<210> SEQ ID NO 427
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 427
attcctatta gatctgtcgc                                                    20

<210> SEQ ID NO 428
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
gggggatttg agaaaataaa attac                                              25

<210> SEQ ID NO 429
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
atttgagaaa ataaaattac cttga                                              25

<210> SEQ ID NO 430
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
ctagcctgga gaagaagaa taaaa                                               25

<210> SEQ ID NO 431
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
agaaaataaa attaccttga cttgc                                              25

<210> SEQ ID NO 432
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
ttcttctagc ctggagaaag aagaa                                              25

<210> SEQ ID NO 433
<211> LENGTH: 25
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 433
ataaaattac cttgacttgc tcaag                                            25

<210> SEQ ID NO 434
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
ttttgttctt ctagcctgga gaaag                                            25

<210> SEQ ID NO 435
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
attaccttga cttgctcaag ctttt                                            25

<210> SEQ ID NO 436
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
tattcttttg ttcttctagc ctgga                                            25

<210> SEQ ID NO 437
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
cttgacttgc tcaagctttt ctttt                                            25

<210> SEQ ID NO 438
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 438
caagatattc ttttgttctt ctagc                                            25

<210> SEQ ID NO 439
<211> LENGTH: 25
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 439
cttttagttg ctgctctttt ccagg                                              25

<210> SEQ ID NO 440
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
ccaggttcaa gtgggatact agcaa                                              25

<210> SEQ ID NO 441
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
atctctttga aattctgaca agata                                              25

<210> SEQ ID NO 442
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
agcaatgtta tctgcttcct ccaac                                              25

<210> SEQ ID NO 443
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
aacaaattca tttaaatctc tttga                                              25

<210> SEQ ID NO 444
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 444
ccaaccataa aacaaattca tttaa                                              25

<210> SEQ ID NO 445
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 445
ttcctccaac cataaaacaa attca                                    25

<210> SEQ ID NO 446
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446
tttaaatctc tttgaaattc tgaca                                    25

<210> SEQ ID NO 447
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 447
tgacaagata ttcttttgtt cttct                                    25

<210> SEQ ID NO 448
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448
ttcaagtggg atactagcaa tgtta                                    25

<210> SEQ ID NO 449
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 449
agatattctt ttgttcttct agcct                                    25

<210> SEQ ID NO 450
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 450
ctgctctttt ccaggttcaa gtggg                                    25

<210> SEQ ID NO 451
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
ttcttttgtt cttctagcct ggaga                                              25

<210> SEQ ID NO 452
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452 cttttcttt agttgctgct ctttt                                               25

<210> SEQ ID NO 453
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
ttgttcttct agcctggaga aagaa                                              25

<210> SEQ ID NO 454
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
cttctagcct ggagaaagaa gaata                                              25

<210> SEQ ID NO 455
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
agcctggaga agaagaata aaatt                                               25

<210> SEQ ID NO 456
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
ctggagaaag aagaataaaa ttgtt                                              25

<210> SEQ ID NO 457
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
gaaagaagaa taaaattgtt                                              20

<210> SEQ ID NO 458
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
ggagaaagaa gaataaaatt                                              20

<210> SEQ ID NO 459
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
agcctggaga aagaagaata                                              20

<210> SEQ ID NO 460
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
cttctagcct ggagaaagaa                                              20

<210> SEQ ID NO 461
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
ttgttcttct agcctggaga                                              20

<210> SEQ ID NO 462
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
ttcttttgtt cttctagcct                                              20

<210> SEQ ID NO 463
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463

```
tgacaagata ttcttttgtt                                              20

<210> SEQ ID NO 464
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
atctctttga aattctgaca                                              20

<210> SEQ ID NO 465
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
aacaaattca tttaaatctc                                              20

<210> SEQ ID NO 466
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
ttcctccaac cataaaacaa                                              20

<210> SEQ ID NO 467
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
agcaatgtta tctgcttcct                                              20

<210> SEQ ID NO 468
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
ttcaagtggg atactagcaa                                              20

<210> SEQ ID NO 469
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
ctgctctttt ccaggttcaa                                              20
```

<210> SEQ ID NO 470
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
cttttctttt agttgctgct                                              20

<210> SEQ ID NO 471
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
cttgacttgc tcaagctttt                                              20

<210> SEQ ID NO 472
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
attaccttga cttgctcaag                                              20

<210> SEQ ID NO 473
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
ataaaattac cttgacttgc                                              20

<210> SEQ ID NO 474
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
agaaaataaa attaccttga                                              20

<210> SEQ ID NO 475
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
atttgagaaa ataaaattac                                              20

<210> SEQ ID NO 476
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
gggggatttg agaaaataaa                                              20

<210> SEQ ID NO 477
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
ctgaaacaga caaatgcaac aacgt                                        25

<210> SEQ ID NO 478
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
agtaactgaa acagacaaat gcaac                                        25

<210> SEQ ID NO 479
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 479
ccaccagtaa ctgaaacaga caaat                                        25

<210> SEQ ID NO 480
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
ctcttccacc agtaactgaa acaga                                        25

<210> SEQ ID NO 481
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
ggcaactctt ccaccagtaa ctgaa                                        25

```
<210> SEQ ID NO 482
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
gcaggggcaa ctcttccacc agtaa                                              25

<210> SEQ ID NO 483
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
ctggcgcagg ggcaactctt ccacc                                              25

<210> SEQ ID NO 484
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
tttaattgtt tgagaattcc ctggc                                              25

<210> SEQ ID NO 485
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485
ttgtttgaga attccctggc gcagg                                              25

<210> SEQ ID NO 486
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
gcacgggtcc tccagtttca tttaa                                              25

<210> SEQ ID NO 487
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
tccagtttca tttaattgtt tgaga                                              25

<210> SEQ ID NO 488
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
gcttatggga gcacttacaa gcacg                                        25

<210> SEQ ID NO 489
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
tacaagcacg ggtcctccag tttca                                        25

<210> SEQ ID NO 490
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
agtttatctt gctcttctgg gctta                                        25

<210> SEQ ID NO 491
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
tctgcttgag cttattttca agttt                                        25

<210> SEQ ID NO 492
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 492
atcttgctct tctgggctta tggga                                        25

<210> SEQ ID NO 493
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
ctttatccac tggagatttg tctgc                                        25

<210> SEQ ID NO 494
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 494
cttattttca agtttatctt gctct                                            25

<210> SEQ ID NO 495
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 495
ctaaccttta tccactggag atttg                                            25

<210> SEQ ID NO 496
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
atttgtctgc ttgagcttat tttca                                            25

<210> SEQ ID NO 497
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
aatgtctaac ctttatccac tggag                                            25

<210> SEQ ID NO 498
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
tggttaatgt ctaaccttta tccac                                            25

<210> SEQ ID NO 499
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
agagatggtt aatgtctaac cttta                                            25

<210> SEQ ID NO 500
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 500
acggaagaga tggttaatgt ctaac                                          25

<210> SEQ ID NO 501
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
acagacaaat gcaacaacgt                                                20

<210> SEQ ID NO 502
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
ctgaaacaga caaatgcaac                                                20

<210> SEQ ID NO 503
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
agtaactgaa acagacaaat                                                20

<210> SEQ ID NO 504
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
ccaccagtaa ctgaaacaga                                                20

<210> SEQ ID NO 505
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505
ctcttccacc agtaactgaa                                                20

<210> SEQ ID NO 506
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 506
ggcaactctt ccaccagtaa                                              20

<210> SEQ ID NO 507
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
ctggcgcagg ggcaactctt                                              20

<210> SEQ ID NO 508
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508
ttgtttgaga attccctggc                                              20

<210> SEQ ID NO 509
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
tccagtttca tttaattgtt                                              20

<210> SEQ ID NO 510
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
tacaagcacg ggtcctccag                                              20

<210> SEQ ID NO 511
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 511
gcttatggga gcacttacaa                                              20

<210> SEQ ID NO 512
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 512
atcttgctct tctgggctta                                                    20

<210> SEQ ID NO 513
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
cttattttca agtttatctt                                                    20

<210> SEQ ID NO 514
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 514
atttgtctgc ttgagcttat                                                    20

<210> SEQ ID NO 515
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515
ctttatccac tggagatttg                                                    20

<210> SEQ ID NO 516
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 516
ctaaccttta tccactggag                                                    20

<210> SEQ ID NO 517
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 517
aatgtctaac ctttatccac                                                    20

<210> SEQ ID NO 518
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 518
tggttaatgt ctaaccttta                                           20

<210> SEQ ID NO 519
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
agagatggtt aatgtctaac                                           20

<210> SEQ ID NO 520
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
acggaagaga tggttaatgt                                           20

<210> SEQ ID NO 521
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
ctgaaaggaa aatacatttt aaaaa                                     25

<210> SEQ ID NO 522
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
cctgaaagga aaatacattt taaaa                                     25

<210> SEQ ID NO 523
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
gaaacctgaa aggaaaatac atttt                                     25

<210> SEQ ID NO 524
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 524
ggaaacctga aaggaaaata cattt                                           25

<210> SEQ ID NO 525
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
ctctggaaac ctgaaaggaa aatac                                           25

<210> SEQ ID NO 526
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
gctctggaaa cctgaaagga aaata                                           25

<210> SEQ ID NO 527
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
taaagctctg gaaacctgaa aggaa                                           25

<210> SEQ ID NO 528
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
gtaaagctct ggaaacctga aagga                                           25

<210> SEQ ID NO 529
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 529
tcaggtaaag ctctggaaac ctgaa                                           25

<210> SEQ ID NO 530
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 530
ctcaggtaaa gctctggaaa cctga                                         25

<210> SEQ ID NO 531
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531
gtttctcagg taaagctctg gaaac                                         25

<210> SEQ ID NO 532
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
tgtttctcag gtaaagctct ggaaa                                         25

<210> SEQ ID NO 533
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533
aatttctcct tgtttctcag gtaaa                                         25

<210> SEQ ID NO 534
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
tttgagcttc aatttctcct tgttt                                         25

<210> SEQ ID NO 535
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 535
ttttatttga gcttcaattt ctcct                                         25

<210> SEQ ID NO 536
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
```
aagctgccca aggtctttta tttga					25

<210> SEQ ID NO 537
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
aggtcttcaa gctttttttc aagct					25

<210> SEQ ID NO 538
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 538
ttcaagcttt ttttcaagct gccca					25

<210> SEQ ID NO 539
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
gatgatttaa ctgctcttca aggtc					25

<210> SEQ ID NO 540
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540
ctgctcttca aggtcttcaa gcttt					25

<210> SEQ ID NO 541
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541
aggagataac cacagcagca gatga					25

<210> SEQ ID NO 542
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542
cagcagatga tttaactgct cttca                                         25

<210> SEQ ID NO 543
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543
atttccaact gattcctaat aggag                                         25

<210> SEQ ID NO 544
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
cttggtttgg ttggttataa atttc                                         25

<210> SEQ ID NO 545
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 545
caactgattc ctaataggag ataac                                         25

<210> SEQ ID NO 546
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
cttaacgtca aatggtcctt cttgg                                         25

<210> SEQ ID NO 547
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 547
ttggttataa atttccaact gattc                                         25

<210> SEQ ID NO 548
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
cctaccttaa cgtcaaatgg tcctt                                         25

<210> SEQ ID NO 549
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 549
tccttcttgg tttggttggt tataa                                          25

<210> SEQ ID NO 550
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550
agttccctac cttaacgtca aatgg                                          25

<210> SEQ ID NO 551
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551
caaaaagttc cctaccttaa cgtca                                          25

<210> SEQ ID NO 552
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 552
taaagcaaaa agttccctac cttaa                                          25

<210> SEQ ID NO 553
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553
atatttaaag caaaaagttc cctac                                          25

<210> SEQ ID NO 554
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554
aggaaaatac attttaaaaa                                                20

<210> SEQ ID NO 555
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555
aaggaaaata cattttaaaa                                                    20

<210> SEQ ID NO 556
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
cctgaaagga aaatacattt                                                    20

<210> SEQ ID NO 557
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 557
ggaaacctga aaggaaaata                                                    20

<210> SEQ ID NO 558
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 558
gctctggaaa cctgaaagga                                                    20

<210> SEQ ID NO 559
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 559
gtaaagctct ggaaacctga                                                    20

<210> SEQ ID NO 560
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 560
ctcaggtaaa gctctggaaa                                                    20

```
<210> SEQ ID NO 561
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561
aatttctcct tgtttctcag                                              20

<210> SEQ ID NO 562
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 562
ttttatttga gcttcaattt                                              20

<210> SEQ ID NO 563
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 563
aagctgccca aggtctttta                                              20

<210> SEQ ID NO 564
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 564
ttcaagcttt ttttcaagct                                              20

<210> SEQ ID NO 565
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 565
ctgctcttca aggtcttcaa                                              20

<210> SEQ ID NO 566
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 566
cagcagatga tttaactgct                                              20

<210> SEQ ID NO 567
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 567
aggagataac cacagcagca                                                   20

<210> SEQ ID NO 568
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 568
caactgattc ctaataggag                                                   20

<210> SEQ ID NO 569
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 569
ttggttataa atttccaact                                                   20

<210> SEQ ID NO 570
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 570
tccttcttgg tttggttggt                                                   20

<210> SEQ ID NO 571
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 571
cttaacgtca aatggtcctt                                                   20

<210> SEQ ID NO 572
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 572
cctaccttaa cgtcaaatgg                                                   20

<210> SEQ ID NO 573
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 573
agttccctac cttaacgtca                                               20

<210> SEQ ID NO 574
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 574
caaaaagttc cctaccttaa                                               20

<210> SEQ ID NO 575
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 575
taaagcaaaa agttccctac                                               20

<210> SEQ ID NO 576
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 576
atatttaaag caaaaagttc                                               20

<210> SEQ ID NO 577
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 577
ctggggaaaa gaacccatat agtgc                                         25

<210> SEQ ID NO 578
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 578
tcctggggaa aagaacccat atagt                                         25

<210> SEQ ID NO 579
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 579
gtttcctggg gaaaagaacc catat                                              25

<210> SEQ ID NO 580
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 580
cagtttcctg gggaaaagaa cccat                                              25

<210> SEQ ID NO 581
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 581
tttcagtttc ctggggaaaa gaacc                                              25

<210> SEQ ID NO 582
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 582
tatttcagtt tcctggggaa aagaa                                              25

<210> SEQ ID NO 583
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 583
tgctatttca gtttcctggg gaaaa                                              25

<210> SEQ ID NO 584
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 584
actgctattt cagtttcctg gggaa                                              25

<210> SEQ ID NO 585
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 585
tgaactgcta tttcagtttc ctggg                                              25

<210> SEQ ID NO 586
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 586
cttgaactgc tatttcagtt tcctg                                              25

<210> SEQ ID NO 587
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 587
tagcttgaac tgctatttca gtttc                                              25

<210> SEQ ID NO 588
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 588
tttagcttga actgctattt cagtt                                              25

<210> SEQ ID NO 589
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 589
ttccacatcc ggttgtttag cttga                                              25

<210> SEQ ID NO 590
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 590
tgccctttag acaaaatctc ttcca                                              25

<210> SEQ ID NO 591
<211> LENGTH: 25
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 591
tttagacaaa atctcttcca catcc                                              25

<210> SEQ ID NO 592
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 592
gttttccctt gtacaaatgc tgccc                                              25

<210> SEQ ID NO 593
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 593
gtacaaatgc tgcccttag acaaa                                               25

<210> SEQ ID NO 594
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 594
cttcactggc tgagtggctg gtttt                                              25

<210> SEQ ID NO 595
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 595
ggctggtttt tccttgtaca aatgc                                              25

<210> SEQ ID NO 596
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 596
attaccttca ctggctgagt ggctg                                              25

<210> SEQ ID NO 597
<211> LENGTH: 25
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 597
gcttcattac cttcactggc tgagt                                              25

<210> SEQ ID NO 598
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 598
aggttgcttc attaccttca ctggc                                              25

<210> SEQ ID NO 599
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 599
gctagaggtt gcttcattac cttca                                              25

<210> SEQ ID NO 600
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 600
atattgctag aggttgcttc attac                                              25

<210> SEQ ID NO 601
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 601
gaaaagaacc catatagtgc                                                    20

<210> SEQ ID NO 602
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 602
gggaaaagaa cccatatagt                                                    20

<210> SEQ ID NO 603
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 603
tcctggggaa aagaacccat					20

<210> SEQ ID NO 604
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 604
cagtttcctg gggaaaagaa					20

<210> SEQ ID NO 605
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 605
tatttcagtt tcctggggaa					20

<210> SEQ ID NO 606
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606
actgctattt cagtttcctg					20

<210> SEQ ID NO 607
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 607
cttgaactgc tatttcagtt					20

<210> SEQ ID NO 608
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 608
tttagcttga actgctattt					20

<210> SEQ ID NO 609
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 609
ttccacatcc ggttgtttag                                               20

<210> SEQ ID NO 610
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 610
tttagacaaa atctcttcca                                               20

<210> SEQ ID NO 611
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 611
gtacaaatgc tgccctttag                                               20

<210> SEQ ID NO 612
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 612
ggctggtttt tccttgtaca                                               20

<210> SEQ ID NO 613
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 613
cttcactggc tgagtggctg                                               20

<210> SEQ ID NO 614
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 614
attaccttca ctggctgagt                                               20

<210> SEQ ID NO 615
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 615
gcttcattac cttcactggc                                                20

<210> SEQ ID NO 616
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 616
aggttgcttc attaccttca                                                20

<210> SEQ ID NO 617
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 617
gctagaggtt gcttcattac                                                20

<210> SEQ ID NO 618
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 618
atattgctag aggttgcttc                                                20

<210> SEQ ID NO 619
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 619
ctttaacaga aaagcataca catta                                          25

<210> SEQ ID NO 620
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 620
tcctctttaa cagaaaagca tacac                                          25

<210> SEQ ID NO 621
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 621

```
ttcctctttta acagaaaagc ataca                                              25
```

```
<210> SEQ ID NO 622
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 622
taacttcctc tttaacagaa aagca                                               25
```

```
<210> SEQ ID NO 623
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 623
ctaacttcct ctttaacaga aaagc                                               25
```

```
<210> SEQ ID NO 624
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 624
tcttctaact tcctctttaa cagaa                                               25
```

```
<210> SEQ ID NO 625
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 625
atcttctaac ttcctctttta acaga                                              25
```

```
<210> SEQ ID NO 626
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 626
tcagatcttc taacttcctc tttaa                                               25
```

```
<210> SEQ ID NO 627
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 627
ctcagatctt ctaacttcct cttta                                               25
```

<210> SEQ ID NO 628
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 628
agagctcaga tcttctaact tcctc                                               25

<210> SEQ ID NO 629
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 629
cagagctcag atcttctaac ttcct                                               25

<210> SEQ ID NO 630
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 630
cactcagagc tcagatcttc tact                                                24

<210> SEQ ID NO 631
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 631
ccttccactc agagctcaga tcttc                                               25

<210> SEQ ID NO 632
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 632
gtaaacggtt taccgccttc cactc                                               25

<210> SEQ ID NO 633
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 633
ctttgccctc agctcttgaa gtaaa                                               25

<210> SEQ ID NO 634
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 634
ccctcagctc ttgaagtaaa cggtt                                              25

<210> SEQ ID NO 635
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 635
ccaggagcta ggtcaggctg ctttg                                              25

<210> SEQ ID NO 636
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 636
ggtcaggctg ctttgccctc agctc                                              25

<210> SEQ ID NO 637
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 637
aggctccaat agtggtcagt ccagg                                              25

<210> SEQ ID NO 638
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 638
tcagtccagg agctaggtca ggctg                                              25

<210> SEQ ID NO 639
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 639
cttacaggct ccaatagtgg tcagt                                              25

```
<210> SEQ ID NO 640
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 640
gtatacttac aggctccaat agtgg                                              25

<210> SEQ ID NO 641
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 641
atccagtata cttacaggct ccaat                                              25

<210> SEQ ID NO 642
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 642
atgggatcca gtatacttac aggct                                              25

<210> SEQ ID NO 643
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 643
agagaatggg atccagtata cttac                                              25

<210> SEQ ID NO 644
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 644
acagaaaagc atacacatta                                                    20

<210> SEQ ID NO 645
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 645
tttaacagaa aagcatacac                                                    20

<210> SEQ ID NO 646
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 646
tcctctttaa cagaaaagca                                                 20

<210> SEQ ID NO 647
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 647
taacttcctc tttaacagaa                                                 20

<210> SEQ ID NO 648
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 648
tcttctaact tcctctttaa                                                 20

<210> SEQ ID NO 649
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 649
tcagatcttc taacttcctc                                                 20

<210> SEQ ID NO 650
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 650
ccttccactc agagctcaga                                                 20

<210> SEQ ID NO 651
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 651
gtaaacggtt taccgccttc                                                 20

<210> SEQ ID NO 652
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 652
ccctcagctc ttgaagtaaa                                              20

<210> SEQ ID NO 653
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 653
ggtcaggctg ctttgccctc                                              20

<210> SEQ ID NO 654
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 654
tcagtccagg agctaggtca                                              20

<210> SEQ ID NO 655
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 655
aggctccaat agtggtcagt                                              20

<210> SEQ ID NO 656
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 656
cttacaggct ccaatagtgg                                              20

<210> SEQ ID NO 657
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 657
gtatacttac aggctccaat                                              20

<210> SEQ ID NO 658
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 658
atccagtata cttacaggct                                               20

<210> SEQ ID NO 659
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 659
atgggatcca gtatacttac                                               20

<210> SEQ ID NO 660
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 660
agagaatggg atccagtata                                               20

<210> SEQ ID NO 661
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 661
ctaaaatatt tgggtttttt gcaaaa                                        26

<210> SEQ ID NO 662
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 662
gctaaaatat tttgggtttt tgcaaa                                        26

<210> SEQ ID NO 663
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 663
taggagctaa aatattttgg gttttt                                        26

<210> SEQ ID NO 664
<211> LENGTH: 25
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 664
agtaggagct aaaatatttt gggtt                                              25

<210> SEQ ID NO 665
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 665
tgagtaggag ctaaaatatt ttggg                                              25

<210> SEQ ID NO 666
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 666
ctgagtagga gctaaaatat tttggg                                             26

<210> SEQ ID NO 667
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 667
cagtctgagt aggagctaaa atatt                                              25

<210> SEQ ID NO 668
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 668
acagtctgag taggagctaa aatatt                                             26

<210> SEQ ID NO 669
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 669
gagtaacagt ctgagtagga gctaaa                                             26

<210> SEQ ID NO 670
<211> LENGTH: 25
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 670
cagagtaaca gtctgagtag gagct                                          25

<210> SEQ ID NO 671
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 671
caccagagta acagtctgag taggag                                         26

<210> SEQ ID NO 672
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 672
gtcaccagag taacagtctg agtag                                          25

<210> SEQ ID NO 673
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 673
aaccacaggt tgtgtcacca gagtaa                                         26

<210> SEQ ID NO 674
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 674
gttgtgtcac cagagtaaca gtctg                                          25

<210> SEQ ID NO 675
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 675
tggcagtttc cttagtaacc acaggt                                         26

<210> SEQ ID NO 676
<211> LENGTH: 26
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 676
atttctagtt tggagatggc agtttc                                26

<210> SEQ ID NO 677
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 677
ggaagatggc atttctagtt tggag                                 25

<210> SEQ ID NO 678
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 678
catcaaggaa gatggcattt ctagtt                                26

<210> SEQ ID NO 679
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 679
gagcaggtac ctccaacatc aaggaa                                26

<210> SEQ ID NO 680
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 680
atctgccaga gcaggtacct ccaac                                 25

<210> SEQ ID NO 681
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 681
aagttctgtc caagcccggt tgaaat                                26

<210> SEQ ID NO 682
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 682
cggttgaaat ctgccagagc aggtac                                             26

<210> SEQ ID NO 683
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 683
gagaaagcca gtcggtaagt tctgtc                                             26

<210> SEQ ID NO 684
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 684
gtcggtaagt tctgtccaag cccgg                                              25

<210> SEQ ID NO 685
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 685
ataacttgat caagcagaga aagcca                                             26

<210> SEQ ID NO 686
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 686
aagcagagaa agccagtcgg taagt                                              25

<210> SEQ ID NO 687
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 687
caccctctgt gattttataa cttgat                                             26

<210> SEQ ID NO 688
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 688
caaggtcacc caccatcacc ctctgt                                          26

<210> SEQ ID NO 689
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 689
catcaccctc tgtgatttta taact                                           25

<210> SEQ ID NO 690
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 690
cttctgcttg atgatcatct cgttga                                          26

<210> SEQ ID NO 691
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 691
ccttctgctt gatgatcatc tcgttg                                          26

<210> SEQ ID NO 692
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 692
atctcgttga tatcctcaag gtcacc                                          26

<210> SEQ ID NO 693
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 693
tcataccttc tgcttgatga tcatct                                          26

<210> SEQ ID NO 694
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 694
```
tcattttttc tcataccttc tgcttg                                    26

<210> SEQ ID NO 695
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 695
ttttctcata ccttctgctt gatgat                                    26

<210> SEQ ID NO 696
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 696
ttttatcatt ttttctcata ccttct                                    26

<210> SEQ ID NO 697
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 697
ccaactttta tcattttttc tcatac                                    26

<210> SEQ ID NO 698
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 698
atattttggg tttttgcaaa                                           20

<210> SEQ ID NO 699
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 699
aaaatatttt gggtttttgc                                           20

<210> SEQ ID NO 700
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 700
gagctaaaat attttgggtt                                            20

<210> SEQ ID NO 701
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 701
agtaggagct aaaatatttt                                            20

<210> SEQ ID NO 702
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 702
gtctgagtag gagctaaaat                                            20

<210> SEQ ID NO 703
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 703
taacagtctg agtaggagct                                            20

<210> SEQ ID NO 704
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 704
cagagtaaca gtctgagtag                                            20

<210> SEQ ID NO 705
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 705
cacaggttgt gtcaccagag                                            20

<210> SEQ ID NO 706
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 706
agtttcctta gtaaccacag                                            20

<210> SEQ ID NO 707
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 707
tagtttggag atggcagttt                                             20

<210> SEQ ID NO 708
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 708
ggaagatggc atttctagtt                                             20

<210> SEQ ID NO 709
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 709
tacctccaac atcaaggaag                                             20

<210> SEQ ID NO 710
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 710
atctgccaga gcaggtacct                                             20

<210> SEQ ID NO 711
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 711
ccaagcccgg ttgaaatctg                                             20

<210> SEQ ID NO 712
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 712
gtcggtaagt tctgtccaag                                             20

<210> SEQ ID NO 713
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 713
aagcagagaa agccagtcgg                                             20

<210> SEQ ID NO 714
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 714
ttttataact tgatcaagca                                             20

<210> SEQ ID NO 715
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 715
catcaccctc tgtgatttta                                             20

<210> SEQ ID NO 716
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 716
ctcaaggtca cccaccatca                                             20

<210> SEQ ID NO 717
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 717
catctcgttg atatcctcaa                                             20

<210> SEQ ID NO 718
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 718
cttctgcttg atgatcatct                                             20

```
<210> SEQ ID NO 719
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 719
cataccttct gcttgatgat                                                   20

<210> SEQ ID NO 720
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 720
tttctcatac cttctgcttg                                                   20

<210> SEQ ID NO 721
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 721
cattttttct cataccttct                                                   20

<210> SEQ ID NO 722
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 722
tttatcattt tttctcatac                                                   20

<210> SEQ ID NO 723
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 723
caacttttat cattttttct                                                   20

<210> SEQ ID NO 724
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 724
ctgtaagaac aaatatccct tagta                                             25

<210> SEQ ID NO 725
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 725
tgcctgtaag aacaaatatc cctta                                              25

<210> SEQ ID NO 726
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 726
gttgcctgta agaacaaata tccct                                              25

<210> SEQ ID NO 727
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 727
attgttgcct gtaagaacaa atatc                                              25

<210> SEQ ID NO 728
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 728
gcattgttgc ctgtaagaac aaata                                              25

<210> SEQ ID NO 729
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 729
cctgcattgt tgcctgtaag aacaa                                              25

<210> SEQ ID NO 730
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 730
atcctgcatt gttgcctgta agaac                                              25

<210> SEQ ID NO 731
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 731
caaatcctgc attgttgcct gtaag                                          25

<210> SEQ ID NO 732
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 732
tccaaatcct gcattgttgc ctgta                                          25

<210> SEQ ID NO 733
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 733
tgttccaaat cctgcattgt tgcct                                          25

<210> SEQ ID NO 734
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 734
tctgttccaa atcctgcatt gttgc                                          25

<210> SEQ ID NO 735
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 735
aactggggac gcctctgttc caaat                                          25

<210> SEQ ID NO 736
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 736
gcctctgttc caaatcctgc attgt                                          25

<210> SEQ ID NO 737
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 737
cagcggtaat gagttcttcc aactg                                           25

<210> SEQ ID NO 738
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 738
cttccaactg gggacgcctc tgttc                                           25

<210> SEQ ID NO 739
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 739 cttgttttc aaattttggg cagcg                                            25

<210> SEQ ID NO 740
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 740
ctagcctctt gattgctggt cttgt                                           25

<210> SEQ ID NO 741
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 741
ttttcaaatt tgggcagcg gtaat                                            25

<210> SEQ ID NO 742
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 742
ttcgatccgt aatgattgtt ctagc                                           25

<210> SEQ ID NO 743
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 743
gattgctggt cttgtttttc aaatt                                           25

<210> SEQ ID NO 744
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 744
cttacttcga tccgtaatga ttgtt                                           25

<210> SEQ ID NO 745
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 745
ttgttctagc ctcttgattg ctggt                                           25

<210> SEQ ID NO 746
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 746
aaaaacttac ttcgatccgt aatga                                           25

<210> SEQ ID NO 747
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 747
tgttaaaaaa cttacttcga tccgt                                           25

<210> SEQ ID NO 748
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 748
atgcttgtta aaaacttac ttcga                                            25

<210> SEQ ID NO 749
<211> LENGTH: 25
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 749
gtcccatgct tgttaaaaaa cttac                                          25

<210> SEQ ID NO 750
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 750
agaacaaata tcccttagta                                                20

<210> SEQ ID NO 751
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 751
gtaagaacaa atatccctta                                                20

<210> SEQ ID NO 752
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 752
tgcctgtaag aacaaatatc                                                20

<210> SEQ ID NO 753
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 753
attgttgcct gtaagaacaa                                                20

<210> SEQ ID NO 754
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 754
cctgcattgt tgcctgtaag                                                20

<210> SEQ ID NO 755
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 755
caaatcctgc attgttgcct                                          20

<210> SEQ ID NO 756
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 756
gcctctgttc caaatcctgc                                          20

<210> SEQ ID NO 757
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 757
cttccaactg gggacgcctc                                          20

<210> SEQ ID NO 758
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 758
cagcggtaat gagttcttcc                                          20

<210> SEQ ID NO 759
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 759
ttttcaaatt ttgggcagcg                                          20

<210> SEQ ID NO 760
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 760
gattgctggt cttgttttc                                           20

<210> SEQ ID NO 761
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 761
ttgttctagc ctcttgattg                                          20

<210> SEQ ID NO 762
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 762
ttcgatccgt aatgattgtt                                          20

<210> SEQ ID NO 763
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 763
cttacttcga tccgtaatga                                          20

<210> SEQ ID NO 764
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 764
aaaaacttac ttcgatccgt                                          20

<210> SEQ ID NO 765
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 765
tgttaaaaaa cttacttcga                                          20

<210> SEQ ID NO 766
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 766
atgcttgtta aaaaacttac                                          20

<210> SEQ ID NO 767
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 767
gtcccatgct tgttaaaaaa                                              20

<210> SEQ ID NO 768
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 768
ctagaataaa aggaaaaata aatat                                        25

<210> SEQ ID NO 769
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 769
aactagaata aaaggaaaaa taaat                                        25

<210> SEQ ID NO 770
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 770
ttcaactaga ataaaggaa aaata                                         25

<210> SEQ ID NO 771
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 771
ctttcaacta gaataaagg aaaaa                                         25

<210> SEQ ID NO 772
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 772
attctttcaa ctagaataaa aggaa                                        25

<210> SEQ ID NO 773
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 773
```
gaattctttc aactagaata aaagg                                              25

<210> SEQ ID NO 774
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 774
tctgaattct ttcaactaga ataaa                                              25

<210> SEQ ID NO 775
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 775
attctgaatt ctttcaacta gaata                                              25

<210> SEQ ID NO 776
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 776
ctgattctga attctttcaa ctaga                                              25

<210> SEQ ID NO 777
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 777
cactgattct gaattctttc aacta                                              25

<210> SEQ ID NO 778
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 778
tcccactgat tctgaattct ttcaa                                              25

<210> SEQ ID NO 779
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 779

```
catcccactg attctgaatt ctttc                                         25

<210> SEQ ID NO 780
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 780
tacttcatcc cactgattct gaatt                                         25

<210> SEQ ID NO 781
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 781
ctgaaggtgt tcttgtactt catcc                                         25

<210> SEQ ID NO 782
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 782
cggttctgaa ggtgttcttg tact                                          24

<210> SEQ ID NO 783
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 783
ctgttgcctc cggttctgaa ggtgt                                         25

<210> SEQ ID NO 784
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 784
tttcattcaa ctgttgcctc cggtt                                         25

<210> SEQ ID NO 785
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 785
taacatttca ttcaactgtt gcctc                                         25
```

<210> SEQ ID NO 786
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 786
ttgtgttgaa tcctttaaca tttca                                        25

<210> SEQ ID NO 787
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 787
tcttccttag cttccagcca ttgtg                                        25

<210> SEQ ID NO 788
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 788
cttagcttcc agccattgtg ttgaa                                        25

<210> SEQ ID NO 789
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 789
gtcctaagac ctgctcagct tcttc                                        25

<210> SEQ ID NO 790
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 790
ctgctcagct tcttccttag cttcc                                        25

<210> SEQ ID NO 791
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 791
ctcaagcttg gctctggcct gtcct                                        25

```
<210> SEQ ID NO 792
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 792
ggcctgtcct aagacctgct cagct                                               25

<210> SEQ ID NO 793
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 793
tagggaccct ccttccatga ctcaa                                               25

<210> SEQ ID NO 794
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 794
tttggattgc atctactgta taggg                                               25

<210> SEQ ID NO 795
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 795
accctccttc catgactcaa gcttg                                               25

<210> SEQ ID NO 796
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 796
cttggtttct gtgattttct tttgg                                               25

<210> SEQ ID NO 797
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 797
atctactgta tagggaccct ccttc                                               25
```

```
<210> SEQ ID NO 798
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 798
ctaaccttgg tttctgtgat tttct                                         25

<210> SEQ ID NO 799
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 799
tttcttttgg attgcatcta ctgta                                         25

<210> SEQ ID NO 800
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 800
tgatactaac cttggtttct gtgat                                         25

<210> SEQ ID NO 801
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 801
atctttgata ctaaccttgg tttct                                         25

<210> SEQ ID NO 802
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 802
aaggtatctt tgatactaac cttgg                                         25

<210> SEQ ID NO 803
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 803 ttaaaaggt atctttgata ctaac                                          25

<210> SEQ ID NO 804
```

<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 804
ataaaaggaa aaataaatat                                             20

<210> SEQ ID NO 805
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 805
gaataaaagg aaaaataaat                                             20

<210> SEQ ID NO 806
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 806
aactagaata aaaggaaaaa                                             20

<210> SEQ ID NO 807
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 807
ctttcaacta gaataaaagg                                             20

<210> SEQ ID NO 808
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 808
gaattctttc aactagaata                                             20

<210> SEQ ID NO 809
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 809
attctgaatt ctttcaacta                                             20

<210> SEQ ID NO 810
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 810
tacttcatcc cactgattct                                            20

<210> SEQ ID NO 811
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 811
ctgaaggtgt tcttgtact                                             19

<210> SEQ ID NO 812
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 812
ctgttgcctc cggttctgaa                                            20

<210> SEQ ID NO 813
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 813
taacatttca ttcaactgtt                                            20

<210> SEQ ID NO 814
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 814
ttgtgttgaa tcctttaaca                                            20

<210> SEQ ID NO 815
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 815
cttagcttcc agccattgtg                                            20

<210> SEQ ID NO 816
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 816
ctgctcagct tcttccttag                                                  20

<210> SEQ ID NO 817
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 817
ggcctgtcct aagacctgct                                                  20

<210> SEQ ID NO 818
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 818
ctcaagcttg gctctggcct                                                  20

<210> SEQ ID NO 819
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 819
accctccttc catgactcaa                                                  20

<210> SEQ ID NO 820
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 820
atctactgta tagggaccct                                                  20

<210> SEQ ID NO 821
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 821
tttcttttgg attgcatcta                                                  20

<210> SEQ ID NO 822
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 822
cttggtttct gtgattttct                                                    20

<210> SEQ ID NO 823
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 823
ctaaccttgg tttctgtgat                                                    20

<210> SEQ ID NO 824
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 824
tgatactaac cttggtttct                                                    20

<210> SEQ ID NO 825
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 825
atctttgata ctaaccttgg                                                    20

<210> SEQ ID NO 826
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 826
aaggtatctt tgatactaac                                                    20

<210> SEQ ID NO 827
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 827
ttaaaaaggt atctttgata                                                    20

<210> SEQ ID NO 828
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 828
ctatagattt ttatgagaaa gaga                                          24

<210> SEQ ID NO 829
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 829
aactgctata gatttttatg agaaa                                         25

<210> SEQ ID NO 830
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 830
tggccaactg ctatagattt ttatg                                         25

<210> SEQ ID NO 831
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 831
gtctttggcc aactgctata gattt                                         25

<210> SEQ ID NO 832
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 832
cggaggtctt tggccaactg ctata                                         25

<210> SEQ ID NO 833
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 833
actggcggag gtctttggcc aactg                                         25

<210> SEQ ID NO 834
<211> LENGTH: 25
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 834
tttgtctgcc actggcggag gtctt                                        25

<210> SEQ ID NO 835
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 835
agtcatttgc cacatctaca tttgt                                        25

<210> SEQ ID NO 836
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 836
tttgccacat ctacatttgt ctgcc                                        25

<210> SEQ ID NO 837
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 837
ccggagaagt ttcagggcca agtca                                        25

<210> SEQ ID NO 838
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 838
gtatcatctg cagaataatc ccgga                                        25

<210> SEQ ID NO 839
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 839
taatcccgga gaagtttcag ggcca                                        25

<210> SEQ ID NO 840
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 840
ttatcatgtg gacttttctg gtatc                                        25

<210> SEQ ID NO 841
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 841
agaggcattg atattctctg ttatc                                        25

<210> SEQ ID NO 842
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 842
atgtggactt ttctggtatc atctg                                        25

<210> SEQ ID NO 843
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 843
cttttatgaa tgcttctcca agagg                                        25

<210> SEQ ID NO 844
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 844
atattctctg ttatcatgtg gactt                                        25

<210> SEQ ID NO 845
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 845 cataccttttt atgaatgctt ctcca                                       25

<210> SEQ ID NO 846
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 846
ctccaagagg cattgatatt ctctg                                         25

<210> SEQ ID NO 847
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 847
taattcatac cttttatgaa tgctt                                         25

<210> SEQ ID NO 848
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 848
cttttatgaa tgcttctcca agagg                                         25

<210> SEQ ID NO 849
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 849
taatgtaatt catacctttt atgaa                                         25

<210> SEQ ID NO 850
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 850
agaaataatg taattcatac ctttt                                         25

<210> SEQ ID NO 851
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 851
gttttagaaa taatgtaatt catac                                         25

<210> SEQ ID NO 852
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 852
gatttttatg agaaagaga                                            19

<210> SEQ ID NO 853
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 853
ctatagattt ttatgagaaa                                           20

<210> SEQ ID NO 854
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 854
aactgctata gatttttatg                                           20

<210> SEQ ID NO 855
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 855
tggccaactg ctatagattt                                           20

<210> SEQ ID NO 856
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 856
gtctttggcc aactgctata                                           20

<210> SEQ ID NO 857
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 857
cggaggtctt tggccaactg                                           20

<210> SEQ ID NO 858
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 858
tttgtctgcc actggcggag                                          20

<210> SEQ ID NO 859
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 859
tttgccacat ctacatttgt                                          20

<210> SEQ ID NO 860
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 860
ttcagggcca agtcatttgc                                          20

<210> SEQ ID NO 861
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 861
taatcccgga gaagtttcag                                          20

<210> SEQ ID NO 862
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 862
gtatcatctg cagaataatc                                          20

<210> SEQ ID NO 863
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 863
atgtggactt ttctggtatc                                          20

<210> SEQ ID NO 864
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 864
atattctctg ttatcatgtg                                          20

<210> SEQ ID NO 865
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 865
ctccaagagg cattgatatt                                              20

<210> SEQ ID NO 866
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 866
cttttatgaa tgcttctcca                                              20

<210> SEQ ID NO 867
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 867
catacctttt atgaatgctt                                              20

<210> SEQ ID NO 868
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 868
taattcatac cttttatgaa                                              20

<210> SEQ ID NO 869
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 869
taatgtaatt catacctttt                                              20

<210> SEQ ID NO 870
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 870
agaaataatg taattcatac                                              20

<210> SEQ ID NO 871
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 871
gttttagaaa taatgtaatt                                                   20

<210> SEQ ID NO 872
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 872
ctgcaaagga ccaaatgttc agatg                                             25

<210> SEQ ID NO 873
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 873
tcaccctgca aaggaccaaa tgttc                                             25

<210> SEQ ID NO 874
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 874
ctcactcacc ctgcaaagga ccaaa                                             25

<210> SEQ ID NO 875
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 875
tctcgctcac tcaccctgca aagga                                             25

<210> SEQ ID NO 876
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 876
cagcctctcg ctcactcacc ctgca                                             25

```
<210> SEQ ID NO 877
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 877
caaagcagcc tctcgctcac tcacc                                         25

<210> SEQ ID NO 878
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 878
tcttccaaag cagcctctcg ctcac                                         25

<210> SEQ ID NO 879
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 879
tctatgagtt tcttccaaag cagcc                                         25

<210> SEQ ID NO 880
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 880
gttgcagtaa tctatgagtt tcttc                                         25

<210> SEQ ID NO 881
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 881
gaactgttgc agtaatctat gagtt                                         25

<210> SEQ ID NO 882
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 882
ttccaggtcc aggggggaact gttgc                                        25

<210> SEQ ID NO 883
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 883
gtaagccagg caagaaactt ttcca                                         25

<210> SEQ ID NO 884
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 884
ccaggcaaga aactttccca ggtcc                                         25

<210> SEQ ID NO 885
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 885
tggcagttgt ttcagcttct gtaag                                         25

<210> SEQ ID NO 886
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 886
ttcagcttct gtaagccagg caaga                                         25

<210> SEQ ID NO 887
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 887
ggtagcatcc tgtaggacat tggca                                         25

<210> SEQ ID NO 888
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 888
gacattggca gttgtttcag cttct                                         25

<210> SEQ ID NO 889
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 889
tctaggagcc tttccttacg ggtag                                           25

<210> SEQ ID NO 890
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 890
cttttactcc cttggagtct tctag                                           25

<210> SEQ ID NO 891
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 891
gagcctttcc ttacgggtag catcc                                           25

<210> SEQ ID NO 892
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 892
ttgccattgt ttcatcagct ctttt                                           25

<210> SEQ ID NO 893
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 893
cttggagtct tctaggagcc tttcc                                           25

<210> SEQ ID NO 894
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 894
cttacttgcc attgtttcat cagct                                           25

<210> SEQ ID NO 895
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 895 cagctcttttt actcccttgg agtct                                              25

<210> SEQ ID NO 896
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 896
cctgacttac ttgccattgt ttcat                                               25

<210> SEQ ID NO 897
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 897
aaatgcctga cttacttgcc attgt                                               25

<210> SEQ ID NO 898
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 898
agcggaaatg cctgacttac ttgcc                                               25

<210> SEQ ID NO 899
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 899
gctaaagcgg aaatgcctga cttac                                               25

<210> SEQ ID NO 900
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 900
aaggaccaaa tgttcagatg                                                     20

<210> SEQ ID NO 901
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 901
ctgcaaagga ccaaatgttc                                                 20

<210> SEQ ID NO 902
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 902
tcaccctgca aaggaccaaa                                                 20

<210> SEQ ID NO 903
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 903
ctcactcacc ctgcaaagga                                                 20

<210> SEQ ID NO 904
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 904
tctcgctcac tcaccctgca                                                 20

<210> SEQ ID NO 905
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 905
cagcctctcg ctcactcacc                                                 20

<210> SEQ ID NO 906
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 906
caaagcagcc tctcgctcac                                                 20

<210> SEQ ID NO 907
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 907
tctatgagtt tcttccaaag                                                   20

<210> SEQ ID NO 908
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 908
gaactgttgc agtaatctat                                                   20

<210> SEQ ID NO 909
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 909
ttccaggtcc aggggggaact                                                  20

<210> SEQ ID NO 910
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 910
ccaggcaaga aactttttcca                                                  20

<210> SEQ ID NO 911
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 911
ttcagcttct gtaagccagg                                                   20

<210> SEQ ID NO 912
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 912
gacattggca gttgtttcag                                                   20

<210> SEQ ID NO 913
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 913
ggtagcatcc tgtaggacat                                              20

<210> SEQ ID NO 914
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 914
gagcctttcc ttacgggtag                                              20

<210> SEQ ID NO 915
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 915
cttggagtct tctaggagcc                                              20

<210> SEQ ID NO 916
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 916
cagctctttt actcccttgg                                              20

<210> SEQ ID NO 917
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 917
ttgccattgt ttcatcagct                                              20

<210> SEQ ID NO 918
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 918
cttacttgcc attgtttcat                                              20

<210> SEQ ID NO 919
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 919
cctgacttac ttgccattgt                                              20

<210> SEQ ID NO 920
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 920
aaatgcctga cttacttgcc                                              20

<210> SEQ ID NO 921
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 921
agcggaaatg cctgacttac                                              20

<210> SEQ ID NO 922
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 922
gctaaagcgg aaatgcctga                                              20

<210> SEQ ID NO 923
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 923
ccactcagag ctcagatctt ctaacttcc                                    29

<210> SEQ ID NO 924
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 924
gggatccagt atacttacag gctcc                                        25

<210> SEQ ID NO 925
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 925
cttccactca gagctcagat cttctaa                                27

<210> SEQ ID NO 926
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 926
acatcaagga agatggcatt tctagtttgg                             30

<210> SEQ ID NO 927
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 927
ctccaacatc aaggaagatg gcatttctag                             30

<210> SEQ ID NO 928
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 928
ttctgtccaa gcccggttga aatc                                   24

<210> SEQ ID NO 929
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 929
cacccaccat caccctcygt g                                      21

<210> SEQ ID NO 930
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 930
atcatctcgt tgatatcctc aa                                     22

<210> SEQ ID NO 931
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 931
acatcaagga agatggcatt tctag					25

<210> SEQ ID NO 932
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 932
accagagtaa cagtctgagt aggagc					26

<210> SEQ ID NO 933
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 933
tcaaggaaga tggcatttct					20

<210> SEQ ID NO 934
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 934
cctctgtgat tttataactt gat					23

<210> SEQ ID NO 935
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 935
atcatttttt ctcatacctt ctgct					25

<210> SEQ ID NO 936
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 936
ctcatacctt ctgcttgatg atc					23

<210> SEQ ID NO 937
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 937
tggcatttct agtttgg                                                17

<210> SEQ ID NO 938
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 938
ccagagcagg tacctccaac atc                                         23

<210> SEQ ID NO 939
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 939
tgttcagctt ctgttagcca ctga                                        24

<210> SEQ ID NO 940
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 940
tttgtgtctt tctgagaaac                                             20

<210> SEQ ID NO 941
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 941
cgccgccatt tctcaacag                                              19

<210> SEQ ID NO 942
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 942
atctgtcaaa tcgcctgcag                                             20

<210> SEQ ID NO 943
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 943 tgttttgag gattgctgaa                                              20

<210> SEQ ID NO 944
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 944
gctgaattat ttcttcccc                                             19

<210> SEQ ID NO 945
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 945
gcccaatgcc atcctgg                                               17

<210> SEQ ID NO 946
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 946
ccaatgccat cctggagttc ctgtaa                                     26

<210> SEQ ID NO 947
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 947
cattcaactg ttgcctccgg ttctgaaggt g                               31

<210> SEQ ID NO 948
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 948
ctgaaggtgt tcttgtactt catcc                                      25

<210> SEQ ID NO 949
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 949
ctgttgcctc cggttctg                                              18

<210> SEQ ID NO 950
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 950
attctttcaa ctagaataaa ag                                          22

<210> SEQ ID NO 951
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 951
gccatcctgg agttcctgta agataccaaa                                  30

<210> SEQ ID NO 952
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 952
ccaatgccat cctggagttc ctgtaagata                                  30

<210> SEQ ID NO 953
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 953
gccgctgccc aatgccatcc tggagttcct                                  30

<210> SEQ ID NO 954
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 954
gtttgccgct gcccaatgcc atcctggagt                                  30

<210> SEQ ID NO 955
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 955
caacagtttg ccgctgccca atgccatcct                                  30

<210> SEQ ID NO 956
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 956
ctgacaacag tttgccgctg cccaatgcca                                            30

<210> SEQ ID NO 957
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 957
tgttctgaca acagtttgcc gctgcccaat                                            30

<210> SEQ ID NO 958
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 958
caatgttctg acaacagttt gccgctgccc                                            30

<210> SEQ ID NO 959
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 959
cattcaatgt tctgacaaca gtttgccgct                                            30

<210> SEQ ID NO 960
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 960
tatttcttcc ccagttgcat tcaatgttct                                            30

<210> SEQ ID NO 961
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 961
gctgaattat ttcttcccca gttgcattca                                            30

<210> SEQ ID NO 962

<210> SEQ ID NO 962
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 962
ggattgctga attatttctt ccccagttgc                                       30

<210> SEQ ID NO 963
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 963
tttgaggatt gctgaattat tcttcccca                                        30

<210> SEQ ID NO 964
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 964
gtacttcatc ccactgattc tgaattcttt                                       30

<210> SEQ ID NO 965
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 965
tcttgtactt catcccactg attctgaatt                                       30

<210> SEQ ID NO 966
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 966
tgttcttgta cttcatccca ctgattctga                                       30

<210> SEQ ID NO 967
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 967
cggttctgaa ggtgttcttg tacttcatcc                                       30

<210> SEQ ID NO 968
<211> LENGTH: 30

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 968
ctccggttct gaaggtgttc ttgtacttca                                      30

<210> SEQ ID NO 969
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 969
tgcctccggt tctgaaggtg ttcttgtact                                      30

<210> SEQ ID NO 970
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 970
tgttgcctcc ggttctgaag gtgttcttgt                                      30

<210> SEQ ID NO 971
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 971
aactgttgcc tccggttctg aaggtgttct                                      30

<210> SEQ ID NO 972
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 972
ttcaactgtt gcctccggtt ctgaaggtgt                                      30

<210> SEQ ID NO 973
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 973

Gly Gly Phe Gly
1

<210> SEQ ID NO 974
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 974

Ala Leu Ala Leu
1

<210> SEQ ID NO 975
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 975

Gly Phe Leu Gly
1

<210> SEQ ID NO 976
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 976
gggaaattac agaatcacat aaaaac                                          26

<210> SEQ ID NO 977
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 977
gggaaattac aggctctgca aagttcttt                                       29
```

NUCLEIC ACID-POLYPEPTIDE COMPOSITIONS AND METHODS OF INDUCING EXON SKIPPING

CROSS-REFERENCE

This application is a continuation of U.S. application Ser. No. 16/129,696, filed Sep. 12, 2018, which is a continuation of U.S. application Ser. No. 16/128,450 filed Sep. 11, 2018, which is a continuation of the International Application No. PCT/US2018/012672, filed Jan. 5, 2018, which claims the benefit of U.S. Provisional Patent Application No. 62/561,939 filed on Sep. 22, 2017 and 62/443,514 filed on Jan. 6, 2017, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Sep. 12, 2018, is named 45532-715_303_SL.txt and is 210,679 bytes in size.

BACKGROUND OF THE DISCLOSURE

Modulation of RNA function is a developing area of therapeutic interest. Drugs that affect mRNA stability like antisense oligonucleotides and short interfering RNAs are one way to modulate RNA function. Another group of oligonucleotides can modulate RNA function by altering the processing of pre-mRNA to include or exclude specific regions of pre-mRNAs from the ultimate gene product: the encoded protein. As such, oligonucleotide therapeutics represent a means of modulating protein expression in disease states and as such have utility as therapeutics.

SUMMARY OF THE DISCLOSURE

Disclosed herein, in certain embodiments, are molecules and pharmaceutical compositions for modulating RNA processing.

Disclosed herein, in certain embodiments, are methods of treating a disease or disorder caused by an incorrectly spliced mRNA transcript in a subject in need thereof, the method comprising: administering to the subject a polynucleic acid molecule conjugate; wherein the polynucleic acid molecule conjugate is conjugated to a cell targeting binding moiety; wherein the polynucleotide optionally comprises at least one 2' modified nucleotide, at least one modified internucleotide linkage, or at least one inverted abasic moiety; wherein the polynucleic acid molecule conjugate induces insertion, deletion, duplication, or alteration in the incorrectly spliced mRNA transcript to induce exon skipping or exon inclusion in the incorrectly spliced mRNA transcript to generate a fully processed mRNA transcript; and wherein the fully processed mRNA transcript encodes a functional protein, thereby treating the disease or disorder in the subject. In some embodiments, the disease or disorder is further characterized by one or more mutations in the mRNA. In some embodiments, the disease or disorder comprises a neuromuscular disease, a genetic disease, cancer, a hereditary disease, or a cardiovascular disease. In some embodiments, the disease or disorder is muscular dystrophy. In some embodiments, the disease or disorder is Duchenne muscular dystrophy. In some embodiments, the exon skipping is of exon 8, 23, 35, 43, 44, 45, 50, 51, 52, 53, or 55 of the DMD gene. In some embodiments, the exon skipping is of exon 23 of the DMD gene. In some embodiments, the polynucleic acid molecule conjugate comprises a structure of Formula (I):

$$A\text{-}X\text{---}B \quad\quad \text{Formula I}$$

wherein,
A comprises a binding moiety;
B consists of a polynucleotide; and
X consists of a bond or first linker.
In some embodiments, the polynucleic acid molecule conjugate comprises a structure of Formula (II):

$$A\text{-}X\text{---}B\text{---}Y\text{---}C \quad\quad \text{Formula II}$$

wherein,
A comprises a binding moiety;
B consists of a polynucleotide;
C consists of a polymer;
X consists of a bond or first linker; and
Y consists of a bond or second linker.
In some embodiments, the polynucleic acid molecule conjugate comprises a structure of Formula (III):

$$A\text{-}X\text{---}C\text{---}Y\text{---}B \quad\quad \text{Formula III}$$

wherein,
A comprises a binding moiety;
B consists of a polynucleotide;
C consists of a polymer;
X consists of a bond or first linker; and
Y consists of a bond or second linker.
In some embodiments, the at least one 2' modified nucleotide comprises a morpholino, 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified nucleotide. In some embodiments, the at least one 2' modified nucleotide comprises locked nucleic acid (LNA), ethylene nucleic acid (ENA), or a peptide nucleic acid (PNA). In some embodiments, the at least one 2' modified nucleotide comprises a morpholino. In some embodiments, the at least one inverted basic moiety is at least one terminus. In some embodiments, the at least one modified internucleotide linkage comprises a phosphorothioate linkage or a phosphorodithioate linkage. In some embodiments, the polynucleic acid molecule is at least from about 10 to about 30 nucleotides in length. In some embodiments, the polynucleic acid molecule is at least one of: from about 15 to about 30, from about 18 to about 25, from about 18 to about 24, from about 19 to about 23, or from about 20 to about 22 nucleotides in length. In some embodiments, the polynucleic acid molecule is at least about 16, 17, 18, 19, 20, 21, 22, 23, 24, or 25 nucleotides in length. In some embodiments, the polynucleic acid molecule comprises at least one of: from about 5% to about 100% modification, from about 10% to about 100% modification, from about 20% to about 100% modification, from about 30% to about 100% modification, from about 40% to about 100% modification, from about 50% to about 100% modification, from about 60% to about 100% modification, from about 70% to about 100% modification, from about 80% to about 100% modification, and from about 90% to about 100% modification. In some embodiments, the polynucleic acid molecule comprises at least one of: from about 10% to about 90% modification, from about 20% to about 90% modification, from about 30% to about 90% modification, from about 40% to about 90% modification, from about 50% to about 90% modification, from about 60% to about 90% modification, from about 70% to about 90% modification, and from about 80% to about 100% modification. In some embodiments, the polynucleic acid molecule comprises at least one of: from about 10% to about 80% modification, from about 20% to about 80% modification, from about 30% to about 80% modification, from about 40% to about 80% modification, from about 50% to about 80% modification, from about 60% to about 80% modification, and from about 70% to about 80% modification. In some embodiments, the polynucleic acid molecule comprises at least one of: from about 10% to about 70% modification, from about 20% to about 70% modification, from about 30% to about 70% modification, from about 40% to about 70% modification, from about 50% to about 70% modification, and from about 60% to about 70% modification. In some embodiments, the polynucleic acid molecule comprises at least one of: from about 10% to about 60% modification, from about 20% to about 60% modification, from about 30% to about 60% modification, from about 40% to about 60% modification, and from about 50% to about 60% modification. In some embodiments, the polynucleic acid molecule comprises at least one of: from about 10% to about 50% modification, from about 20% to about 50% modification, from about 30% to about 50% modification, and from about 40% to about 50% modification. In some embodiments, the polynucleic acid molecule comprises at least one of: from about 10% to about 40% modification, from about 20% to about 40% modification, and from about 30% to about 40% modification. In some embodiments, the polynucleic acid molecule comprises at least one of: from about 10% to about 30% modification, and from about 20% to about 30% modification. In some embodiments, the polynucleic acid molecule comprises from about 10% to about 20% modification. In some embodiments, the polynucleic acid molecule comprises from about 15% to about 90%, from about 20% to about 80%, from about 30% to about 70%, or from about 40% to about 60% modifications. In some embodiments, the polynucleic acid molecule comprises at least about 15%, 20%, 30%, 40%, 50%, 60%, 70%, 80%, 90%, 95%, or 99% modification. In some embodiments, the polynucleic acid molecule comprises at least about 3, about 4, about 5, about 6, about 7, about 8, about 9, about 10, about 11, about 12, about 13, about 14, about 15, about 16, about 17, about 18, about 19, about 20, about 21, about 22 or more modifications. In some embodiments, the polynucleic acid molecule comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22 or more modified nucleotides. In some embodiments, the polynucleic acid molecule comprises a single strand. In some embodiments, the polynucleic acid molecule comprises two or more strands. In some embodiments, the polynucleic acid molecule comprises a first polynucleotide and a second polynucleotide hybridized to the first polynucleotide to form a double-stranded polynucleic acid molecule. In some embodiments, the second polynucleotide comprises at least one modification. In some embodiments, the first polynucleotide and the second polynucleotide are RNA molecules. In some embodiments, the first polynucleotide and the second polynucleotide are siRNA molecules. In some embodiments, X and Y are independently a bond, a degradable linker, a non-degradable linker, a cleavable linker, or a non-polymeric linker group. In some embodiments, X is a bond. In some embodiments, X is a $C_1$-$C_6$ alkyl group. In some embodiments, Y is a $C_1$-$C_6$ alkyl group. In some embodiments, X is a homobifunctional linker or a heterobifunctional linker, optionally conjugated to a $C_1$-$C_6$ alkyl group. In some embodiments, Y is a homobifunctional linker or a heterobifunctional linker. In some embodiments, the binding moiety is an antibody or binding fragment thereof. In some embodiments, the antibody or binding fragment thereof comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof. In some embodiments, C is polyethylene glycol. In some embodiments, C has a molecular weight of about 5000 Da. In some embodiments, A-X is conjugated to the 5' end of B and Y—C is conjugated to the 3' end of B. In some embodiments, Y—C is conjugated to the 5' end of B and A-X is conjugated to the 3' end of B. In some embodiments, A-X, Y—C or a combination thereof is conjugated to an internucleotide linkage group. In some embodiments, methods further comprise D. In some embodiments, D is conjugated to C or to A. In some embodiments, D is conjugated to the molecule conjugate of Formula (II) according to Formula (IV):

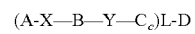  Formula IV wherein,
A comprises a binding moiety;
B consists of a polynucleotide;
C consists of a polymer;
X consists of a bond or first linker;
Y consists of a bond or second linker;
L consists of a bond or third linker;
D consists of an endosomolytic moiety; and
c is an integer between 0 and 1; and
wherein the polynucleotide comprises at least one 2' modified nucleotide, at least one modified internucleotide linkage, or an inverted abasic moiety; and D is conjugated anywhere on A, B, or C.

In some embodiments, D is INF7 or melittin. In some embodiments, L is a $C_1$-$C_6$ alkyl group. In some embodiments, L is a homobifunctional linker or a heterobifunctional linker. In some embodiments, methods further comprise at least a second binding moiety A. In some embodiments, the at least second binding moiety A is conjugated to A, to B, or to C.

Disclosed herein, in some embodiments, are methods of inducing an insertion, deletion, duplication, or alteration in the incorrectly spliced mRNA transcript to induce exon skipping or exon inclusion in the incorrectly spliced mRNA transcript, the method comprising: contacting a target cell with a polynucleic acid molecule conjugate, wherein the polynucleotide comprises at least one 2' modified nucleotide, at least one modified internucleotide linkage, or at least one inverted abasic moiety; hybridizing the polynucleic acid molecule conjugate to the incorrectly spliced mRNA transcript within the target cell to induce an insertion, deletion, duplication, or alteration in the incorrectly spliced mRNA transcript to induce exon skipping or exon inclusion, wherein the incorrectly spliced mRNA transcript is capable of encoding a functional form of a protein; and translating the functional form of a protein from a fully processed mRNA transcript of the previous step. In some embodiments, the target cell is a target cell of a subject. In some embodiments, the incorrectly spliced mRNA transcript further induces a disease or disorder. In some embodiments, the disease or disorder is further characterized by one or more mutations in the mRNA. In some embodiments, the disease or disorder comprises a neuromuscular disease, a genetic disease, cancer, a hereditary disease, or a cardiovascular disease. In some embodiments, the disease or disorder is muscular dystrophy. In some embodiments, the disease or disorder is Duchenne muscular dystrophy. In some embodiments, the exon skipping is of exon 8, 23, 35, 43, 44, 45, 50, 51, 52, 53, or 55 of the DMD gene. In some embodiments, the exon skipping is of exon 23 of the DMD gene. In some embodiments, the polynucleic acid molecule conjugate comprises a structure of Formula (I):

A-X—B             Formula I wherein,
A comprises a binding moiety;
B consists of a polynucleotide; and
X consists of a bond or first linker.

In some embodiments, the polynucleic acid molecule conjugate comprises a structure of Formula (II):

A-X—B—Y—C        Formula II wherein,
A comprises a binding moiety;
B consists of a polynucleotide;
C consists of a polymer;
X consists of a bond or first linker; and
Y consists of a bond or second linker.

In some embodiments, the polynucleic acid molecule conjugate comprises a structure of Formula (III):

A-X—C—Y—B        Formula III wherein,
A comprises a binding moiety;
B consists of a polynucleotide;
C consists of a polymer;
X consists of a bond or first linker; and
Y consists of a bond or second linker.

In some embodiments, the at least one 2' modified nucleotide comprises a morpholino, 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified nucleotide. In some embodiments, the at least one 2' modified nucleotide comprises locked nucleic acid (LNA), ethylene nucleic acid (ENA), peptide nucleic acid (PNA). In some embodiments, the at least one 2' modified nucleotide comprises a morpholino. In some embodiments, the at least one inverted basic moiety is at least one terminus. In some embodiments, the at least one modified internucleotide linkage comprises a phosphorothioate linkage or a phosphorodithioate linkage. In some embodiments, the polynucleic acid molecule is at least from about 10 to about 30 nucleotides in length. In some embodiments, the polynucleic acid molecule is at least one of: from about 15 to about 30, from about 18 to about 25, from about 18 to about 24, from about 19 to about 23, or from about 20 to about 22 nucleotides in length. In some embodiments, the polynucleic acid molecule is at least about 16, 17, 18, 19, 20, 21, 22, 23, 24, or 25 nucleotides in length. In some embodiments, the polynucleic acid molecule comprises at least one of: from about 5% to about 100% modification, from about 10% to about 100% modification, from about 20% to about 100% modification, from about 30% to about 100% modification, from about 40% to about 100% modification, from about 50% to about 100% modification, from about 60% to about 100% modification, from about 70% to about 100% modification, from about 80% to about 100% modification, and from about 90% to about 100% modification. In some embodiments, the polynucleic acid molecule comprises at least one of: from about 10% to about 90% modification, from about 20% to about 90% modification, from about 30% to about 90% modification, from about 40% to about 90% modification, from about 50% to about 90% modification, from about 60% to about 90% modification, from about 70% to about 90% modification, and from about 80% to about 100% modification. In some embodiments, the polynucleic acid molecule comprises at least one of: from about 10% to about 80% modification, from about 20% to about 80% modification, from about 30% to about 80% modification, from about 40% to about 80% modification, from about 50% to about 80% modification, from about 60% to about 80% modification, and from about 70% to about 80% modification. In some embodiments, the polynucleic acid molecule comprises at least one of: from about 10% to about 70% modification, from about 20% to about 70% modification, from about 30% to about 70% modification, from about 40% to about 70% modification, from about 50% to about 70% modification, and from about 60% to about 70% modification. In some embodiments, the polynucleic acid molecule comprises at least one of: from about 10% to about 60% modification, from about 20% to about 60% modification, from about 30% to about 60% modification, from about 40% to about 60% modification, and from about 50% to about 60% modification. In some embodiments, the polynucleic acid molecule comprises at least one of: from about 10% to about 50% modification, from about 20% to about 50% modification, from about 30% to about 50% modification, and from about 40% to about 50% modification. In some embodiments, the polynucleic acid molecule comprises at least one of: from about 10% to about 40% modification, from about 20% to about 40% modification, and from about 30% to about 40% modification. In some embodiments, the polynucleic acid molecule comprises at least one of: from about 10% to about 30% modification, and from about 20% to about 30% modification. In some embodiments, the polynucleic acid molecule comprises from about 10% to about 20% modification. In some embodiments, the polynucleic acid molecule comprises from about 15% to about 90%, from about 20% to about 80%, from about 30% to about 70%, or from about 40% to about 60% modifications. In some embodiments, the polynucleic acid molecule comprises at least about 15%, 20%, 30%, 40%, 50%, 60%, 70%, 80%, 90%, 95%, or 99% modification. In some embodiments, the polynucleic acid molecule comprises at least about 3, about 4, about 5, about 6, about 7, about 8, about 9, about 10, about 11, about 12, about 13, about 14, about 15, about 16, about 17, about 18, about 19, about 20, about 21, about 22 or more modifications. In some embodiments, the polynucleic acid molecule comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22 or more modified nucleotides. In some embodiments, the polynucleic acid molecule comprises a single strand. In some embodiments, the polynucleic acid molecule comprises two or more strands. In some embodiments, the polynucleic acid molecule comprises a first polynucleotide and a second polynucleotide hybridized to the first polynucleotide to form a double-stranded polynucleic acid molecule. In some embodiments, the second polynucleotide comprises at least one modification. In some embodiments, the first polynucleotide and the second polynucleotide are RNA molecules. In some embodiments, the first polynucleotide and the second polynucleotide are siRNA molecules. In some embodiments, X and Y are independently a bond, a degradable linker, a non-degradable linker, a cleavable linker, or a non-polymeric linker group. In some embodiments, X is a bond. In some embodiments, X is a $C_1$-$C_6$ alkyl group. In some embodiments, Y is a $C_1$-$C_6$ alkyl group. In some embodiments, X is a homobifunctional linker or a heterobifunctional linker, optionally conjugated to a $C_1$-$C_6$ alkyl group. In some embodiments, Y is a homobifunctional linker or a heterobifunctional linker. In some embodiments, the binding moiety is an antibody or binding fragment thereof. In some embodiments, the antibody or binding fragment thereof comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof. In some embodiments, C is polyethylene glycol. In some embodiments, C has a molecular weight of about 5000 Da. In some embodiments, A-X is conjugated to the 5' end of B and Y—C is conjugated to the 3' end of B. In some embodiments, Y—C is conjugated to the 5' end of B and A-X is conjugated to the 3' end of B. In some embodiments, A-X, Y—C or a combination thereof is conjugated to an internucleotide linkage group. In some embodiments, methods further comprise D. In some embodiments, D is conjugated to C or to A. In some embodiments, D is conjugated to the molecule conjugate of Formula (II) according to Formula (IV):

(A-X—B—Y—$C_c$)L-D <span style="float:right">Formula IV</span> wherein,
A comprises a binding moiety;
B consists of a polynucleotide;
C consists of a polymer;
X consists of a bond or first linker;
Y is a bond or second linker;
L consists of a bond or third linker;
D consists of an endosomolytic moiety; and
c is an integer between 0 and 1; and
wherein the polynucleotide comprises at least one 2' modified nucleotide, at least one modified internucleotide linkage, or an inverted abasic moiety; and D is conjugated anywhere on A, B, or C.

In some embodiments, D is INF7 or melittin. In some embodiments, L is a $C_1$-$C_6$ alkyl group. In some embodiments, L is a homobifunctional linker or a heterobifunctional linker. In some embodiments, methods further comprise at least a second binding moiety A. In some embodiments, the at least second binding moiety A is conjugated to A, to B, or to C. In some embodiments, the method is an in vivo method. In some embodiments, the method is an in vitro method. In some embodiments, the subject is a human.

Disclosed herein, in certain embodiments, are pharmaceutical compositions comprising: a molecule obtained by any one of the methods disclosed herein and a pharmaceutically acceptable excipient. In some embodiments, the pharmaceutical composition is formulated as a nanoparticle formulation. In some embodiments, the pharmaceutical composition is formulated for parenteral, oral, intranasal, buccal, rectal, or transdermal administration.

Disclosed herein, in certain embodiments, are kits comprising a molecule obtained by any one of the methods disclosed herein.

Disclosed herein, in certain embodiments, are compositions comprising a polynucleic acid molecule conjugate, wherein the polynucleic acid molecule conjugate comprises a polynucleotide comprising a sequence having at least 60%, 65%, 70%, 75%, 80%, 85%, 90%, 95%, 96%, 97%, 98%, 99%, or 100% sequence identity to SEQ ID NOs: 54-972. Disclosed herein, in certain embodiments, are compositions comprising a polynucleic acid molecule conjugate, wherein the polynucleic acid molecule conjugate comprises a polynucleotide comprising a sequence having at least 80%, 85%, 90%, 95%, 96%, 97%, 98%, 99%, or 100% sequence identity to SEQ ID NOs: 54-972. In certain embodiments, the polynucleic acid molecule conjugate comprises a structure of Formula (I):

A-X—B <span style="float:right">Formula I</span> wherein,
A comprises a binding moiety;
B consists of the polynucleotide; and
X consists of a bond or first linker.

In certain embodiments, the polynucleic acid molecule conjugate comprises a structure of Formula (II):

A-X—B—Y—C <span style="float:right">Formula II</span> wherein,
A comprises a binding moiety;
B consists of the polynucleotide;
C consists of a polymer;
X consists of a bond or first linker; and
Y consists of a bond or second linker.

In certain embodiments, the polynucleic acid molecule conjugate comprises a structure of Formula (III):

A-X—C—Y—B <span style="float:right">Formula III</span> wherein,
A comprises a binding moiety;
B consists of the polynucleotide;
C consists of a polymer;
X consists of a bond or first linker; and
Y consists of a bond or second linker.

In certain embodiments, the at least one 2' modified nucleotide comprises a morpholino, 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified nucleotide. In certain embodiments, the at least one 2' modified nucleotide comprises a morpholino.

Disclosed herein, in certain embodiments, are methods of treating a disease or disorder comprising: administering to a subject a polynucleic acid molecule conjugate; wherein the polynucleic acid molecule conjugate comprises a target cell binding moiety and a targeted pre-mRNA specific splice modulating polynucleic acid moiety; wherein the target cell binding moiety specifically binds to a targeted cell, and the targeted pre-mRNA specific splice modulating polynucleic acid moiety induces insertion, deletion, duplication, or alteration of a targeted pre-mRNA transcript in the targeted cell to induce a splicing event in the targeted pre-mRNA transcript to generate a mRNA transcript; and wherein the mRNA transcript encodes a protein that is modified when compared to the same protein in untreated target cells, thereby treating the disease or disorder in the subject. In certain embodiments, the splicing event is exon skipping. In certain embodiments, the splicing event is exon inclusion. In certain embodiments, the disease or disorder is further characterized by one or more mutations in the pre-mRNA. In certain embodiments, the disease or disorder comprises a neuromuscular disease, a genetic disease, cancer, a hereditary disease, or a cardiovascular disease. In certain embodiments, the disease or disorder is muscular dystrophy. In certain embodiments, the disease or disorder is Duchenne muscular dystrophy. In certain embodiments, the splicing event is of exon 8, 23, 35, 43, 44, 45, 50, 51, 52, 53, or 55 of DMD gene. In certain embodiments, the splicing event is of exon 23 of DMD gene. In certain embodiments, the splicing event is of an exon of PAH, MSTN, or K-Ras gene. In certain embodiments, the polynucleic acid molecule conjugate comprises a structure of Formula (I):

A-X—B <span></span> Formula I wherein,
A comprises a binding moiety;
B consists of a polynucleotide; and
X consists of a bond or first linker.
In certain embodiments, the polynucleic acid molecule conjugate comprises a structure of Formula (II):

A-X—B—Y—C <span></span> Formula II wherein,
A comprises a binding moiety;
B consists of a polynucleotide;
C consists of a polymer;
X consists a bond or first linker; and
Y consists of a bond or second linker.
In certain embodiments, the polynucleic acid molecule conjugate comprises a structure of Formula (III):

A-X—C—Y—B <span></span> Formula III wherein,
A comprises a binding moiety;
B consists of a polynucleotide;
C consists of a polymer;
X consists of a bond or first linker; and
Y consists of a bond or second linker.
In certain embodiments, the polynucleic acid molecule conjugate optionally comprises at least one 2' modified nucleotide, at least one modified internucleotide linkage, or at least one inverted abasic moiety. In certain embodiments, the at least one 2' modified nucleotide comprises a morpholino, 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified nucleotide. In certain embodiments, the at least one 2' modified nucleotide comprises locked nucleic acid (LNA), ethylene nucleic acid (ENA), or a peptide nucleic acid (PNA). In certain embodiments, the at least one 2' modified nucleotide comprises a morpholino. In certain embodiments, the at least one inverted basic moiety is at least one terminus. In certain embodiments, the at least one modified internucleotide linkage comprises a phosphorothioate linkage or a phosphorodithioate linkage. In certain embodiments, the polynucleic acid molecule comprises at least from about 10 to about 30 nucleotides in length. In certain embodiments, the polynucleic acid molecule comprises at least about 15%, 20%, 30%, 40%, 50%, 60%, 70%, 80%, 90%, 95%, or 99% modification. In certain embodiments, the polynucleic acid molecule comprises a single strand. In certain embodiments, the polynucleic acid molecule comprises two or more strands. In certain embodiments, the polynucleic acid molecule comprises a first polynucleotide and a second polynucleotide hybridized to the first polynucleotide to form a double-stranded polynucleic acid molecule. In certain embodiments, the second polynucleotide comprises at least one modification. In certain embodiments, the first polynucleotide and the second polynucleotide comprise RNA molecules. In certain embodiments, the first polynucleotide and the second polynucleotide comprise siRNA molecules. In certain embodiments, X is a bond. In certain embodiments, X and Y are independently a bond, a degradable linker, a non-degradable linker, a cleavable linker, or a non-polymeric linker group. In certain embodiments, X and Y are independently a bond, a degradable linker, a non-degradable linker, a cleavable linker, or a non-polymeric linker group. In certain embodiments, X is a $C_1$-$C_6$ alkyl group. In certain embodiments, X or Y is a $C_1$-$C_6$ alkyl group. In certain embodiments, X or Y is a $C_1$-$C_6$ alkyl group. In certain embodiments, the binding moiety is an antibody or binding fragment thereof. In certain embodiments, the binding moiety is an antibody or binding fragment thereof. In certain embodiments, the binding moiety is an antibody or binding fragment thereof. In certain embodiments, C is polyethylene glycol. In certain embodiments, C is polyethylene glycol. In certain embodiments, A-X is conjugated to the 5' end of B and Y—C is conjugated to the 3' end of B. In certain embodiments, Y—C is conjugated to the 5' end of B and A-X is conjugated to the 3' end of B. In certain embodiments, methods further comprise D. In certain embodiments, D is conjugated to C or to A. In certain embodiments, methods further comprise at least a second binding moiety A. In certain embodiments, methods further comprise at least a second binding moiety A. In certain embodiments, methods further comprise at least a second binding moiety A.

Disclosed herein, in certain embodiments, are methods of inducing a splicing event in a targeted pre-mRNA transcript, comprising: (a) contacting a target cell with a polynucleic acid molecule conjugate, wherein the polynucleic acid molecule conjugate comprises a target cell binding moiety and a targeted pre-mRNA splice modulating polynucleic acid moiety; (b) hybridizing the targeted pre-mRNA splice modulating polynucleic acid moiety to the targeted pre-mRNA transcript within the target cell to induce the splicing event in the targeted pre-mRNA transcript to produce a mRNA transcript; and (c) optionally, translating the mRNA transcript of step (b) in the target cell to produce a protein. In certain embodiments, the splicing event is exon skipping. In certain embodiments, the splicing event is exon inclusion. In certain embodiments, the targeted pre-mRNA transcript induces a disease or disorder. In certain embodiments, the disease or disorder comprises a neuromuscular disease, a genetic disease, cancer, a hereditary disease, or a cardiovascular disease. In certain embodiments, the polynucleic acid molecule conjugate:
a) comprises a structure of Formula (I):

A-X—B <span></span> Formula I wherein,
A comprises a binding moiety;
B consists of the polynucleotide; and
X consists of a bond or first linker;
b) comprises a structure of Formula (II):

A-X—B—Y—C <span></span> Formula II wherein,
A comprises a binding moiety;
B consists of the polynucleotide;
C consists of a polymer;
X consists of a bond or first linker; and
Y consists of a bond or second linker; or
c) comprises a structure of Formula (III):

A-X—C—Y—B  Formula III wherein,
A comprises a binding moiety;
B consists of the polynucleotide;
C consists of a polymer;
X consists of a bond or first linker; and
Y consists of a bond or second linker.

In certain embodiments, the polynucleic acid molecule conjugate optionally comprises at least one 2' modified nucleotide, at least one modified internucleotide linkage, or at least one inverted abasic moiety. In certain embodiments, the at least one 2' modified nucleotide comprises a morpholino, 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified nucleotide. In certain embodiments, the at least one 2' modified nucleotide comprises locked nucleic acid (LNA), ethylene nucleic acid (ENA), peptide nucleic acid (PNA). In certain embodiments, the at least one 2' modified nucleotide comprises a morpholino. In certain embodiments, the at least one inverted basic moiety is at least one terminus. In certain embodiments, the at least one modified internucleotide linkage comprises a phosphorothioate linkage or a phosphorodithioate linkage. In certain embodiments, the polynucleic acid molecule comprises at least from about 10 to about 30 nucleotides in length. In certain embodiments, the polynucleic acid molecule comprises at least about 15%, 20%, 30%, 40%, 50%, 60%, 70%, 80%, 90%, 95%, or 99% modification. In certain embodiments, the polynucleic acid molecule comprises at least about 3, about 4, about 5, about 6, about 7, about 8, about 9, about 10, about 11, about 12, about 13, about 14, about 15, about 16, about 17, about 18, about 19, about 20, about 21, about 22 or more modifications. In certain embodiments, X and Y are independently a bond, a degradable linker, a non-degradable linker, a cleavable linker, or a non-polymeric linker group. In certain embodiments, X is a bond. In certain embodiments, X is a $C_1$-$C_6$ alkyl group. In certain embodiments, Y is a $C_1$-$C_6$ alkyl group. In certain embodiments, X is a homobifunctional linker or a heterobifunctional linker, optionally conjugated to a $C_1$-$C_6$ alkyl group. In certain embodiments, Y is a homobifunctional linker or a heterobifunctional linker. In certain embodiments, the binding moiety is an antibody or binding fragment thereof. In certain embodiments, C is polyethylene glycol. In certain embodiments, A-X is conjugated to the 5' end of B and Y—C is conjugated to the 3' end of B. In certain embodiments, Y—C is conjugated to the 5' end of B and A-X is conjugated to the 3' end of B. In certain embodiments, A-X, Y—C or a combination thereof is conjugated to an internucleotide linkage group. In certain embodiments, methods further comprise D. In certain embodiments, D is conjugated to C or to A. In certain embodiments, methods further comprise at least a second binding moiety A.

Disclosed herein, in certain embodiments, are polynucleic acid molecule conjugate compositions comprising a target cell binding moiety and a targeted pre-mRNA specific splice modulating polynucleic acid moiety wherein the targeted pre-mRNA specific splice modulating polynucleic acid moiety comprises a sequence having at least 60%, 65%, 70%, 75%, 80%, 85%, 90%, 95%, 96%, 97%, 98%, 99%, or 100% sequence identity to SEQ ID NOs: 54-972. In certain embodiments, the polynucleic acid molecule conjugate:
a) comprises a structure of Formula (I):

A-X—B  Formula I wherein,
A comprises a binding moiety;
B consists of the polynucleotide; and
X consists of a bond or first linker;
b) comprises a structure of Formula (II):

A-X—B—Y—C  Formula II wherein,
A comprises a binding moiety;
B consists of the polynucleotide;
C consists of a polymer;
X consists of a bond or first linker; and
Y consists of a bond or second linker; or
c) comprises a structure of Formula (III):

A-X—C—Y—B  Formula III wherein,
A comprises a binding moiety;
B consists of the polynucleotide;
C consists of a polymer;
X consists of a bond or first linker; and
Y consists of a bond or second linker.

In certain embodiments, the pharmaceutical composition is formulated as a nanoparticle formulation.

DESCRIPTION OF THE DRAWINGS

FIG. 19A-FIG. 19L illustrate cartoon representations of molecules described herein.

DETAILED DESCRIPTION OF THE DISCLOSURE

Figure 1:
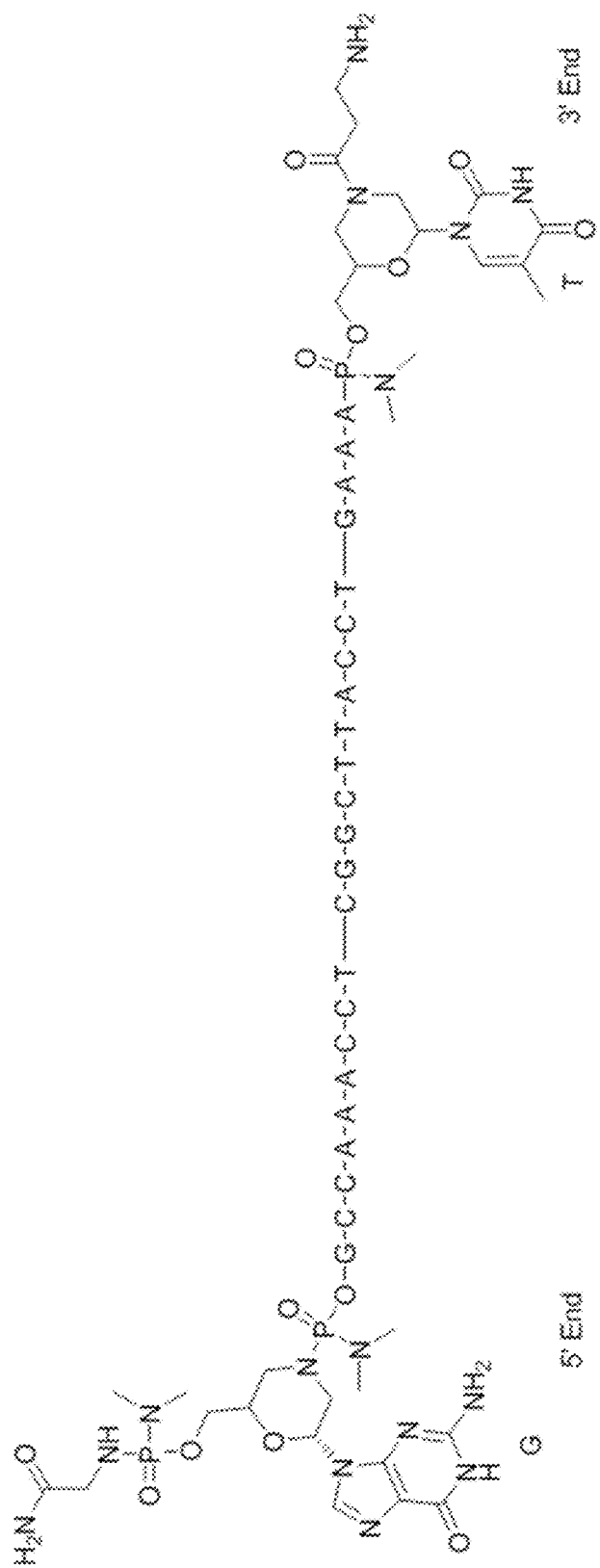
FIG. 1 depicts a phosphorodiamidate morpholino oligomer (PMO) sequence with end nucleotides expanded (SEQ ID NO: 28).

Nucleic acid (e.g., RNAi) therapy is a targeted therapy with high selectivity and specificity. However, in some instances, nucleic acid therapy is also hindered by poor intracellular uptake, insufficient intracellular concentrations in target cells, and low efficacy. To address these issues, various modifications of the nucleic acid composition are explored, such as for example, novel linkers for better stabilizing and/or lower toxicity, optimization of binding moiety for increased target specificity and/or target delivery, and nucleic acid polymer modifications for increased stability and/or reduced off-target effect.

In some instances, one such area where oligonucleotide is used is for treating muscular dystrophy. Muscular dystrophy encompasses several diseases that affect the muscle. Duchenne muscular dystrophy is a severe form of muscular dystrophy and caused by mutations in the DMD gene. In some instances, mutations in the DMD gene disrupt the translational reading frame and results in non-functional dystrophin protein.

Described herein, in certain embodiments, are methods and compositions relating nucleic acid therapy to induce an insertion, deletion, duplication, or alteration in an incorrectly spliced mRNA transcript to induce exon skipping or exon inclusion, which is used to restore the translational reading frame. In some embodiments, also described herein include methods and compositions for treating a disease or disorder characterized by an incorrectly processed mRNA transcript, in which after removal of an exon, the mRNA is capable of encoding a functional protein, thereby treating the disease or disorder. In additional embodiments, described herein include pharmaceutical compositions and kits for treating the same.

RNA Processing

RNA has a central role in regulation of gene expression and cell physiology. Proper processing of RNA is important for translational of functional protein. Alterations in RNA processing such as a result of incorrect splicing of RNA can result in disease. For example, mutations in a splice site causes exposure of a premature stop codon, a loss of an exon, or inclusion of an intron. In some instances, alterations in RNA processing results in an insertion, deletion, or duplication. In some instances, alterations in RNA processing results in an insertion, deletion, or duplication of an exon. Alterations in RNA processing, in some cases, results in an insertion, deletion, or duplication of an intron.

Alternative transcriptional or splicing events include, but are not limited to, exon skipping, alternative 3' splice site selection, alternative 5' splice site selection, intron retention, mutually exclusive exons, alternative promoter usage, and alternative polyadenylation. Splicing events, in some embodiments, results in an insertion, deletion, or duplication of an exon, for example, by exon skipping or exon inclusion.

Exon Skipping

Exon skipping is a form of RNA splicing. In some cases, exon skipping occurs when an exon is skipped over or is spliced out of the processed mRNA. As a result of exon skipping, the processed mRNA does not contain the skipped exon. In some instances, exon skipping results in expression of an altered product.

In some instances, antisense oligonucleotides (AONs) are used to induce exon skipping. In some instances, AONs are short nucleic acid sequences that bind to specific mRNA or pre-mRNA sequences. For example, AONs bind splice sites or exonic enhancers. In some instances, binding of AONs to specific mRNA or pre-mRNA sequences generates double-stranded regions. In some instances, formation of double-stranded regions occurs at sites where the spliceosome or proteins associated with the spliceosome would normally bind and causes exons to be skipped. In some instances, skipping of exons results in restoration of the transcript reading frame and allows for production of a partially functional protein.

Exon Inclusion

In some instances, a mutation in RNA results in exon skipping. In some cases, a mutation is at least one of at the splice site, near the splice site, and at a distance from the splice site. In some instances, the mutations result in at least one of inactivating or weakening the splice site, disrupting exon splice enhancer or intron splice enhancer, and creating an exon splice silencer or intron splice enhancer. Mutations in some instances alter RNA secondary structure. In some cases, a mutation alters a RNA secondary structure result in disrupting the accessibility of signals important for exon recognition.

In some instances, use of AONs results in inclusion of the skipped exon. In some instances, the AONs bind to at least one of a splice site, a site near a splice site, and a site distant to a splice site. In some cases, AONs bind at site in the RNA to prevent disruption of an exon splice enhancer or intron splice enhancer. In some instances, AONs bind at site in the RNA to prevent creation of an exon splice silencer or intron splice silencer.

Intron Retention

In some instances, a mutation in RNA results in intron retention. Intron retention results in an intron remaining in the mature mRNA transcript. In some instances, presence of a retained intron prevents or reduces translation of a functional protein. In some instances, intron retention occurs in a coding region, a non-coding region, at the 5' UTR, or at the 3' UTR. Where intron retention occurs in a coding region, in some instances, the retained intron encodes amino acids in frame, or is in misalignment which generates truncated proteins or non-functional proteins due to stop codon or frame shifts. In some instances, the intron is retained between two exons, located at the 5' UTR, or located at the 3' UTR.

In some instances, AONs are used to hybridize to a partially processed mRNA to initiate removal of a retained intron. In some instances, the AONs hybridize to an intronic splicing enhancer or an intronic splicing silencer. In some instances, the AONs hybridize at or a distance from a 5' splice site, 3' splice site, branchpoint, polypyrimidine tract, an intron silencer site, a cryptic intron splice site, a pseudo splice site, or an intron enhancer of the intron. In some instances, the AONs hybridize to an internal region of the intron.

Indications

In some embodiments, a polynucleic acid molecule or a pharmaceutical composition described herein is used for the treatment of a disease or disorder characterized with a defective mRNA. In some embodiments, a polynucleic acid molecule or a pharmaceutical composition described herein is used for the treatment of disease or disorder by inducing an insertion, deletion, duplication, or alteration in an incorrectly spliced mRNA transcript to induce a splicing event. In some embodiments, the splicing event is exon skipping or exon inclusion. In some embodiments, the splicing event is intron retention.

In some embodiments, a polynucleic acid molecule or a pharmaceutical composition described herein is used for the treatment of disease or disorder by inducing an insertion, deletion, duplication, or alteration in an incorrectly spliced mRNA transcript to induce exon skipping or exon inclusion.

A large percentage of human protein-coding genes are alternatively spliced. In some instances, a mutation results in improperly spliced or partially spliced mRNA. For example, a mutation is in at least one of a splice site in a protein coding gene, a silencer or enhancer sequence, exonic sequences, or intronic sequences. In some instances, a mutation results in gene dysfunction. In some instances, a mutation results in a disease or disorder.

In some instances, a disease or disorder resulting from improperly spliced or partially spliced mRNA includes, but not limited to, a neuromuscular disease, a genetic disease, cancer, a hereditary disease, or a cardiovascular disease.

In some instances, genetic diseases or disorders include an autosomal dominant disorder, an autosomal recessive disorder, X-linked dominant disorder, X-linked recessive disorder, Y-linked disorder, mitochondrial disease, or multifactorial or polygenic disorder.

In some instances, cardiovascular disease such as hypercholesterolemia results from improperly spliced or partially spliced mRNA. In hypercholesterolemia, it has been shown that a single nucleotide polymorphism in exon 12 of the low density lipoprotein receptor (LDLR) promotes exon skipping.

In some instances, improperly spliced or partially spliced mRNA results in cancer. For example, improperly spliced or partially spliced mRNA affects cellular processes involved in cancer including, but not limited to, proliferation, motility, and drug response. In some instances is a solid cancer or a hematologic cancer. In some instances, the cancer is bladder cancer, lung cancer, brain cancer, melanoma, breast cancer, Non-Hodgkin lymphoma, cervical cancer, ovarian cancer, colorectal cancer, pancreatic cancer, esophageal cancer, prostate cancer, kidney cancer, skin cancer, leukemia, thyroid cancer, liver cancer, or uterine cancer.

Improperly spliced or partially spliced mRNA in some instances causes a neuromuscular disease or disorder. Exemplary neuromuscular diseases include muscular dystrophy such as Duchenne muscular dystrophy, Becker muscular dystrophy, facioscapulohumeral muscular dystrophy, congenital muscular dystrophy, or myotonic dystrophy. In some instances, muscular dystrophy is genetic. In some instances, muscular dystrophy is caused by a spontaneous mutation. Becker muscular dystrophy and Duchenne muscular dystrophy have been shown to involve mutations in the DMD gene, which encodes the protein dystrophin. Facioscapulohumeral muscular dystrophy has been shown to involve mutations in double homeobox, 4 (DUX4) gene.

In some instances, improperly spliced or partially spliced mRNA causes Duchenne muscular dystrophy. Duchenne muscular dystrophy results in severe muscle weakness and is caused by mutations in the DMD gene that abolishes the production of functional dystrophin. In some instances, Duchenne muscular dystrophy is a result of a mutation in an exon in the DMD gene. In some instances, Duchenne muscular dystrophy is a result of a mutation in at least one of exon 1, 2, 3, 4, 5, 6, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78 and 79 in the DMD gene. In some instances, Duchenne muscular dystrophy is a result of a mutation in at least one of exon 3, 4, 5, 6, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, and 63 in the DMD gene. In some instances, Duchenne muscular dystrophy is a result of a mutation in at least one of exon 8, 23, 35, 43, 44, 45, 50, 51, 52, 53, and 55 in the DMD gene. In some instances, multiple exons are mutated. For example, mutation of exons 48-50 is common in Duchenne muscular dystrophy patients. In some instances, Duchenne muscular dystrophy is a result of mutation of exon 51. In some instances, Duchenne muscular dystrophy is a result of mutation of exon 23. In some instances, a mutation involves a deletion of an exon. In some instances, a mutation involves a duplication of an exon. In some instances, a mutation involves a point mutation in an exon. For example, it has been shown that some patients have a nonsense point mutation in exon 51 of the DMD gene.

In some instances, a polynucleic acid molecule or a pharmaceutical composition described herein is used for the treatment of muscular dystrophy. In some instances, a polynucleic acid molecule or a pharmaceutical composition described herein is used for the treatment of Duchenne muscular dystrophy, Becker muscular dystrophy, facioscapulohumeral muscular dystrophy, congenital muscular dystrophy, or myotonic dystrophy. In some instances, a polynucleic acid molecule or a pharmaceutical composition described herein is used for the treatment of Duchenne muscular dystrophy.

Polynucleic Acid Molecule

In some embodiments, a polynucleic acid molecule described herein that induces an insertion, deletion, duplication, or alteration in an incorrectly spliced mRNA transcript to induce exon skipping or exon inclusion. In some instances, the polynucleic acid molecule restores the translational reading frame. In some instances, the polynucleic acid molecule results in a functional and truncated protein.

In some instances, a polynucleic acid molecule targets a mRNA sequence. In some instances, the polynucleic acid molecule targets a splice site. In some instances, the polynucleic acid molecule targets a cis-regulatory element. In some instances, the polynucleic molecule targets a trans-regulatory element. In some instances, the polynucleic acid molecule targets exonic splice enhancers or intronic splice enhancers. In some instances, the polynucleic acid molecule targets exonic splice silencers or intronic splice silencers.

In some instances, a polynucleic acid molecule targets a sequence found in introns or exons. For example, the polynucleic acid molecule targets a sequence found in an exon that mediates splicing of said exon. In some instances, the polynucleic acid molecule targets an exon recognition sequence. In some instances, the polynucleic acid molecule targets a sequence upstream of an exon. In some instances, the polynucleic acid molecule targets a sequence downstream of an exon.

As described above, a polynucleic acid molecule targets an incorrectly processed mRNA transcript which results in a disease or disorder not limited to a neuromuscular disease, a genetic disease, cancer, a hereditary disease, or a cardiovascular disease.

In some instances, a polynucleic acid molecule targets an exon that is mutated in a gene that causes a disease or disorder. Exemplary diseases or disorders include, but are not limited to, familial dysautonomia (FD), spinal muscular atrophy (SMA), medium-chain acyl-CoA dehydrogenase (MCAD) deficiency, Hutchinson-Gilford progeria syndrome (HGPS), myotonic dystrophy type I (DM1), myotonic dystrophy type II (DM2), autosomal dominant retinitis pigmentosa (RP), Duchenne muscular dystrophy (DMD), microcephalic osteodysplastic primordial dwarfism type 1 (MOPD1) (Taybi-Linder syndrome (TALS)), frontotemporal dementia with parkinsonism-17 (FTDP-17), Fukuyama congenital muscular dystrophy (FCMD), amyotrophic lateral sclerosis (ALS), hypercholesterolemia, and cystic fibrosis (CF). Exemplary genes that are involved in the disease or disorder include, but are not limited to, IKBKAP, SMN2, MCAD, LMNA, DMPK, ZNF9, MAPT, FKTN, TDP-43, LDLR, CFTR, DMD, PAH, MSTN, and K-Ras. In some embodiments, the gene is DMD, PAH, MSTN, or K-Ras.

In some instances, a polynucleic acid molecule described herein targets a region that is at the exon-intron junction of an exon of a gene that causes a disease or disorder. In some embodiments, the gene is IKBKAP, SMN2, MCAD, LMNA, DMPK, ZNF9, MAPT, FKTN, TDP-43, LDLR, CFTR, DMD, PAH, MSTN, or K-Ras. In some embodiments, a polynucleic acid molecule described herein targets a region that is at the exon-intron junction of exon 1, 2, or 3 of MSTN. In some embodiments, a polynucleic acid molecule described herein targets a region that is at the exon-intron junction of exon 2 of MSTN. In some embodiments, a polynucleic acid molecule described herein targets a region that is at the exon-intron junction of exon 1, 2, 3, 4, 5, 6, 7, 8, 9, 10, 11, 12, 13, 14, 15, 16, 17, 18, 19, 20, or 21 of PAH. In some embodiments, a polynucleic acid molecule described herein targets a region that is at the exon-intron junction of exon 11 of PAH.

In some instances, the polynucleic acid molecule hybridizes to a target region that is at either the 5' intron-exon junction or the 3' exon-intron junction of at least one of an exon of a gene that causes a disease or disorder. In some embodiments, the gene is IKBKAP, SMN2, MCAD, LMNA, DMPK, ZNF9, MAPT, FKTN, TDP-43, LDLR, CFTR, DMD, PAH, MSTN, or K-Ras. In some embodiments, a polynucleic acid molecule described herein targets either the 5' intron-exon junction or the 3' exon-intron junction of exon 1, 2, or 3 of MSTN. In some embodiments, a polynucleic acid molecule described herein targets a region that is either the 5' intron-exon junction or the 3' exon-intron junction of exon 2 of MSTN. In some embodiments, a polynucleic acid molecule described herein targets a region that is either the 5' intron-exon junction or the 3' exon-intron junction of exon 1, 2, 3, 4, 5, 6, 7, 8, 9, 10, 11, 12, 13, 14, 15, 16, 17, 18, 19, 20, or 21 of PAH. In some embodiments, a polynucleic acid molecule described herein targets a region that is either the 5' intron-exon junction or the 3' exon-intron junction of exon 11 of PAH.

In some cases, the polynucleic acid molecule hybridizes to a target region that is at the 5' intron-exon junction of at least one of exon of a gene that causes a disease or disorder. In some embodiments, the gene is IKBKAP, SMN2, MCAD, LMNA, DMPK, ZNF9, MAPT, FKTN, TDP-43, LDLR, CFTR, DMD, PAH, MSTN, or K-Ras. In some embodiments, a polynucleic acid molecule described herein targets a region that is at the 5' intron-exon junction of exon 1, 2, or 3 of MSTN. In some embodiments, a polynucleic acid molecule described herein targets a region that is at the 5' intron-exon junction of exon 2 of MSTN. In some embodiments, a polynucleic acid molecule described herein targets a region that is at the 5' intron-exon junction of exon 1, 2, 3, 4, 5, 6, 7, 8, 9, 10, 11, 12, 13, 14, 15, 16, 17, 18, 19, 20, or 21 of PAH. In some embodiments, a polynucleic acid molecule described herein targets a region that is at the 5' intron-exon junction of exon 11 of PAH.

In some cases, the polynucleic acid molecule hybridizes to a target region that is at the 3' exon-intron junction of at least one of exon of a gene that causes a disease or disorder. In some embodiments, the gene is IKBKAP, SMN2, MCAD, LMNA, DMPK, ZNF9, MAPT, FKTN, TDP-43, LDLR, CFTR, DMD, PAH, MSTN, or K-Ras. In some embodiments, a polynucleic acid molecule described herein targets a region that is at the 3' exon-intron junction of exon 1, 2, or 3 of MSTN. In some embodiments, a polynucleic acid molecule described herein targets a region that is at the 3' exon-intron junction of exon 2 of MSTN. In some embodiments, a polynucleic acid molecule described herein targets a region that is at the 3' exon-intron junction of exon 1, 2, 3, 4, 5, 6, 7, 8, 9, 10, 11, 12, 13, 14, 15, 16, 17, 18, 19, 20, or 21 of PAH. In some embodiments, a polynucleic acid molecule described herein targets a region that is at the 3' exon-intron junction of exon 11 of PAH.

In some cases, the polynucleic acid molecule described herein targets a splice site of an exon of a gene that causes a disease or disorder. In some embodiments, the gene is IKBKAP, SMN2, MCAD, LMNA, DMPK, ZNF9, MAPT, FKTN, TDP-43, LDLR, CFTR, DMD, PAH, MSTN, or K-Ras. In some embodiments, a polynucleic acid molecule described herein targets a splice site of exon 1, 2, or 3 of MSTN. In some embodiments, a polynucleic acid molecule described herein targets a splice site of exon 2 of MSTN. In some embodiments, a polynucleic acid molecule described herein targets a splice site of exon 1, 2, 3, 4, 5, 6, 7, 8, 9, 10, 11, 12, 13, 14, 15, 16, 17, 18, 19, 20, or 21 of PAH. In some embodiments, a polynucleic acid molecule described herein targets a splice site of exon 11 of PAH. As used herein, a splice site includes a canonical splice site, a cryptic splice site or an alternative splice site that is capable of inducing an insertion, deletion, duplication, or alteration in an incorrectly spliced mRNA transcript to induce exon skipping or exon inclusion.

In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt upstream (or from the 5') of an exon of a gene that causes a disease or disorder. In some embodiments, the gene is IKBKAP, SMN2, MCAD, LMNA, DMPK, ZNF9, MAPT, FKTN, TDP-43, LDLR, CFTR, DMD, PAH, MSTN, or K-Ras. In some instances, a polynucleic acid molecule described herein targets a region at least 1000 nt, 500 nt, 400 nt, 300 nt, 200 nt, 100 nt, 80 nt, 60 nt, 50 nt, 40 nt, 30 nt, 20 nt, 10 nt, or 5 nt upstream (or from the 5') of exon 1, 2, or 3 of the MSTN gene. In some instances, a polynucleic acid molecule described herein targets a region at least 1000 nt, 500 nt, 400 nt, 300 nt, 200 nt, 100 nt, 80 nt, 60 nt, 50 nt, 40 nt, 30 nt, 20 nt, 10 nt, or 5 nt upstream (or from the 5') of exon 2 of the MSTN gene. In some instances, a polynucleic acid molecule described herein targets a region at least 1000 nt, 500 nt, 400 nt, 300 nt, 200 nt, 100 nt, 80 nt, 60 nt, 50 nt, 40 nt, 30 nt, 20 nt, 10 nt, or 5 nt upstream (or from the 5') of exon 1, 2, 3, 4, 5, 6, 7, 8, 9, 10, 11, 12, 13, 14, 15, 16, 17, 18, 19, 20, or 21 of PAH gene. In some instances, a polynucleic acid molecule described herein targets a region at least 1000 nt, 500 nt, 400 nt, 300 nt, 200 nt, 100 nt, 80 nt, 60 nt, 50 nt, 40 nt, 30 nt, 20 nt, 10 nt, or 5 nt upstream (or from the 5') of exon 11 of the PAH gene.

In some instances, the polynucleic acid molecule hybridizes to a target region that is upstream (or 5') to at least one of an exon of a gene that causes a disease or disorder. In some embodiments, the gene is IKBKAP, SMN2, MCAD, LMNA, DMPK, ZNF9, MAPT, FKTN, TDP-43, LDLR, CFTR, DMD, PAH, MSTN, or K-Ras. In some instances, the polynucleic acid molecule hybridizes to a target region that is upstream (or 5') to at least one of exon 1, 2, or 3 of the MSTN gene. In some instances, the polynucleic acid molecule hybridizes to a target region that is about 5, 10, 15, 20, 50, 100, 200, 300, 400 or 500 bp upstream (or 5') to at least one of exon 2 of the MSTN gene. In some instances, the polynucleic acid molecule hybridizes to a target region that is upstream (or 5') to at least one of exon 1, 2, 3, 4, 5, 6, 7, 8, 9, 10, 11, 12, 13, 14, 15, 16, 17, 18, 19, 20, or 21 of the PAH gene. In some instances, the polynucleic acid molecule hybridizes to a target region that is about 5, 10, 15, 20, 50, 100, 200, 300, 400 or 500 bp upstream (or 5') to at least one of exon 11 of the PAH gene.

In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt downstream (or from the 3') of an exon of a gene that causes a disease or disorder. In some embodiments, the gene is IKBKAP, SMN2, MCAD, LMNA, DMPK, ZNF9, MAPT, FKTN, TDP-43, LDLR, CFTR, DMD, PAH, MSTN, or K-Ras. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt downstream (or from the 3') of exon 1, 2, or 3 of the MSTN gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt downstream (or from the 3') of exon 2 of the MSTN gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt downstream (or from the 3') of exon 1, 2, 3, 4, 5, 6, 7, 8, 9, 10, 11, 12, 13, 14, 15, 16, 17, 18, 19, 20, or 21 of the PAH gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt downstream (or from the 3') of exon 11 of the PAH gene.

In some instances, the polynucleic acid molecule hybridizes to a target region that is downstream (or 3') to at least one of an exon of a gene that causes a disease or disorder. In some embodiments, the gene is IKBKAP, SMN2, MCAD, LMNA, DMPK, ZNF9, MAPT, FKTN, TDP-43, LDLR, CFTR, DMD, PAH, MSTN, or K-Ras. In some instances, the polynucleic acid molecule hybridizes to a target region that is about 5, 10, 15, 20, 50, 100, 200, 300, 400 or 500 bp downstream (or 3') to at least one of exon 1, 2, or 3 of the MSTN gene. In some instances, the polynucleic acid molecule hybridizes to a target region that is about 5, 10, 15, 20, 50, 100, 200, 300, 400 or 500 bp downstream (or 3') to at least one of exon 2 of the MSTN gene. In some instances, the polynucleic acid molecule hybridizes to a target region that is about 5, 10, 15, 20, 50, 100, 200, 300, 400 or 500 bp downstream (or 3') to at least one of exon 1, 2, 3, 4, 5, 6, 7, 8, 9, 10, 11, 12, 13, 14, 15, 16, 17, 18, 19, 20, or 21 of the PAH gene. In some instances, the polynucleic acid molecule hybridizes to a target region that is about 5, 10, 15, 20, 50, 100, 200, 300, 400 or 500 bp downstream (or 3') to at least one of exon 11 of the PAH gene.

In some instances, a polynucleic acid molecule described herein targets an internal region within an exon of a gene that causes a disease or disorder. In some embodiments, the gene is IKBKAP, SMN2, MCAD, LMNA, DMPK, ZNF9, MAPT, FKTN, TDP-43, LDLR, CFTR, DMD, PAH, MSTN, or K-Ras. In some instances, a polynucleic acid molecule described herein targets an internal region within exon 1, 2, or 3 of the MSTN gene. In some instances, a polynucleic acid molecule described herein targets an internal region within exon 2 of the MSTN gene. In some instances, a polynucleic acid molecule described herein targets an internal region within 1, 2, 3, 4, 5, 6, 7, 8, 9, 10, 11, 12, 13, 14, 15, 16, 17, 18, 19, 20, or 21 of the PAH gene. In some instances, a polynucleic acid molecule described herein targets an internal region within exon 11 of the PAH gene.

In some cases, a polynucleic acid molecule targets an incorrectly processed mRNA transcript which results in a neuromuscular disease or disorder. In some cases, a neuromuscular disease or disorder is Duchenne muscular dystrophy, Becker muscular dystrophy, facioscapulohumeral muscular dystrophy, congenital muscular dystrophy, or myotonic dystrophy. In some cases, a polynucleic acid molecule targets an incorrectly processed mRNA transcript which results in Duchenne muscular dystrophy, Becker muscular dystrophy, facioscapulohumeral muscular dystrophy, congenital muscular dystrophy, or myotonic dystrophy. In some cases, a polynucleic acid molecule targets an incorrectly processed mRNA transcript which results in Duchenne muscular dystrophy.

In some instances, a polynucleic acid molecule targets an exon that is mutated in the DMD gene that causes Duchenne muscular dystrophy. Exemplary exons that are mutated in the DMD gene that causes Duchenne muscular dystrophy include, but not limited to, exon 3, 4, 5, 6, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, and 63. In some instances, the polynucleic acid molecule targets a sequence adjacent to a mutated exon. For example, if there is a deletion of exon 50, the polynucleic acid molecule targets a sequence in exon 51 so that exon 51 is skipped. In another instance, if there is a mutation in exon 23, the polynucleic acid molecule targets a sequence in exon 22 so that exon 23 is skipped.

In some instances, a polynucleic acid molecule described herein targets a region that is at the exon-intron junction of exon 3, 4, 5, 6, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 63 of the DMD gene. In some instances, a polynucleic acid molecule described herein targets a region that is at the exon-intron junction of exon 8, 23, 35, 43, 44, 45, 50, 51, 52, 53, or 55 of the DMD gene. In some cases, a polynucleic acid molecule described herein targets a region that is at the exon-intron junction of exon 8 of the DMD gene. In some cases, a polynucleic acid molecule described herein targets a region that is at the exon-intron junction of exon 23 of the DMD gene. In some cases, a polynucleic acid molecule described herein targets a region that is at the exon-intron junction of exon 35 of the DMD gene. In some cases, a polynucleic acid molecule described herein targets a region that is at the exon-intron junction of exon 43 of the DMD gene. In some cases, a polynucleic acid molecule described herein targets a region that is at the exon-intron junction of exon 44 of the DMD gene. In some cases, a polynucleic acid molecule described herein targets a region that is at the exon-intron junction of exon 45 of the DMD gene. In some cases, a polynucleic acid molecule described herein targets a region that is at the exon-intron junction of exon 48 of the DMD gene. In some cases, a polynucleic acid molecule described herein targets a region that is at the exon-intron junction of exon 49 of the DMD gene. In some cases, a polynucleic acid molecule described herein targets a region that is at the exon-intron junction of exon 50 of the DMD gene. In some cases, a polynucleic acid molecule described herein targets a region that is at the exon-intron junction of exon 51 of the DMD gene. In some cases, a polynucleic acid molecule described herein targets a region that is at the exon-intron junction of exon 52 of the DMD gene. In some cases, a polynucleic acid molecule described herein targets a region that is at the exon-intron junction of exon 53 of the DMD gene. In some cases, a polynucleic acid molecule described herein targets a region that is at the exon-intron junction of exon 55 of the DMD gene.

In some instances, the polynucleic acid molecule hybridizes to a target region that is at either the 5' intron-exon junction or the 3' exon-intron junction of at least one of exon 3, 4, 5, 6, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 52, 53, 54, 55, 56, 57, 58, 59, 60, 61, 62, and 63 of the DMD gene. In some instances, the polynucleic acid molecule hybridizes to a target region that is at either the 5' intron-exon junction or the 3' exon-intron junction of exon 8, 23, 35, 43, 44, 45, 50, 51, 52, 53, or 55 of the DMD gene.

In some cases, the polynucleic acid molecule hybridizes to a target region that is at the 5' intron-exon junction of at least one of exon 3, 4, 5, 6, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 52, 53, 54, 55, 56, 57, 58, 59, 60, 61, 62, and 63 of the DMD gene. In some cases, the polynucleic acid molecule hybridizes to a target region that is at the 5' intron-exon junction of exon 8, 23, 35, 43, 44, 45, 50, 51, 52, 53, or 55 of the DMD gene. In some cases, the polynucleic acid molecule hybridizes to a target region that is at the 5' intron-exon junction of exon 8 of the DMD gene. In some cases, the polynucleic acid molecule hybridizes to a target region that is at the 5' intron-exon junction of exon 23 of the DMD gene. In some cases, the polynucleic acid molecule hybridizes to a target region that is at the 5' intron-exon junction of exon 35 of the DMD gene. In some cases, the polynucleic acid molecule hybridizes to a target region that is at the 5' intron-exon junction of exon 43 of the DMD gene. In some cases, the polynucleic acid molecule hybridizes to a target region that is at the 5' intron-exon junction of exon 44 of the DMD gene. In some cases, the polynucleic acid molecule hybridizes to a target region that is at the 5' intron-exon junction of exon 45 of the DMD gene. In some cases, the polynucleic acid molecule hybridizes to a target region that is at the 5' intron-exon junction of exon 50 of the DMD gene. In some cases, the polynucleic acid molecule hybridizes to a target region that is at the 5' intron-exon junction of exon 51 of the DMD gene. In some cases, the polynucleic acid molecule hybridizes to a target region that is at the 5' intron-exon junction of exon 52 of the DMD gene. In some cases, the polynucleic acid molecule hybridizes to a target region that is at the 5' intron-exon junction of exon 53 of the DMD gene. In some cases, the polynucleic acid molecule hybridizes to a target region that is at the 5' intron-exon junction of exon 55 of the DMD gene.

In some cases, the polynucleic acid molecule hybridizes to a target region that is at the 3' exon-intron junction of at least one of exon 3, 4, 5, 6, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 52, 53, 54, 55, 56, 57, 58, 59, 60, 61, 62, and 63 of the DMD gene. In some cases, the polynucleic acid molecule hybridizes to a target region that is at the 3' exon-intron junction of exon 8, 23, 35, 43, 44, 45, 50, 51, 52, 53, or 55 of the DMD gene. In some cases, the polynucleic acid molecule hybridizes to a target region that is at the 3' exon-intron junction of exon 8 of the DMD gene. In some cases, the polynucleic acid molecule hybridizes to a target region that is at the 3' exon-intron junction of exon 23 of the DMD gene. In some cases, the polynucleic acid molecule hybridizes to a target region that is at the 3' exon-intron junction of exon 35 of the DMD gene. In some cases, the polynucleic acid molecule hybridizes to a target region that is at the 3' exon-intron junction of exon 43 of the DMD gene. In some cases, the polynucleic acid molecule hybridizes to a target region that is at the 3' exon-intron junction of exon 44 of the DMD gene. In some cases, the polynucleic acid molecule hybridizes to a target region that is at the 3' exon-intron junction of exon 45 of the DMD gene. In some cases, the polynucleic acid molecule hybridizes to a target region that is at the 3' exon-intron junction of exon 50 of the DMD gene. In some cases, the polynucleic acid molecule hybridizes to a target region that is at the 3' exon-intron junction of exon 51 of the DMD gene. In some cases, the polynucleic acid molecule hybridizes to a target region that is at the 3' exon-intron junction of exon 52 of the DMD gene. In some cases, the polynucleic acid molecule hybridizes to a target region that is at the 3' exon-intron junction of exon 53 of the DMD gene. In some cases, the polynucleic acid molecule hybridizes to a target region that is at the 3' exon-intron junction of exon 55 of the DMD gene.

In some instances, a polynucleic acid molecule described herein targets a splice site of exon 3, 4, 5, 6, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 63 of the DMD gene. In some instances, a polynucleic acid molecule described herein targets a splice site of exon 8, 23, 35, 43, 44, 45, 50, 51, 52, 53, or 55 of the DMD gene. In some cases, a polynucleic acid molecule described herein targets a splice site of exon 8 of the DMD gene. In some instances, a polynucleic acid molecule described herein targets a splice site of exon 23 of the DMD gene. In some cases, a polynucleic acid molecule described herein targets a splice site of exon 35 of the DMD gene. In some cases, a polynucleic acid molecule described herein targets a splice site of exon 43 of the DMD gene. In some cases, a polynucleic acid molecule described herein targets a splice site of exon 44 of the DMD gene. In some cases, a polynucleic acid molecule described herein targets a splice site of exon 45 of the DMD gene. In some instances, a polynucleic acid molecule described herein targets a splice site of exon 48 of the DMD gene. In some instances, a polynucleic acid molecule described herein targets a splice site of exon 49 of the DMD gene. In some instances, a polynucleic acid molecule described herein targets a splice site of exon 50 of the DMD gene. In some instances, a polynucleic acid molecule described herein targets a splice site of exon 51 of the DMD gene. In some cases, a polynucleic acid molecule described herein targets a splice site of exon 52 of the DMD gene. In some cases, a polynucleic acid molecule described herein targets a splice site of exon 53 of the DMD gene. In some cases, a polynucleic acid molecule described herein targets a splice site of exon 55 of the DMD gene. As used herein, a splice site includes a canonical splice site, a cryptic splice site or an alternative splice site that is capable of inducing an insertion, deletion, duplication, or alteration in an incorrectly spliced mRNA transcript to induce exon skipping or exon inclusion.

In some embodiments, a polynucleic acid molecule described herein target a partially spliced mRNA sequence comprising additional exons involved in Duchenne muscular dystrophy such as exon 3, 4, 5, 6, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 52, 53, 54, 55, 56, 57, 58, 59, 60, 61, 62, or 63.

In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt upstream (or from the 5') of exon 3, 4, 5, 6, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 63 of the DMD gene. In some instances, a polynucleic acid molecule described herein targets a region at least 1000 nt, 500 nt, 400 nt, 300 nt, 200 nt, 100 nt, 80 nt, 60 nt, 50 nt, 40 nt, 30 nt, 20 nt, 10 nt, or 5 nt upstream (or from the 5') of exon 8, 23, 35, 43, 44, 45, 50, 51, 52, 53, or 55 of the DMD gene. In some instances, a polynucleic acid molecule described herein targets a region at least 1000 nt, 500 nt, 400 nt, 300 nt, 200 nt, 100 nt, 80 nt, 60 nt, 50 nt, 40 nt, 30 nt, 20 nt, 10 nt, or 5 nt upstream (or from the 5') of exon 8 of the DMD gene. In some instances, a polynucleic acid molecule described herein targets a region at least 1000 nt, 500 nt, 400 nt, 300 nt, 200 nt, 100 nt, 80 nt, 60 nt, 50 nt, 40 nt, 30 nt, 20 nt, 10 nt, or 5 nt upstream (or from the 5') of exon 23 of the DMD gene. In some instances, a polynucleic acid molecule described herein targets a region at least 1000 nt, 500 nt, 400 nt, 300 nt, 200 nt, 100 nt, 80 nt, 60 nt, 50 nt, 40 nt, 30 nt, 20 nt, 10 nt, or 5 nt upstream (or from the 5')

of exon 35 of the DMD gene. In some instances, a polynucleic acid molecule described herein targets a region at least 1000 nt, 500 nt, 400 nt, 300 nt, 200 nt, 100 nt, 80 nt, 60 nt, 50 nt, 40 nt, 30 nt, 20 nt, 10 nt, or 5 nt upstream (or from the 5') of exon 43 of the DMD gene. In some instances, a polynucleic acid molecule described herein targets a region at least 1000 nt, 500 nt, 400 nt, 300 nt, 200 nt, 100 nt, 80 nt, 60 nt, 50 nt, 40 nt, 30 nt, 20 nt, 10 nt, or 5 nt upstream (or from the 5') of exon 44 of the DMD gene. In some instances, a polynucleic acid molecule described herein targets a region at least 1000 nt, 500 nt, 400 nt, 300 nt, 200 nt, 100 nt, 80 nt, 60 nt, 50 nt, 40 nt, 30 nt, 20 nt, 10 nt, or 5 nt upstream (or from the 5') of exon 45 of the DMD gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt upstream (or from the 5') of exon 48 of the DMD gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt upstream (or from the 5') of exon 49 of the DMD gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt upstream (or from the 5') of exon 50 of the DMD gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt upstream (or from the 5') of exon 51 of the DMD gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt upstream (or from the 5') of exon 52 of the DMD gene. In some instances, a polynucleic acid molecule described herein targets a region at least 1000 nt, 500 nt, 400 nt, 300 nt, 200 nt, 100 nt, 80 nt, 60 nt, 50 nt, 40 nt, 30 nt, 20 nt, 10 nt, or 5 nt upstream (or from the 5') of exon 53 of the DMD gene. In some instances, a polynucleic acid molecule described herein targets a region at least 1000 nt, 500 nt, 400 nt, 300 nt, 200 nt, 100 nt, 80 nt, 60 nt, 50 nt, 40 nt, 30 nt, 20 nt, 10 nt, or 5 nt upstream (or from the 5') of exon 55 of the DMD gene.

In some instances, the polynucleic acid molecule hybridizes to a target region that is upstream (or 5') to at least one of exon 3, 4, 5, 6, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 52, 53, 54, 55, 56, 57, 58, 59, 60, 61, 62, and 63 of the DMD gene. In some instances, the polynucleic acid molecule hybridizes to a target region that is upstream (or 5') to at least one of exon 8, 23, 35, 43, 44, 45, 50, 51, 52, 53, or 55 of the DMD gene. In some instances, the polynucleic acid molecule hybridizes to a target region that is about 5, 10, 15, 20, 50, 100, 200, 300, 400 or 500 bp upstream (or 5') to at least one of exon 3, 4, 5, 6, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 52, 53, 54, 55, 56, 57, 58, 59, 60, 61, 62, and 63 of the DMD gene.

In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt downstream (or from the 3') of exon 3, 4, 5, 6, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 63 of the DMD gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt downstream (or from the 3') of exon 8, 23, 35, 43, 44, 45, 50, 51, 52, 53, or 55 of the DMD gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt downstream (or from the 3') of exon 8 of the DMD gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt downstream (or from the 3') of exon 23 of the DMD gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt downstream (or from the 3') of exon 35 of the DMD gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt downstream (or from the 3') of exon 43 of the DMD gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt downstream (or from the 3') of exon 44 of the DMD gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt downstream (or from the 3') of exon 45 of the DMD gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt downstream (or from the 3') of exon 48 of the DMD gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt downstream (or from the 3') of exon 49 of the DMD gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt downstream (or from the 3') of exon 50 of the DMD gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt downstream (or from the 3') of exon 51 of the DMD gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt downstream (or from the 3') of exon 52 of the DMD gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt downstream (or from the 3') of exon 53 of the DMD gene. In some instances, a polynucleic acid molecule described herein targets a region at least 1000 nucleotides (nt), 500 nt, 400 nt, 300 nt, 200 nt, 100 nt, 80 nt, 60 nt, 50 nt, 40 nt, 30 nt, 20 nt, 10 nt, or 5 nt downstream (or from the 3') of exon 55 of the DMD gene.

In some instances, the polynucleic acid molecule hybridizes to a target region that is downstream (or 3') to at least one of exon 3, 4, 5, 6, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 52, 53, 54, 55, 56, 57, 58, 59, 60, 61, 62, and 63 of the DMD gene. In some instances, the polynucleic acid molecule hybridizes to a target region that is about 5, 10, 15, 20, 50, 100, 200, 300, 400 or 500 bp downstream (or 3') to at least one of exon 3, 4, 5, 6, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 52, 53, 54, 55, 56, 57, 58, 59, 60, 61, 62, and 63 of the DMD gene. In some instances, the polynucleic acid molecule hybridizes to a target region that is about 5, 10, 15, 20, 50, 100, 200, 300, 400 or 500 bp downstream (or 3') to at least one of exon 8, 23, 35, 43, 44, 45, 50, 51, 52, 53, or 55 of the DMD gene.

In some instances, a polynucleic acid molecule described herein targets an internal region within exon 3, 4, 5, 6, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 63 of the DMD gene. In some instances, a polynucleic acid molecule described herein targets an internal region within exon 8, 23, 35, 43, 44, 45, 50, 51, 52, 53, or 55 of the DMD gene. In some instances, a polynucleic acid molecule described herein targets an internal region within exon 8 of the DMD gene. In some instances, a polynucleic acid molecule described herein targets an internal region within exon 23 of the DMD gene. In some instances, a polynucleic acid molecule described herein targets an internal region within exon 35 of the DMD gene. In some instances, a polynucleic acid molecule described herein targets an internal region within exon 43 of the DMD gene. In some instances, a polynucleic acid molecule described herein targets an internal region within exon 44 of the DMD gene. In some instances, a polynucleic acid molecule described herein targets an internal region within exon 45 of the DMD gene. In some instances, a polynucleic acid molecule described herein targets an internal region within exon 48 of the DMD gene. In some instances, a polynucleic acid molecule described herein targets an internal region within exon 49 of the DMD gene. In some instances, a polynucleic acid molecule described herein targets an internal region within exon 50 of the DMD gene. In some instances, a polynucleic acid molecule described herein targets an internal region within exon 51 of the DMD gene. In some instances, a polynucleic acid molecule described herein targets an internal region within exon 52 of the DMD gene. In some instances, a polynucleic acid molecule described herein targets an internal region within exon 53 of the DMD gene. In some instances, a polynucleic acid molecule described herein targets an internal region within exon 55 of the DMD gene.

In some instances, the polynucleic acid molecule hybridizes to a target region that is within at least one of exon 3, 4, 5, 6, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 52, 53, 54, 55, 56, 57, 58, 59, 60, 61, 62, and 63 of the DMD gene. In some instances, the polynucleic acid molecule hybridizes to a target region that is within at least one of exon 8, 23, 35, 43, 44, 45, 50, 51, 52, 53, or 55 of the DMD gene.

In some embodiments, a polynucleic acid molecule described herein targets a partially spliced mRNA sequence comprising exon 51. In some instances, the polynucleic acid molecule hybridizes to a target region that is upstream (or 5') to exon 51. In some instances, the polynucleic acid molecule hybridizes to a target region that is about 5, 10, 15, 20, 50, 100, 200, 300, 400 or 500 bp upstream (or 5') to exon 51. In some instances, the polynucleic acid molecule hybridizes to a target region that is downstream (or 3') to exon 51. In some instances, the polynucleic acid molecule hybridizes to a target region that is about 5, 10, 15, 20, 50, 100, 200, 300, 400 or 500 bp downstream (or 3') to exon 51.

In some instances, the polynucleic acid molecule hybridizes to a target region that is within exon 51. In some instances, the polynucleic acid molecule hybridizes to a target region that is at either the 5' intron-exon 51 junction or the 3' exon 51-intron junction.

In some embodiments, the polynucleic acid molecule comprises a sequence having at least 50%, 55%, 60%, 65%, 70%, 75%, 80%, 85%, 90%, 95%, 96%, 97%, 98%, 99%, or 100% sequence identity to a target sequence of interest. In some embodiments, the polynucleic acid molecule comprises a sequence having at least 50% sequence identity to a target sequence of interest. In some embodiments, the polynucleic acid molecule comprises a sequence having at least 60% sequence identity to a target sequence of interest. In some embodiments, the polynucleic acid molecule comprises a sequence having at least 70% sequence identity to a target sequence of interest. In some embodiments, the polynucleic acid molecule comprises a sequence having at least 75% sequence identity to a target sequence of interest. In some embodiments, the polynucleic acid molecule comprises a sequence having at least 80% sequence identity to a target sequence of interest. In some embodiments, the polynucleic acid molecule comprises a sequence having at least 85% sequence identity to a target sequence of interest. In some embodiments, the polynucleic acid molecule comprises a sequence having at least 90% sequence identity to a target sequence of interest. In some embodiments, the polynucleic acid molecule comprises a sequence having at least 95% sequence identity to a target sequence of interest. In some embodiments, the polynucleic acid molecule comprises a sequence having at least 96% sequence identity to a target sequence of interest. In some embodiments, the polynucleic acid molecule comprises a sequence having at least 97% sequence identity to a target sequence of interest. In some embodiments, the polynucleic acid molecule comprises a sequence having at least 98% sequence identity to a target sequence of interest. In some embodiments, the polynucleic acid molecule comprises a sequence having at least 99% sequence identity to a target sequence of interest. In some embodiments, the polynucleic acid molecule consists of a target sequence of interest.

In some embodiments, the polynucleic acid molecule comprises a first polynucleotide and a second polynucleotide. In some instances, the first polynucleotide comprises a sequence having at least 50%, 55%, 60%, 65%, 70%, 75%, 80%, 85%, 90%, 95%, 96%, 97%, 98%, 99%, or 100% sequence identity to a target sequence of interest. In some cases, the second polynucleotide comprises a sequence having at least 50%, 55%, 60%, 65%, 70%, 75%, 80%, 85%, 90%, 95%, 96%, 97%, 98%, 99%, or 100% sequence identity to a target sequence of interest. In some cases, the polynucleic acid molecule comprises a first polynucleotide having at least 50%, 55%, 60%, 65%, 70%, 75%, 80%, 85%, 90%, 95%, 96%, 97%, 98%, 99%, or 100% sequence identity to a target sequence of interest and a second polynucleotide having at least 50%, 55%, 60%, 65%, 70%, 75%, 80%, 85%, 90%, 95%, 96%, 97%, 98%, 99%, or 100% sequence identity to a target sequence of interest.

In some embodiments, the polynucleic acid molecule described herein comprises RNA or DNA. In some cases, the polynucleic acid molecule comprises RNA. In some instances, RNA comprises short interfering RNA (siRNA), short hairpin RNA (shRNA), microRNA (miRNA), double-stranded RNA (dsRNA), transfer RNA (tRNA), ribosomal RNA (rRNA), or heterogeneous nuclear RNA (hnRNA). In some instances, RNA comprises shRNA. In some instances, RNA comprises miRNA. In some instances, RNA comprises dsRNA. In some instances, RNA comprises tRNA. In some instances, RNA comprises rRNA. In some instances, RNA comprises hnRNA. In some instances, the RNA comprises siRNA. In some instances, the polynucleic acid molecule comprises siRNA.

In some embodiments, the polynucleic acid molecule is from about 10 to about 50 nucleotides in length. In some instances, the polynucleic acid molecule is from about 10 to about 30, from about 15 to about 30, from about 18 to about 25, form about 18 to about 24, from about 19 to about 23, or from about 20 to about 22 nucleotides in length.

In some embodiments, the polynucleic acid molecule is about 50 nucleotides in length. In some instances, the polynucleic acid molecule is about 45 nucleotides in length. In some instances, the polynucleic acid molecule is about 40 nucleotides in length. In some instances, the polynucleic acid molecule is about 35 nucleotides in length. In some instances, the polynucleic acid molecule is about 30 nucleotides in length. In some instances, the polynucleic acid molecule is about 25 nucleotides in length. In some instances, the polynucleic acid molecule is about 20 nucleotides in length. In some instances, the polynucleic acid molecule is about 19 nucleotides in length. In some instances, the polynucleic acid molecule is about 18 nucleotides in length. In some instances, the polynucleic acid molecule is about 17 nucleotides in length. In some instances, the polynucleic acid molecule is about 16 nucleotides in length. In some instances, the polynucleic acid molecule is about 15 nucleotides in length. In some instances, the polynucleic acid molecule is about 14 nucleotides in length. In some instances, the polynucleic acid molecule is about 13 nucleotides in length. In some instances, the polynucleic acid molecule is about 12 nucleotides in length. In some instances, the polynucleic acid molecule is about 11 nucleotides in length. In some instances, the polynucleic acid molecule is about 10 nucleotides in length. In some instances, the polynucleic acid molecule is between about 10 and about 50 nucleotides in length. In some instances, the polynucleic acid molecule is between about 10 and about 45 nucleotides in length. In some instances, the polynucleic acid molecule is between about 10 and about 40 nucleotides in length. In some instances, the polynucleic acid molecule is between about 10 and about 35 nucleotides in length. In some instances, the polynucleic acid molecule is between about 10 and about 30 nucleotides in length. In some instances, the polynucleic acid molecule is between about 10 and about 25 nucleotides in length. In some instances, the polynucleic acid molecule is between about 10 and about 20 nucleotides in length. In some instances, the polynucleic acid molecule is between about 15 and about 25 nucleotides in length. In some instances, the polynucleic acid molecule is between about 15 and about 30 nucleotides in length. In some instances, the polynucleic acid molecule is between about 12 and about 30 nucleotides in length.

In some embodiments, the polynucleic acid molecule comprises a first polynucleotide. In some instances, the polynucleic acid molecule comprises a second polynucleotide. In some instances, the polynucleic acid molecule comprises a first polynucleotide and a second polynucleotide. In some instances, the first polynucleotide is a sense strand or passenger strand. In some instances, the second polynucleotide is an antisense strand or guide strand.

In some embodiments, the polynucleic acid molecule is a first polynucleotide. In some embodiments, the first polynucleotide is from about 10 to about 50 nucleotides in length. In some instances, the first polynucleotide is from about 10 to about 30, from about 15 to about 30, from about 18 to about 25, form about 18 to about 24, from about 19 to about 23, or from about 20 to about 22 nucleotides in length.

In some instances, the first polynucleotide is about 50 nucleotides in length. In some instances, the first polynucleotide is about 45 nucleotides in length. In some instances, the first polynucleotide is about 40 nucleotides in length. In some instances, the first polynucleotide is about 35 nucleotides in length. In some instances, the first polynucleotide is about 30 nucleotides in length. In some instances, the first polynucleotide is about 25 nucleotides in length. In some instances, the first polynucleotide is about 20 nucleotides in length. In some instances, the first polynucleotide is about 19 nucleotides in length. In some instances, the first polynucleotide is about 18 nucleotides in length. In some instances, the first polynucleotide is about 17 nucleotides in length. In some instances, the first polynucleotide is about 16 nucleotides in length. In some instances, the first polynucleotide is about 15 nucleotides in length. In some instances, the first polynucleotide is about 14 nucleotides in length. In some instances, the first polynucleotide is about 13 nucleotides in length. In some instances, the first polynucleotide is about 12 nucleotides in length. In some instances, the first polynucleotide is about 11 nucleotides in length. In some instances, the first polynucleotide is about 10 nucleotides in length. In some instances, the first polynucleotide is between about 10 and about 50 nucleotides in length. In some instances, the first polynucleotide is between about 10 and about 45 nucleotides in length. In some instances, the first polynucleotide is between about 10 and about 40 nucleotides in length. In some instances, the first polynucleotide is between about 10 and about 35 nucleotides in length. In some instances, the first polynucleotide is between about 10 and about 30 nucleotides in length. In some instances, the first polynucleotide is between about 10 and about 25 nucleotides in length. In some instances, the first polynucleotide is between about 10 and about 20 nucleotides in length. In some instances, the first polynucleotide is between about 15 and about 25 nucleotides in length. In some instances, the first polynucleotide is between about 15 and about 30 nucleotides in length. In some instances, the first polynucleotide is between about 12 and about 30 nucleotides in length.

In some embodiments, the polynucleic acid molecule is a second polynucleotide. In some embodiments, the second polynucleotide is from about 10 to about 50 nucleotides in length. In some instances, the second polynucleotide is from about 10 to about 30, from about 15 to about 30, from about 18 to about 25, form about 18 to about 24, from about 19 to about 23, or from about 20 to about 22 nucleotides in length.

In some instances, the second polynucleotide is about 50 nucleotides in length. In some instances, the second polynucleotide is about 45 nucleotides in length. In some instances, the second polynucleotide is about 40 nucleotides in length. In some instances, the second polynucleotide is about 35 nucleotides in length. In some instances, the second polynucleotide is about 30 nucleotides in length. In some instances, the second polynucleotide is about 25 nucleotides in length. In some instances, the second polynucleotide is about 20 nucleotides in length. In some instances, the second polynucleotide is about 19 nucleotides in length. In some instances, the second polynucleotide is about 18 nucleotides in length. In some instances, the second polynucleotide is about 17 nucleotides in length. In some instances, the second polynucleotide is about 16 nucleotides in length. In some instances, the second polynucleotide is about 15 nucleotides in length. In some instances, the second polynucleotide is about 14 nucleotides in length. In some instances, the second polynucleotide is about 13 nucleotides in length. In some instances, the second polynucleotide is about 12 nucleotides in length. In some instances, the second polynucleotide is about 11 nucleotides in length. In some instances, the second polynucleotide is about 10 nucleotides in length. In some instances, the second polynucleotide is between about 10 and about 50 nucleotides in length. In some instances, the second polynucleotide is between about 10 and about 45 nucleotides in length. In some instances, the second polynucleotide is between about 10 and about 40 nucleotides in length. In some instances, the second polynucleotide is between about 10 and about 35 nucleotides in length. In some instances, the second polynucleotide is between about 10 and about 30 nucleotides in length. In some instances, the second polynucleotide is between about 10 and about 25 nucleotides in length. In some instances, the second polynucleotide is between about 10 and about 20 nucleotides in length. In some instances, the second polynucleotide is between about 15 and about 25 nucleotides in length. In some instances, the second polynucleotide is between about 15 and about 30 nucleotides in length. In some instances, the second polynucleotide is between about 12 and about 30 nucleotides in length.

In some embodiments, the polynucleic acid molecule comprises a first polynucleotide and a second polynucleotide. In some instances, the polynucleic acid molecule further comprises a blunt terminus, an overhang, or a combination thereof. In some instances, the blunt terminus is a 5' blunt terminus, a 3' blunt terminus, or both. In some cases, the overhang is a 5' overhang, 3' overhang, or both. In some cases, the overhang comprises 1, 2, 3, 4, 5, 6, 7, 8, 9, or 10 non-base pairing nucleotides. In some cases, the overhang comprises 1, 2, 3, 4, 5, or 6 non-base pairing nucleotides. In some cases, the overhang comprises 1, 2, 3, or 4 non-base pairing nucleotides. In some cases, the overhang comprises 1 non-base pairing nucleotide. In some cases, the overhang comprises 2 non-base pairing nucleotides. In some cases, the overhang comprises 3 non-base pairing nucleotides. In some cases, the overhang comprises 4 non-base pairing nucleotides.

In some embodiments, the sequence of the polynucleic acid molecule is at least 40%, 50%, 55%, 60%, 65%, 70%, 75% 80%, 85%, 90%, 95% 98%, 99%, or 99.5% complementary to a target sequence described herein. In some embodiments, the sequence of the polynucleic acid molecule is at least 50% complementary to a target sequence described herein. In some embodiments, the sequence of the polynucleic acid molecule is at least 60% complementary to a target sequence described herein. In some embodiments, the sequence of the polynucleic acid molecule is at least 70% complementary to a target sequence described herein. In some embodiments, the sequence of the polynucleic acid molecule is at least 80% complementary to a target sequence described herein. In some embodiments, the sequence of the polynucleic acid molecule is at least 90% complementary to a target sequence described herein. In some embodiments, the sequence of the polynucleic acid molecule is at least 95% complementary to a target sequence described herein. In some embodiments, the sequence of the polynucleic acid molecule is at least 99% complementary to a target sequence described herein. In some instances, the sequence of the polynucleic acid molecule is 100% complementary to a target sequence described herein.

In some embodiments, the sequence of the polynucleic acid molecule has 5 or less mismatches to a target sequence described herein. In some embodiments, the sequence of the polynucleic acid molecule has 4 or less mismatches to a target sequence described herein. In some instances, the sequence of the polynucleic acid molecule has 3 or less mismatches to a target sequence described herein. In some cases, the sequence of the polynucleic acid molecule has 2 or less mismatches to a target sequence described herein. In some cases, the sequence of the polynucleic acid molecule has 1 or less mismatches to a target sequence described herein.

In some embodiments, the specificity of the polynucleic acid molecule that hybridizes to a target sequence described herein is a 95%, 98%, 99%, 99.5% or 100% sequence complementarity of the polynucleic acid molecule to a target sequence. In some instances, the hybridization is a high stringent hybridization condition.

In some embodiments, the polynucleic acid molecule has reduced off-target effect. In some instances, "off-target" or "off-target effects" refer to any instance in which a polynucleic acid polymer directed against a given target causes an unintended effect by interacting either directly or indirectly with another mRNA sequence, a DNA sequence or a cellular protein or other moiety. In some instances, an "off-target effect" occurs when there is a simultaneous degradation of other transcripts due to partial homology or complementarity between that other transcript and the sense and/or antisense strand of the polynucleic acid molecule.

In some embodiments, the polynucleic acid molecule comprises natural or synthetic or artificial nucleotide analogues or bases. In some cases, the polynucleic acid molecule comprises combinations of DNA, RNA and/or nucleotide analogues. In some instances, the synthetic or artificial nucleotide analogues or bases comprise modifications at one or more of ribose moiety, phosphate moiety, nucleoside moiety, or a combination thereof.

In some embodiments, nucleotide analogues or artificial nucleotide base comprise a nucleic acid with a modification at a 2' hydroxyl group of the ribose moiety. In some instances, the modification includes an H, OR, R, halo, SH, SR, NH2, NHR, NR2, or CN, wherein R is an alkyl moiety. Exemplary alkyl moiety includes, but is not limited to, halogens, sulfurs, thiols, thioethers, thioesters, amines (primary, secondary, or tertiary), amides, ethers, esters, alcohols and oxygen. In some instances, the alkyl moiety further comprises a modification. In some instances, the modification comprises an azo group, a keto group, an aldehyde group, a carboxyl group, a nitro group, a nitroso, group, a nitrile group, a heterocycle (e.g., imidazole, hydrazino or hydroxylamino) group, an isocyanate or cyanate group, or a sulfur containing group (e.g., sulfoxide, sulfone, sulfide, and disulfide). In some instances, the alkyl moiety further comprises a hetero substitution. In some instances, the carbon of the heterocyclic group is substituted by a nitrogen, oxygen or sulfur. In some instances, the heterocyclic substitution includes but is not limited to, morpholino, imidazole, and pyrrolidino.

In some instances, the modification at the 2' hydroxyl group is a 2'-O-methyl modification or a 2'-O-methoxyethyl (2'-O-MOE) modification. In some cases, the 2'-O-methyl modification adds a methyl group to the 2' hydroxyl group of the ribose moiety whereas the 2'O-methoxyethyl modification adds a methoxyethyl group to the 2' hydroxyl group of the ribose moiety. Exemplary chemical structures of a 2'-O-methyl modification of an adenosine molecule and 2'O-methoxyethyl modification of an uridine are illustrated below.

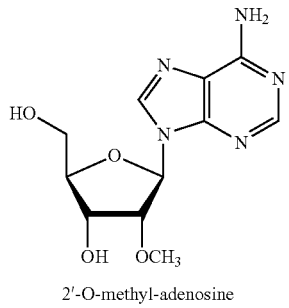

2'-O-methyl-adenosine

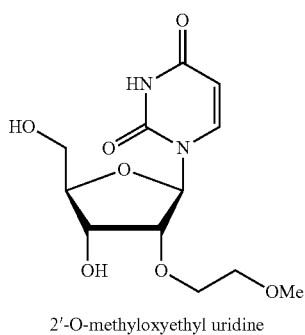

2'-O-methyloxyethyl uridine

In some instances, the modification at the 2' hydroxyl group is a 2'-O-aminopropyl modification in which an extended amine group comprising a propyl linker binds the amine group to the 2' oxygen. In some instances, this modification neutralizes the phosphate derived overall negative charge of the oligonucleotide molecule by introducing one positive charge from the amine group per sugar and thereby improves cellular uptake properties due to its zwitterionic properties. An exemplary chemical structure of a 2'-O-aminopropyl nucleoside phosphoramidite is illustrated below.

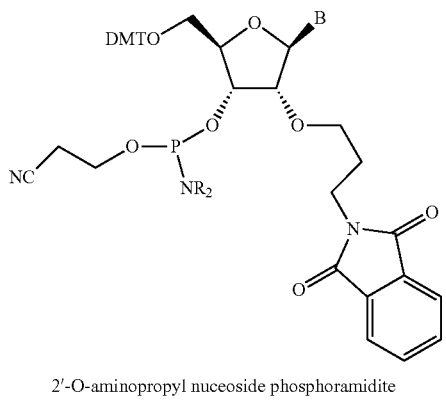

2'-O-aminopropyl nuceoside phosphoramidite

In some instances, the modification at the 2' hydroxyl group is a locked or bridged ribose modification (e.g., locked nucleic acid or LNA) in which the oxygen molecule bound at the 2' carbon is linked to the 4' carbon by a methylene group, thus forming a 2'-C,4'-C-oxy-methylene-linked bicyclic ribonucleotide monomer. Exemplary representations of the chemical structure of LNA are illustrated below. The representation shown to the left highlights the chemical connectivities of an LNA monomer. The representation shown to the right highlights the locked 3'-endo ($^3$E) conformation of the furanose ring of an LNA monomer.

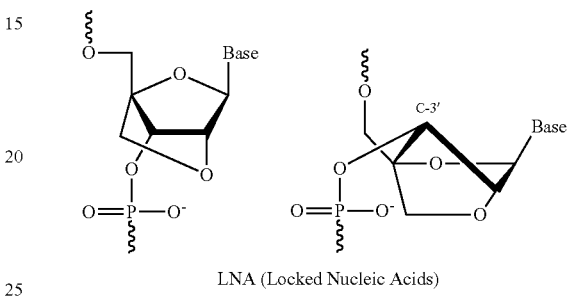

LNA (Locked Nucleic Acids)

In some instances, the modification at the 2' hydroxyl group comprises ethylene nucleic acids (ENA) such as for example 2'-4'-ethylene-bridged nucleic acid, which locks the sugar conformation into a C3'-endo sugar puckering conformation. ENA are part of the bridged nucleic acids class of modified nucleic acids that also comprises LNA. Exemplary chemical structures of the ENA and bridged nucleic acids are illustrated below.

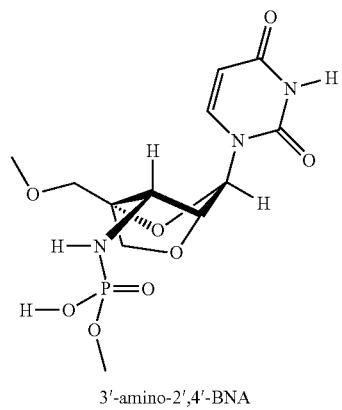

3'-amino-2',4'-BNA

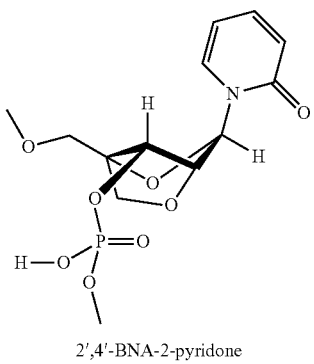

2',4'-BNA-2-pyridone

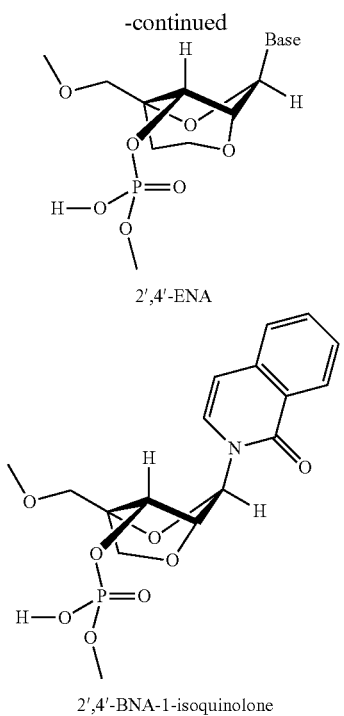

2',4'-ENA

2',4'-BNA-1-isoquinolone

In some embodiments, additional modifications at the 2' hydroxyl group include 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA).

In some embodiments, nucleotide analogues comprise modified bases such as, but not limited to, 5-propynyluridine, 5-propynylcytidine, 6-methyladenine, 6-methylguanine, N, N, -dimethyladenine, 2-propyladenine, 2propylguanine, 2-aminoadenine, 1-methylinosine, 3-methyluridine, 5-methylcytidine, 5-methyluridine and other nucleotides having a modification at the 5 position, 5-(2-amino) propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2, 2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxy acetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyi nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties, in some cases are or be based on, mannoses, arabinoses, glucopyranoses, galactopyranoses, 4'-thioribose, and other sugars, heterocycles, or carbocycles. The term nucleotide also includes what are known in the art as universal bases. By way of example, universal bases include but are not limited to 3-nitropyrrole, 5-nitroindole, or nebularine.

In some embodiments, nucleotide analogues further comprise morpholinos, peptide nucleic acids (PNAs), methylphosphonate nucleotides, thiolphosphonate nucleotides, 2'-fluoro N3-P5'-phosphoramidites, 1', 5'-anhydrohexitol nucleic acids (HNAs), or a combination thereof. Morpholino or phosphorodiamidate morpholino oligo (PMO) comprises synthetic molecules whose structure mimics natural nucleic acid structure by deviates from the normal sugar and phosphate structures. In some instances, the five member ribose ring is substituted with a six member morpholino ring containing four carbons, one nitrogen and one oxygen. In some cases, the ribose monomers are linked by a phosphordiamidate group instead of a phosphate group. In such cases, the backbone alterations remove all positive and negative charges making morpholinos neutral molecules capable of crossing cellular membranes without the aid of cellular delivery agents such as those used by charged oligonucleotides.

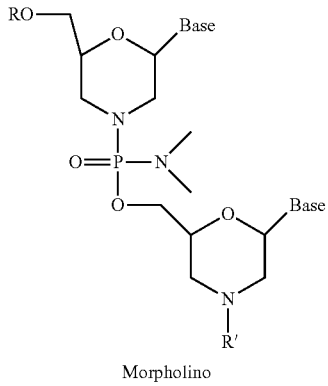

Morpholino

In some embodiments, peptide nucleic acid (PNA) does not contain sugar ring or phosphate linkage and the bases are attached and appropriately spaced by oligoglycine-like molecules, therefore, eliminating a backbone charge.

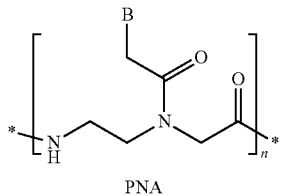

PNA

In some embodiments, one or more modifications optionally occur at the internucleotide linkage. In some instances, modified internucleotide linkage include, but is not limited to, phosphorothioates, phosphorodithioates, methylphosphonates, 5'-alkylenephosphonates, 5'-methylphosphonate, 3'-alkylene phosphonates, borontrifluoridates, borano phosphate esters and selenophosphates of 3'-5'linkage or 2'-5'linkage, phosphotriesters, thionoalkylphosphotriesters, hydrogen phosphonate linkages, alkyl phosphonates, alkylphosphonothioates, arylphosphonothioates, phosphoroselenoates, phosphorodiselenoates, phosphinates, phosphoramidates, 3'-alkylphosphoramidates, aminoalkylphosphoramidates, thionophosphoramidates, phosphoropiperazidates, phosphoroanilothioates, phosphoroanilidates, ketones, sulfones, sulfonamides, carbonates, carbamates, methylenehydrazos, methylenedimethylhydrazos, formacetals, thioformacetals, oximes, methyleneiminos, methylenemethyliminos, thioamidates, linkages with riboacetyl groups, aminoethyl glycine, silyl or siloxane linkages, alkyl or cycloalkyl linkages with or without heteroatoms of, for example, 1 to 10 carbons that are saturated or unsaturated and/or substituted and/or contain heteroatoms, linkages with morpholino structures, amides, polyamides wherein the bases are attached to the aza nitrogens of the backbone directly or indirectly, and combinations thereof. Phosphorothioate antisene oligonucleotides (PS ASO) are antisense oligonucleotides comprising a phosphorothioate linkage. An exemplary PS ASO is illustrated below.

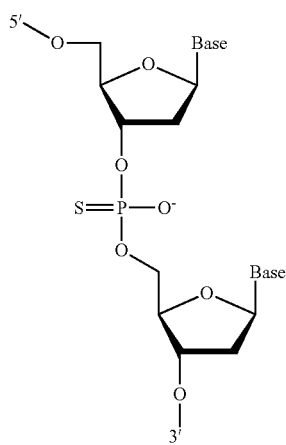

In some instances, the modification is a methyl or thiol modification such as methylphosphonate or thiolphosphonate modification. Exemplary thiolphosphonate nucleotide (left) and methylphosphonate nucleotide (right) are illustrated below.

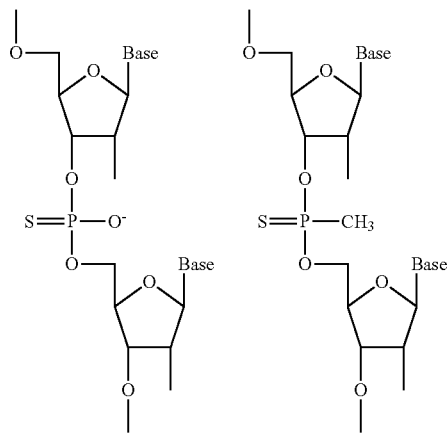

In some instances, a modified nucleotide includes, but is not limited to, 2'-fluoro N3-P5'-phosphoramidites illustrated as:

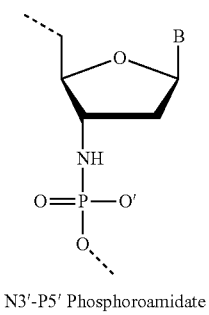

N3'-P5' Phosphoroamidate

In some instances, a modified nucleotide includes, but is not limited to, hexitol nucleic acid (or 1', 5'-anhydrohexitol nucleic acids (HNA)) illustrated as:

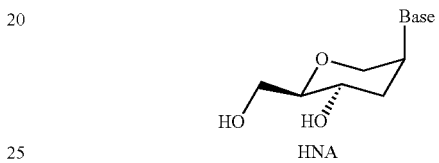

HNA

In some embodiments, one or more modifications further optionally include modifications of the ribose moiety, phosphate backbone and the nucleoside, or modifications of the nucleotide analogues at the 3' or the 5' terminus. For example, the 3' terminus optionally include a 3 cationic group, or by inverting the nucleoside at the 3'-terminus with a 3'-3 linkage. In another alternative, the 3'-terminus is optionally conjugated with an aminoalkyl group, e.g., a 3' C5-aminoalkyl dT. In an additional alternative, the 3'-terminus is optionally conjugated with an abasic site, e.g., with an apurinic or apyrimidinic site. In some instances, the 5-terminus is conjugated with an aminoalkyl group, e.g., a 5'-O-alkylamino substituent. In some cases, the 5'-terminus is conjugated with an abasic site, e.g., with an apurinic or apyrimidinic site.

In some embodiments, the polynucleic acid molecule comprises one or more of the artificial nucleotide analogues described herein. In some instances, the polynucleic acid molecule comprises 1, 2, 3, 4, 5, 6, 7, 8, 9, 10, 11, 12, 13, 14, 15, 16, 17, 18, 20, 25, or more of the artificial nucleotide analogues described herein. In some embodiments, the artificial nucleotide analogues include 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the polynucleic acid molecule comprises 1, 2, 3, 4, 5, 6, 7, 8, 9, 10, 11, 12, 13, 14, 15, 16, 17, 18, 20, 25, or more of the artificial nucleotide analogues selected from 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof. In some instances, the polynucleic acid molecule comprises 1, 2, 3, 4, 5, 6, 7, 8, 9, 10, 11, 12, 13, 14, 15, 16, 17, 18, 20, 25, or more of 2'-O-methyl modified nucleotides. In some instances, the polynucleic acid molecule comprises 1, 2, 3, 4, 5, 6, 7, 8, 9, 10, 11, 12, 13, 14, 15, 16, 17, 18, 20, 25, or more of 2'-O-methoxyethyl (2'-O-MOE) modified nucleotides. In some instances, the polynucleic acid molecule comprises 1, 2, 3, 4, 5, 6, 7, 8, 9, 10, 11, 12, 13, 14, 15, 16, 17, 18, 20, 25, or more of thiolphosphonate nucleotides.

In some instances, the polynucleic acid molecule comprises at least one of: from about 5% to about 100% modification, from about 10% to about 100% modification, from about 20% to about 100% modification, from about 30% to about 100% modification, from about 40% to about 100% modification, from about 50% to about 100% modification, from about 60% to about 100% modification, from about 70% to about 100% modification, from about 80% to about 100% modification, and from about 90% to about 100% modification.

In some cases, the polynucleic acid molecule comprises at least one of: from about 10% to about 90% modification, from about 20% to about 90% modification, from about 30% to about 90% modification, from about 40% to about 90% modification, from about 50% to about 90% modification, from about 60% to about 90% modification, from about 70% to about 90% modification, and from about 80% to about 100% modification.

In some cases, the polynucleic acid molecule comprises at least one of: from about 10% to about 80% modification, from about 20% to about 80% modification, from about 30% to about 80% modification, from about 40% to about 80% modification, from about 50% to about 80% modification, from about 60% to about 80% modification, and from about 70% to about 80% modification.

In some instances, the polynucleic acid molecule comprises at least one of: from about 10% to about 70% modification, from about 20% to about 70% modification, from about 30% to about 70% modification, from about 40% to about 70% modification, from about 50% to about 70% modification, and from about 60% to about 70% modification.

In some instances, the polynucleic acid molecule comprises at least one of: from about 10% to about 60% modification, from about 20% to about 60% modification, from about 30% to about 60% modification, from about 40% to about 60% modification, and from about 50% to about 60% modification.

In some cases, the polynucleic acid molecule comprises at least one of: from about 10% to about 50% modification, from about 20% to about 50% modification, from about 30% to about 50% modification, and from about 40% to about 50% modification.

In some cases, the polynucleic acid molecule comprises at least one of: from about 10% to about 40% modification, from about 20% to about 40% modification, and from about 30% to about 40% modification.

In some cases, the polynucleic acid molecule comprises at least one of: from about 10% to about 30% modification, and from about 20% to about 30% modification.

In some cases, the polynucleic acid molecule comprises from about 10% to about 20% modification.

In some cases, the polynucleic acid molecule comprises from about 15% to about 90%, from about 20% to about 80%, from about 30% to about 70%, or from about 40% to about 60% modifications.

In additional cases, the polynucleic acid molecule comprises at least about 15%, 20%, 30%, 40%, 50%, 60%, 70%, 80%, 90%, 95%, or 99% modification.

In some embodiments, the polynucleic acid molecule comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22 or more modifications.

In some instances, the polynucleic acid molecule comprises at least about 1, about 2, about 3, about 4, about 5, about 6, about 7, about 8, about 9, about 10, about 11, about 12, about 13, about 14, about 15, about 16, about 17, about 18, about 19, about 20, about 21, about 22 or more modified nucleotides.

In some instances, from about 5% to about 100% of the polynucleic acid molecule comprise the artificial nucleotide analogues described herein. In some instances, about 5%, 10%, 15%, 20%, 25%, 30%, 35%, 40%, 45%, 50%, 55%, 60%, 65%, 70%, 75%, 80%, 85%, 90%, 95% or 100% of the polynucleic acid molecule comprise the artificial nucleotide analogues described herein. In some instances, about 5% of a polynucleic acid molecule comprise the artificial nucleotide analogues described herein. In some instances, about 10% of a polynucleic acid molecule comprise the artificial nucleotide analogues described herein. In some instances, about 15% of a polynucleic acid molecule comprise the artificial nucleotide analogues described herein. In some instances, about 20% of a polynucleic acid molecule comprise the artificial nucleotide analogues described herein. In some instances, about 25% of a polynucleic acid molecule comprise the artificial nucleotide analogues described herein. In some instances, about 30% of a polynucleic acid molecule comprise the artificial nucleotide analogues described herein. In some instances, about 35% of a polynucleic acid molecule comprise the artificial nucleotide analogues described herein. In some instances, about 40% of a polynucleic acid molecule comprise the artificial nucleotide analogues described herein. In some instances, about 45% of a polynucleic acid molecule comprise the artificial nucleotide analogues described herein. In some instances, about 50% of a polynucleic acid molecule comprise the artificial nucleotide analogues described herein. In some instances, about 55% of a polynucleic acid molecule comprise the artificial nucleotide analogues described herein. In some instances, about 60% of a polynucleic acid molecule comprise the artificial nucleotide analogues described herein. In some instances, about 65% of a polynucleic acid molecule comprise the artificial nucleotide analogues described herein. In some instances, about 70% of a polynucleic acid molecule comprise the artificial nucleotide analogues described herein. In some instances, about 75% of a polynucleic acid molecule comprise the artificial nucleotide analogues described herein. In some instances, about 80% of a polynucleic acid molecule comprise the artificial nucleotide analogues described herein. In some instances, about 85% of a polynucleic acid molecule comprise the artificial nucleotide analogues described herein. In some instances, about 90% of a polynucleic acid molecule comprise the artificial nucleotide analogues described herein. In some instances, about 95% of a polynucleic acid molecule comprise the artificial nucleotide analogues described herein. In some instances, about 96% of a polynucleic acid molecule comprise the artificial nucleotide analogues described herein. In some instances, about 97% of a polynucleic acid molecule comprise the artificial nucleotide analogues described herein. In some instances, about 98% of a polynucleic acid molecule comprise the artificial nucleotide analogues described herein. In some instances, about 99% of a polynucleic acid molecule comprise the artificial nucleotide analogues described herein. In some instances, about 100% of a polynucleic acid molecule comprise the artificial nucleotide analogues described herein. In some embodiments, the artificial nucleotide analogues include 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or a combination thereof.

In some embodiments, the polynucleic acid molecule comprises from about 1 to about 25 modifications in which the modification comprises an artificial nucleotide analogues described herein. In some embodiments, a polynucleic acid molecule comprises about 1 modification in which the modification comprises an artificial nucleotide analogue described herein. In some embodiments, a polynucleic acid molecule comprises about 2 modifications in which the modifications comprise an artificial nucleotide analogue described herein. In some embodiments, a polynucleic acid molecule comprises about 3 modifications in which the modifications comprise an artificial nucleotide analogue described herein. In some embodiments, a polynucleic acid molecule comprises about 4 modifications in which the modifications comprise an artificial nucleotide analogue described herein. In some embodiments, a polynucleic acid molecule comprises about 5 modifications in which the modifications comprise an artificial nucleotide analogue described herein. In some embodiments, a polynucleic acid molecule comprises about 6 modifications in which the modifications comprise an artificial nucleotide analogue described herein. In some embodiments, a polynucleic acid molecule comprises about 7 modifications in which the modifications comprise an artificial nucleotide analogue described herein. In some embodiments, a polynucleic acid molecule comprises about 8 modifications in which the modifications comprise an artificial nucleotide analogue described herein. In some embodiments, a polynucleic acid molecule comprises about 9 modifications in which the modifications comprise an artificial nucleotide analogue described herein. In some embodiments, a polynucleic acid molecule comprises about 10 modifications in which the modifications comprise an artificial nucleotide analogue described herein. In some embodiments, a polynucleic acid molecule comprises about 11 modifications in which the modifications comprise an artificial nucleotide analogue described herein. In some embodiments, a polynucleic acid molecule comprises about 12 modifications in which the modifications comprise an artificial nucleotide analogue described herein. In some embodiments, a polynucleic acid molecule comprises about 13 modifications in which the modifications comprise an artificial nucleotide analogue described herein. In some embodiments, a polynucleic acid molecule comprises about 14 modifications in which the modifications comprise an artificial nucleotide analogue described herein. In some embodiments, a polynucleic acid molecule comprises about 15 modifications in which the modifications comprise an artificial nucleotide analogue described herein. In some embodiments, a polynucleic acid molecule comprises about 16 modifications in which the modifications comprise an artificial nucleotide analogue described herein. In some embodiments, a polynucleic acid molecule comprises about 17 modifications in which the modifications comprise an artificial nucleotide analogue described herein. In some embodiments, a polynucleic acid molecule comprises about 18 modifications in which the modifications comprise an artificial nucleotide analogue described herein. In some embodiments, a polynucleic acid molecule comprises about 19 modifications in which the modifications comprise an artificial nucleotide analogue described herein. In some embodiments, a polynucleic acid molecule comprises about 20 modifications in which the modifications comprise an artificial nucleotide analogue described herein. In some embodiments, a polynucleic acid molecule comprises about 21 modifications in which the modifications comprise an artificial nucleotide analogue described herein. In some embodiments, a polynucleic acid molecule comprises about 22 modifications in which the modifications comprise an artificial nucleotide analogue described herein. In some embodiments, a polynucleic acid molecule comprises about 23 modifications in which the modifications comprise an artificial nucleotide analogue described herein. In some embodiments, a polynucleic acid molecule comprises about 24 modifications in which the modifications comprise an artificial nucleotide analogue described herein. In some embodiments, a polynucleic acid molecule comprises about 25 modifications in which the modifications comprise an artificial nucleotide analogue described herein.

In some embodiments, a polynucleic acid molecule is assembled from two separate polynucleotides wherein one polynucleotide comprises the sense strand and the second polynucleotide comprises the antisense strand of the polynucleic acid molecule. In other embodiments, the sense strand is connected to the antisense strand via a linker molecule, which in some instances is a polynucleotide linker or a non-nucleotide linker.

In some embodiments, a polynucleic acid molecule comprises a sense strand and antisense strand, wherein pyrimidine nucleotides in the sense strand comprises 2'-O-methylpyrimidine nucleotides and purine nucleotides in the sense strand comprise 2'-deoxy purine nucleotides. In some embodiments, a polynucleic acid molecule comprises a sense strand and antisense strand, wherein pyrimidine nucleotides present in the sense strand comprise 2'-deoxy-2'-fluoro pyrimidine nucleotides and wherein purine nucleotides present in the sense strand comprise 2'-deoxy purine nucleotides.

In some embodiments, a polynucleic acid molecule comprises a sense strand and antisense strand, wherein the pyrimidine nucleotides when present in said antisense strand are 2'-deoxy-2'-fluoro pyrimidine nucleotides and the purine nucleotides when present in said antisense strand are 2'-O-methyl purine nucleotides.

In some embodiments, a polynucleic acid molecule comprises a sense strand and antisense strand, wherein the pyrimidine nucleotides when present in said antisense strand are 2'-deoxy-2'-fluoro pyrimidine nucleotides and wherein the purine nucleotides when present in said antisense strand comprise 2'-deoxy-purine nucleotides.

In some embodiments, a polynucleic acid molecule comprises a sense strand and antisense strand, wherein the sense strand includes a terminal cap moiety at the 5'-end, the 3'-end, or both of the 5' and 3' ends of the sense strand. In other embodiments, the terminal cap moiety is an inverted deoxy abasic moiety.

In some embodiments, a polynucleic acid molecule comprises a sense strand and an antisense strand, wherein the antisense strand comprises a phosphate backbone modification at the 3' end of the antisense strand. In some instances, the phosphate backbone modification is a phosphorothioate.

In some embodiments, a polynucleic acid molecule comprises a sense strand and an antisense strand, wherein the antisense strand comprises a glyceryl modification at the 3' end of the antisense strand.

In some embodiments, a polynucleic acid molecule comprises a sense strand and an antisense strand, in which the sense strand comprises one or more, for example, about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or about one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and in which the antisense strand comprises about 1 to about 10 or more, specifically about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10, or more, pyrimidine nucleotides of the sense and/or antisense strand are chemically-modified with 2'-deoxy, 2'-O-methyl and/or 2'-deoxy-2'-fluoro nucleotides, with or without one or more, for example about 1, 2, 3, 4, 5, 6, 7, 8, 9, 10, or more, phosphorothioate internucleotide linkages and/or a terminal cap molecule at the 3'-end, the 5'-end, or both of the 3'- and 5'-ends, being present in the same or different strand.

In some embodiments, a polynucleic acid molecule comprises a sense strand and an antisense strand, in which the sense strand comprises about 1 to about 25, for example, about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10, or more) 2'-deoxy, 2'-O-methyl, 2'-deoxy-2'-fluoro, and/or one or more (e.g., about 1, 2, 3, 4, 5, 6, 7, 8, 9, 10, or more) universal base modified nucleotides, and optionally a terminal cap molecule at the 3-end, the 5'-end, or both of the 3'- and 5'-ends of the sense strand; and in which the antisense strand comprises about 1 to about 25 or more, for example about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10, or more, pyrimidine nucleotides of the sense and/or antisense strand are chemically-modified with 2'-deoxy, 2'-O-methyl and/or 2'-deoxy-2'-fluoro nucleotides, with or without about 1 to about 25 or more, for example about 1, 2, 3, 4, 5, 6, 7, 8, 9, 10, 11, 12, 13, 14, 15, 16, 17, 18, 19, 20, or more phosphorothioate internucleotide linkages and/or a terminal cap molecule at the 3'-end, the 5'-end, or both of the 3'- and 5'-ends, being present in the same or different strand.

In some embodiments, a polynucleic acid molecule comprises a sense strand and an antisense strand, in which the antisense strand comprises one or more, for example, about 1, 2, 3, 4, 5, 6, 7, 8, 9, 10, 11, 12, 13, 14, 15, 16, 17, 18, 19, 20, or more phosphorothioate internucleotide linkages, and/or about one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises about 1 to about 10 or more, specifically about 1, 2, 3, 4, 5, 6, 7, 8, 9, 10 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10, 11, 12, 13, 14, 15, 16, 17, 18, 19, 20, or more pyrimidine nucleotides of the sense and/or antisense strand are chemically-modified with 2'-deoxy, 2'-O-methyl and/or 2'-deoxy-2'-fluoro nucleotides, with or without one or more, for example, about 1, 2, 3, 4, 5, 6, 7, 8, 9, 10 or more phosphorothioate internucleotide linkages and/or a terminal cap molecule at the 3'-end, the 5'-end, or both of the 3' and 5'-ends, being present in the same or different strand.

In some embodiments, a polynucleic acid molecule comprises a sense strand and an antisense strand, in which the antisense strand comprises about 1 to about 25 or more, for example, about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises about 1 to about 25 or more, for example about 1, 2, 3, 4, 5, 6, 7, 8, 9, 10, 11, 12, 13, 14, 15, 16, 17, 18, 19, 20, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In other embodiments, one or more, for example about 1, 2, 3, 4, 5, 6, 7, 8, 9, 10 or more pyrimidine nucleotides of the sense and/or antisense strand are chemically-modified with 2'-deoxy, 2'-O-methyl and/or 2'-deoxy-2'-fluoro nucleotides, with or without about 1 to about 5, for example about 1, 2, 3, 4, 5 or more phosphorothioate internucleotide linkages and/or a terminal cap molecule at the 3'-end, the 5'-end, or both of the 3'- and 5'-ends, being present in the same or different strand.

In some embodiments, a polynucleic acid molecule described herein is a chemically-modified short interfering nucleic acid molecule having about 1 to about 25, for example, about 1, 2, 3, 4, 5, 6, 7, 8, 9, 10, 11, 12, 13, 14, 15, 16, 17, 18, 19, 20 or more phosphorothioate internucleotide linkages in each strand of the polynucleic acid molecule.

In another embodiment, a polynucleic acid molecule described herein comprises 2'-5' internucleotide linkages. In some instances, the 2'-5' internucleotide linkage(s) is at the 3'-end, the 5'-end, or both of the 3'- and 5'-ends of one or both sequence strands. In addition instances, the 2'-5' internucleotide linkage(s) is present at various other positions within one or both sequence strands, for example, about 1, 2, 3, 4, 5, 6, 7, 8, 9, 10, or more including every internucleotide linkage of a pyrimidine nucleotide in one or both strands of the polynucleic acid molecule comprise a 2'-5' internucleotide linkage, or about 1, 2, 3, 4, 5, 6, 7, 8, 9, 10, or more including every internucleotide linkage of a purine nucleotide in one or both strands of the polynucleic acid molecule comprise a 2'-5' internucleotide linkage.

In some embodiments, a polynucleic acid molecule is a single stranded polynucleic acid molecule that mediates RNAi activity in a cell or reconstituted in vitro system, wherein the polynucleic acid molecule comprises a single stranded polynucleotide having complementarity to a target nucleic acid sequence, and wherein one or more pyrimidine nucleotides present in the polynucleic acid are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any purine nucleotides present in the polynucleic acid are 2'-deoxy purine nucleotides (e.g., wherein all purine nucleotides are 2'-deoxy purine nucleotides or alternately a plurality of purine nucleotides are 2'-deoxy purine nucleotides), and a terminal cap modification, that is optionally present at the 3'-end, the 5'-end, or both of the 3' and 5'-ends of the antisense sequence, the polynucleic acid molecule optionally further comprising about 1 to about 4 (e.g., about 1, 2, 3, or 4) terminal 2'-deoxynucleotides at the 3'-end of the polynucleic acid molecule, wherein the terminal nucleotides further comprise one or more (e.g., 1, 2, 3, or 4) phosphorothioate internucleotide linkages, and wherein the polynucleic acid molecule optionally further comprises a terminal phosphate group, such as a 5'-terminal phosphate group.

In some cases, one or more of the artificial nucleotide analogues described herein are resistant toward nucleases such as for example ribonuclease such as RNase H, deoxyribonuclease such as DNase, or exonuclease such as 5'-3' exonuclease and 3'-5' exonuclease when compared to natural polynucleic acid molecules. In some instances, artificial nucleotide analogues comprising 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or combinations thereof are resistant toward nucleases such as for example ribonuclease such as RNase H, deoxyribonuclease such as DNase, or exonuclease such as 5'-3' exonuclease and 3'-5' exonuclease. In some instances, 2'-O-methyl modified polynucleic acid molecule is nuclease resistance (e.g., RNase H, DNase, 5'-3' exonuclease or 3'-5' exonuclease resistance). In some instances, 2'O-methoxyethyl (2'-O-MOE) modified polynucleic acid molecule is nuclease resistance (e.g., RNase H, DNase, 5'-3' exonuclease or 3'-5' exonuclease resistance). In some instances, 2'-O-aminopropyl modified polynucleic acid molecule is nuclease resistance (e.g., RNase H, DNase, 5'-3' exonuclease or 3'-5' exonuclease resistance). In some instances, 2'-deoxy modified polynucleic acid molecule is nuclease resistance (e.g., RNase H, DNase, 5'-3' exonuclease or 3'-5' exonuclease resistance). In some instances, T-deoxy-2'-fluoro modified polynucleic acid molecule is nuclease resistance (e.g., RNase H, DNase, 5'-3' exonuclease or 3'-5' exonuclease resistance). In some instances, 2'-O-aminopropyl (2'-O-AP) modified polynucleic acid molecule is nuclease resistance (e.g., RNase H, DNase, 5'-3' exonuclease or 3'-5' exonuclease resistance). In some instances, 2'-O-dimethylaminoethyl (2'-O-DMAOE) modified polynucleic acid molecule is nuclease resistance (e.g., RNase H, DNase, 5'-3' exonuclease or 3'-5' exonuclease resistance). In some instances, 2'-O-dimethylaminopropyl (2'-O-DMAP) modified polynucleic acid molecule is nuclease resistance (e.g., RNase H, DNase, 5'-3' exonuclease or 3'-5' exonuclease resistance). In some instances, T-O-dimethylaminoethyloxyethyl (2'-O-DMAEOE) modified polynucleic acid molecule is nuclease resistance (e.g., RNase H, DNase, 5'-3' exonuclease or 3'-5' exonuclease resistance). In some instances, 2'-O—N-methylacetamido (2'-O-NMA) modified polynucleic acid molecule is nuclease resistance (e.g., RNase H, DNase, 5'-3' exonuclease or 3'-5' exonuclease resistance). In some instances, LNA modified polynucleic acid molecule is nuclease resistance (e.g., RNase H, DNase, 5'-3' exonuclease or 3'-5' exonuclease resistance). In some instances, ENA modified polynucleic acid molecule is nuclease resistance (e.g., RNase H, DNase, 5'-3' exonuclease or 3'-5' exonuclease resistance). In some instances, HNA modified polynucleic acid molecule is nuclease resistance (e.g., RNase H, DNase, 5'-3' exonuclease or 3'-5' exonuclease resistance). In some instances, morpholinos is nuclease resistance (e.g., RNase H, DNase, 5'-3' exonuclease or 3'-5' exonuclease resistance). In some instances, PNA modified polynucleic acid molecule is resistant to nucleases (e.g., RNase H, DNase, 5'-3' exonuclease or 3'-5' exonuclease resistance). In some instances, methylphosphonate nucleotides modified polynucleic acid molecule is nuclease resistance (e.g., RNase H, DNase, 5'-3' exonuclease or 3'-5' exonuclease resistance). In some instances, thiolphosphonate nucleotides modified polynucleic acid molecule is nuclease resistance (e.g., RNase H, DNase, 5'-3' exonuclease or 3'-5' exonuclease resistance). In some instances, polynucleic acid molecule comprising 2'-fluoro N3-P5'-phosphoramidites is nuclease resistance (e.g., RNase H, DNase, 5'-3' exonuclease or 3'-5' exonuclease resistance). In some instances, the 5' conjugates described herein inhibit 5'-3' exonucleolytic cleavage. In some instances, the 3° conjugates described herein inhibit 3-5' exonucleolytic cleavage.

In some embodiments, one or more of the artificial nucleotide analogues described herein have increased binding affinity toward their mRNA target relative to an equivalent natural polynucleic acid molecule. The one or more of the artificial nucleotide analogues comprising 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, or 2'-fluoro N3-P5'-phosphoramidites have increased binding affinity toward their mRNA target relative to an equivalent natural polynucleic acid molecule. In some instances, 2'-O-methyl modified polynucleic acid molecule has increased binding affinity toward their mRNA target relative to an equivalent natural polynucleic acid molecule. In some instances, 2'-O-methoxyethyl (2'-O-MOE) modified polynucleic acid molecule has increased binding affinity toward their mRNA target relative to an equivalent natural polynucleic acid molecule. In some instances, 2'-O-aminopropyl modified polynucleic acid molecule has increased binding affinity toward their mRNA target relative to an equivalent natural polynucleic acid molecule. In some instances, 2'-deoxy modified polynucleic acid molecule has increased binding affinity toward their mRNA target relative to an equivalent natural polynucleic acid molecule. In some instances, T-deoxy-2'-fluoro modified polynucleic acid molecule has increased binding affinity toward their mRNA target relative to an equivalent natural polynucleic acid molecule. In some instances, 2'-O-aminopropyl (2'-O-AP) modified polynucleic acid molecule has increased binding affinity toward their mRNA target relative to an equivalent natural polynucleic acid molecule. In some instances, 2'-O-dimethylaminoethyl (2'-O-DMAOE) modified polynucleic acid molecule has increased binding affinity toward their mRNA target relative to an equivalent natural polynucleic acid molecule. In some instances, 2'-O-dimethylaminopropyl (2'-O-DMAP) modified polynucleic acid molecule has increased binding affinity toward their mRNA target relative to an equivalent natural polynucleic acid molecule. In some instances, T-O-dimethylaminoethyloxyethyl (2'-O-DMAEOE) modified polynucleic acid molecule has increased binding affinity toward their mRNA target relative to an equivalent natural polynucleic acid molecule. In some instances, 2'-O—N-methylacetamido (2'-O-NMA) modified polynucleic acid molecule has increased binding affinity toward their mRNA target relative to an equivalent natural polynucleic acid molecule. In some instances, LNA modified polynucleic acid molecule has increased binding affinity toward their mRNA target relative to an equivalent natural polynucleic acid molecule. In some instances, ENA modified polynucleic acid molecule has increased binding affinity toward their mRNA target relative to an equivalent natural polynucleic acid molecule. In some instances, PNA modified polynucleic acid molecule has increased binding affinity toward their mRNA target relative to an equivalent natural polynucleic acid molecule. In some instances, HNA modified polynucleic acid molecule has increased binding affinity toward their mRNA target relative to an equivalent natural polynucleic acid molecule. In some instances, morpholino modified polynucleic acid molecule has increased binding affinity toward their mRNA target relative to an equivalent natural polynucleic acid molecule. In some instances, methylphosphonate nucleotides modified polynucleic acid molecule has increased binding affinity toward their mRNA target relative to an equivalent natural polynucleic acid molecule. In some instances, thiolphosphonate nucleotides modified polynucleic acid molecule has increased binding affinity toward their mRNA target relative to an equivalent natural polynucleic acid molecule. In some instances, polynucleic acid molecule comprising 2'-fluoro N3-P5'-phosphoramidites has increased binding affinity toward their mRNA target relative to an equivalent natural polynucleic acid molecule. In some cases, the increased affinity is illustrated with a lower Kd, a higher melt temperature (Tm), or a combination thereof.

In some embodiments, a polynucleic acid molecule described herein is a chirally pure (or stereo pure) polynucleic acid molecule, or a polynucleic acid molecule comprising a single enantiomer. In some instances, the polynucleic acid molecule comprises L-nucleotide. In some instances, the polynucleic acid molecule comprises D-nucleotides. In some instance, a polynucleic acid molecule composition comprises less than 30%, 25%, 20%, 15%, 10%, 5%, 4%, 3%, 2%, 1%, or less of its mirror enantiomer. In some cases, a polynucleic acid molecule composition comprises less than 30%, 25%, 20%, 15%, 10%, 5%, 4%, 3%, 2%, 1%, or less of a racemic mixture. In some instances, the polynucleic acid molecule is a polynucleic acid molecule described in: U.S. Patent Publication Nos: 2014/194610 and 2015/211006; and PCT Publication No.: WO2015107425.

In some embodiments, a polynucleic acid molecule described herein is further modified to include an aptamer conjugating moiety. In some instances, the aptamer conjugating moiety is a DNA aptamer conjugating moiety. In some instances, the aptamer conjugating moiety is Alphamer (Centauri Therapeutics), which comprises an aptamer portion that recognizes a specific cell-surface target and a portion that presents a specific epitopes for attaching to circulating antibodies. In some instance, a polynucleic acid molecule described herein is further modified to include an aptamer conjugating moiety as described in: U.S. Pat. Nos. 8,604,184, 8,591,910, and 7,850,975.

In additional embodiments, a polynucleic acid molecule described herein is modified to increase its stability. In some embodiment, the polynucleic acid molecule is RNA (e.g., siRNA). In some instances, the polynucleic acid molecule is modified by one or more of the modifications described above to increase its stability. In some cases, the polynucleic acid molecule is modified at the 2' hydroxyl position, such as by 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modification or by a locked or bridged ribose conformation (e.g., LNA or ENA). In some cases, the polynucleic acid molecule is modified by 2'-O-methyl and/or 2'-O-methoxyethyl ribose. In some cases, the polynucleic acid molecule also includes morpholinos, PNAs, HNA, methylphosphonate nucleotides, thiolphosphonate nucleotides, and/or 2'-fluoro N3-P5'-phosphoramidites to increase its stability. In some instances, the polynucleic acid molecule is a chirally pure (or stereo pure) polynucleic acid molecule. In some instances, the chirally pure (or stereo pure) polynucleic acid molecule is modified to increase its stability. Suitable modifications to the RNA to increase stability for delivery will be apparent to the skilled person.

In some embodiments, a polynucleic acid molecule describe herein has RNAi activity that modulates expression of RNA encoded by a gene involved in a disease or disorder such as, but not limited to, IKBKAP, SMN2, MCAD, LMNA, DMPK, ZNF9, MAPT, FKTN, TDP-43, LDLR, CFTR, DMD, PAH, MSTN, or K-Ras. In some instances, a polynucleic acid molecule describe herein is a double-stranded siRNA molecule that down-regulates expression of at least one of IKBKAP, SMN2, MCAD, LMNA, DMPK, ZNF9, MAPT, FKTN, TDP-43, LDLR, CFTR, DMD, PAH, MSTN, or K-Ras, wherein one of the strands of the double-stranded siRNA molecule comprises a nucleotide sequence that is complementary to a nucleotide sequence of at least one of IKBKAP, SMN2, MCAD, LMNA, DMPK, ZNF9, MAPT, FKTN, TDP-43, LDLR, CFTR, DMD, PAH, MSTN, or K-Ras or RNA encoded by at least one of IKBKAP, SMN2, MCAD, LMNA, DMPK, ZNF9, MAPT, FKTN, TDP-43, LDLR, CFTR, DMD, PAH, MSTN, or K-Ras or a portion thereof, and wherein the second strand of the double-stranded siRNA molecule comprises a nucleotide sequence substantially similar to the nucleotide sequence of at least one of IKBKAP, SMN2, MCAD, LMNA, DMPK, ZNF9, MAPT, FKTN, TDP-43, LDLR, CFTR, DMD, PAH, MSTN, or K-Ras or RNA encoded by at least one of IKBKAP, SMN2, MCAD, LMNA, DMPK, ZNF9, MAPT, FKTN, TDP-43, LDLR, CFTR, DMD, PAH, MSTN, or K-Ras or a portion thereof. In some cases, a polynucleic acid molecule describe herein is a double-stranded siRNA molecule that down-regulates expression of at least one of IKBKAP, SMN2, MCAD, LMNA, DMPK, ZNF9, MAPT, FKTN, TDP-43, LDLR, CFTR, DMD, PAH, MSTN, or K-Ras, wherein each strand of the siRNA molecule comprises about 15 to 25, 18 to 24, or 19 to about 23 nucleotides, and wherein each strand comprises at least about 14, 17, or 19 nucleotides that are complementary to the nucleotides of the other strand. In some cases, a polynucleic acid molecule describe herein is a double-stranded siRNA molecule that down-regulates expression of at least one of IKBKAP, SMN2, MCAD, LMNA, DMPK, ZNF9, MAPT, FKTN, TDP-43, LDLR, CFTR, DMD, PAH, MSTN, or K-Ras, wherein each strand of the siRNA molecule comprises about 19 to about 23 nucleotides, and wherein each strand comprises at least about 19 nucleotides that are complementary to the nucleotides of the other strand. In some instances, the RNAi activity occurs within a cell. In other instances, the RNAi activity occurs in a reconstituted in vitro system.

In some embodiments, a polynucleic acid molecule describe herein has RNAi activity that modulates expression of RNA encoded by a gene involved in muscular dystrophy such as, but not limited to, DMD, DUX4, DYSF, EMD, or LMNA. In some instances, a polynucleic acid molecule describe herein is a double-stranded siRNA molecule that down-regulates expression of at least one of DMD, DUX4, DYSF, EMD, or LMNA, wherein one of the strands of the double-stranded siRNA molecule comprises a nucleotide sequence that is complementary to a nucleotide sequence of at least one of DMD, DUX4, DYSF, EMD, or LMINA or RNA encoded by at least one of DMD, DUX4, DYSF, EMD, or LMINA or a portion thereof, and wherein the second strand of the double-stranded siRNA molecule comprises a nucleotide sequence substantially similar to the nucleotide sequence of at least one of DMD, DUX4, DYSF, EMD, or LMINA or RNA encoded by at least one of DMD, DUX4, DYSF, EMD, or LMINA or a portion thereof. In some cases, a polynucleic acid molecule describe herein is a double-stranded siRNA molecule that down-regulates expression of at least one of DMD, DUX4, DYSF, EMD, or LMNA, wherein each strand of the siRNA molecule comprises about 15 to 25, 18 to 24, or 19 to about 23 nucleotides, and wherein each strand comprises at least about 14, 17, or 19 nucleotides that are complementary to the nucleotides of the other strand. In some cases, a polynucleic acid molecule describe herein is a double-stranded siRNA molecule that down-regulates expression of at least one of DMD, DUX4, DYSF, EMD, or LMNA, wherein each strand of the siRNA molecule comprises about 19 to about 23 nucleotides, and wherein each strand comprises at least about 19 nucleotides that are complementary to the nucleotides of the other strand. In some instances, the RNAi activity occurs within a cell. In other instances, the RNAi activity occurs in a reconstituted in vitro system.

In some embodiments, a polynucleic acid molecule describe herein has RNAi activity that modulates expression of RNA encoded by the DMD gene. In some instances, a polynucleic acid molecule describe herein is a single-stranded siRNA molecule that down-regulates expression of DMD, wherein the single-stranded siRNA molecule comprises a nucleotide sequence that is complementary to a nucleotide sequence of DMD or RNA encoded by DMD or a portion thereof. In some cases, a polynucleic acid molecule describe herein is a single-stranded siRNA molecule that down-regulates expression of DMD, wherein the siRNA molecule comprises about 15 to 25, 18 to 24, or 19 to about 23 nucleotides. In some cases, a polynucleic acid molecule describe herein is a single-stranded siRNA molecule that down-regulates expression of DMD, wherein the siRNA molecule comprises about 19 to about 23 nucleotides. In some instances, the RNAi activity occurs within a cell. In other instances, the RNAi activity occurs in a reconstituted in vitro system.

In some instances, the polynucleic acid molecule is a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. In some instances, the polynucleic acid molecule is assembled from two separate polynucleotides, where one strand is the sense strand and the other is the antisense strand, wherein the antisense and sense strands are self-complementary (e.g., each strand comprises nucleotide sequence that is complementary to nucleotide sequence in the other strand; such as where the antisense strand and sense strand form a duplex or double stranded structure, for example wherein the double stranded region is about 19, 20, 21, 22, 23, or more base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the polynucleic acid molecule is assembled from a single oligonucleotide, where the self-complementary sense and antisense regions of the polynucleic acid molecule are linked by means of a nucleic acid based or non-nucleic acid-based linker(s).

In some cases, the polynucleic acid molecule is a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. In other cases, the polynucleic acid molecule is a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide is processed either in vivo or in vitro to generate an active polynucleic acid molecule capable of mediating RNAi. In additional cases, the polynucleic acid molecule also comprises a single stranded polynucleotide having nucleotide sequence complementary to nucleotide sequence in a target nucleic acid molecule or a portion thereof (for example, where such polynucleic acid molecule does not require the presence within the polynucleic acid molecule of nucleotide sequence corresponding to the target nucleic acid sequence or a portion thereof), wherein the single stranded polynucleotide further comprises a terminal phosphate group, such as a 5'-phosphate (see for example Martinez et al., 2002, *Cell*, 110, 563-574 and Schwarz et al., 2002, *Molecular Cell*, 10, 537-568), or 5',3'-diphosphate.

In some instances, an asymmetric is a linear polynucleic acid molecule comprising an antisense region, a loop portion that comprises nucleotides or non-nucleotides, and a sense region that comprises fewer nucleotides than the antisense region to the extent that the sense region has enough complimentary nucleotides to base pair with the antisense region and form a duplex with loop. For example, an asymmetric hairpin polynucleic acid molecule comprises an antisense region having length sufficient to mediate RNAi in a cell or in vitro system (e.g. about 19 to about 22 nucleotides) and a loop region comprising about 4 to about 8 nucleotides, and a sense region having about 3 to about 18 nucleotides that are complementary to the antisense region. In some cases, the asymmetric hairpin polynucleic acid molecule also comprises a 5'-terminal phosphate group that is chemically modified. In additional cases, the loop portion of the asymmetric hairpin polynucleic acid molecule comprises nucleotides, non-nucleotides, linker molecules, or conjugate molecules.

In some embodiments, an asymmetric duplex is a polynucleic acid molecule having two separate strands comprising a sense region and an antisense region, wherein the sense region comprises fewer nucleotides than the antisense region to the extent that the sense region has enough complimentary nucleotides to base pair with the antisense region and form a duplex. For example, an asymmetric duplex polynucleic acid molecule comprises an antisense region having length sufficient to mediate RNAi in a cell or in vitro system (e.g. about 19 to about 22 nucleotides) and a sense region having about 3 to about 18 nucleotides that are complementary to the antisense region.

In some cases, an universal base refers to nucleotide base analogs that form base pairs with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see for example Loakes, 2001, *Nucleic Acids Research*, 29, 2437-2447).

Polynucleic Acid Molecule Synthesis

In some embodiments, a polynucleic acid molecule described herein is constructed using chemical synthesis and/or enzymatic ligation reactions using procedures known in the art. For example, a polynucleic acid molecule is chemically synthesized using naturally occurring nucleotides or variously modified nucleotides designed to increase the biological stability of the molecules or to increase the physical stability of the duplex formed between the polynucleic acid molecule and target nucleic acids. Exemplary methods include those described in: U.S. Pat. Nos. 5,142,047; 5,185,444; 5,889,136; 6,008,400; and 6,111,086; PCT Publication No. WO2009099942; or European Publication No. 1579015. Additional exemplary methods include those described in: Griffey et al., "2'-O-aminopropyl ribonucleotides: a zwitterionic modification that enhances the exonuclease resistance and biological activity of antisense oligonucleotides," *J. Med. Chem.* 39(26):5100-5109 (1997)); Obika, et al. "Synthesis of 2'-O,4'-C-methyleneuridine and -cytidine. Novel bicyclic nucleosides having a fixed C3, -endo sugar puckering". *Tetrahedron Letters* 38 (50): 8735 (1997); Koizumi, M. "ENA oligonucleotides as therapeutics". *Current opinion in molecular therapeutics* 8 (2): 144-149 (2006); and Abramova et al., "Novel oligonucleotide analogues based on morpholino nucleoside subunits-antisense technologies: new chemical possibilities," Indian Journal of Chemistry 48B:1721-1726 (2009). Alternatively, the polynucleic acid molecule is produced biologically using an expression vector into which a polynucleic acid molecule has been subcloned in an antisense orientation (i.e., RNA transcribed from the inserted polynucleic acid molecule will be of an antisense orientation to a target polynucleic acid molecule of interest).

In some embodiments, a polynucleic acid molecule is synthesized via a tandem synthesis methodology, wherein both strands are synthesized as a single contiguous oligonucleotide fragment or strand separated by a cleavable linker which is subsequently cleaved to provide separate fragments or strands that hybridize and permit purification of the duplex.

In some instances, a polynucleic acid molecule is also assembled from two distinct nucleic acid strands or fragments wherein one fragment includes the sense region and the second fragment includes the antisense region of the molecule.

Additional modification methods for incorporating, for example, sugar, base and phosphate modifications include: Eckstein et al., International Publication PCT No. WO 92/07065; Perrault et al. *Nature*, 1990, 344, 565-568; Pieken et al. *Science*, 1991, 253, 314-317; Usman and Cedergren, *Trends in Biochem. Sci.*, 1992, 17, 334-339; Usman et al. International Publication PCT No. WO 93/15187; Sproat, U.S. Pat. No. 5,334,711 and Beigelman et al., 1995, *J. Biol. Chem.*, 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, *Tetrahedron Lett.*, 39, 1131; Earnshaw and Gait, 1998, *Biopolymers (Nucleic Acid Sciences)*, 48, 39-55; Verma and Eckstein, 1998, *Annu. Rev. Biochem.*, 67, 99-134; and Burlina et al., 1997, *Bioorg. Med. Chem.*, 5, 1999-2010. Such publications describe general methods and strategies to determine the location of incorporation of sugar, base and/or phosphate modifications and the like into nucleic acid molecules without modulating catalysis.

In some instances, while chemical modification of the polynucleic acid molecule internucleotide linkages with phosphorothioate, phosphorodithioate, and/or 5'-methylphosphonate linkages improves stability, excessive modifications sometimes cause toxicity or decreased activity. Therefore, when designing nucleic acid molecules, the amount of these internucleotide linkages in some cases is minimized. In such cases, the reduction in the concentration of these linkages lowers toxicity, increases efficacy and higher specificity of these molecules.

Nucleic Acid-Polypeptide Conjugate

In some embodiments, a polynucleic acid molecule is further conjugated to a polypeptide A for delivery to a site of interest. In some cases, a polynucleic acid molecule is conjugated to a polypeptide A and optionally a polymeric moiety.

In some instances, at least one polypeptide A is conjugated to at least one B. In some instances, the at least one polypeptide A is conjugated to the at least one B to form an A-B conjugate. In some embodiments, at least one A is conjugated to the 5' terminus of B, the 3' terminus of B, an internal site on B, or in any combinations thereof. In some instances, the at least one polypeptide A is conjugated to at least two B. In some instances, the at least one polypeptide A is conjugated to at least 2, 3, 4, 5, 6, 7, 8, or more B.

In some embodiments, at least one polypeptide A is conjugated at one terminus of at least one B while at least one C is conjugated at the opposite terminus of the at least one B to form an A-B—C conjugate. In some instances, at least one polypeptide A is conjugated at one terminus of the at least one B while at least one of C is conjugated at an internal site on the at least one B. In some instances, at least one polypeptide A is conjugated directly to the at least one C. In some instances, the at least one B is conjugated indirectly to the at least one polypeptide A via the at least one C to form an A-C—B conjugate.

In some instances, at least one B and/or at least one C, and optionally at least one D are conjugated to at least one polypeptide A. In some instances, the at least one B is conjugated at a terminus (e.g., a 5' terminus or a 3' terminus) to the at least one polypeptide A or are conjugated via an internal site to the at least one polypeptide A. In some cases, the at least one C is conjugated either directly to the at least one polypeptide A or indirectly via the at least one B. If indirectly via the at least one B, the at least one C is conjugated either at the same terminus as the at least one polypeptide A on B, at opposing terminus from the at least one polypeptide A, or independently at an internal site. In some instances, at least one additional polypeptide A is further conjugated to the at least one polypeptide A, to B, or to C. In additional instances, the at least one D is optionally conjugated either directly or indirectly to the at least one polypeptide A, to the at least one B, or to the at least one C. If directly to the at least one polypeptide A, the at least one D is also optionally conjugated to the at least one B to form an A-D-B conjugate or is optionally conjugated to the at least one B and the at least one C to form an A-D-B—C conjugate. In some instances, the at least one D is directly conjugated to the at least one polypeptide A and indirectly to the at least one B and the at least one C to form a D-A-B—C conjugate. If indirectly to the at least one polypeptide A, the at least one D is also optionally conjugated to the at least one B to form an A-B-D conjugate or is optionally conjugated to the at least one B and the at least one C to form an A-B-D-C conjugate. In some instances, at least one additional D is further conjugated to the at least one polypeptide A, to B, or to C.

In some embodiments, a polynucleic acid molecule conjugate comprises a construct as illustrated in FIG. 19A.

In some embodiments, a polynucleic acid molecule conjugate comprises a construct as illustrated in FIG. 19B.

In some embodiments, a polynucleic acid molecule conjugate comprises a construct as illustrated in FIG. 19C.

In some embodiments, a polynucleic acid molecule conjugate comprises a construct as illustrated in FIG. 19D.

In some embodiments, a polynucleic acid molecule conjugate comprises a construct as illustrated in FIG. 19E.

In some embodiments, a polynucleic acid molecule conjugate comprises a construct as illustrated in FIG. 19F.

In some embodiments, a polynucleic acid molecule conjugate comprises a construct as illustrated in FIG. 19G.

In some embodiments, a polynucleic acid molecule conjugate comprises a construct as illustrated in FIG. 19H.

In some embodiments, a polynucleic acid molecule conjugate comprises a construct as illustrated in FIG. 19I.

In some embodiments, a polynucleic acid molecule conjugate comprises a construct as illustrated in FIG. 19J.

In some embodiments, a polynucleic acid molecule conjugate comprises a construct as illustrated in FIG. 19K.

In some embodiments, a polynucleic acid molecule conjugate comprises a construct as illustrated in FIG. 19L.

The antibody as illustrated above is for representation purposes only and encompasses a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof.

Binding Moiety

In some embodiments, the binding moiety A is a polypeptide. In some instances, the polypeptide is an antibody or its fragment thereof. In some cases, the fragment is a binding fragment. In some instances, the antibody or binding fragment thereof comprises a humanized antibody or binding fragment thereof, murine antibody or binding fragment thereof, chimeric antibody or binding fragment thereof, monoclonal antibody or binding fragment thereof, monovalent Fab', divalent Fab$_2$, F(ab)'$_3$ fragments, single-chain variable fragment (scFv), bis-scFv, (scFv)$_2$, diabody, minibody, nanobody, triabody, tetrabody, disulfide stabilized Fv protein (dsFv), single-domain antibody (sdAb), Ig NAR, camelid antibody or binding fragment thereof, bispecific antibody or biding fragment thereof, or a chemically modified derivative thereof.

In some instances, A is an antibody or binding fragment thereof. In some instances, A is a humanized antibody or binding fragment thereof, murine antibody or binding fragment thereof, chimeric antibody or binding fragment thereof, monoclonal antibody or binding fragment thereof, monovalent Fab', divalent Fab$_2$, F(ab)'$_3$ fragments, single-chain variable fragment (scFv), bis-scFv, (scFv)$_2$, diabody, minibody, nanobody, triabody, tetrabody, disulfide stabilized Fv protein ("dsFv"), single-domain antibody (sdAb), Ig NAR, camelid antibody or binding fragment thereof, bispecific antibody or biding fragment thereof, or a chemically modified derivative thereof. In some instances, A is a humanized antibody or binding fragment thereof. In some instances, A is a murine antibody or binding fragment thereof. In some instances, A is a chimeric antibody or binding fragment thereof. In some instances, A is a monoclonal antibody or binding fragment thereof. In some instances, A is a monovalent Fab'. In some instances, A is a diavalent Fab$_2$. In some instances, A is a single-chain variable fragment (scFv).

In some embodiments, the binding moiety A is a bispecific antibody or binding fragment thereof. In some instances, the bispecific antibody is a trifunctional antibody or a bispecific mini-antibody. In some cases, the bispecific antibody is a trifunctional antibody. In some instances, the trifunctional antibody is a full length monoclonal antibody comprising binding sites for two different antigens.

In some cases, the bispecific antibody is a bispecific mini-antibody. In some instances, the bispecific mini-antibody comprises divalent Fab$_2$, F(ab)'$_3$ fragments, bis-scFv, (scFv)$_2$, diabody, minibody, triabody, tetrabody or a bi-specific T-cell engager (BiTE). In some embodiments, the bi-specific T-cell engager is a fusion protein that contains two single-chain variable fragments (scFvs) in which the two scFvs target epitopes of two different antigens.

In some embodiments, the binding moiety A is a bispecific mini-antibody. In some instances, A is a bispecific Fab$_2$. In some instances, A is a bispecific F(ab)'$_3$ fragment. In some cases, A is a bispecific bis-scFv. In some cases, A is a bispecific (scFv)$_2$. In some embodiments, A is a bispecific diabody. In some embodiments, A is a bispecific minibody. In some embodiments, A is a bispecific triabody. In other embodiments, A is a bispecific tetrabody. In other embodiments, A is a bi-specific T-cell engager (BiTE).

In some embodiments, the binding moiety A is a trispecific antibody. In some instances, the trispecific antibody comprises F(ab)'$_3$ fragments or a triabody. In some instances, A is a trispecific F(ab)'$_3$ fragment. In some cases, A is a triabody. In some embodiments, A is a trispecific antibody as described in Dimas, et al., "Development of a trispecific antibody designed to simultaneously and efficiently target three different antigens on tumor cells," *Mol. Pharmaceutics,* 12(9): 3490-3501 (2015).

In some embodiments, the binding moiety A is an antibody or binding fragment thereof that recognizes a cell surface protein. In some instances, the binding moiety A is an antibody or binding fragment thereof that recognizes a cell surface protein on a muscle cell. Exemplary cell surface proteins recognized by an antibody or binding fragment thereof include, but are not limited to, Sca-1, CD34, Myo-D, myogenin, MRF4, NCAM, CD43, and CD95 (Fas).

In some instances, the cell surface protein comprises clusters of differentiation (CD) cell surface markers. Exemplary CD cell surface markers include, but are not limited to, CD1, CD2, CD3, CD4, CD5, CD6, CD7, CD8, CD9, CD10, CD11a, CD11b, CD11c, CD11d, CDw12, CD13, CD14, CD15, CD15s, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD45RO, CD45RA, CD45RB, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L (L-selectin), CD62P, CD63, CD64, CD65, CD66a, CD66b, CD66c, CD66d, CD66e, CD79 (e.g., CD79a, CD79b), CD90, CD95 (Fas), CD103, CD104, CD125 (IL5RA), CD134 (OX40), CD137 (4-1BB), CD152 (CTLA-4), CD221, CD274, CD279 (PD-1), CD319 (SLAMF7), CD326 (EpCAM), and the like.

In some instances, the binding moiety A is an antibody or binding fragment thereof that recognizes a CD cell surface marker. In some instances, the binding moiety A is an antibody or binding fragment thereof that recognizes CD1, CD2, CD3, CD4, CD5, CD6, CD7, CD8, CD9, CD10, CD11a, CD11b, CD11c, CD11d, CDw12, CD13, CD14, CD15, CD15s, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD45RO, CD45RA, CD45RB, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L (L-selectin), CD62P, CD63, CD64, CD65, CD66a, CD66b, CD66c, CD66d, CD66e, CD79 (e.g., CD79a, CD79b), CD90, CD95 (Fas), CD103, CD104, CD125 (IL5RA), CD134 (OX40), CD137 (4-1BB), CD152 (CTLA-4), CD221, CD274, CD279 (PD-1), CD319 (SLAMF7), CD326 (EpCAM), or a combination thereof.

In some embodiments, the binding moiety A is conjugated to a polynucleic acid molecule (B) non-specifically. In some instances, the binding moiety A is conjugated to a polynucleic acid molecule (B) via a lysine residue or a cysteine residue, in a non-site specific manner. In some instances, the binding moiety A is conjugated to a polynucleic acid molecule (B) via a lysine residue in a non-site specific manner. In some cases, the binding moiety A is conjugated to a polynucleic acid molecule (B) via a cysteine residue in a non-site specific manner.

In some embodiments, the binding moiety A is conjugated to a polynucleic acid molecule (B) in a site-specific manner. In some instances, the binding moiety A is conjugated to a polynucleic acid molecule (B) through a lysine residue, a cysteine residue, at the 5'-terminus, at the 3'-terminus, an unnatural amino acid, or an enzyme-modified or enzyme-catalyzed residue, via a site-specific manner. In some instances, the binding moiety A is conjugated to a polynucleic acid molecule (B) through a lysine residue via a site-specific manner. In some instances, the binding moiety A is conjugated to a polynucleic acid molecule (B) through a cysteine residue via a site-specific manner. In some instances, the binding moiety A is conjugated to a polynucleic acid molecule (B) at the 5'-terminus via a site-specific manner. In some instances, the binding moiety A is conjugated to a polynucleic acid molecule (B) at the 3'-terminus via a site-specific manner. In some instances, the binding moiety A is conjugated to a polynucleic acid molecule (B) through an unnatural amino acid via a site-specific manner. In some instances, the binding moiety A is conjugated to a polynucleic acid molecule (B) through an enzyme-modified or enzyme-catalyzed residue via a site-specific manner.

In some embodiments, one or more polynucleic acid molecule (B) is conjugated to a binding moiety A. In some instances, about 1, 2, 3, 4, 5, 6, 7, 8, 9, 10, 11, 12, 13, 14, 15, 16, or more polynucleic acid molecules are conjugated to one binding moiety A. In some instances, about 1 polynucleic acid molecule is conjugated to one binding moiety A. In some instances, about 2 polynucleic acid molecules are conjugated to one binding moiety A. In some instances, about 3 polynucleic acid molecules are conjugated to one binding moiety A. In some instances, about 4 polynucleic acid molecules are conjugated to one binding moiety A. In some instances, about 5 polynucleic acid molecules are conjugated to one binding moiety A. In some instances, about 6 polynucleic acid molecules are conjugated to one binding moiety A. In some instances, about 7 polynucleic acid molecules are conjugated to one binding moiety A. In some instances, about 8 polynucleic acid molecules are conjugated to one binding moiety A. In some instances, about 9 polynucleic acid molecules are conjugated to one binding moiety A. In some instances, about 10 polynucleic acid molecules are conjugated to one binding moiety A. In some instances, about 11 polynucleic acid molecules are conjugated to one binding moiety A. In some instances, about 12 polynucleic acid molecules are conjugated to one binding moiety A. In some instances, about 13 polynucleic acid molecules are conjugated to one binding moiety A. In some instances, about 14 polynucleic acid molecules are conjugated to one binding moiety A. In some instances, about 15 polynucleic acid molecules are conjugated to one binding moiety A. In some instances, about 16 polynucleic acid molecules are conjugated to one binding moiety A. In some cases, the one or more polynucleic acid molecules are the same. In other cases, the one or more polynucleic acid molecules are different.

In some embodiments, the number of polynucleic acid molecule (B) conjugated to a binding moiety A forms a ratio. In some instances, the ratio is referred to as a DAR (drug-to-antibody) ratio, in which the drug as referred to herein is the polynucleic acid molecule (B). In some instances, the DAR ratio of the polynucleic acid molecule (B) to binding moiety A is about 1, 2, 3, 4, 5, 6, 7, 8, 9, 10, 11, 12, 13, 14, 15, 16, or greater. In some instances, the DAR ratio of the polynucleic acid molecule (B) to binding moiety A is about 1 or greater. In some instances, the DAR ratio of the polynucleic acid molecule (B) to binding moiety A is about 2 or greater. In some instances, the DAR ratio of the polynucleic acid molecule (B) to binding moiety A is about 3 or greater. In some instances, the DAR ratio of the polynucleic acid molecule (B) to binding moiety A is about 4 or greater. In some instances, the DAR ratio of the polynucleic acid molecule (B) to binding moiety A is about 5 or greater. In some instances, the DAR ratio of the polynucleic acid molecule (B) to binding moiety A is about 6 or greater. In some instances, the DAR ratio of the polynucleic acid molecule (B) to binding moiety A is about 7 or greater. In some instances, the DAR ratio of the polynucleic acid molecule (B) to binding moiety A is about 8 or greater. In some instances, the DAR ratio of the polynucleic acid molecule (B) to binding moiety A is about 9 or greater. In some instances, the DAR ratio of the polynucleic acid molecule (B) to binding moiety A is about 10 or greater. In some instances, the DAR ratio of the polynucleic acid molecule (B) to binding moiety A is about 11 or greater. In some instances, the DAR ratio of the polynucleic acid molecule (B) to binding moiety A is about 12 or greater.

In some instances, the DAR ratio of the polynucleic acid molecule (B) to binding moiety A is about 1, 2, 3, 4, 5, 6, 7, 8, 9, 10, 11, 12, 13, 14, 15, or 16. In some instances, the DAR ratio of the polynucleic acid molecule (B) to binding moiety A is about 1. In some instances, the DAR ratio of the polynucleic acid molecule (B) to binding moiety A is about 2. In some instances, the DAR ratio of the polynucleic acid molecule (B) to binding moiety A is about 3. In some instances, the DAR ratio of the polynucleic acid molecule (B) to binding moiety A is about 4. In some instances, the DAR ratio of the polynucleic acid molecule (B) to binding moiety A is about 5. In some instances, the DAR ratio of the polynucleic acid molecule (B) to binding moiety A is about 6. In some instances, the DAR ratio of the polynucleic acid molecule (B) to binding moiety A is about 7. In some instances, the DAR ratio of the polynucleic acid molecule (B) to binding moiety A is about 8. In some instances, the DAR ratio of the polynucleic acid molecule (B) to binding moiety A is about 9. In some instances, the DAR ratio of the polynucleic acid molecule (B) to binding moiety A is about 10. In some instances, the DAR ratio of the polynucleic acid molecule (B) to binding moiety A is about 11. In some instances, the DAR ratio of the polynucleic acid molecule (B) to binding moiety A is about 12. In some instances, the DAR ratio of the polynucleic acid molecule (B) to binding moiety A is about 13. In some instances, the DAR ratio of the polynucleic acid molecule (B) to binding moiety A is about 14. In some instances, the DAR ratio of the polynucleic acid molecule (B) to binding moiety A is about 15. In some instances, the DAR ratio of the polynucleic acid molecule (B) to binding moiety A is about 16.

In some instances, the DAR ratio of the polynucleic acid molecule (B) to binding moiety A is 1, 2, 3, 4, 5, 6, 7, 8, 9, 10, 11, 12, 13, 14, 15, or 16. In some instances, the DAR ratio of the polynucleic acid molecule (B) to binding moiety A is 1. In some instances, the DAR ratio of the polynucleic acid molecule (B) to binding moiety A is 2. In some instances, the DAR ratio of the polynucleic acid molecule (B) to binding moiety A is 4. In some instances, the DAR ratio of the polynucleic acid molecule (B) to binding moiety A is 6. In some instances, the DAR ratio of the polynucleic acid molecule (B) to binding moiety A is 8. In some instances, the DAR ratio of the polynucleic acid molecule (B) to binding moiety A is 12.

In some instances, a conjugate comprising polynucleic acid molecule (B) and binding moiety A has improved activity as compared to a conjugate comprising polynucleic acid molecule (B) without a binding moiety A. In some instances, improved activity results in enhanced biologically relevant functions, e.g., improved stability, affinity, binding, functional activity, and efficacy in treatment or prevention of a disease state. In some instances, the disease state is a result of one or more mutated exons of a gene. In some instances, the conjugate comprising polynucleic acid molecule (B) and binding moiety A results in increased exon skipping of the one or more mutated exons as compared to the conjugate comprising polynucleic acid molecule (B) without a binding moiety A. In some instances, exon skipping is increased by at least or about 5%, 10%, 20%, 25%, 30%, 40%, 50%, 60%, 70%, 80%, 90%, 95%, or more than 95% in the conjugate comprising polynucleic acid molecule (B) and binding moiety A as compared to the conjugate comprising polynucleic acid molecule (B) without a binding moiety A.

In some embodiments, an antibody or its binding fragment is further modified using conventional techniques known in the art, for example, by using amino acid deletion, insertion, substitution, addition, and/or by recombination and/or any other modification (e.g. posttranslational and chemical modifications, such as glycosylation and phosphorylation) known in the art either alone or in combination. In some instances, the modification further comprises a modification for modulating interaction with Fc receptors. In some instances, the one or more modifications include those described in, for example, International Publication No. WO97/34631, which discloses amino acid residues involved in the interaction between the Fc domain and the FcRn receptor. Methods for introducing such modifications in the nucleic acid sequence underlying the amino acid sequence of an antibody or its binding fragment is well known to the person skilled in the art.

In some instances, an antibody binding fragment further encompasses its derivatives and includes polypeptide sequences containing at least one CDR.

In some instances, the term "single-chain" as used herein means that the first and second domains of a bi-specific single chain construct are covalently linked, preferably in the form of a co-linear amino acid sequence encodable by a single nucleic acid molecule.

In some instances, a bispecific single chain antibody construct relates to a construct comprising two antibody derived binding domains. In such embodiments, bi-specific single chain antibody construct is tandem bi-scFv or diabody. In some instances, a scFv contains a VH and VL domain connected by a linker peptide. In some instances, linkers are of a length and sequence sufficient to ensure that each of the first and second domains can, independently from one another, retain their differential binding specificities.

In some embodiments, binding to or interacting with as used herein defines a binding/interaction of at least two antigen-interaction-sites with each other. In some instances, antigen-interaction-site defines a motif of a polypeptide that shows the capacity of specific interaction with a specific antigen or a specific group of antigens. In some cases, the binding/interaction is also understood to define a specific recognition. In such cases, specific recognition refers to that the antibody or its binding fragment is capable of specifically interacting with and/or binding to at least two amino acids of each of a target molecule. For example, specific recognition relates to the specificity of the antibody molecule, or to its ability to discriminate between the specific regions of a target molecule. In additional instances, the specific interaction of the antigen-interaction-site with its specific antigen results in an initiation of a signal, e.g. due to the induction of a change of the conformation of the antigen, an oligomerization of the antigen, etc. In further embodiments, the binding is exemplified by the specificity of a "key-lock-principle". Thus in some instances, specific motifs in the amino acid sequence of the antigen-interaction-site and the antigen bind to each other as a result of their primary, secondary or tertiary structure as well as the result of secondary modifications of said structure. In such cases, the specific interaction of the antigen-interaction-site with its specific antigen results as well in a simple binding of the site to the antigen.

In some instances, specific interaction further refers to a reduced cross-reactivity of the antibody or its binding fragment or a reduced off-target effect. For example, the antibody or its binding fragment that bind to the polypeptide/protein of interest but do not or do not essentially bind to any of the other polypeptides are considered as specific for the polypeptide/protein of interest. Examples for the specific interaction of an antigen-interaction-site with a specific antigen comprise the specificity of a ligand for its receptor, for example, the interaction of an antigenic determinant (epitope) with the antigenic binding site of an antibody.

Conjugation Chemistry

In some embodiments, a polynucleic acid molecule B is conjugated to a binding moiety. In some instances, the binding moiety comprises amino acids, peptides, polypeptides, proteins, antibodies, antigens, toxins, hormones, lipids, nucleotides, nucleosides, sugars, carbohydrates, polymers such as polyethylene glycol and polypropylene glycol, as well as analogs or derivatives of all of these classes of substances. Additional examples of binding moiety also include steroids, such as cholesterol, phospholipids, di- and triacylglycerols, fatty acids, hydrocarbons (e.g., saturated, unsaturated, or contains substitutions), enzyme substrates, biotin, digoxigenin, and polysaccharides. In some instances, the binding moiety is an antibody or binding fragment thereof. In some instances, the polynucleic acid molecule is further conjugated to a polymer, and optionally an endosomolytic moiety.

In some embodiments, the polynucleic acid molecule is conjugated to the binding moiety by a chemical ligation process. In some instances, the polynucleic acid molecule is conjugated to the binding moiety by a native ligation. In some instances, the conjugation is as described in: Dawson, et al. "Synthesis of proteins by native chemical ligation," *Science* 1994, 266, 776-779; Dawson, et al. "Modulation of Reactivity in Native Chemical Ligation through the Use of Thiol Additives," *J. Am. Chem. Soc.* 1997, 119, 4325-4329; Hackeng, et al. "Protein synthesis by native chemical ligation: Expanded scope by using straightforward methodology.," *Proc. Natl. Acad. Sci. USA* 1999, 96, 10068-10073; or Wu, et al. "Building complex glycopeptides: Development of a cysteine-free native chemical ligation protocol," *Angew. Chem. Int. Ed.* 2006, 45, 4116-4125. In some instances, the conjugation is as described in U.S. Pat. No. 8,936,910. In some embodiments, the polynucleic acid molecule is conjugated to the binding moiety either site-specifically or non-specifically via native ligation chemistry.

In some instances, the polynucleic acid molecule is conjugated to the binding moiety by a site-directed method utilizing a "traceless" coupling technology (Philochem). In some instances, the "traceless" coupling technology utilizes an N-terminal 1,2-aminothiol group on the binding moiety which is then conjugate with a polynucleic acid molecule containing an aldehyde group. (see Casi et al., "Site-specific traceless coupling of potent cytotoxic drugs to recombinant antibodies for pharmacodelivery," *JACS* 134(13): 5887-5892 (2012))

In some instances, the polynucleic acid molecule is conjugated to the binding moiety by a site-directed method utilizing an unnatural amino acid incorporated into the binding moiety. In some instances, the unnatural amino acid comprises p-acetylphenylalanine (pAcPhe). In some instances, the keto group of pAcPhe is selectively coupled to an alkoxy-amine derivatived conjugating moiety to form an oxime bond. (see Axup et al., "Synthesis of site-specific antibody-drug conjugates using unnatural amino acids," *PNAS* 109(40): 16101-16106 (2012)).

In some instances, the polynucleic acid molecule is conjugated to the binding moiety by a site-directed method utilizing an enzyme-catalyzed process. In some instances, the site-directed method utilizes SMARTag™ technology (Redwood). In some instances, the SMARTag™ technology comprises generation of a formylglycine (FGly) residue from cysteine by formylglycine-generating enzyme (FGE) through an oxidation process under the presence of an aldehyde tag and the subsequent conjugation of FGly to an alkylhydraine-functionalized polynucleic acid molecule via hydrazino-Pictet-Spengler (HIPS) ligation. (see Wu et al., "Site-specific chemical modification of recombinant proteins produced in mammalian cells by using the genetically encoded aldehyde tag," *PNAS* 106(9): 3000-3005 (2009); Agarwal, et al., "A Pictet-Spengler ligation for protein chemical modification," *PNAS* 110(1): 46-51 (2013))

In some instances, the enzyme-catalyzed process comprises microbial transglutaminase (mTG). In some cases, the polynucleic acid molecule is conjugated to the binding moiety utilizing a microbial transglutaminze catalyzed process. In some instances, mTG catalyzes the formation of a covalent bond between the amide side chain of a glutamine within the recognition sequence and a primary amine of a functionalized polynucleic acid molecule. In some instances, mTG is produced from *Streptomyces mobarensis*. (see Strop et al., "Location matters: site of conjugation modulates stability and pharmacokinetics of antibody drug conjugates," *Chemistry and Biology* 20(2) 161-167 (2013))

In some instances, the polynucleic acid molecule is conjugated to the binding moiety by a method as described in PCT Publication No. WO2014/140317, which utilizes a sequence-specific transpeptidase.

In some instances, the polynucleic acid molecule is conjugated to the binding moiety by a method as described in U.S. Patent Publication Nos. 2015/0105539 and 2015/0105540.

Production of Antibodies or Binding Fragments Thereof

In some embodiments, polypeptides described herein (e.g., antibodies and its binding fragments) are produced using any method known in the art to be useful for the synthesis of polypeptides (e.g., antibodies), in particular, by chemical synthesis or by recombinant expression, and are preferably produced by recombinant expression techniques.

In some instances, an antibody or its binding fragment thereof is expressed recombinantly, and the nucleic acid encoding the antibody or its binding fragment is assembled from chemically synthesized oligonucleotides (e.g., as described in Kutmeier et al., 1994, *BioTechniques* 17:242), which involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody is optionally generated from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

In some instances, an antibody or its binding is optionally generated by immunizing an animal, such as a rabbit, to generate polyclonal antibodies or, more preferably, by generating monoclonal antibodies, e.g., as described by Kohler and Milstein (1975, *Nature* 256:495-497) or, as described by Kozbor et al. (1983, *Immunology Today* 4:72) or Cole et al. (1985 in *Monoclonal Antibodies and Cancer Therapy*, Alan R. Liss, Inc., pp. 77-96). Alternatively, a clone encoding at least the Fab portion of the antibody is optionally obtained by screening Fab expression libraries (e.g., as described in Huse et al., 1989, *Science* 246:1275-1281) for clones of Fab fragments that bind the specific antigen or by screening antibody libraries (See, e.g., Clackson et al., 1991, *Nature* 352:624; Hane et al., 1997 *Proc. Natl. Acad. Sci. USA* 94:4937).

In some embodiments, techniques developed for the production of "chimeric antibodies" (Morrison et al., 1984, *Proc. Natl. Acad. Sci.* 81:851-855; Neuberger et al., 1984, *Nature* 312:604-608; Takeda et al., 1985, *Nature* 314:452-454) by splicing genes from a mouse antibody molecule of appropriate antigen specificity together with genes from a human antibody molecule of appropriate biological activity are used. A chimeric antibody is a molecule in which different portions are derived from different animal species, such as those having a variable region derived from a murine monoclonal antibody and a human immunoglobulin constant region, e.g., humanized antibodies.

In some embodiments, techniques described for the production of single chain antibodies (U.S. Pat. No. 4,694,778; Bird, 1988, *Science* 242:423-42; Huston et al., 1988, *Proc. Natl. Acad. Sci. USA* 85:5879-5883; and Ward et al., 1989, *Nature* 334:544-54) are adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* are also optionally used (Skerra et al., 1988, *Science* 242:1038-1041).

In some embodiments, an expression vector comprising the nucleotide sequence of an antibody or the nucleotide sequence of an antibody is transferred to a host cell by conventional techniques (e.g., electroporation, liposomal transfection, and calcium phosphate precipitation), and the transfected cells are then cultured by conventional techniques to produce the antibody. In specific embodiments, the expression of the antibody is regulated by a constitutive, an inducible or a tissue, specific promoter.

In some embodiments, a variety of host-expression vector systems is utilized to express an antibody or its binding fragment described herein. Such host-expression systems represent vehicles by which the coding sequences of the antibody is produced and subsequently purified, but also represent cells that are, when transformed or transfected with the appropriate nucleotide coding sequences, express an antibody or its binding fragment in situ. These include, but are not limited to, microorganisms such as bacteria (e.g., *E. coli* and *B. subtilis*) transformed with recombinant bacteriophage DNA, plasmid DNA or cosmid DNA expression vectors containing an antibody or its binding fragment coding sequences; yeast (e.g., *Saccharomyces Pichia*) transformed with recombinant yeast expression vectors containing an antibody or its binding fragment coding sequences; insect cell systems infected with recombinant virus expression vectors (e.g., baculovirus) containing an antibody or its binding fragment coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing an antibody or its binding fragment coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g. the adenovirus late promoter; the vaccinia virus 7.5K promoter).

For long-term, high-yield production of recombinant proteins, stable expression is preferred. In some instances, cell lines that stably express an antibody are optionally engineered. Rather than using expression vectors that contain viral origins of replication, host cells are transformed with DNA controlled by appropriate expression control elements (e.g., promoter, enhancer, sequences, transcription terminators, polyadenylation sites, etc.), and a selectable marker. Following the introduction of the foreign DNA, engineered cells are then allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn are cloned and expanded into cell lines. This method can advantageously be used to engineer cell lines which express the antibody or its binding fragments.

In some instances, a number of selection systems are used, including but not limited to the herpes simplex virus thymidine kinase (Wigler et al., 1977, *Cell* 11:223), hypoxanthine-guanine phosphoribosyltransferase (Szybalska & Szybalski, 192, *Proc. Natl. Acad. Sci. USA* 48:202), and adenine phosphoribosyltransferase (Lowy et al., 1980, *Cell* 22:817) genes are employed in tk–, hgprt– or aprt– cells, respectively. Also, antimetabolite resistance are used as the basis of selection for the following genes: dhfr, which confers resistance to methotrexate (Wigler et al., 1980, *Proc. Natl. Acad. Sci. USA* 77:357; O'Hare et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (Clinical Pharmacy 12:488-505; Wu and Wu, 1991, *Biotherapy* 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217; May, 1993, *TIB TECH* 11(5):155-215) and hygro, which confers resistance to hygromycin (Santerre et al., 1984, *Gene* 30:147). Methods commonly known in the art of recombinant DNA technology which can be used are described in Ausubel et al. (eds., 1993, *Current Protocols in Molecular Biology*, John Wiley & Sons, NY; Kriegler, 1990, Gene Transfer and Expression, *A Laboratory Manual*, Stockton Press, NY; and in Chapters 12 and 13, Dracopoli et al. (eds), 1994, *Current Protocols in Human Genetics*, John Wiley & Sons, NY.; Colberre-Garapin et al., 1981, *J. Mol. Biol.* 150:1).

In some instances, the expression levels of an antibody are increased by vector amplification (for a review, see Bebbington and Hentschel, *The use of vectors based on gene amplification for the expression of cloned genes in mammalian cells in DNA cloning*, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (Crouse et al., 1983, *Mol. Cell Biol.* 3:257).

In some instances, any method known in the art for purification or analysis of an antibody or antibody conjugates is used, for example, by chromatography (e.g., ion exchange, affinity, particularly by affinity for the specific antigen after Protein A, and sizing column chromatography), centrifugation, differential solubility, or by any other standard technique for the purification of proteins. Exemplary chromatography methods included, but are not limited to, strong anion exchange chromatography, hydrophobic interaction chromatography, size exclusion chromatography, and fast protein liquid chromatography.

Polymer Conjugating Moiety

In some embodiments, a polymer moiety C is further conjugated to a polynucleic acid molecule described herein, a binding moiety described herein, or in combinations thereof. In some instances, a polymer moiety C is conjugated a polynucleic acid molecule. In some cases, a polymer moiety C is conjugated to a binding moiety. In other cases, a polymer moiety C is conjugated to a polynucleic acid molecule-binding moiety molecule. In additional cases, a polymer moiety C is conjugated, as illustrated supra.

In some instances, the polymer moiety C is a natural or synthetic polymer, consisting of long chains of branched or unbranched monomers, and/or cross-linked network of monomers in two or three dimensions. In some instances, the polymer moiety C includes a polysaccharide, lignin, rubber, or polyalkylen oxide (e.g., polyethylene glycol). In some instances, the at least one polymer moiety C includes, but is not limited to, alpha-, omega-dihydroxylpolyethyleneglycol, biodegradable lactone-based polymer, e.g. polyacrylic acid, polylactide acid (PLA), poly(glycolic acid) (PGA), polypropylene, polystyrene, polyolefin, polyamide, polycyanoacrylate, polyimide, polyethylenterephthalat (PET, PETG), polyethylene terephthalate (PETE), polytetramethylene glycol (PTG), or polyurethane as well as mixtures thereof. As used herein, a mixture refers to the use of different polymers within the same compound as well as in reference to block copolymers. In some cases, block copolymers are polymers wherein at least one section of a polymer is build up from monomers of another polymer. In some instances, the polymer moiety C comprises polyalkylene oxide. In some instances, the polymer moiety C comprises PEG. In some instances, the polymer moiety C comprises polyethylene imide (PEI) or hydroxy ethyl starch (HES).

In some instances, C is a PEG moiety. In some instances, the PEG moiety is conjugated at the 5' terminus of the polynucleic acid molecule while the binding moiety is conjugated at the 3' terminus of the polynucleic acid molecule. In some instances, the PEG moiety is conjugated at the 3' terminus of the polynucleic acid molecule while the binding moiety is conjugated at the 5' terminus of the polynucleic acid molecule. In some instances, the PEG moiety is conjugated to an internal site of the polynucleic acid molecule. In some instances, the PEG moiety, the binding moiety, or a combination thereof, are conjugated to an internal site of the polynucleic acid molecule. In some instances, the conjugation is a direct conjugation. In some instances, the conjugation is via native ligation.

In some embodiments, the polyalkylene oxide (e.g., PEG) is a polydispers or monodispers compound. In some instances, polydispers material comprises disperse distribution of different molecular weight of the material, characterized by mean weight (weight average) size and dispersity. In some instances, the monodisperse PEG comprises one size of molecules. In some embodiments, C is poly- or monodispersed polyalkylene oxide (e.g., PEG) and the indicated molecular weight represents an average of the molecular weight of the polyalkylene oxide, e.g., PEG, molecules.

In some embodiments, the molecular weight of the polyalkylene oxide (e.g., PEG) is about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da.

In some embodiments, C is polyalkylene oxide (e.g., PEG) and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some embodiments, C is PEG and has a molecular weight of about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da. In some instances, the molecular weight of C is about 200 Da. In some instances, the molecular weight of C is about 300 Da. In some instances, the molecular weight of C is about 400 Da. In some instances, the molecular weight of C is about 500 Da. In some instances, the molecular weight of C is about 600 Da. In some instances, the molecular weight of C is about 700 Da. In some instances, the molecular weight of C is about 800 Da. In some instances, the molecular weight of C is about 900 Da. In some instances, the molecular weight of C is about 1000 Da. In some instances, the molecular weight of C is about 1100 Da. In some instances, the molecular weight of C is about 1200 Da. In some instances, the molecular weight of C is about 1300 Da. In some instances, the molecular weight of C is about 1400 Da. In some instances, the molecular weight of C is about 1450 Da. In some instances, the molecular weight of C is about 1500 Da. In some instances, the molecular weight of C is about 1600 Da. In some instances, the molecular weight of C is about 1700 Da. In some instances, the molecular weight of C is about 1800 Da. In some instances, the molecular weight of C is about 1900 Da. In some instances, the molecular weight of C is about 2000 Da. In some instances, the molecular weight of C is about 2100 Da. In some instances, the molecular weight of C is about 2200 Da. In some instances, the molecular weight of C is about 2300 Da. In some instances, the molecular weight of C is about 2400 Da. In some instances, the molecular weight of C is about 2500 Da. In some instances, the molecular weight of C is about 2600 Da. In some instances, the molecular weight of C is about 2700 Da. In some instances, the molecular weight of C is about 2800 Da. In some instances, the molecular weight of C is about 2900 Da. In some instances, the molecular weight of C is about 3000 Da. In some instances, the molecular weight of C is about 3250 Da. In some instances, the molecular weight of C is about 3350 Da. In some instances, the molecular weight of C is about 3500 Da. In some instances, the molecular weight of C is about 3750 Da. In some instances, the molecular weight of C is about 4000 Da. In some instances, the molecular weight of C is about 4250 Da. In some instances, the molecular weight of C is about 4500 Da. In some instances, the molecular weight of C is about 4600 Da. In some instances, the molecular weight of C is about 4750 Da. In some instances, the molecular weight of C is about 5000 Da. In some instances, the molecular weight of C is about 5500 Da. In some instances, the molecular weight of C is about 6000 Da. In some instances, the molecular weight of C is about 6500 Da. In some instances, the molecular weight of C is about 7000 Da. In some instances, the molecular weight of C is about 7500 Da. In some instances, the molecular weight of C is about 8000 Da. In some instances, the molecular weight of C is about 10,000 Da. In some instances, the molecular weight of C is about 12,000 Da. In some instances, the molecular weight of C is about 20,000 Da. In some instances, the molecular weight of C is about 35,000 Da. In some instances, the molecular weight of C is about 40,000 Da. In some instances, the molecular weight of C is about 50,000 Da. In some instances, the molecular weight of C is about 60,000 Da. In some instances, the molecular weight of C is about 100,000 Da.

In some embodiments, the polyalkylene oxide (e.g., PEG) comprises discrete ethylene oxide units (e.g., four to about 48 ethylene oxide units). In some instances, the polyalkylene oxide comprising the discrete ethylene oxide units is a linear chain. In other cases, the polyalkylene oxide comprising the discrete ethylene oxide units is a branched chain.

In some instances, the polymer moiety C is a polyalkylene oxide (e.g., PEG) comprising discrete ethylene oxide units. In some cases, the polymer moiety C comprises between about 4 and about 48 ethylene oxide units. In some cases, the polymer moiety C comprises about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, or about 48 ethylene oxide units.

In some instances, the polymer moiety C is a discrete PEG comprising, e.g., between about 4 and about 48 ethylene oxide units. In some cases, the polymer moiety C is a discrete PEG comprising, e.g., about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, or about 48 ethylene oxide units. In some cases, the polymer moiety C is a discrete PEG comprising, e.g., about 4 ethylene oxide units. In some cases, the polymer moiety C is a discrete PEG comprising, e.g., about 5 ethylene oxide units. In some cases, the polymer moiety C is a discrete PEG comprising, e.g., about 6 ethylene oxide units. In some cases, the polymer moiety C is a discrete PEG comprising, e.g., about 7 ethylene oxide units. In some cases, the polymer moiety C is a discrete PEG comprising, e.g., about 8 ethylene oxide units. In some cases, the polymer moiety C is a discrete PEG comprising, e.g., about 9 ethylene oxide units. In some cases, the polymer moiety C is a discrete PEG comprising, e.g., about 10 ethylene oxide units. In some cases, the polymer moiety C is a discrete PEG comprising, e.g., about 11 ethylene oxide units. In some cases, the polymer moiety C is a discrete PEG comprising, e.g., about 12 ethylene oxide units. In some cases, the polymer moiety C is a discrete PEG comprising, e.g., about 13 ethylene oxide units. In some cases, the polymer moiety C is a discrete PEG comprising, e.g., about 14 ethylene oxide units. In some cases, the polymer moiety C is a discrete PEG comprising, e.g., about 15 ethylene oxide units. In some cases, the polymer moiety C is a discrete PEG comprising, e.g., about 16 ethylene oxide units. In some cases, the polymer moiety C is a discrete PEG comprising, e.g., about 17 ethylene oxide units. In some cases, the polymer moiety C is a discrete PEG comprising, e.g., about 18 ethylene oxide units. In some cases, the polymer moiety C is a discrete PEG comprising, e.g., about 19 ethylene oxide units. In some cases, the polymer moiety C is a discrete PEG comprising, e.g., about 20 ethylene oxide units. In some cases, the polymer moiety C is a discrete PEG comprising, e.g., about 21 ethylene oxide units. In some cases, the polymer moiety C is a discrete PEG comprising, e.g., about 22 ethylene oxide units. In some cases, the polymer moiety C is a discrete PEG comprising, e.g., about 23 ethylene oxide units. In some cases, the polymer moiety C is a discrete PEG comprising, e.g., about 24 ethylene oxide units. In some cases, the polymer moiety C is a discrete PEG comprising, e.g., about 25 ethylene oxide units. In some cases, the polymer moiety C is a discrete PEG comprising, e.g., about 26 ethylene oxide units. In some cases, the polymer moiety C is a discrete PEG comprising, e.g., about 27 ethylene oxide units. In some cases, the polymer moiety C is a discrete PEG comprising, e.g., about 28 ethylene oxide units. In some cases, the polymer moiety C is a discrete PEG comprising, e.g., about 29 ethylene oxide units. In some cases, the polymer moiety C is a discrete PEG comprising, e.g., about 30 ethylene oxide units. In some cases, the polymer moiety C is a discrete PEG comprising, e.g., about 31 ethylene oxide units. In some cases, the polymer moiety C is a discrete PEG comprising, e.g., about 32 ethylene oxide units. In some cases, the polymer moiety C is a discrete PEG comprising, e.g., about 33 ethylene oxide units. In some cases, the polymer moiety C is a discrete PEG comprising, e.g., about 34 ethylene oxide units. In some cases, the polymer moiety C is a discrete PEG comprising, e.g., about 35 ethylene oxide units. In some cases, the polymer moiety C is a discrete PEG comprising, e.g., about 36 ethylene oxide units. In some cases, the polymer moiety C is a discrete PEG comprising, e.g., about 37 ethylene oxide units. In some cases, the polymer moiety C is a discrete PEG comprising, e.g., about 38 ethylene oxide units. In some cases, the polymer moiety C is a discrete PEG comprising, e.g., about 39 ethylene oxide units. In some cases, the polymer moiety C is a discrete PEG comprising, e.g., about 40 ethylene oxide units. In some cases, the polymer moiety C is a discrete PEG comprising, e.g., about 41 ethylene oxide units. In some cases, the polymer moiety C is a discrete PEG comprising, e.g., about 42 ethylene oxide units. In some cases, the polymer moiety C is a discrete PEG comprising, e.g., about 43 ethylene oxide units. In some cases, the polymer moiety C is a discrete PEG comprising, e.g., about 44 ethylene oxide units. In some cases, the polymer moiety C is a discrete PEG comprising, e.g., about 45 ethylene oxide units. In some cases, the polymer moiety C is a discrete PEG comprising, e.g., about 46 ethylene oxide units. In some cases, the polymer moiety C is a discrete PEG comprising, e.g., about 47 ethylene oxide units. In some cases, the polymer moiety C is a discrete PEG comprising, e.g., about 48 ethylene oxide units.

In some cases, the polymer moiety C is dPEG® (Quanta Biodesign Ltd).

In some embodiments, the polymer moiety C comprises a cationic mucic acid-based polymer (cMAP). In some instances, cMAP comprises one or more subunit of at least one repeating subunit, and the subunit structure is represented as Formula (V):

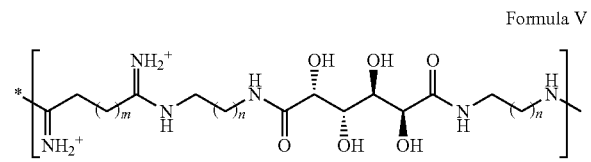

Formula V wherein m is independently at each occurrence 1, 2, 3, 4, 5, 6, 7, 8, 9, or 10, preferably 4-6 or 5; and n is independently at each occurrence 1, 2, 3, 4, or 5. In some embodiments, m and n are, for example, about 10.

In some instances, cMAP is further conjugated to a PEG moiety, generating a cMAP-PEG copolymer, an mPEG-cMAP-PEGm triblock polymer, or a cMAP-PEG-cMAP triblock polymer. In some instances, the PEG moiety is in a range of from about 500 Da to about 50,000 Da. In some instances, the PEG moiety is in a range of from about 500 Da to about 1000 Da, greater than 1000 Da to about 5000 Da, greater than 5000 Da to about 10,000 Da, greater than 10,000 to about 25,000 Da, greater than 25,000 Da to about 50,000 Da, or any combination of two or more of these ranges.

In some instances, the polymer moiety C is cMAP-PEG copolymer, an mPEG-cMAP-PEGm triblock polymer, or a cMAP-PEG-cMAP triblock polymer. In some cases, the polymer moiety C is cMAP-PEG copolymer. In other cases, the polymer moiety C is an mPEG-cMAP-PEGm triblock polymer. In additional cases, the polymer moiety C is a cMAP-PEG-cMAP triblock polymer.

In some embodiments, the polymer moiety C is conjugated to the polynucleic acid molecule, the binding moiety, and optionally to the endosomolytic moiety as illustrated supra.

Endosomolytic Moiety

In some embodiments, a molecule of Formula (I): A-X—B—Y—C, further comprises an additional conjugating moiety. In some instances, the additional conjugating moiety is an endosomolytic moiety. In some cases, the endosomolytic moiety is a cellular compartmental release component, such as a compound capable of releasing from any of the cellular compartments known in the art, such as the endosome, lysosome, endoplasmic reticulum (ER), golgi apparatus, microtubule, peroxisome, or other vesicular bodies with the cell. In some cases, the endosomolytic moiety comprises an endosomolytic polypeptide, an endosomolytic polymer, an endosomolytic lipid, or an endosomolytic small molecule. In some cases, the endosomolytic moiety comprises an endosomolytic polypeptide. In other cases, the endosomolytic moiety comprises an endosomolytic polymer.

Endosomolytic Polypeptides

In some embodiments, a molecule of Formula (I): A-X—B—Y—C, is further conjugated with an endosomolytic polypeptide. In some cases, the endosomolytic polypeptide is a pH-dependent membrane active peptide. In some cases, the endosomolytic polypeptide is an amphipathic polypeptide. In additional cases, the endosomolytic polypeptide is a peptidomimetic. In some instances, the endosomolytic polypeptide comprises INF, melittin, meucin, or their respective derivatives thereof. In some instances, the endosomolytic polypeptide comprises INF or its derivatives thereof. In other cases, the endosomolytic polypeptide comprises melittin or its derivatives thereof. In additional cases, the endosomolytic polypeptide comprises meucin or its derivatives thereof.

In some instances, INF7 is a 24 residue polypeptide those sequence comprises CGIFGEIEELIEEGLENLIDWGNA (SEQ ID NO: 1), or GLFEAIEGFIENGWEGMIDGWYGC (SEQ ID NO: 2). In some instances, INF7 or its derivatives comprise a sequence of: GLFEAIEGFIENGWEG-MIWDYGSGSCG (SEQ ID NO: 3), GLFEAIEGFIEN-GWEGMIDGWYG-(PEG)6-NH2 (SEQ ID NO: 4), or GLFEAIEGFIENGWEGMIWDYG-SGSC-K(GalNAc)2 (SEQ ID NO: 5).

In some cases, melittin is a 26 residue polypeptide those sequence comprises CLIGAILKVLATGLPTLISWIKNK-RKQ (SEQ ID NO: 6), or GIGAVLKVLTTGLPAL-ISWIKRKRQQ (SEQ ID NO: 7). In some instances, melittin comprises a polypeptide sequence as described in U.S. Pat. No. 8,501,930.

In some instances, meucin is an antimicrobial peptide (AMP) derived from the venom gland of the scorpion *Mesobuthus eupeus*. In some instances, meucin comprises of meucin-13 those sequence comprises IFGAIAGLLKNIF-NH$_2$ (SEQ ID NO: 8) and meucin-18 those sequence comprises FFGHLFKLATKIIPSLFQ (SEQ ID NO: 9).

In some instances, the endosomolytic polypeptide comprises a polypeptide in which its sequence is at least 50%, 60%, 70%, 80%, 90%, 95%, or 99% sequence identity to INF7 or its derivatives thereof, melittin or its derivatives thereof, or meucin or its derivatives thereof. In some instances, the endosomolytic moiety comprises INF7 or its derivatives thereof, melittin or its derivatives thereof, or meucin or its derivatives thereof.

In some instances, the endosomolytic moiety is INF7 or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 1-5. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 1. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 2-5. In some cases, the endosomolytic moiety comprises SEQ ID NO: 1. In some cases, the endosomolytic moiety comprises SEQ ID NO: 2-5. In some cases, the endosomolytic moiety consists of SEQ ID NO: 1. In some cases, the endosomolytic moiety consists of SEQ ID NO: 2-5.

In some instances, the endosomolytic moiety is melittin or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 6 or 7. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 6. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 7. In some cases, the endosomolytic moiety comprises SEQ ID NO: 6. In some cases, the endosomolytic moiety comprises SEQ ID NO: 7. In some cases, the endosomolytic moiety consists of SEQ ID NO: 6. In some cases, the endosomolytic moiety consists of SEQ ID NO: 7.

In some instances, the endosomolytic moiety is meucin or its derivatives thereof. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NOs: 8 or 9. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 8. In some cases, the endosomolytic moiety comprises a polypeptide having at least 50%, 55%, 60%, 65%, 70%, 75%, 80%, 85%, 90%, 95%, 96%, 97%, 98%, 99%, or 100% sequence identity to SEQ ID NO: 9. In some cases, the endosomolytic moiety comprises SEQ ID NO: 8. In some cases, the endosomolytic moiety comprises SEQ ID NO: 9. In some cases, the endosomolytic moiety consists of SEQ ID NO: 8. In some cases, the endosomolytic moiety consists of SEQ ID NO: 9.

In some instances, the endosomolytic moiety comprises a sequence as illustrated in Table 1.

TABLE 1

| Name | Origin | Amino Acid Sequence | SEQ ID NO: | Type |
|---|---|---|---|---|
| Pep-1 | NLS from Simian Virus 40 large antigen and Reverse transcriptase of HIV | KETWWETWWTEWSQPKKKRKV | 10 | Primary amphipathic |
| pVEC | VE-cadherin | LLIILRRRRIRKQAHAHSK | 11 | Primary amphipathic |
| VT5 | Synthetic peptide | DPKGDPKGVTVTVTVTGKGDPKPD | 12 | β-sheet amphipathic |
| C105Y | 1-antitrypsin | CSIPPEVKFNKPFVYLI | 13 | — |
| Transportan | Galanin and mastoparan | GWTLNSAGYLLGKINLKALAALAKKIL | 14 | Primary amphipathic |
| TP10 | Galanin and mastoparan | AGYLLGKINLKALAALAKKIL | 15 | Primary amphipathic |
| MPG | A hydrofobic domain from the fusion sequence of HIV gp41 and NLS of SV40 T antigen | GALFLGFLGAAGSTMGA | 16 | β-sheet amphipathic |
| gH625 | Glycoprotein gH of HSV type I | HGLASTLTRWAHYNALIRAF | 17 | Secondary amphipathic α-helical |
| CADY | PPTG1 peptide | GLWRALWRLLRSLWRLLWRA | 18 | Secondary amphipathic α-helical |
| GALA | Synthetic peptide | WEAALAEALAEALAEHLAEALAEALEALAA | 19 | Secondary amphipathic α-helical |
| INF | Influenza HA2 fusion peptide | GLFEAIEGFIENGWEGMIDGWYGC | 20 | Secondary amphipathic α-helical/ pH-dependent membrane active peptide |
| HA2E5-TAT | Influenza HA2 subunit of influenza virus X31 strain fusion peptide | GLFGAIAGFIENGWEGMIDGWYG | 21 | Secondary amphipathic α-helical/ pH-dependent membrane active peptide |
| HA2-penetratin | Influenza HA2 subunit of influenza virus X31 strain fusion peptide | GLFGAIAGFIENGWEGMIDGRQIKIWFQNRRMKWKK-amide | 22 | pH-dependent membrane active peptide |
| HA-K4 | Influenza HA2 subunit of influenza virus X31 strain fusion peptide | GLFGAIAGFIENGWEGMIDG-SSKKKK | 23 | pH-dependent membrane active peptide |
| HA2E4 | Influenza HA2 subunit of influenza virus X31 strain fusion peptide | GLFEAIAGFIENGWEGMIDGGGYC | 24 | pH-dependent membrane active peptide |

TABLE 1-continued

| Name | Origin | Amino Acid Sequence | SEQ ID NO: | Type |
|---|---|---|---|---|
| H5WYG | HA2 analogue | GLFHAIAHFIHGGWHGLIHGWYG | 25 | pH-dependent membrane active peptide |
| GALA-INF3-(PEG)6-NH | INF3 fusion peptide | GLFEAIEGFIENGWEGLAEALAEAL EALAA-(PEG)6-NH2 | 26 | pH-dependent membrane active peptide |
| CM18-TAT11 | Cecropin-A-Melittin$_{2-12}$ (CM$_{18}$) fusion peptide | KWKLFKKIGAVLKVLTTG-YGRKKRRQRRR | 27 | pH-dependent membrane active peptide |

In some cases, the endosomolytic moiety comprises a Bak BH3 polypeptide which induces apoptosis through antagonization of suppressor targets such as Bcl-2 and/or Bcl-xL. In some instances, the endosomolytic moiety comprises a Bak BH3 polypeptide described in Albarran, et al., "Efficient intracellular delivery of a pro-apoptotic peptide with a pH-responsive carrier," *Reactive & Functional Polymers* 71: 261-265 (2011).

In some instances, the endosomolytic moiety comprises a polypeptide (e.g., a cell-penetrating polypeptide) as described in PCT Publication Nos. WO2013/166155 or WO2015/069587.

Linkers

In some embodiments, a linker described herein is a cleavable linker or a non-cleavable linker. In some instances, the linker is a cleavable linker. In other instances, the linker is a non-cleavable linker.

In some cases, the linker is a non-polymeric linker. A non-polymeric linker refers to a linker that does not contain a repeating unit of monomers generated by a polymerization process. Exemplary non-polymeric linkers include, but are not limited to, $C_1$-$C_6$ alkyl group (e.g., a $C_5$, $C_4$, $C_3$, $C_2$, or $C_1$ alkyl group), homobifunctional cross linkers, heterobifunctional cross linkers, peptide linkers, traceless linkers, self-immolative linkers, maleimide-based linkers, or combinations thereof. In some cases, the non-polymeric linker comprises a $C_1$-$C_6$ alkyl group (e.g., a $C_5$, $C_4$, $C_3$, $C_2$, or $C_1$ alkyl group), a homobifunctional cross linker, a heterobifunctional cross linker, a peptide linker, a traceless linker, a self-immolative linker, a maleimide-based linker, or a combination thereof. In additional cases, the non-polymeric linker does not comprise more than two of the same type of linkers, e.g., more than two homobifunctional cross linkers, or more than two peptide linkers. In further cases, the non-polymeric linker optionally comprises one or more reactive functional groups.

In some instances, the non-polymeric linker does not encompass a polymer that is described above. In some instances, the non-polymeric linker does not encompass a polymer encompassed by the polymer moiety C. In some cases, the non-polymeric linker does not encompass a polyalkylene oxide (e.g., PEG). In some cases, the non-polymeric linker does not encompass a PEG.

In some instances, the linker comprises a homobifunctional linker. Exemplary homobifunctional linkers include, but are not limited to, Lomant's reagent dithiobis (succinimidylpropionate) DSP, 3'3'-dithiobis(sulfosuccinimidyl proprionate) (DTSSP), disuccinimidyl suberate (DSS), bis (sulfosuccinimidyl)suberate (BS), disuccinimidyl tartrate (DST), disulfosuccinimidyl tartrate (sulfo DST), ethylene glycobis(succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[(β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide).

In some embodiments, the linker comprises a heterobifunctional linker. Exemplary heterobifunctional linker include, but are not limited to, amine-reactive and sulfhydryl cross-linkers such as N-succinimidyl 3-(2-pyridyldithio) propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl)amino)hexanoate (sIAX), succinimidyl 6-[6-(((iodoacetyl)amino) hexanoyl)amino]hexanoate (sIAXX), succinimidyl 4-(((iodoacetyl)amino)methyl)cyclohexane-1-carboxylate (sIAC), succinimidyl 6-((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 (M2C2H), 3-(2- pyridyldithio)propionyl hydrazide (PDPH), amine-reactive and photoreactive cross-linkers such as N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido)hexanoate (sulfo-NHs-LC-AsA), sulfosuccinimidyl-2-(p-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(p-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), p-nitrophenyl diazopyruvate (pNPDP), p-nitrophenyl-2-diazo-3,3,3-trifluoropropionate (PNP-DTP), sulfhydryl-reactive and photoreactive cross-linkers such as 1-(p-Azidosalicylamido)-4-(iodoacetamido) butane (AsIB), N-[4-(p-azidosalicylamido)butyl]-3'-(2'-pyridyldithio)propionamide (APDP), benzophenone-4-iodoacetamide, benzophenone-4-maleimide carbonyl-reactive and photoreactive cross-linkers such as p-azidobenzoyl hydrazide (ABH), carboxylate-reactive and photoreactive cross-linkers such as 4-(p-azidosalicylamido) butylamine (AsBA), and arginine-reactive and photoreactive cross-linkers such as p-azidophenyl glyoxal (APG).

In some instances, the linker comprises a reactive functional group. In some cases, the reactive functional group comprises a nucleophilic group that is reactive to an electrophilic group present on a binding moiety. Exemplary electrophilic groups include carbonyl groups-such as aldehyde, ketone, carboxylic acid, ester, amide, enone, acyl halide or acid anhydride. In some embodiments, the reactive functional group is aldehyde. Exemplary nucleophilic groups include hydrazide, oxime, amino, hydrazine, thiosemicarbazone, hydrazine carboxylate, and arylhydrazide.

In some embodiments, the linker comprises a maleimide group. In some instances, the maleimide group is also referred to as a maleimide spacer. In some instances, the maleimide group further encompasses a caproic acid, forming maleimidocaproyl (mc). In some cases, the linker comprises maleimidocaproyl (mc). In some cases, the linker is maleimidocaproyl (mc). In other instances, the maleimide group comprises a maleimidomethyl group, such as succinimidyl-4-(N-maleimidomethyl)cyclohexane-1-carboxylate (sMCC) or sulfosuccinimidyl-4-(N-maleimidomethyl)cyclohexane-1-carboxylate (sulfo-sMCC) described above.

In some embodiments, the maleimide group is a self-stabilizing maleimide. In some instances, the self-stabilizing maleimide utilizes diaminopropionic acid (DPR) to incorporate a basic amino group adjacent to the maleimide to provide intramolecular catalysis of tiosuccinimide ring hydrolysis, thereby eliminating maleimide from undergoing an elimination reaction through a retro-Michael reaction. In some instances, the self-stabilizing maleimide is a maleimide group described in Lyon, et al., "Self-hydrolyzing maleimides improve the stability and pharmacological properties of antibody-drug conjugates," *Nat. Biotechnol.* 32(10): 1059-1062 (2014). In some instances, the linker comprises a self-stabilizing maleimide. In some instances, the linker is a self-stabilizing maleimide.

In some embodiments, the linker comprises a peptide moiety. In some instances, the peptide moiety comprises at least 2, 3, 4, 5, 6, 7, 8, or more amino acid residues. In some instances, the peptide moiety is a cleavable peptide moiety (e.g., either enzymatically or chemically). In some instances, the peptide moiety is a non-cleavable peptide moiety. In some instances, the peptide moiety comprises Val-Cit (valine-citrulline), Gly-Gly-Phe-Gly (SEQ ID NO: 973), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 974), or Gly-Phe-Leu-Gly (SEQ ID NO: 975). In some instances, the linker comprises a peptide moiety such as: Val-Cit (valine-citrulline), Gly-Gly-Phe-Gly (SEQ ID NO: 973), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 974), or Gly-Phe-Leu-Gly (SEQ ID NO: 975). In some cases, the linker comprises Val-Cit. In some cases, the linker is Val-Cit.

In some embodiments, the linker comprises a benzoic acid group, or its derivatives thereof. In some instances, the benzoic acid group or its derivatives thereof comprise paraaminobenzoic acid (PABA). In some instances, the benzoic acid group or its derivatives thereof comprise gamma-aminobutyric acid (GABA).

In some embodiments, the linker comprises one or more of a maleimide group, a peptide moiety, and/or a benzoic acid group, in any combination. In some embodiments, the linker comprises a combination of a maleimide group, a peptide moiety, and/or a benzoic acid group. In some instances, the maleimide group is maleimidocaproyl (mc). In some instances, the peptide group is val-cit. In some instances, the benzoic acid group is PABA. In some instances, the linker comprises a mc-val-cit group. In some cases, the linker comprises a val-cit-PABA group. In additional cases, the linker comprises a mc-val-cit-PABA group.

In some embodiments, the linker is a self-immolative linker or a self-elimination linker. In some cases, the linker is a self-immolative linker. In other cases, the linker is a self-elimination linker (e.g., a cyclization self-elimination linker). In some instances, the linker comprises a linker described in U.S. Pat. No. 9,089,614 or PCT Publication No. WO2015038426.

In some embodiments, the linker is a dendritic type linker. In some instances, the dendritic type linker comprises a branching, multifunctional linker moiety. In some instances, the dendritic type linker is used to increase the molar ratio of polynucleotide B to the binding moiety A. In some instances, the dendritic type linker comprises PAMAM dendrimers.

In some embodiments, the linker is a traceless linker or a linker in which after cleavage does not leave behind a linker moiety (e.g., an atom or a linker group) to a binding moiety A, a polynucleotide B, a polymer C, or an endosomolytic moiety D. Exemplary traceless linkers include, but are not limited to, germanium linkers, silicium linkers, sulfur linkers, selenium linkers, nitrogen linkers, phosphorus linkers, boron linkers, chromium linkers, or phenylhydrazine linker. In some cases, the linker is a traceless aryl-triazene linker as described in Hejesen, et al., "A traceless aryl-triazene linker for DNA-directed chemistry," *Org Biomol Chem* 11(15): 2493-2497 (2013). In some instances, the linker is a traceless linker described in Blaney, et al., "Traceless solid-phase organic synthesis," *Chem. Rev.* 102: 2607-2024 (2002). In some instances, a linker is a traceless linker as described in U.S. Pat. No. 6,821,783.

In some instances, the linker is a linker described in U.S. Pat. Nos. 6,884,869; 7,498,298; 8,288,352; 8,609,105; or 8,697,688; U.S. Patent Publication Nos. 2014/0127239; 2013/028919; 2014/286970; 2013/0309256; 2015/037360; or 2014/0294851; or PCT Publication Nos. WO2015057699; WO2014080251; WO2014197854; WO2014145090; or WO2014177042.

In some embodiments, X, Y, and L are independently a bond or a linker. In some instances, X, Y, and L are independently a bond. In some cases, X, Y, and L are independently a linker.

In some instances, X is a bond or a linker, e.g., a non-polymeric linker. In some instances, X is a bond. In some instances, X is anon-polymeric linker. In some instances, the non-polymeric linker is a $C_1$-$C_6$ alkyl group. In some cases, X is a $C_1$-$C_6$ alkyl group, such as for example, a $C_5$, $C_4$, $C_3$, $C_2$, or $C_1$ alkyl group. In some cases, the $C_1$-$C_6$ alkyl group is an unsubstituted $C_1$-$C_6$ alkyl group. As used in the context of anon-polymeric linker, and in particular in the context of X, alkyl means a saturated straight or branched hydrocarbon radical containing up to six carbon atoms. In some instances, X includes a homobifunctional linker or a heterobifunctional linker described supra. In some cases, X includes a heterobifunctional linker. In some cases, X includes sMCC. In other instances, X includes a heterobifunctional linker optionally conjugated to a $C_1$-$C_6$ alkyl group. In other instances, X includes sMCC optionally conjugated to a $C_1$-$C_6$ alkyl group. In additional instances, X does not encompass a polymer encompassed by the polymer moiety C, e.g., X does not encompass a polyalkylene oxide (e.g., a PEG molecule).

In some instances, Y is a bond or a linker, e.g., a non-polymeric linker. In some instances, Y is a bond. In other cases, Y is a non-polymeric linker. In some embodiments, Y is a $C_1$-$C_6$ alkyl group. In some instances, Y is a homobifunctional linker or a heterobifunctional linker described supra. In some instances, Y is a homobifunctional linker described supra. In some instances, Y is a heterobifunctional linker described supra. In some instances, Y comprises a maleimide group, such as maleimidocaproyl (mc) or a self-stabilizing maleimide group described above. In some instances, Y comprises a peptide moiety, such as Val-Cit. In some instances, Y comprises a benzoic acid group, such as PABA. In additional instances, Y comprises a combination of a maleimide group, a peptide moiety, and/or a benzoic acid group. In additional instances, Y comprises a me group. In additional instances, Y comprises a me-val-cit group. In additional instances, Y comprises a val-cit-PABA group. In additional instances, Y comprises a mc-val-cit-PABA group. In some cases, Y does not encompass a polymer encompassed by the polymer moiety C, e.g., Y does not encompass a polyalkylene oxide (e.g., a PEG molecule).

In some instances, L is a bond or a linker, optionally a non-polymeric linker. In some cases, L is a bond. In other cases, L is a linker, optionally anon-polymeric linker. In some embodiments, L is a $C_1$-$C_6$ alkyl group. In some instances, L is a homobifunctional linker or a heterobifunctional linker described supra. In some instances, L is a homobifunctional linker described supra. In some instances, L is a heterobifunctional linker described supra. In some instances, L comprises a maleimide group, such as maleimidocaproyl (mc) or a self-stabilizing maleimide group described above. In some instances, L comprises a peptide moiety, such as Val-Cit. In some instances, L comprises a benzoic acid group, such as PABA. In additional instances, L comprises a combination of a maleimide group, a peptide moiety, and/or a benzoic acid group. In additional instances, L comprises a me group. In additional instances, L comprises a mc-val-cit group. In additional instances, L comprises a val-cit-PABA group. In additional instances, L comprises a mc-val-cit-PABA group. In some cases, L, when optionally as a non-polymeric linker, does not encompass a polymer encompassed by the polymer moiety C, e.g., Y does not encompass a polyalkylene oxide (e.g., a PEG molecule).

Pharmaceutical Formulation

In some embodiments, the pharmaceutical formulations described herein are administered to a subject by multiple administration routes, including but not limited to, parenteral (e.g., intravenous, subcutaneous, intramuscular), oral, intranasal, buccal, rectal, or transdermal administration routes. In some instances, the pharmaceutical composition describe herein is formulated for parenteral (e.g., intravenous, subcutaneous, intramuscular, intra-arterial, intraperitoneal, intrathecal, intracerebral, intracerebroventricular, or intracranial) administration. In other instances, the pharmaceutical composition describe herein is formulated for oral administration. In still other instances, the pharmaceutical composition describe herein is formulated for intranasal administration.

In some embodiments, the pharmaceutical formulations include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations (e.g., nanoparticle formulations), and mixed immediate and controlled release formulations.

In some instances, the pharmaceutical formulation includes multiparticulate formulations. In some instances, the pharmaceutical formulation includes nanoparticle formulations. In some instances, nanoparticles comprise cMAP, cyclodextrin, or lipids. In some cases, nanoparticles comprise solid lipid nanoparticles, polymeric nanoparticles, self-emulsifying nanoparticles, liposomes, microemulsions, or micellar solutions. Additional exemplary nanoparticles include, but are not limited to, paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes and quantum dots. In some instances, a nanoparticle is a metal nanoparticle, e.g., a nanoparticle of scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum, gold, gadolinium, aluminum, gallium, indium, tin, thallium, lead, bismuth, magnesium, calcium, strontium, barium, lithium, sodium, potassium, boron, silicon, phosphorus, germanium, arsenic, antimony, and combinations, alloys or oxides thereof.

In some instances, a nanoparticle includes a core or a core and a shell, as in a core-shell nanoparticle.

In some instances, a nanoparticle is further coated with molecules for attachment of functional elements (e.g., with one or more of a polynucleic acid molecule or binding moiety described herein). In some instances, a coating comprises chondroitin sulfate, dextran sulfate, carboxymethyl dextran, alginic acid, pectin, carragheenan, fucoidan, agaropectin, porphyran, karaya gum, gellan gum, xanthan gum, hyaluronic acids, glucosamine, galactosamine, chitin (or chitosan), polyglutamic acid, polyaspartic acid, lysozyme, cytochrome C, ribonuclease, trypsinogen, chymotrypsinogen, α-chymotrypsin, polylysine, polyarginine, histone, protamine, ovalbumin or dextrin or cyclodextrin. In some instances, a nanoparticle comprises a graphene-coated nanoparticle.

In some cases, a nanoparticle has at least one dimension of less than about 500 nm, 400 nm, 300 nm, 200 nm, or 100 nm.

In some instances, the nanoparticle formulation comprises paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes or quantum dots. In some instances, a polynucleic acid molecule or a binding moiety described herein is conjugated either directly or indirectly to the nanoparticle. In some instances, at least 1, 5, 10, 15, 20, 30, 40, 50, 60, 70, 80, 90, 100 or more polynucleic acid molecules or binding moieties described herein are conjugated either directly or indirectly to a nanoparticle.

In some embodiments, the pharmaceutical formulation comprise a delivery vector, e.g., a recombinant vector, the delivery of the polynucleic acid molecule into cells. In some instances, the recombinant vector is DNA plasmid. In other instances, the recombinant vector is a viral vector. Exemplary viral vectors include vectors derived from adeno-associated virus, retrovirus, adenovirus, or alphavirus. In some instances, the recombinant vectors capable of expressing the polynucleic acid molecules provide stable expression in target cells. In additional instances, viral vectors are used that provide for transient expression of polynucleic acid molecules.

In some embodiments, the pharmaceutical formulations include a carrier or carrier materials selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrolidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

In some instances, the pharmaceutical formulations further include pH adjusting agents or buffering agents which include acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some instances, the pharmaceutical formulations further include diluent which are used to stabilize compounds because they provide a more stable environment. Salts dissolved in buffered solutions (which also provide pH control or maintenance) are utilized as diluents in the art, including, but not limited to a phosphate buffered saline solution. In certain instances, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

In some cases, the pharmaceutical formulations include disintegration agents or disintegrants to facilitate the breakup or disintegration of a substance. The term "disintegrate" include both the dissolution and dispersion of the dosage form when contacted with gastrointestinal fluid. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In some instances, the pharmaceutical formulations include filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

Lubricants and glidants are also optionally included in the pharmaceutical formulations described herein for preventing, reducing or inhibiting adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

Plasticizers include compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers also function as dispersing agents or wetting agents.

Solubilizers include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

Stabilizers include compounds such as any antioxidation agents, buffers, acids, preservatives and the like.

Suspending agents include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol has a molecular weight of about 300 to about 6000, or about 3350 to about 4000, or about 7000 to about 5400, sodium carboxymethylcellulose, methylcellulose, hydroxypropylmethylcellulose, hydroxyethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Additional surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. Sometimes, surfactants is included to enhance physical stability or for other purposes.

Viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Therapeutic Regimens

In some embodiments, the pharmaceutical compositions described herein are administered for therapeutic applications. In some embodiments, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In some embodiments, one or more pharmaceutical compositions are administered simultaneously, sequentially, or at an interval period of time. In some embodiments, one or more pharmaceutical compositions are administered simultaneously. In some cases, one or more pharmaceutical compositions are administered sequentially. In additional cases, one or more pharmaceutical compositions are administered at an interval period of time (e.g., the first administration of a first pharmaceutical composition is on day one followed by an interval of at least 1, 2, 3, 4, 5, or more days prior to the administration of at least a second pharmaceutical composition).

In some embodiments, two or more different pharmaceutical compositions are coadministered. In some instances, the two or more different pharmaceutical compositions are coadministered simultaneously. In some cases, the two or more different pharmaceutical compositions are coadministered sequentially without a gap of time between administrations. In other cases, the two or more different pharmaceutical compositions are coadministered sequentially with a gap of about 0.5 hour, 1 hour, 2 hour, 3 hour, 12 hours, 1 day, 2 days, or more between administrations.

In the case wherein the patient's status does improve, upon the doctor's discretion the administration of the composition is given continuously; alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages is altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits/Article of Manufacture

Disclosed herein, in certain embodiments, are kits and articles of manufacture for use with one or more of the compositions and methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include target nucleic acid molecule described herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

As used herein the terms "DMD," "DMD gene," and equivalents thereof refer to the DMD gene that encodes for the protein dystrophin. In addition, the terms "DMD" and "DMD gene" are used interchangeable, and both terms refer to the dystrophin gene.

EXAMPLES

These examples are provided for illustrative purposes only and not to limit the scope of the claims provided herein.

Example 1. Antisense Oligonucleotide Sequences and Synthesis

Phosphorodiamidate morpholino oligomers (PMO), phosphorothioate antisense oligonucleotides (PS ASO), and antisense oligonucleotides (ASOs) were synthesized.

The PMO sequence was

5' GGCCAAACCTCGGCTTACCTGAAAT 3'

Primary amine (SEQ ID NO: 28) and can be seen in FIG. 1 with end nucleotides expanded. The PMO contains a C3-NH$_2$ conjugation handle at the 3' end of the molecule for conjugation. PMOs were fully assembled on solid phase using standard solid phase synthesis protocols and purified over HPLC.

Figure 2A:
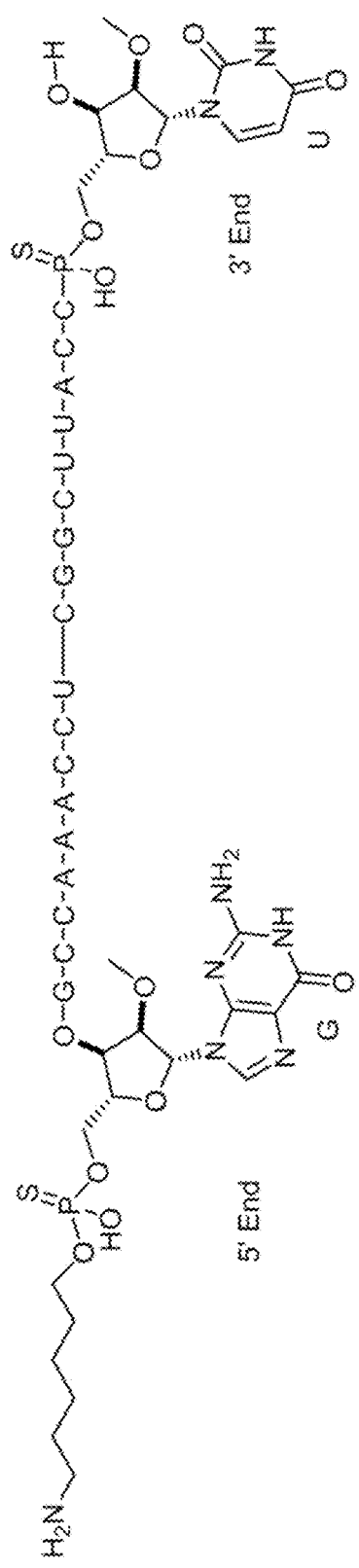
FIG. 2A depicts a phosphorothioate antisense oligonucleotide (PS ASO) sequence with end nucleotides expanded (SEQ ID NO: 29).
Figure 2B:
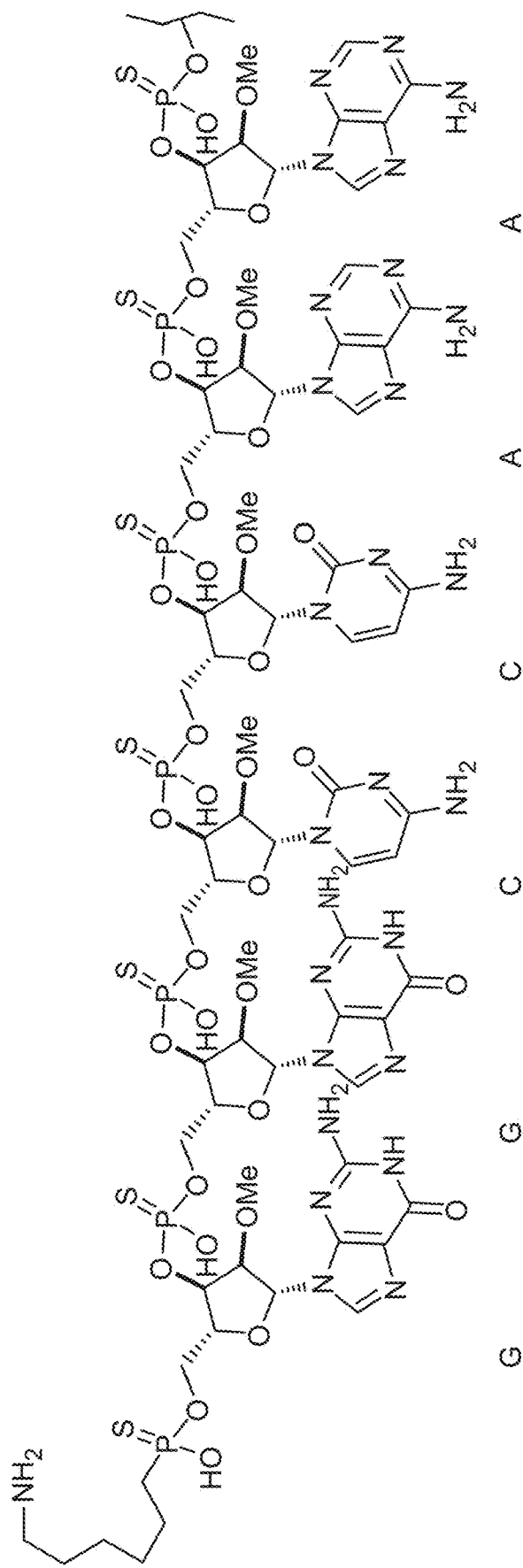
FIG. 2B depicts a fully expanded phosphorothioate antisense oligonucleotide (PS ASO) sequence (SEQ ID NO: 29).

The PS ASO sequence was (SEQ ID NO: 29)
C6-GGCCAAACCUCGGCUUACCU and can be seen in FIGS. 2A-2B with end nucleotides expanded. The structure of the PS ASO comprised a phosphate backbone that was 100% phosphorothioate linkages and all the ribose sugars contained a 2' 2'OMe modification. The PS ASO also contained a C6-NH$_2$ conjugation handle at the 5' end of the molecule for conjugation. The PS ASOs were fully assembled on the solid phase using standard solid phase phosphoramidite chemistry and purified over HPLC.

ASOs were fully assembled on the solid phase using standard solid phase phosphoramidite chemistry and purified over HPLC. ASOs contained a C6-NH$_2$ conjugation handle at the 5' end of the molecule for conjugation.

Example 2. Detection of DMD Exon Skipping

Methods for Determining DMD Exon 23 Skipping in Differentiated C1C12 Cells

Mouse myoblast C2C12 cells were plated at 50,000-100,000/well in 24-well plates in 0.5 mL 10% FBS RPMI 1640 media and incubated at 37° C. with 5% CO$_2$ overnight. On the second day, cells were switched to differentiation media (2% horse serum RPMI 1640 and 1 µM insulin) and incubated for 3-5 days. Following incubation, samples were added and incubated for 24 hours. After the sample treatment, 1 mL of fresh media (with no compounds) was changed every day for 2 more days. At 72 hours after the start of treatments, cells were harvested. RNAs were isolated using InviTrap RNA Cell HTS 96 Kit (B-Bridge International #7061300400) and reverse transcribed using High Capacity cDNA Reverse transcription Kit (ThermoFisher #4368813). PCR reactions were performed using DreamTaq™ PCR Mastermix (ThermoFisher #K1072). The primary PCR used primers in exon 20 (Ex20F 5'-CAGAAT-TCTGCCAATTGCTGAG) (SEQ ID NO; 30) and exon 26 (Ex26R 5'-TTCTTCAGCTTGTGTCATCC) (SEQ ID NO: 31) to amplify both skipped and unskipped molecules using the protocol in Table 2.

TABLE 2

| PCR Protocol | |
|---|---|
| Hot Start | 95°C. for 2 minutes |
| Denaturation | 95°C. for 0.5 minute |
| Annealing of primers | 50°C. for 0.5 minute |
| Primer extension | 72°C. for 1 minute |
| Final extension | 72°C. for 5 minutes |
| Number of Cycles | 10 |

For the nested PCR, primary PCR reactions were diluted with water 100×, and 5 µl was used for nested PCR reaction (50 µl total reaction volume). Nested PCR used primers in exon 20 (Ex20F2: 5'-ACCCAGTCTACCACCCTATC (SEQ ID NO: 32) and exon 25 (Ex25R: 5'-CTCTT-TATCTTCTGCCCACCTT (SEQ ID NO: 33) to amplify both skipped and unskipped molecules using the protocol in Table 3.

TABLE 3

| Nested PCR Protocol | |
|---|---|
| Hot Start | 95°C. for 2 minutes |
| Denaturation | 95°C. for 0.5 minute |
| Annealing of primers | 50°C. for 0.5 minute |
| Primer extension | 72°C. for 1 minute |
| Final extension | 72°C. for 5 minutes |
| Number of Cycles | 35 |

PCR reactions were analyzed using 4% TAE agarose gels. The wild-type (WT) DMD product had an expected size of 788 base pairs and the skipped DMD A23 of 575 base pairs.

Animals

All animal studies were conducted following protocols in accordance with the Institutional Animal Care and Use Committee (IACUC) at Explora BioLabs, which adhere to the regulations outlined in the USDA Animal Welfare Act as well as the "Guide for the Care and Use of Laboratory Animals" (National Research Council publication, 8th Ed., revised in 2011). All mice were obtained from either Charles River Laboratories or Harlan Laboratories.

In Vivo Mouse Model

WT CD-1 mice (4-6 weeks old) were dosed via intravenous (iv) injection with the indicated antisense conjugates (ASCs) and doses. The "naked" PMO or ASO were dosed via intramuscular injection at the indicated doses. After 4, 7, or 14 days, heart and gastrocnemius muscle tissues were harvested and snap-frozen in liquid nitrogen. RNAs were isolated with Trizol and RNeasy Plus 96 Kit (Qiagen, #74192) and reversed transcribed using High Capacity cDNA Reverse transcription Kit (ThermoFisher #4368813). Nested PCR reactions were performed as described. PCR reactions were analyzed in 4% (or 1%) TAE agarose gels which were quantitated by densitometry.

To confirm exon 23 skipping in treated mice, DNA fragments were isolated from the 4% agarose gels and sequenced.

Figure 3:
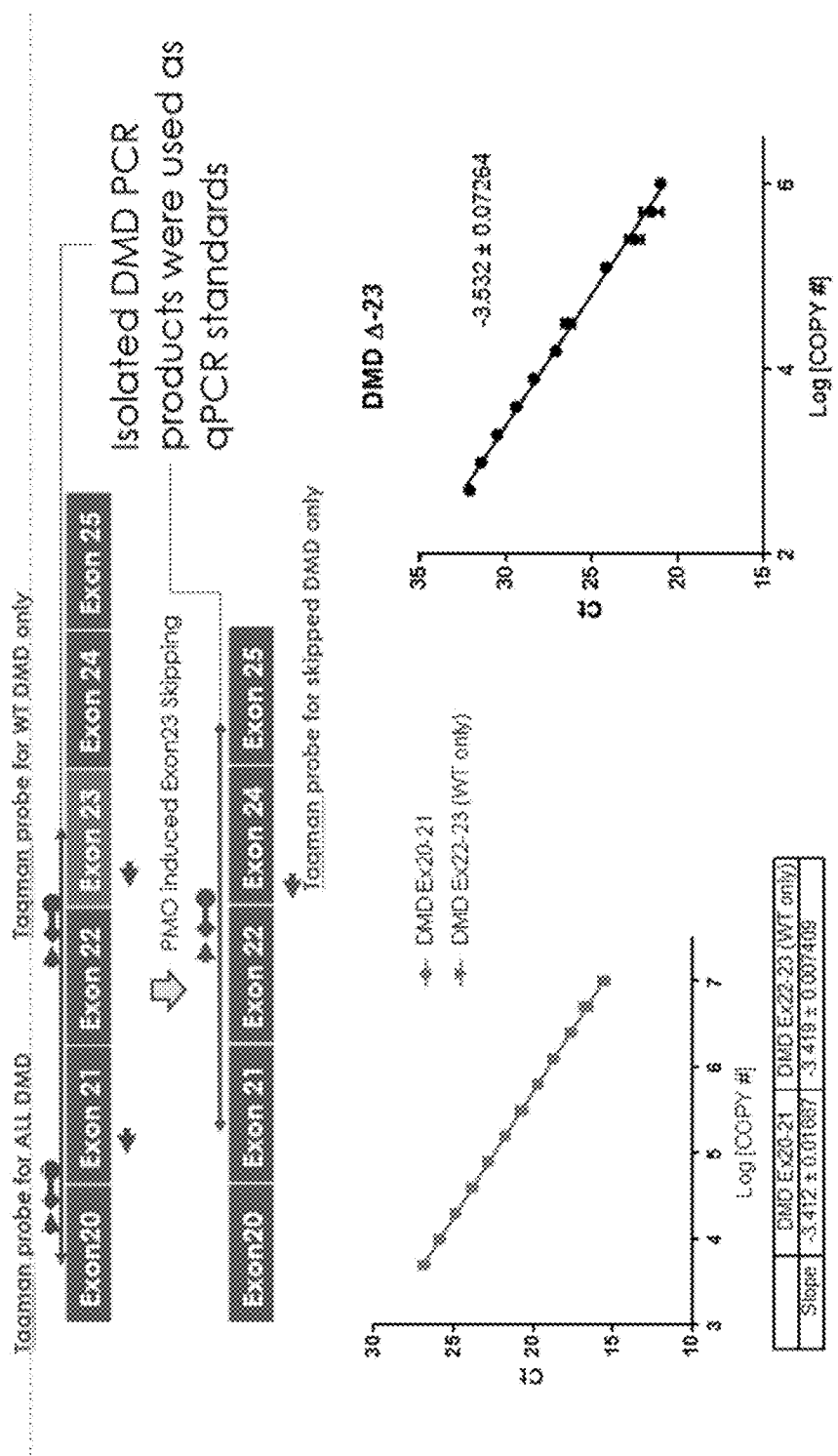
FIG. 3 depicts methods used to quantify skipped DMD mRNA in total RNA using Taqman qPCR.

To quantitatively determine the skipped DMD mRNA copy number, qPCR primer/probe sets were designed to quantify skipped and WT DMD mRNA (FIG. 3). qPCR quantification standards were designed and produced via PCR using designed PCR primers as seen in Table 4. For the qPCR standard for WT and DMD, following PCR a 733 base pair fragment was isolated from the agarose gel. For qPCR standard for skipped DMA, the nested primers were used.

The amplification efficiency of the qPCR primer/probes were determined to be within 10% of expected efficiency.

qPCR reactions were performed in QuantStudio 7 and Tagman™ PCR Universal Mastermix II (ThermoFisher #4440041) according to manufacturer's instructions.

TABLE 4

| | SEQ ID NO | Primer/Probe | Sequence |
|---|---|---|---|
| DMD Δ-23, for Ex23 skipping | 34 | Forward Primer | 5'GCGCTATCAGGA GACAATGAG |
| | 35 | Reverse Primer | 5'GTTTTTATGTGA TTCTGTAATTTCCC |
| | 36 | Probe | 5'CTCTCTGTACCT TATCTTAGTGTT |
| DMD Ex22-23, for WT DMD only | 37 | Forward Primer | 5'TGGAGGAGAGAC TCGGGAAA |
| | 38 | Reverse Primer | 5'TTGAAGCCATTT TGTTGCTCTTT |
| | 39 | Probe | 5'ACAGGCTCTGCA AAGT |
| DMD Ex20-21, for All DMD | 40 | Forward Primer | 5'AACAGATGACAA CTACTGCCGAAA |
| | 41 | Reverse Primer | 5'TTGGCTCTGATA GGGTGGTAGAC |
| | 42 | Probe | 5'CTTGTTGAAAAC CC |
| qPCR standard for WT and all DMD | 43 | Forward Primer | 5'TGAGGGTGTTAA TGCTGAAAGTA |
| | 44 | Reverse Primer | 5'CACCAACTGGGA GGAAAGTT |

Example 3: Conjugate Synthesis

Analytical and Purification Methods

Analytical and purification methods were performed according to Tables 5-11.

TABLE 5

Size exclusion chromatography (SEC) methods

| Size Exclusion Chromatography (SEC) Method | Column | Mobile Phase | Flow Rate |
|---|---|---|---|
| method 1 | TOSOH Biosciences, TSKgelG3000SW XL, 7.8 ×300 mm, 5 μM | 150 mM phosphate buffer | 1.0 mL/minute for 20 minutes |
| method 2 | TOSOH Biosciences, TSKgelG3000SW, 21.5 ×600 mm, 5 μM | PBS pH 7.4 | 1.0 mL/minute for 180 minutes |

TABLE 6

Hydrophobic interaction chromatography (HIC) method 1

| | | Gradient | | |
|---|---|---|---|---|
| Column | Solvent | Column Volume | % A | % B |
| GE, HiScreen Butyl HP, 4.7 mL | Solvent A: 50 mM phosphate buffer, 0.8M Ammonium Sulfate, pH 7.0 Solvent B: 80% 50 mM phosphate buffer, 20% IPA, pH 7.0 Flow Rate: 1.0 mL/minute | 1.00 30 5 | 95 0 0 | 5 100 100 |

TABLE 7

Hydrophobic interaction chromatography (HIC) method 2

| | | Gradient | | |
|---|---|---|---|---|
| Column | Solvent | Time | % A | % B |
| Thermo Scientific, MAbPac HIC-20, 4.6 mm ID × 10 cm, 5 um | Solvent A: 100 mM phosphate buffer, 1.8M Ammonium Sulfate, pH 7.0 Solvent B: 80% 100 mM phosphate buffer, 20% IPA, pH 7.0 Flow Rate: 0.7 mL/minute | 0.00 2.00 22.00 25.00 26.00 30.00 | 100 100 0 0 100 100 | 0 0 100 100 0 0 |

TABLE 8

Hydrophobic interaction chromatography (HIC) method 3

| | | Gradient | | |
|---|---|---|---|---|
| Column | Solvent | Column Volume | % A | % B |
| GE, HiScreen Butyl HP, 4.7 mL | Solvent A: 50 mM phosphate buffer, 0.8M Ammonium Sulfate, pH 7.0 Solvent B: 80% 50 mM phosphate buffer, 20% IPA, pH 7.0 Flow Rate: 1.0 mL/minute | 1 25 1 2 | 100 0 0 0 | 0 80 100 100 |

TABLE 9

Hydrophobic interaction chromatography (HIC) method 4

| | | Gradient | | |
|---|---|---|---|---|
| Column | Solvent | Time | % A | % B |
| Thermo Scientific, MAbPac HIC-20, 4.6 mm ID ×10 cm, 5 um | Solvent A: 100 mM phosphate buffer, 1.8M Ammonium Sulfate, pH 7.0 Solvent B: 80% 100 mM phosphate buffer, 20% IPA, pH 7.0 Flow Rate: 0.5 mL/minute | 0.00 5.00 20.00 25.00 26.00 30.00 | 100 100 0 0 100 100 | 0 0 100 100 0 0 |

TABLE 10

Strong anion exchange chromatography (SAX) method 1

| | | Gradient | | |
|---|---|---|---|---|
| Column | Solvent | Column Volume | % A | % B |
| Tosoh Bioscience, TSKGel SuperQ-5PW, 21.5 mm ID ×15 cm, 13 um | Solvent A: 20 mM TRIS buffer, pH 8.0; Solvent B: 20 mM TRIS, 1.5M NaCl, pH 8.0 Flow Rate: 6.0 mL/minute | 0.5 0.5 17 0.5 0.5 | 100 80 20 0 0 | 0 20 80 100 100 |

TABLE 11

Strong anion exchange chromatography (SAX) method 2

| | | Gradient | | |
|---|---|---|---|---|
| Column | Solvent | Time | % A | % B |
| Thermo Scientific, ProPac ™SAX-10, Bio LC ™, 4 ×250 | Solvent A: 80% 10 mM TRIS pH 8, 20% ethanol Solvent B: 80% 10 mM TRIS | 0.0 3.00 17.00 | 90 90 0 | 10 10 100 |

TABLE 11-continued

Strong anion exchange chromatography (SAX) method 2

| Column | Solvent | Gradient Time | % A | % B |
|---|---|---|---|---|
| mm | pH 8, 20% ethanol, 1.5M NaCl | 21.00 | 0 | 100 |
| | Flow Rate: 0.75 mL/minute | 22.00 | 90 | 10 |
| | | 25.00 | 90 | 10 |

Anti-Transferrin Receptor Antibody

Anti-mouse transferrin receptor antibody or anti-CD71 mAb that was used was a rat IgG2a subclass monoclonal antibody that binds mouse CD71 or mouse transferrin receptor 1 (mTfR1). The antibody was produced by BioXcell and it is commercially available (Catalog #BE0175).

Anti-CD71 Antibody Morpholino Antisense Oligonucleotide Conjugate (Anti-CD71 mAb-PMO)

Anti-CD71 mAb-PMO Conjugation

Figure 4:
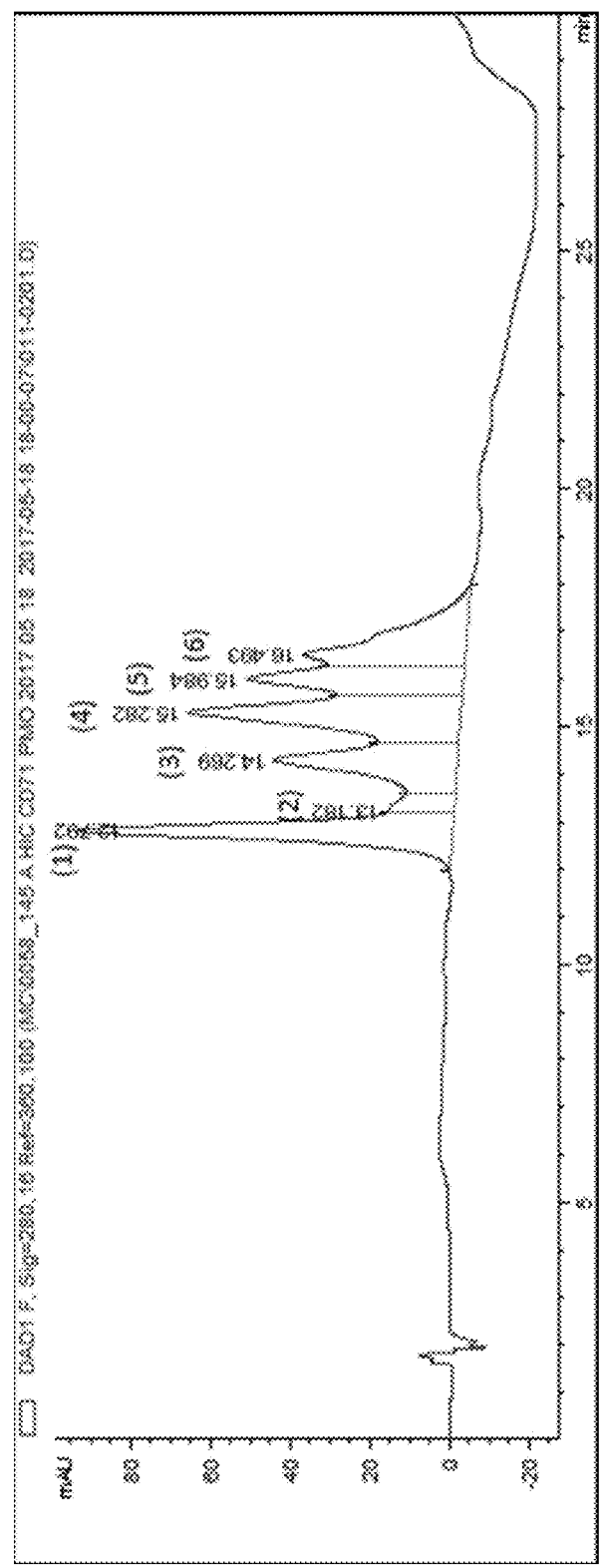
FIG. 4 depicts a chromatogram of anti-CD71 mAb-PMO reaction mixture produced with hydrophobic interaction chromatography (HIC) method 2.

Anti-CD71 antibody (10 mg/mL) in borate buffer (25 mM sodium tetraborate, 25 mM NaCl, 1 mM Diethylene triamine pentaacetic acid, pH 8.0) was reduced by adding 4 equivalents of tris(2-carboxyethyl)phosphine (TCEP) in water and incubating at 37° C. for 4 hours. 4(N-Maleimidomethyl) cyclohexanecarboxylic acid N-hydroxysuccinimide ester (SMCC) was coupled to the primary amine on the 3' end of the phosphorodiamidate morpholino oligomer (PMO) by incubating the PMO (50 mg/mL) in DMSO with 10 equivalents of SMCC (10 mg/mL) in DMSO for one hour. Unconjugated SMCC was removed by ultrafiltration using Amicon Ultra-15 centrifugal filter units with a MWCO of 3 kDa. The PMO-SMCC was washed three times with acetate buffer (10 mM sodium acetate, pH 6.0) and used immediately. The reduced antibody was mixed with 2.25 equivalents of PMO-SMCC and incubated overnight at 4° C. The pH of the reaction mixture was then reduced to 7.5, and 8 equivalents of N-Ethylmaleimide was added to the mixture at room temperature for 30 minutes to quench unreacted cysteines. Analysis of the reaction mixture by hydrophobic interaction chromatography (HIC) method 2 showed antibody-PMO conjugates along with unreacted antibody and PMO (FIG. 4). FIG. 4 shows a chromatogram of anti-CD71 mAb-PMO reaction mixture produced with HIC method 2 showing free antibody peak (1), free PMO (2), DAR 1 (3), DAR 2 (4), DAR 3 (5), DAR >3 (6). "DAR" refers to a drug-to-antibody ratio. The number in parentheses refers to the peak in the chromatogram.

Purification

The reaction mixture was purified with an AKTA Explorer FPLC using HIC method 1. Fractions containing conjugates with a drug to antibody ratio of one (DAR 1) and two (DAR 2) were combined and concentrated with Amicon Ultra-15 centrifugal filter units with a MWCO of 50 kDa separately from conjugates with a DAR greater than 2. Concentrated conjugates were buffer exchanged with PBS (pH 7.4) using Amicon Ultra-15 centrifugal filter units prior to analysis.

Analysis of the Purified Conjugate

Figure 5A:
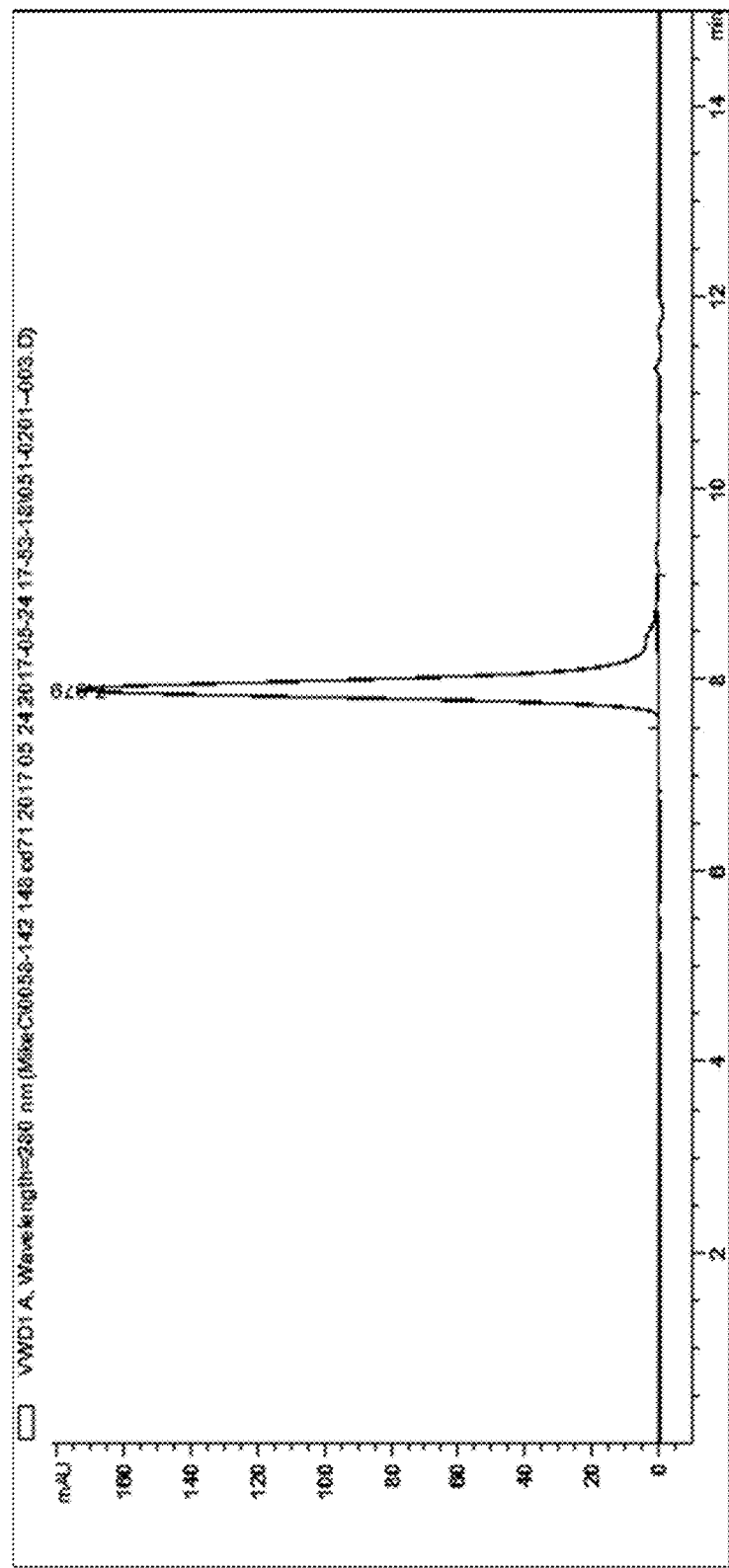
FIG. 5A depicts a chromatogram of anti-CD71 mAb produced using size exclusion chromatography (SEC) method 1.
Figure 5B:
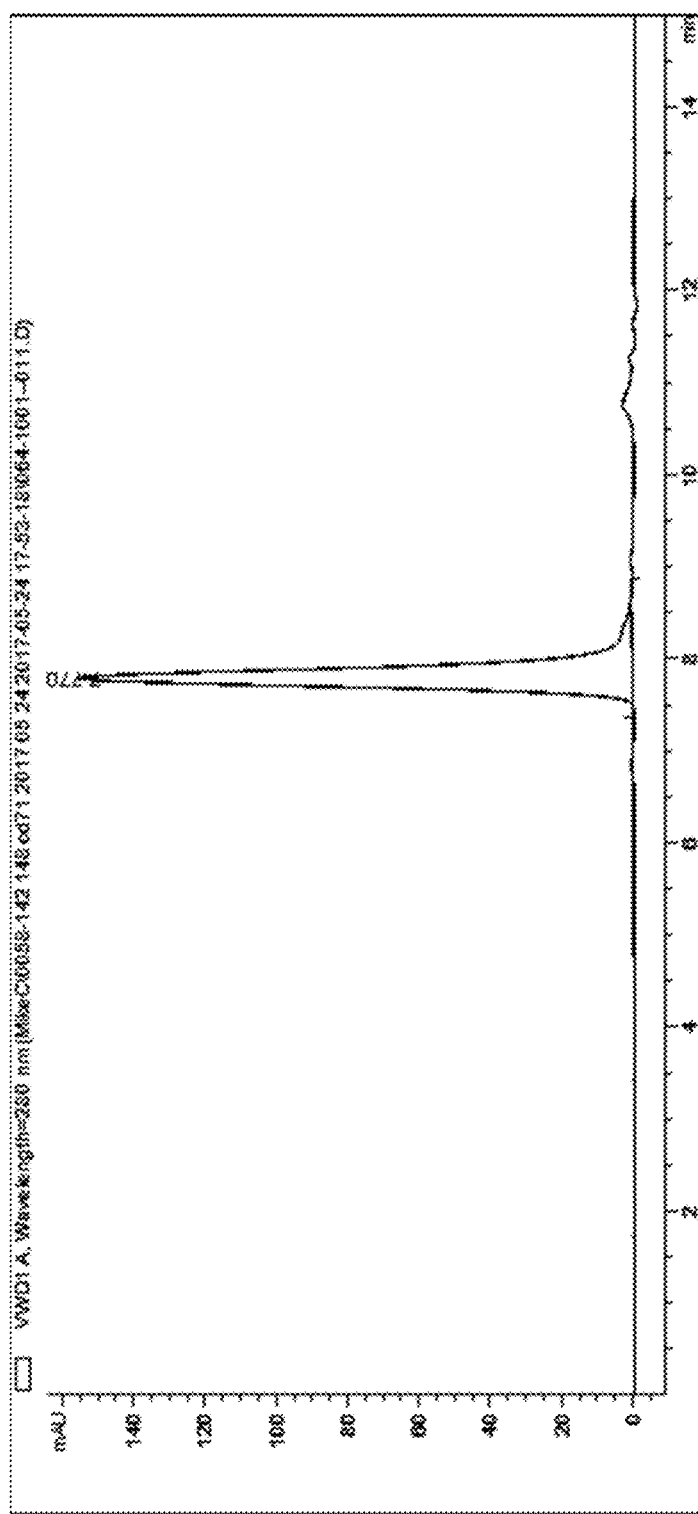
FIG. 5B depicts a chromatogram of anti-CD71 mAb-PMO DAR 1,2 produced using size exclusion chromatography (SEC) method 1.
Figure 5C:
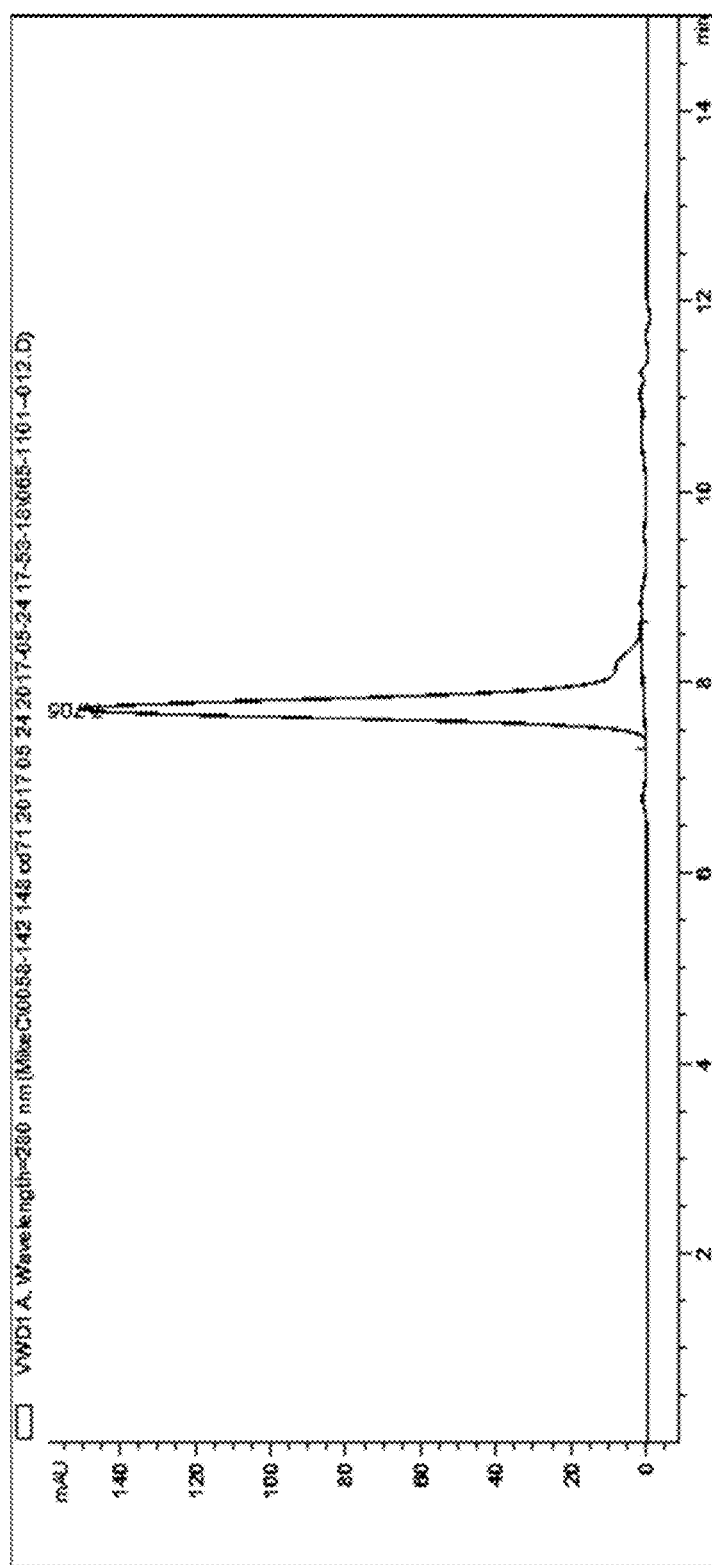
FIG. 5C depicts a chromatogram of anti-CD71 mAb-PMO DAR >2 produced using size exclusion chromatography (SEC) method 1.

The isolated conjugates were characterized by size exclusion chromatography (SEC) and HIC. SEC method 1 was used to confirm the absence of high molecular weight aggregates and unconjugated PMOs (FIGS. 5A-5C). FIG. 5A shows a chromatogram of anti-CD71 mAb produced using SEC method 1. FIG. 5B shows a chromatogram of anti-CD71 mAb-PMO DAR 1,2 produced using SEC method 1. FIG. 5C shows a chromatogram of anti-CD71 mAb-PMO DAR greater than 2 produced using SEC method 1. "DAR" refers to a drug-to-antibody ratio.

Figure 6A:
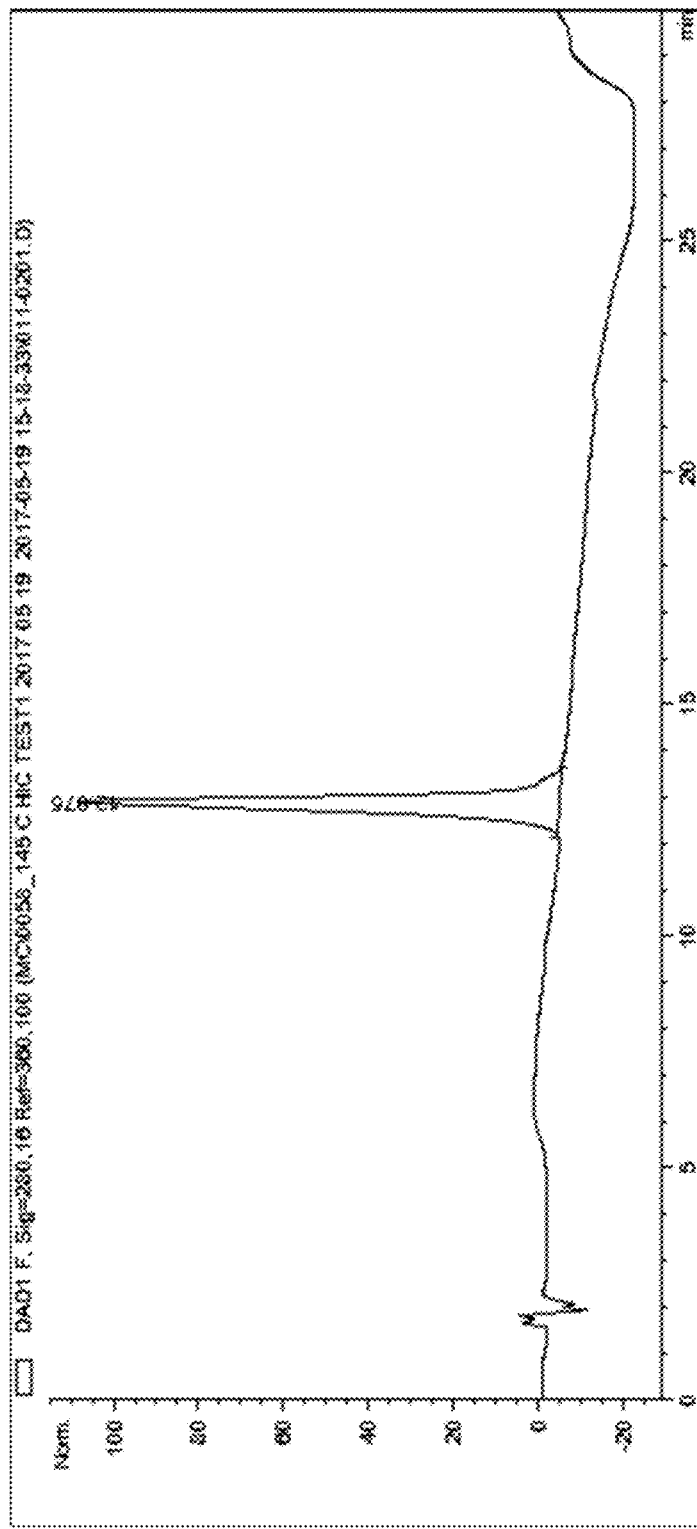
FIG. 6A depicts a chromatogram of anti-CD71 mAb produced using hydrophobic interaction chromatography (HIC) method 2.
Figure 6B:
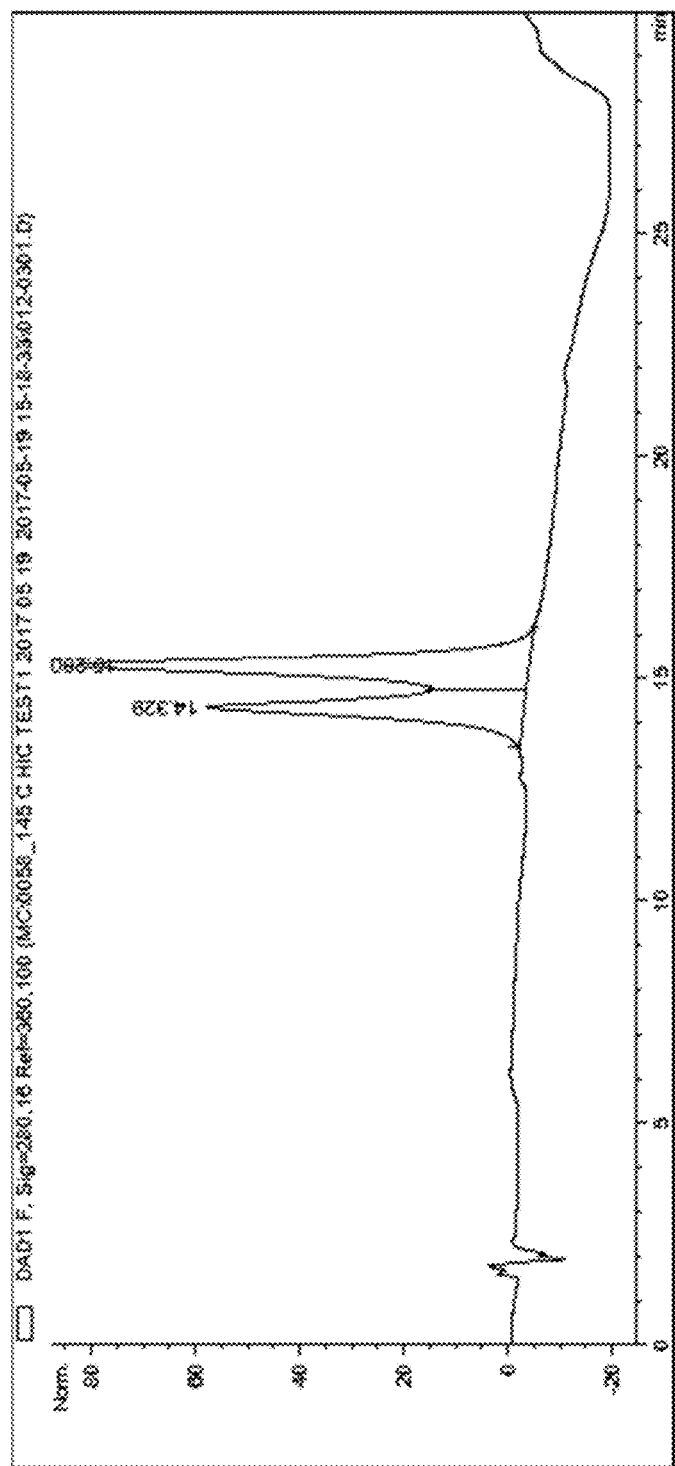
FIG. 6B depicts a chromatogram of purified anti-CD71 mAb-PMO DAR 1,2 conjugate produced using hydrophobic interaction chromatography (HIC) method 2.
Figure 6C:
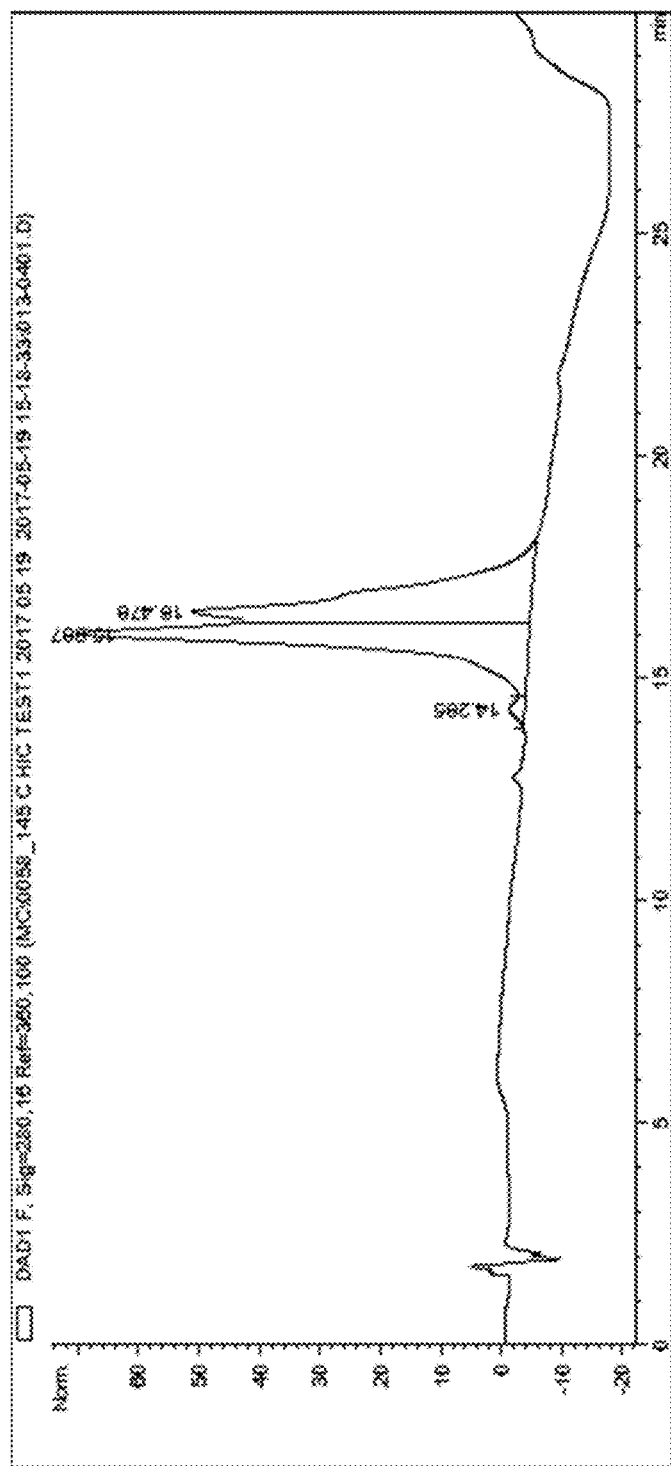
FIG. 6C depicts a chromatogram of purified anti-CD71 mAb-PMO DAR >2 conjugate produced using hydrophobic interaction chromatography (HIC) method 2.

The purity of the conjugate was assessed by analytical HPLC using HIC method 2 (FIGS. 6A-6C). FIG. 6A shows a chromatogram of anti-CD71 mAb produced using HIC method 2. FIG. 6B shows a chromatogram of purified anti-CD71 mAb-PMO DAR 1,2 conjugate produced using HIC method 2. FIG. 6C shows a chromatogram of purified anti-CD71 mAb-PMO DAR >2 conjugate produced using HIC method 2. The 260/280 nm UV absorbance ratio of each sample was compared to a standard curve of known ratios of PMO and antibody to confirm DAR. The DAR 1,2 sample had an average DAR of ~1.6 while the DAR greater than 2 sample had an average DAR of ~3.7. "DAR" refers to a drug-to-antibody ratio.

Anti-CD71 Fab Morpholino Antisense Oligonucleotide Conjugate (Anti-CD71 Fab-PMO)

Antibody Digestion with Pepsin

Anti-CD71 antibody (5 mg/mL) in 20 mM acetate buffer (pH 4.0) was incubated with immobilized pepsin for 3 hours at 37° C. The resin was removed and the reaction mixture was washed with PBS (pH 7.4) using Amicon Ultra-15 centrifugal filter units with a MWCO of 30 kDa. The retentate was collected and purified using size exclusion chromatography (SEC) method 2 to isolate the F(ab')2 fragment.

Anti-CD71 (Fab)-PMO Conjugation

Figure 7A:
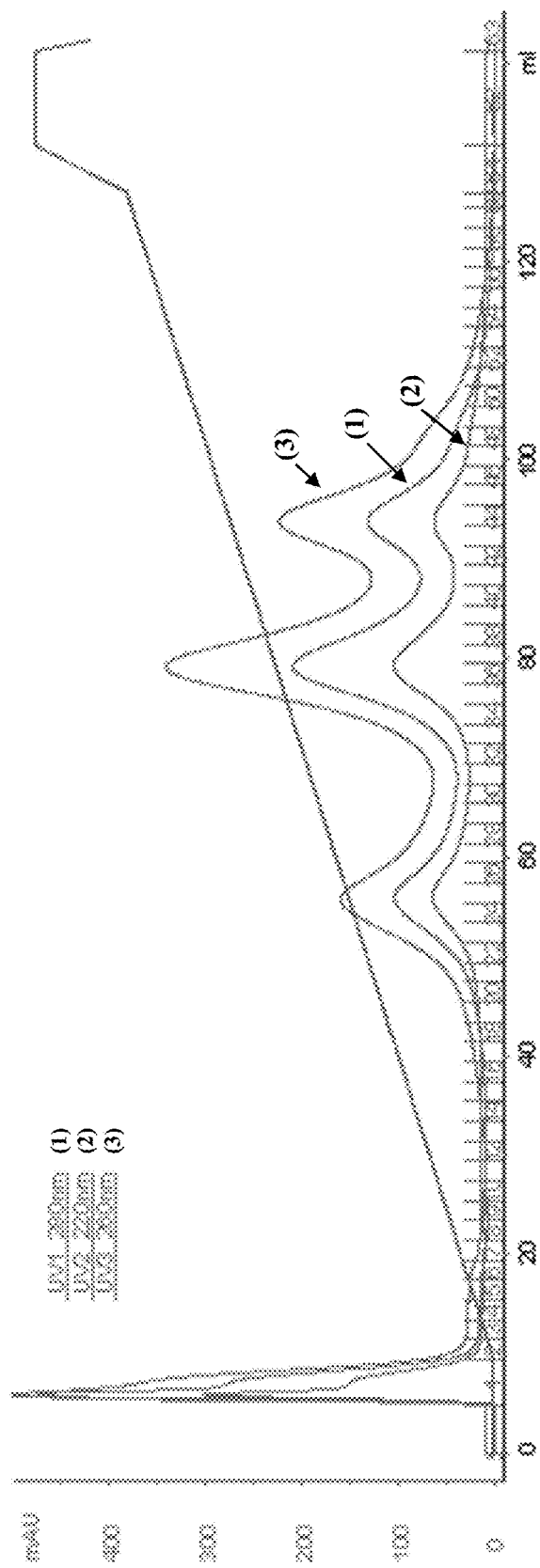
FIG. 7A depicts a chromatogram of fast protein liquid chromatography (FPLC) purification of anti-CD71 Fab-PMO using hydrophobic interaction chromatography (HIC) method 3.

The F(ab')2 fragment (15 mg/mL) in borate buffer (pH 8.0) was reduced by adding 10 equivalents of TCEP in water and incubating at 37° C. for 2 hours. SMCC was added to the primary amine on the 3' end of the PMO by incubating the PMO (50 mg/mL) in DMSO with 10 equivalents of SMCC (10 mg/mL) in DMSO for 1 hour. Unconjugated SMCC was removed by ultrafiltration using Amicon Ultra-15 centrifugal filter units with a MWCO of 3 kDa. The PMO-SMCC was washed three times with acetate buffer (pH 6.0) and used immediately. The reduced F(ab') fragment (Fab) was buffer exchanged into borate buffer (pH 8.0) using Amicon Ultra-15 Centrifugal Filter Units with a MWCO of 10 kDa, and 1.75 equivalents of PMO-SMCC was added and incubated overnight at 4° C. The pH of the reaction mixture was then reduced to 7.5, and 6 equivalents of N-Ethylmaleimide was added to the mixture at room temperature for 30 minutes to quench unreacted cysteines. Analysis of the reaction mixture by hydrophobic interaction chromatography (HIC) method 3 showed anti-CD71 (Fab)-PMO conjugates along with unreacted Fab (FIG. 7A). FIG. 7A shows a chromatogram of FPLC purification of anti-CD71 Fab-PMO using HIC method 3.

Purification

The reaction mixture was purified with an AKTA Explorer FPLC using HIC method 3. Fractions containing conjugates with a DAR of one, two and three were combined and concentrated separately. Concentrated conjugates were buffer exchanged with PBS (pH 7.4) using Amicon Ultra-15 centrifugal filter units with a MWCO of 10 kDa prior to analysis.

Analysis of the Purified Conjugate

Figure 7B:
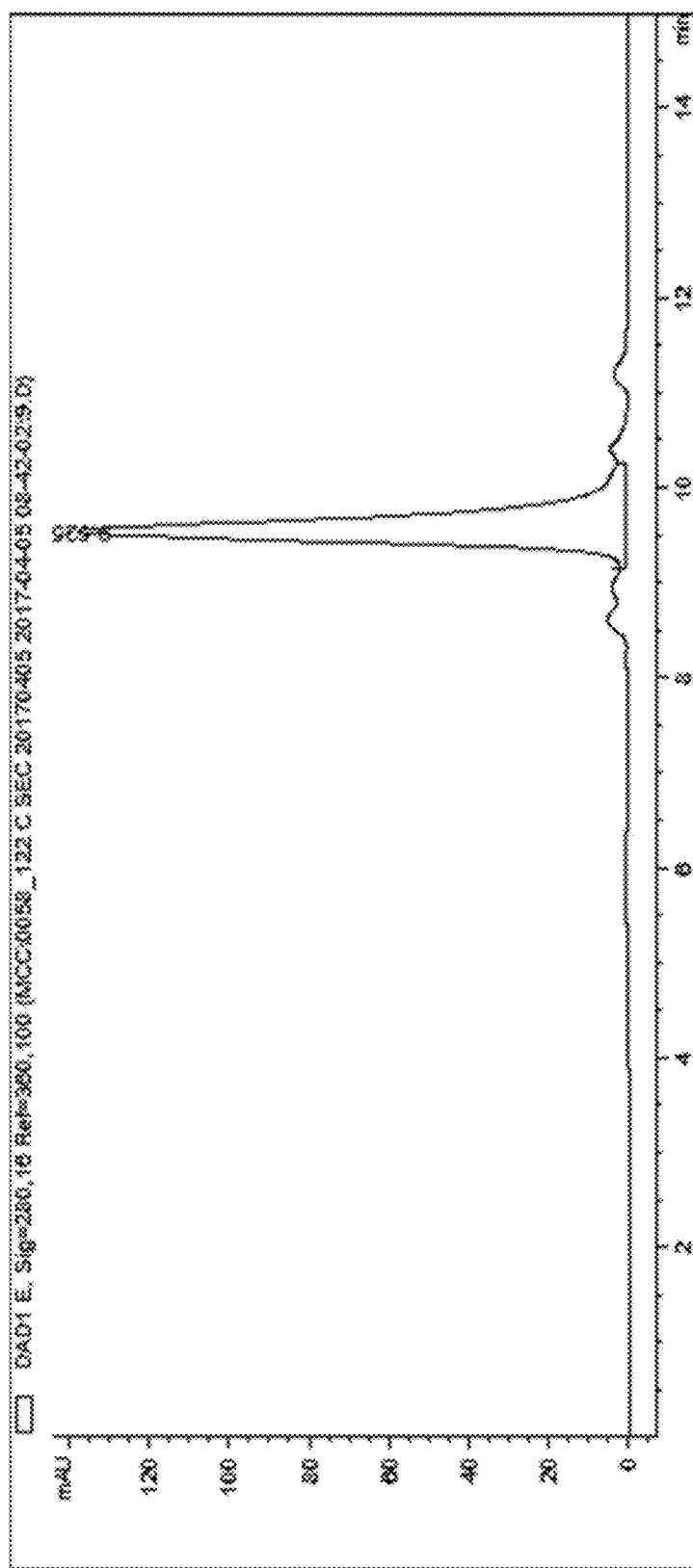
FIG. 7B depicts a chromatogram of anti-CD71 Fab produced using SEC method 1.
Figure 7C:
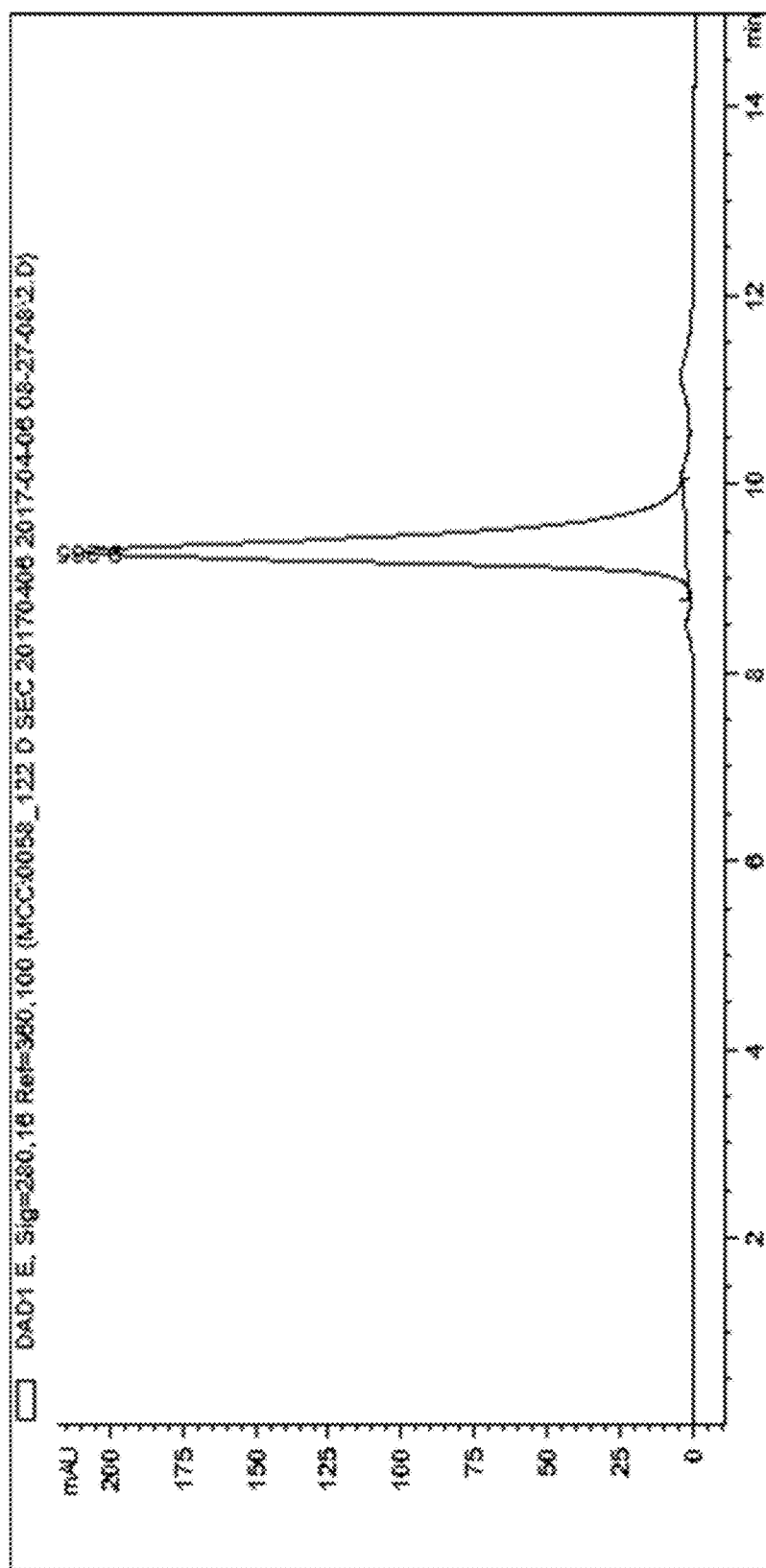
FIG. 7C depicts a chromatogram of anti-CD71 Fab-PMO DAR 1 conjugate produced using SEC method 1.
Figure 7D:
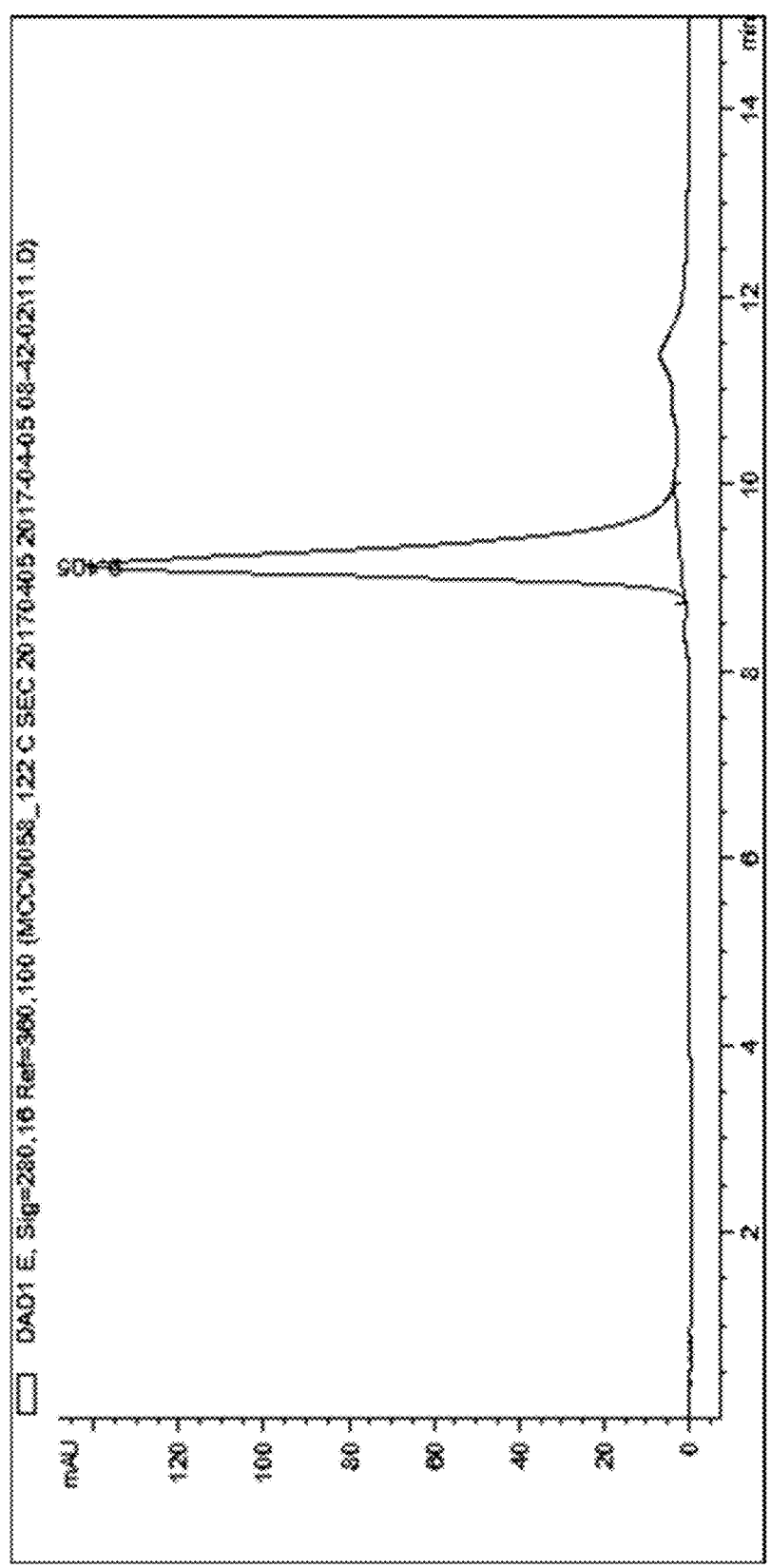
FIG. 7D depicts a chromatogram of anti-CD71 Fab-PMO DAR 2 conjugate produced using SEC method 1.
Figure 7E:
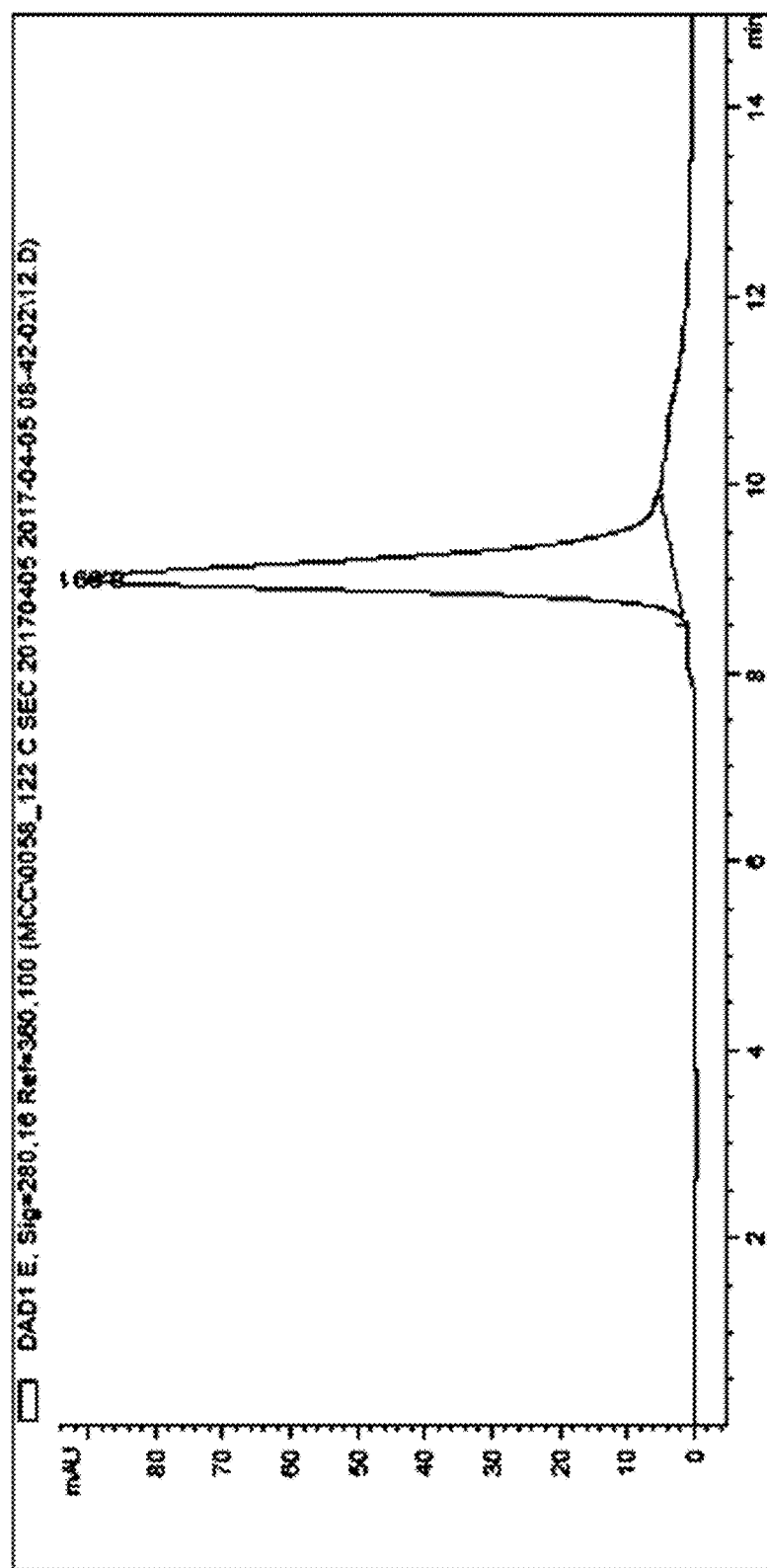
FIG. 7E depicts a chromatogram of anti-CD71 Fab-PMO DAR 3 conjugate produced using SEC method 1.
Figure 7F:
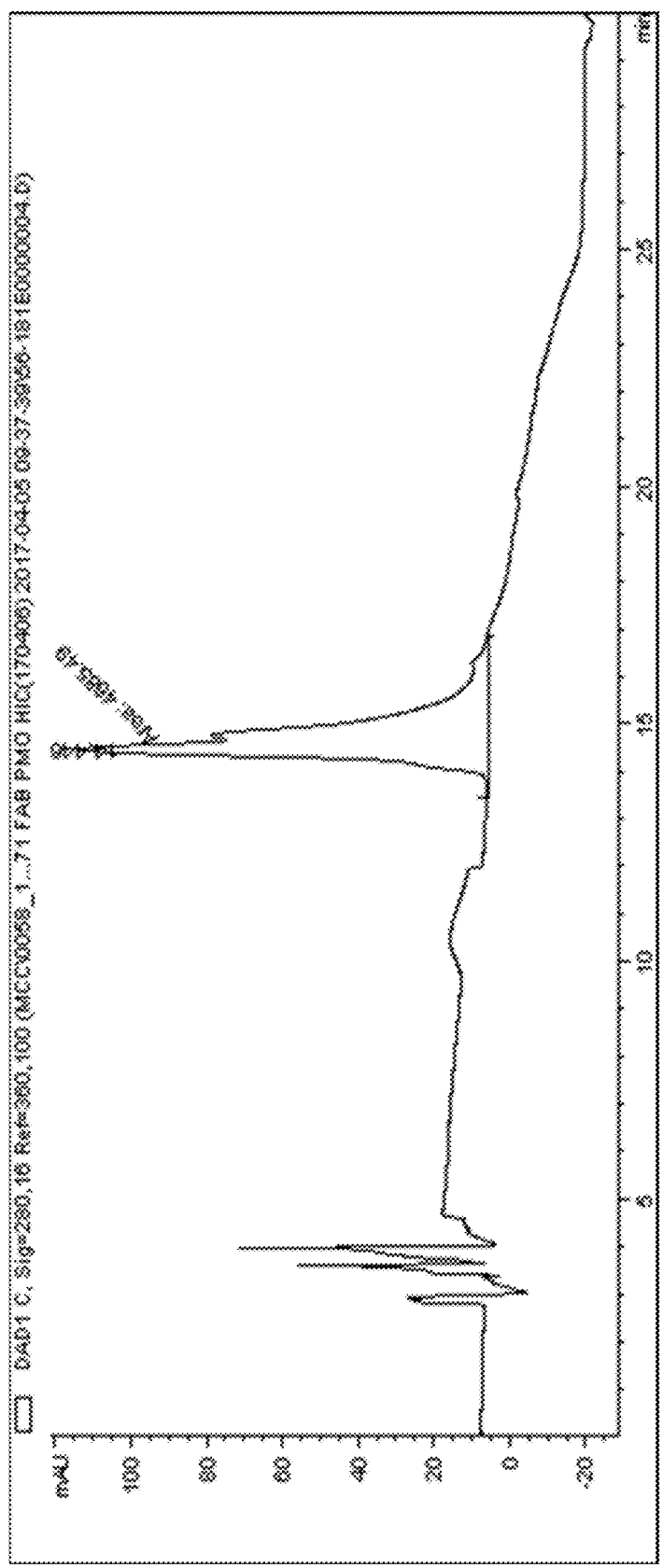
FIG. 7F depicts a chromatogram of anti-CD71 Fab produced using HIC method 4.
Figure 7G:
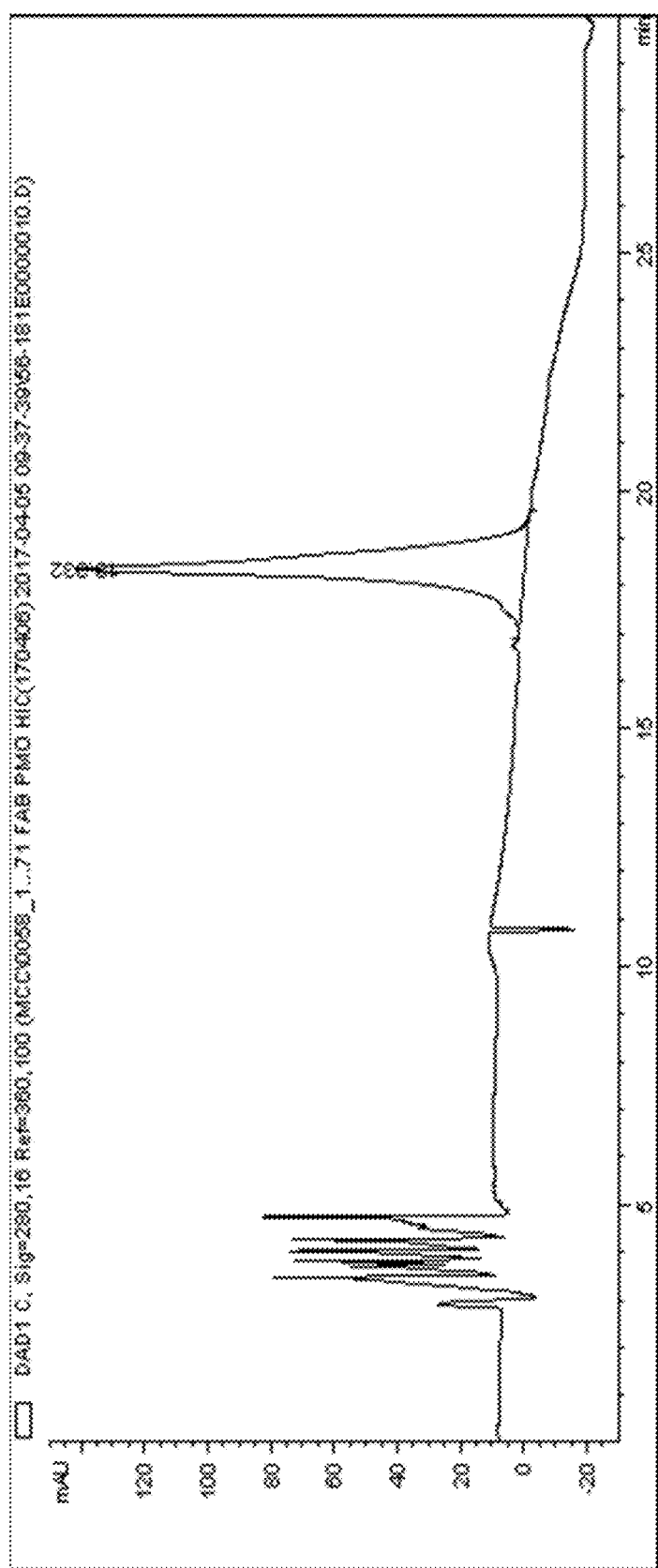
FIG. 7G depicts a chromatogram of anti-CD71 Fab-PMO DAR 1 conjugate produced using HIC method 4.
Figure 7H:
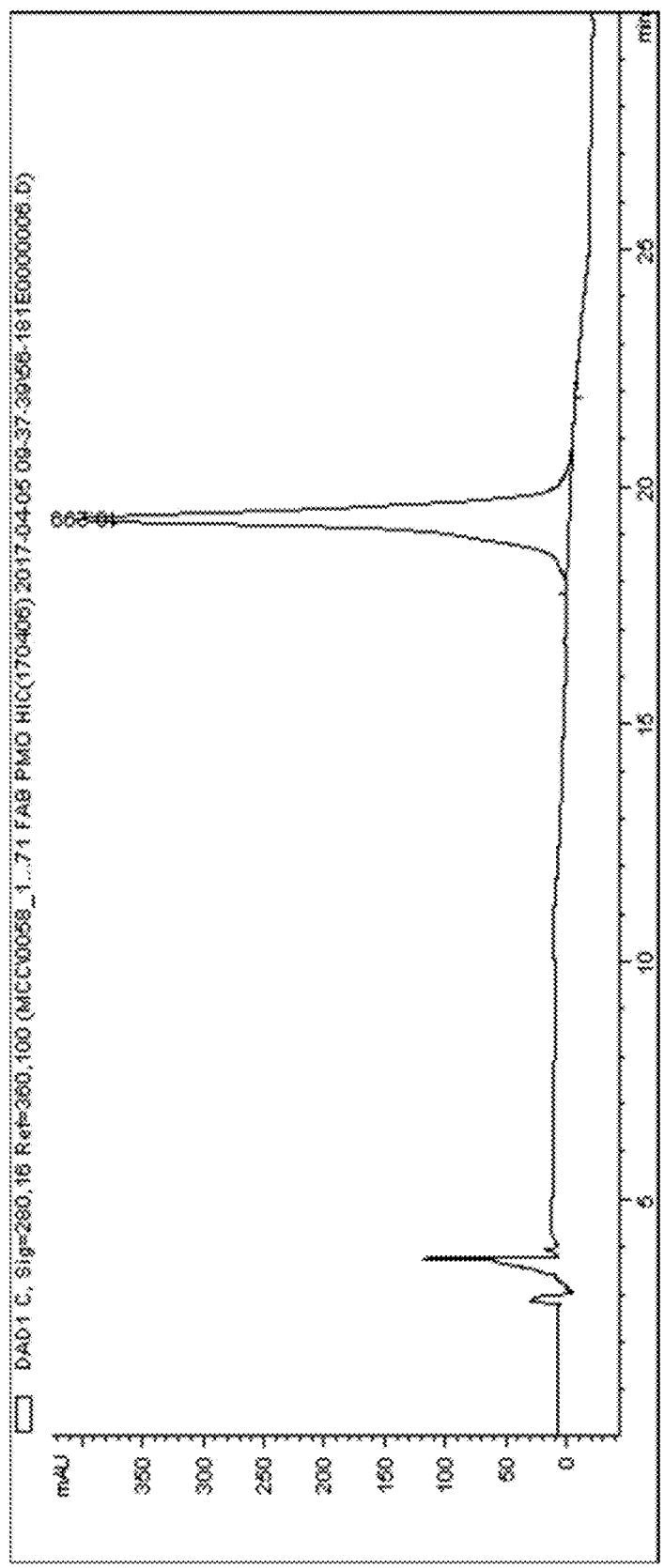
FIG. 7H depicts a chromatogram of anti-CD71 Fab-PMO DAR 2 conjugate produced using HIC method 4.
Figure 7I:
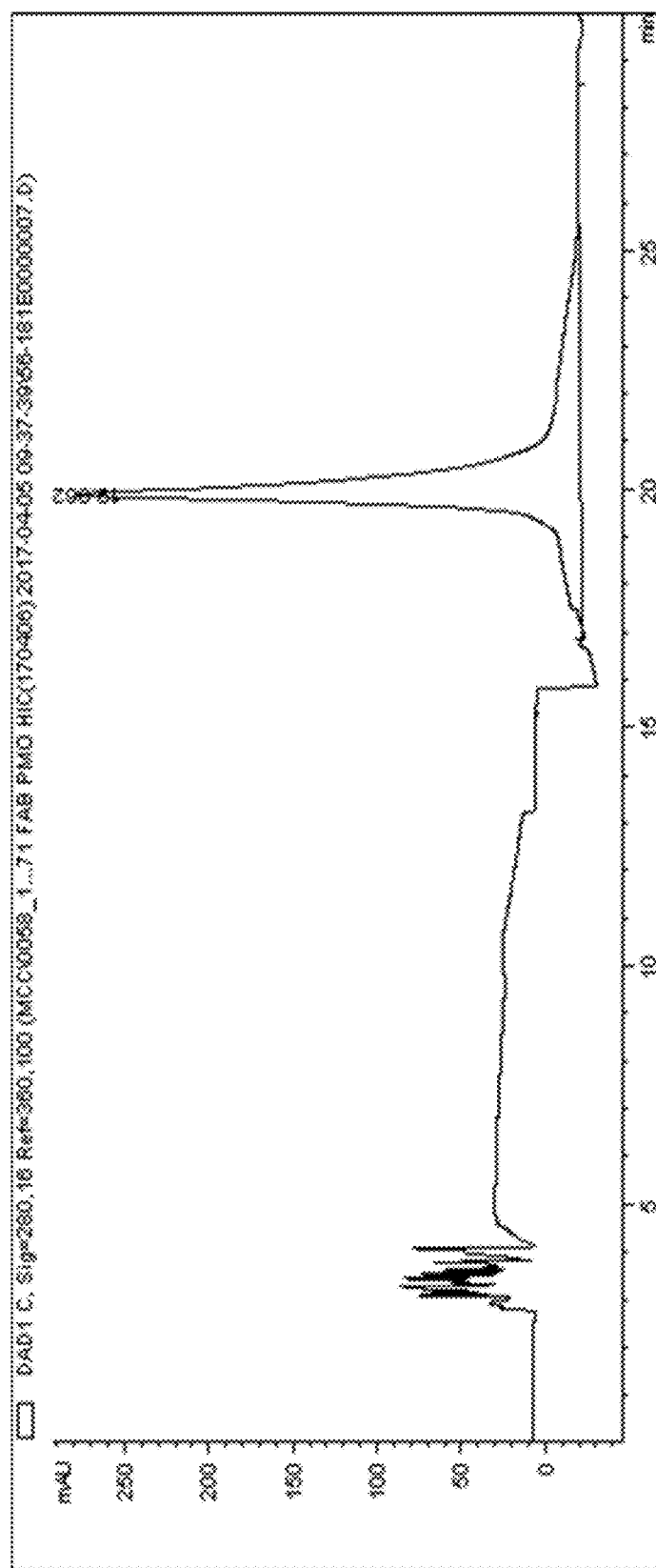
FIG. 7I depicts a chromatogram of anti-CD71 Fab-PMO DAR 3 conjugate produced using HIC method 4.

The isolated conjugates were characterized by SEC, and HIC. SEC method 1 was used to confirm the absence of high molecular weight aggregates and unconjugated PMO. See FIGS. 7B-7E. FIG. 7B shows a chromatogram of anti-CD71 Fab produced using SEC method 1. FIG. 7C shows a chromatogram of anti-CD71 Fab-PMO DAR 1 conjugate produced using SEC method 1. FIG. 7D shows a chromatogram of anti-CD71 Fab-PMO DAR 2 conjugate produced using SEC method 1. FIG. 7E shows a chromatogram of anti-CD71 Fab-PMO DAR 3 conjugate produced using SEC method 1. The purity of the conjugate was assessed by analytical HPLC using HIC method 4. See FIGS. 7F-7I. FIG. 7F shows a chromatogram of anti-CD71 Fab produced using HIC method 4. FIG. 7G shows a chromatogram of anti-CD71 Fab-PMO DAR 1 conjugate produced using HIC method 4. FIG. 7H shows a chromatogram of anti-CD71 Fab-PMO DAR 2 conjugate produced using HIC method 4. FIG. 7I shows a chromatogram of anti-CD71 Fab-PMO DAR 3 conjugate produced using HIC method 4. "DAR" refers to drug-to-antibody ratio. The 260/280 nm UV absorbance ratio of each sample was compared to a standard curve of known ratios of PMO and Fab to confirm DAR.

Anti-CD71 Antibody Phosphorothioate Antisense Oligonucleotide Conjugate (Anti-CD71 mAb-PS ASO)

Anti-CD71 mAb-PS ASO

Figure 8A:
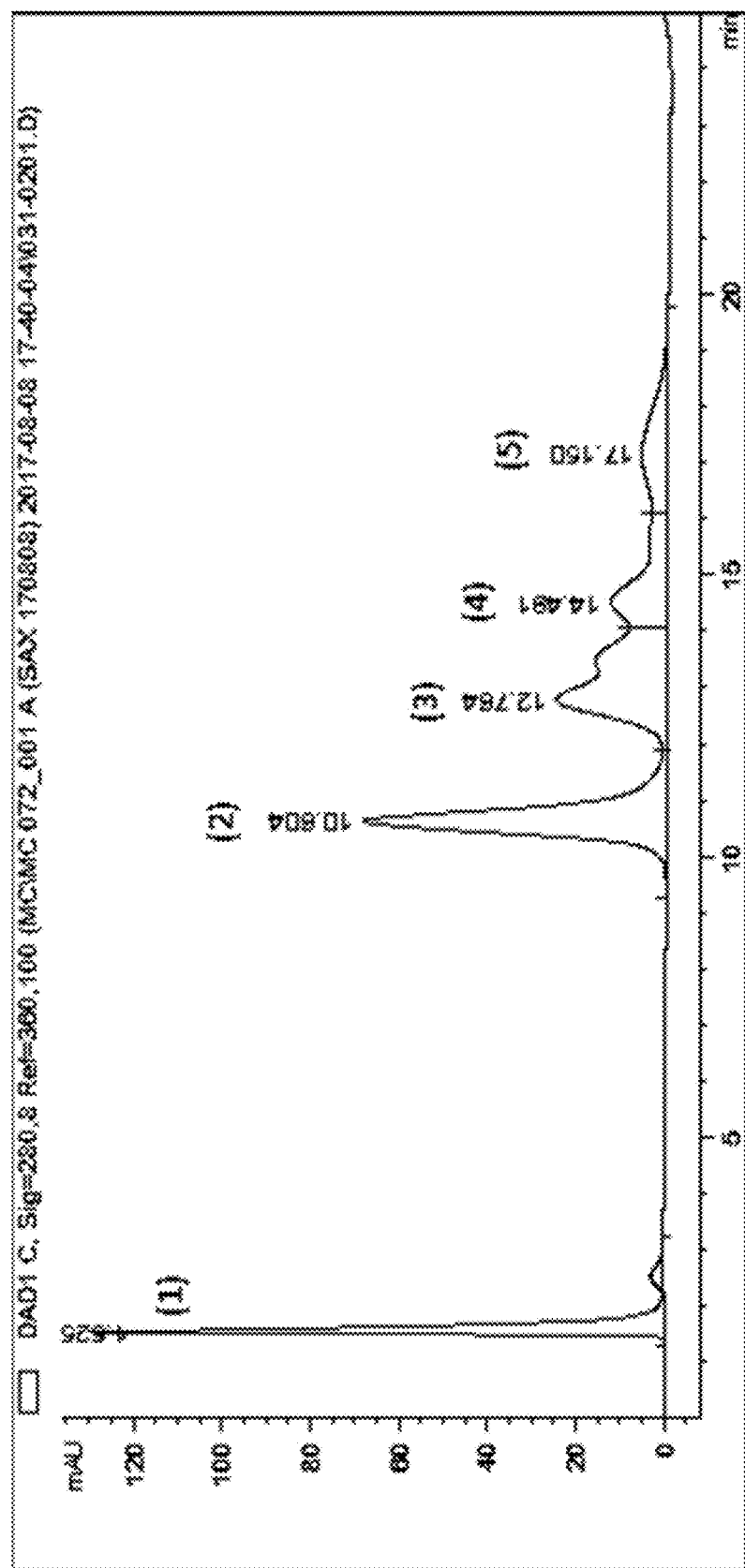
FIG. 8A depicts a chromatogram of anti-CD71 mAb-PS ASO reaction mixture produced with SAX method 2.

Anti-CD71 antibody (10 mg/mL) in borate buffer (pH 8.0) was reduced by adding 4 equivalents of TCEP in water and incubating at 37° C. for 4 hours. 4(N-Maleimidomethyl) cyclohexanecarboxylic acid N-hydroxysuccinimide ester (SMCC) was added to the primary amine on the 5' end of the PS-ASO by incubating the PS ASO (50 mg/mL) in 1:1 mixture of 250 mM PB (pH 7.5) and DMSO with 10 equivalents of SMCC (10 mg/mL) in DMSO for 1 hour. Unconjugated SMCC was removed by ultrafiltration using Amicon Ultra-15 centrifugal filter units with a MWCO of 3 kDa. The PS ASO-SMCC was washed three times with acetate buffer (pH 6.0) and used immediately. The reduced antibody was mixed with 1.7 equivalents of PS ASO-SMCC and incubated overnight at 4° C. The pH of the reaction mixture was then reduced to 7.4, and 8 equivalents of N-Ethylmaleimide was added to the mixture at room temperature for 30 minutes to quench unreacted cysteines. Analysis of the reaction mixture by strong anion exchange chromatography (SAX) method 2 showed antibody-PS ASO conjugates along with unreacted antibody and ASO (FIG. 8A). FIG. 8A shows a chromatogram of anti-CD71 mAb-PS ASO reaction mixture produced with SAX method 2 showing free antibody peak (1), free PS ASO (5), DAR 1 (2), DAR 2 (3), DAR >2 (4). "DAR" refers to a drug-to-antibody ratio. The number in parentheses refers to the peak.

Purification

The reaction mixture was purified with an AKTA Explorer FPLC using SAX method 1. Fractions containing conjugates with a drug-to-antibody ratio (DAR) of one, two and three were combined and concentrated separately and buffer exchanged with PBS (pH 7.4) using Amicon Ultra-15 centrifugal filter units with a MWCO of 50 kDa prior to analysis.

Analysis of the Purified Conjugate

Figure 8B:
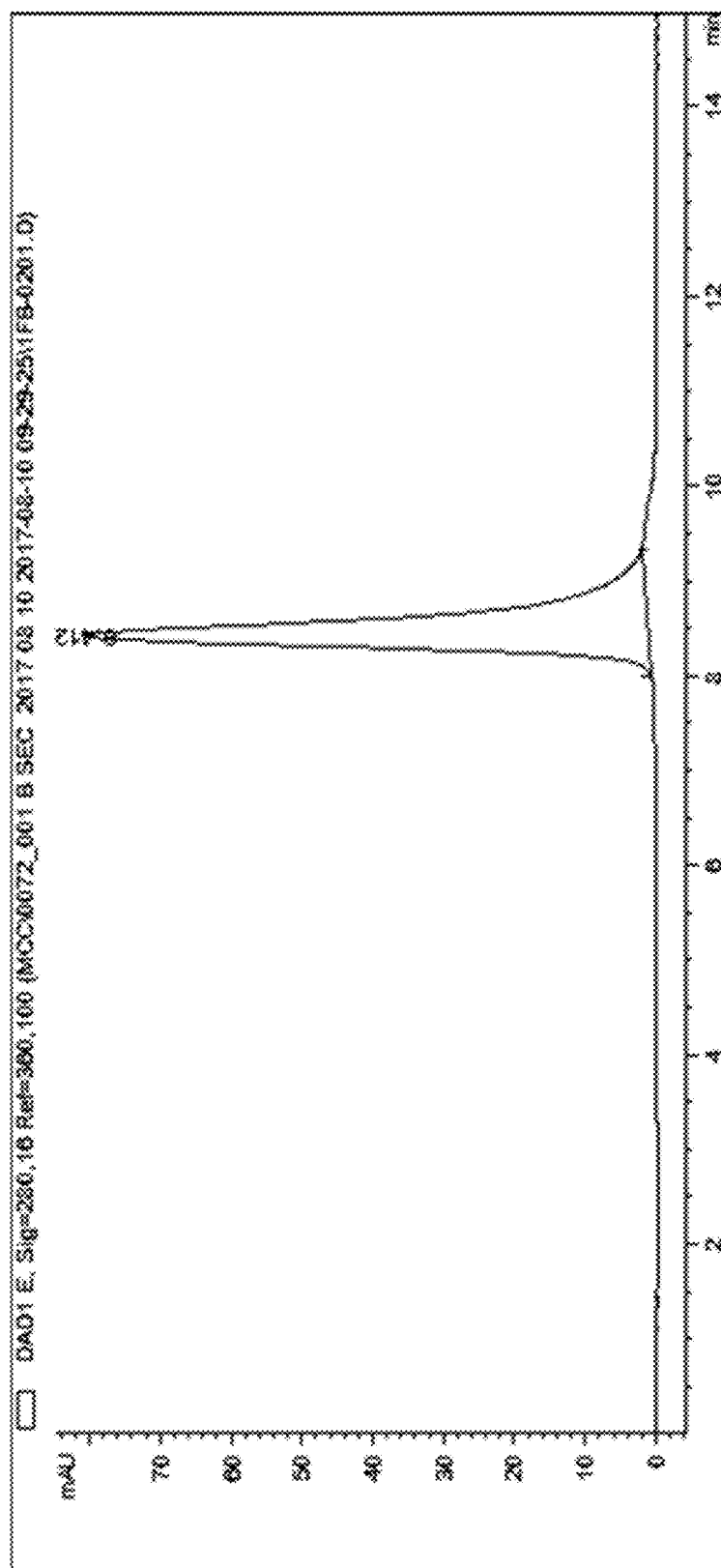
FIG. 8B depicts a chromatogram of anti-CD71 mAb produced using SEC method 1.
Figure 8C:
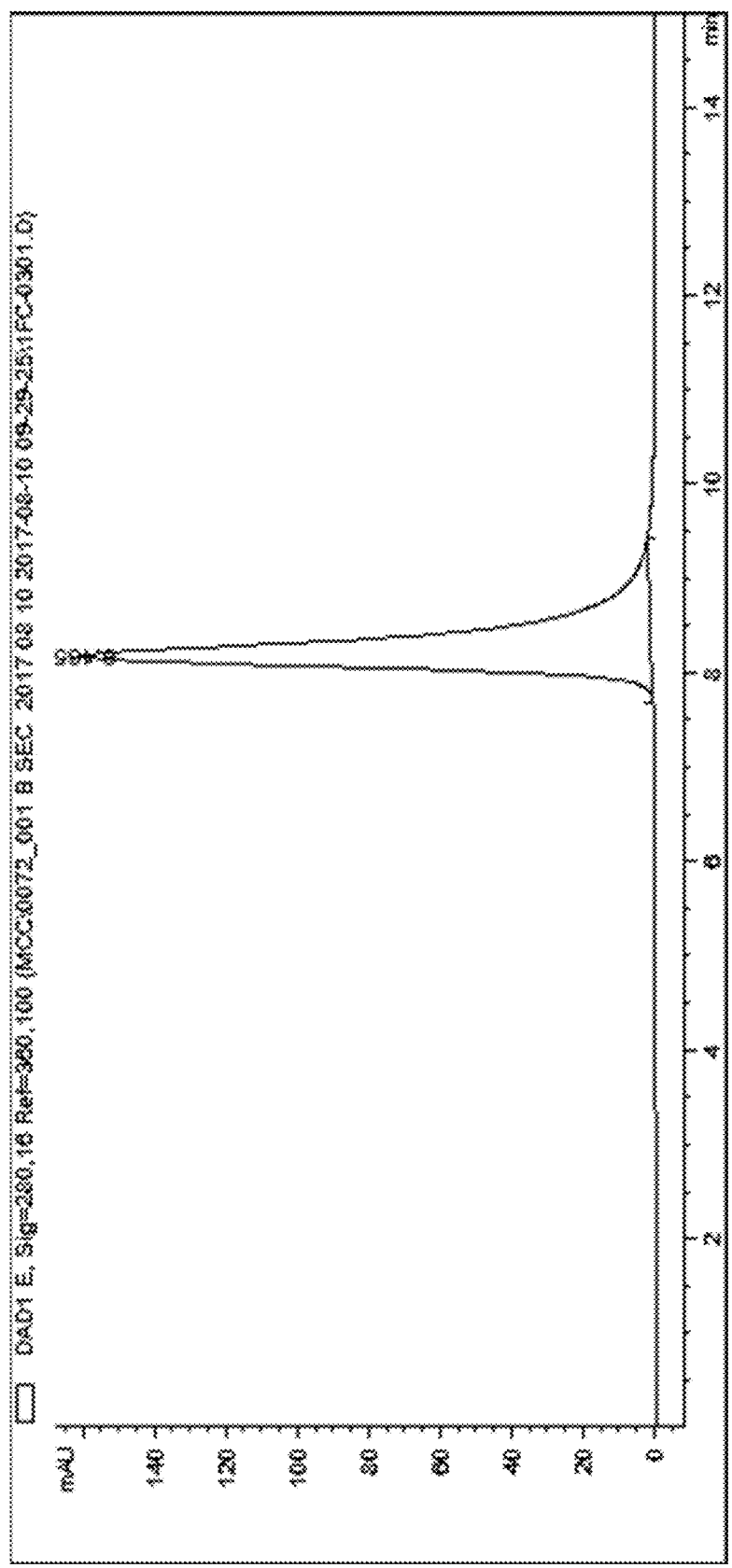
FIG. 8C depicts a chromatogram of anti-CD71 mAb-PS ASO DAR 1 conjugate produced using SEC method 1.
Figure 8D:
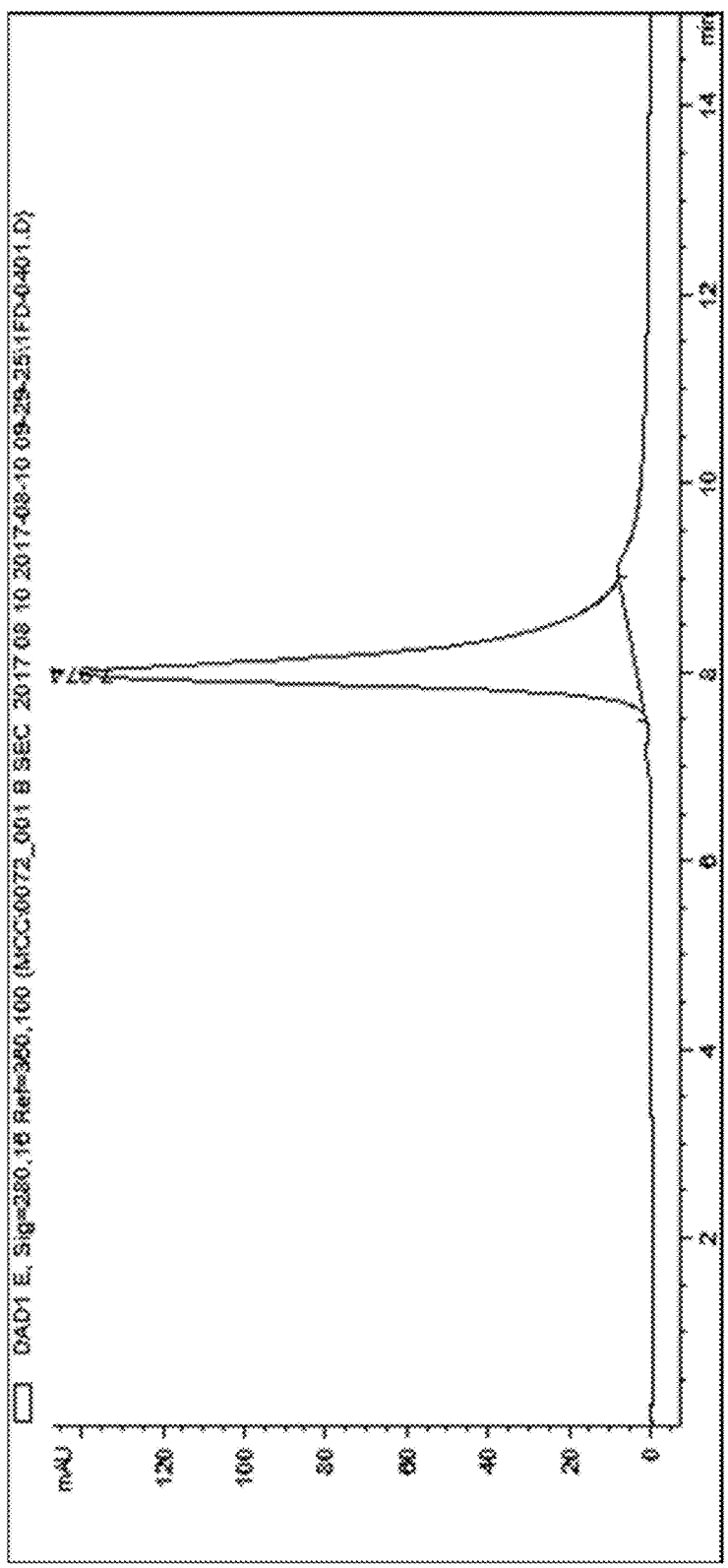
FIG. 8D depicts a chromatogram of anti-CD71 mAb-PS ASO DAR 2 conjugate produced using SEC method 1.
Figure 8E:
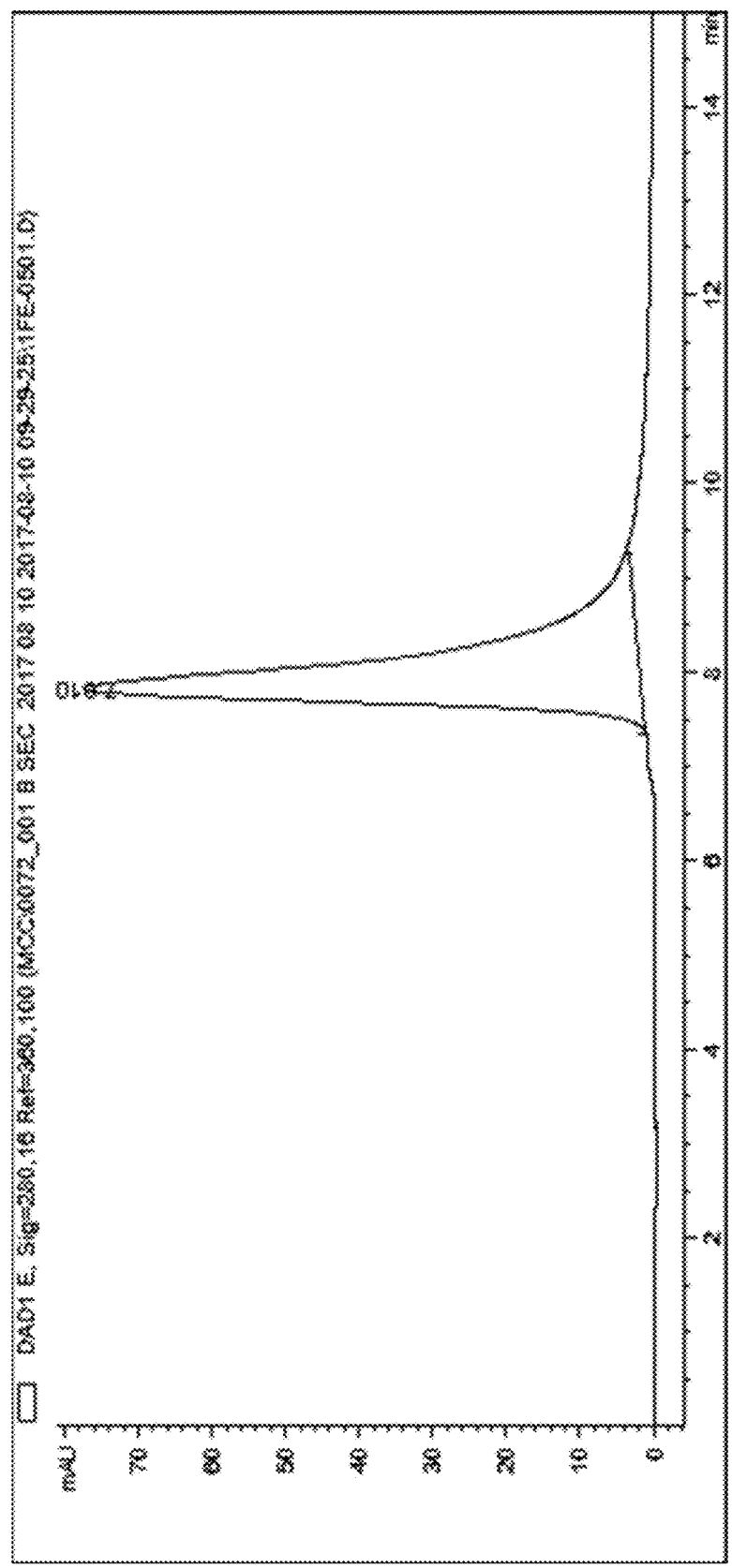
FIG. 8E depicts a chromatogram of anti-CD71 mAb-PS ASO DAR 3 conjugate produced using SEC method 1.
Figure 8F:
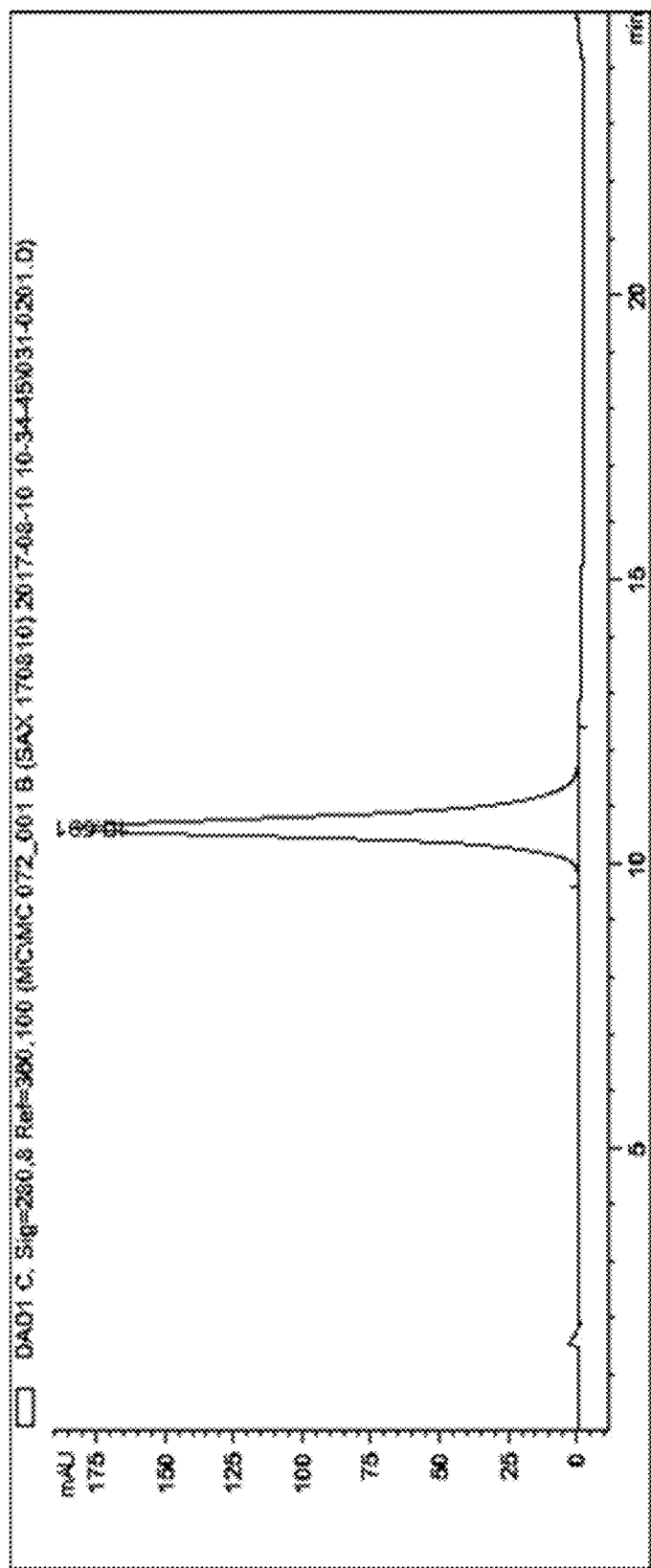
FIG. 8F depicts a chromatogram of anti-CD71 mAb-PS ASO DAR 1 conjugate produced using SAX method 2.
Figure 8G:
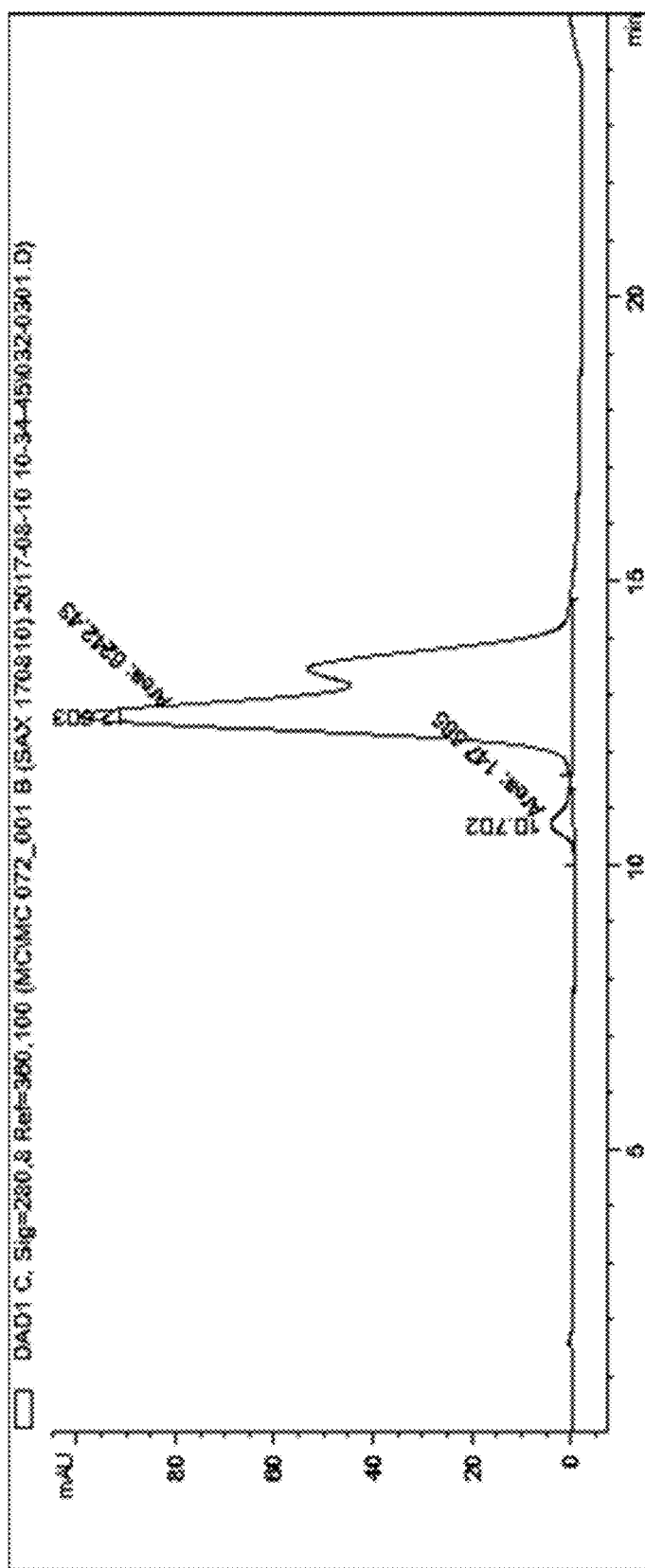
FIG. 8G depicts a chromatogram of anti-CD71 mAb-PS ASO DAR 2 conjugate produced using SAX method 2.
Figure 8H:
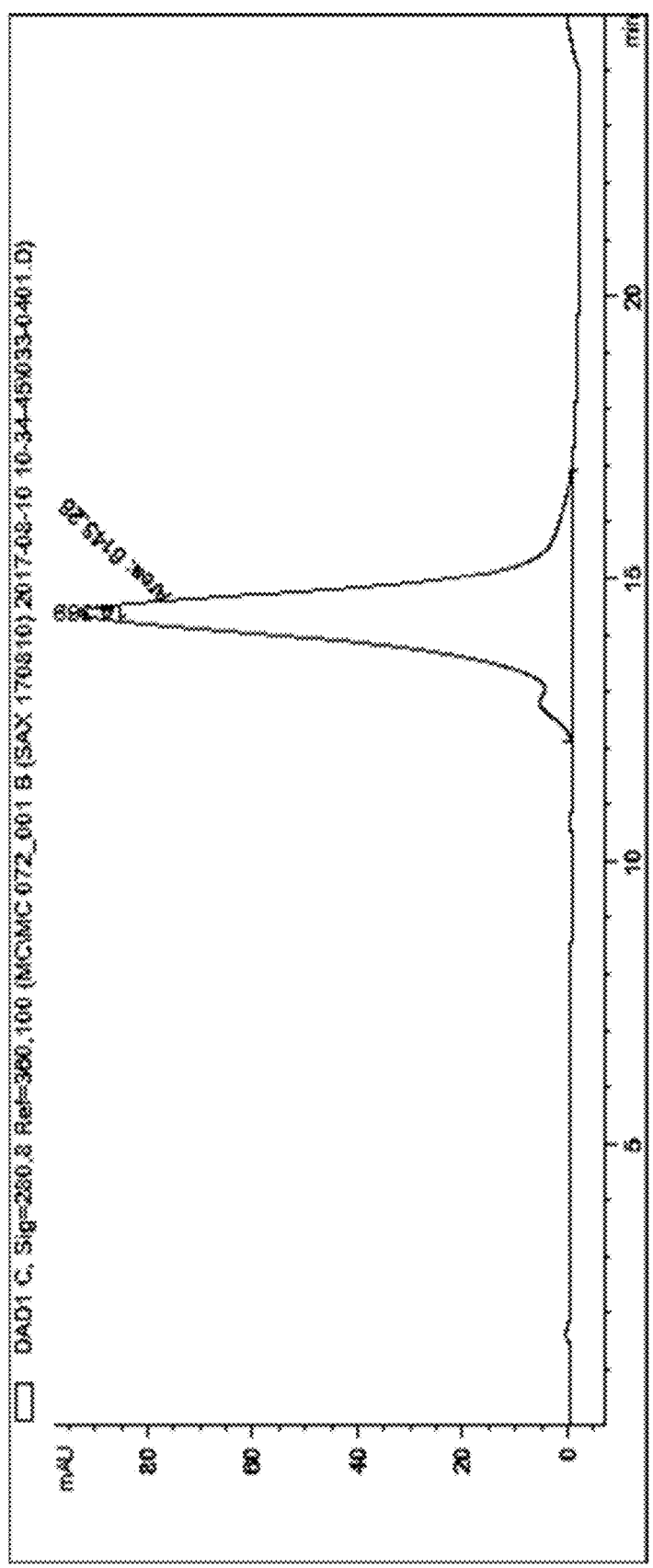
FIG. 8H depicts a chromatogram of anti-CD71 mAb-PS ASO DAR 3 conjugate produced using SAX method 2.

The isolated conjugates were characterized by size exclusion chromatography (SEC) and SAX. Size exclusion chromatography method 1 was used to confirm the absence of high molecular weight aggregates and unconjugated ASO. See FIGS. 8B-8E. FIG. 8B shows a chromatogram of anti-CD71 mAb produced using SEC method 1. FIG. 8C shows a chromatogram of anti-CD71 mAb-PS ASO DAR 1 conjugate produced using SEC method 1. FIG. 8D shows a chromatogram of anti-CD71 mAb-PS ASO DAR 2 conjugate produced using SEC method 1. FIG. 8E shows a chromatogram of anti-CD71 mAb-PS ASO DAR 3 conjugate produced using SEC method 1. The purity of the conjugate was assessed by analytical HPLC using SAX method 2. See FIGS. 8F-8H. FIG. 8F shows a chromatogram of anti-CD71 mAb-PS ASO DAR 1 conjugate produced using SAX method 2. FIG. 8G shows a chromatogram of anti-CD71 mAb-PS ASO DAR 2 conjugate produced using SAX method 2. FIG. 8H shows a chromatogram of anti-CD71 mAb-PS ASO DAR 3 conjugate produced using SAX method 2. The 260/280 nm UV absorbance ratio of each sample was compared to a standard curve of known ratios of ASO and antibody to confirm drug-to-antibody ratio (DAR).

Example 4: In Vitro Activity of Anti-CD71 mAb-PMO Conjugate

The anti-CD71 mAb-PMO conjugate was made and characterized as described in Example 3. The conjugate was assessed for its ability to mediate exon skipping in vitro in differentiated C2C12 cells using nested PCR using methods similar to Example 2. Briefly, the potency of "naked" morpholino ASO ("PMO") was compared to an anti-CD71 mAb-PMO conjugate at multiple concentrations with the relevant vehicle controls. Controls included vehicle ("Veh"), scramble morpholino at 50 uM ("Scr50"), and no antibody ("Neg-Ab"). The concentrations of PMO used included 50 uM, 1 uM, and 0.02 uM. The concentrations of anti-CD71 mAB-PMO DAR 1,2 used included 200 nM, 20 nM, and 2 nM. "DAR" refers to drug-to-antibody ratio.

Following cDNA synthesis, two rounds of PCR amplification (primary and nested PCR) were used to detect exon-skipping. PCR reactions were analyzed in a 4% TAE agarose gel (FIG. 9).

Figure 9:
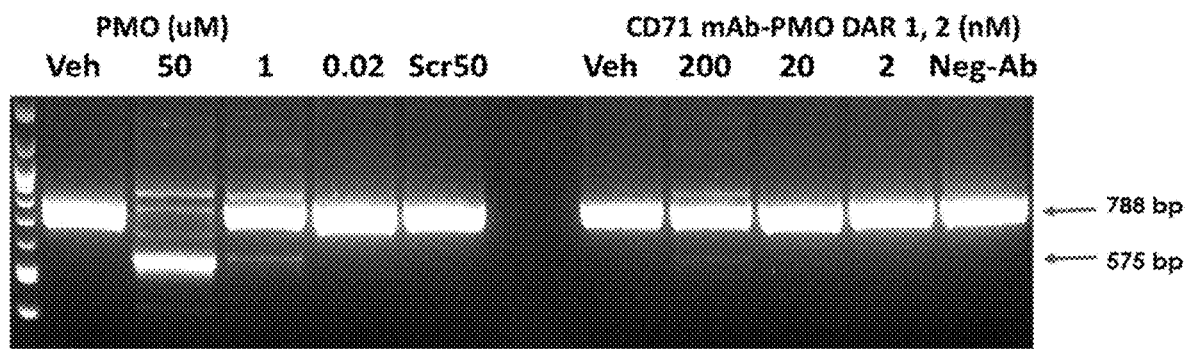
FIG. 9 depicts an agarose gel from nested PCR detecting exon 23 skipping in differentiated C2C12 cells using PMO and anti-CD71 mAb-PMO conjugate.

Referring to FIG. 9, anti-CD71 mAb-PMO conjugate produced measurable exon 23 skipping in differentiated C2C12 cells and lower concentrations than the "naked" PMO control. The wild-type product had an expected size of 788 base pairs and the skipped DMD A23 of 575 base pairs.

Figure 10:
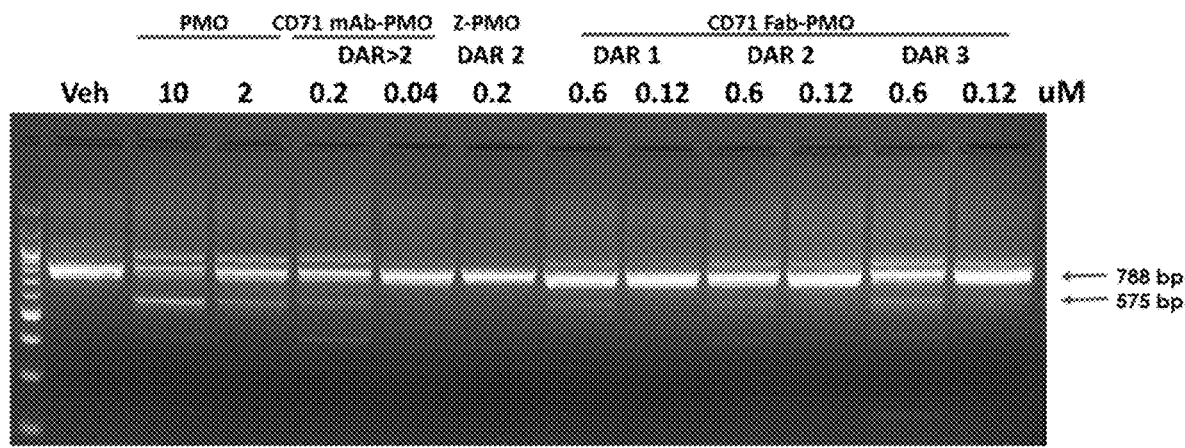
FIG. 10 depicts an agarose gel from nested PCR detecting exon 23 skipping in differentiated C2C12 cells using PMO, anti-CD71 mAb-PMO, and anti-CD71 Fab-PMO conjugates.

A second experiment included an anti-CD71 Fab-PMO conjugate and a PMO targeted with an anti-EGFR ("Z-PMO") as a negative control (FIG. 10). The concentrations of PMO used included 10 uM and 2 uM. The concentrations of anti-CD71 mAb-PMO used included 0.2 uM and 0.04 uM. Anti-CD71 mAb-PMO had a DAR of 2. Z-PMO was used at a concentration of 0.2 uM and had a DAR of 2. Concentrations of anti-CD71 Fab-PMO included 0.6 uM and 0.12 uM. DAR of 1, 2, and 3 for anti-CD71 mAb-PMO at 0.6 uM and 0.12 uM were assayed.

Referring to FIG. 10, Receptor mediated uptake utilizing the transferrin receptor, the anti-CD71 mAb-PMO, and anti-CD71 Fab-PMO conjugates resulted in measurable exon 23 skipping in C2C12 cells and lower concentrations than the "naked" PMO control. There was no measurable exon 23 skipping from the Z-PMO at the concentration tested, which produced skipping from the anti-CD71 conjugates.

Example 5. In Vitro Activity of Anti-CD71-ASO mAb PS Conjugate

Figure 11:
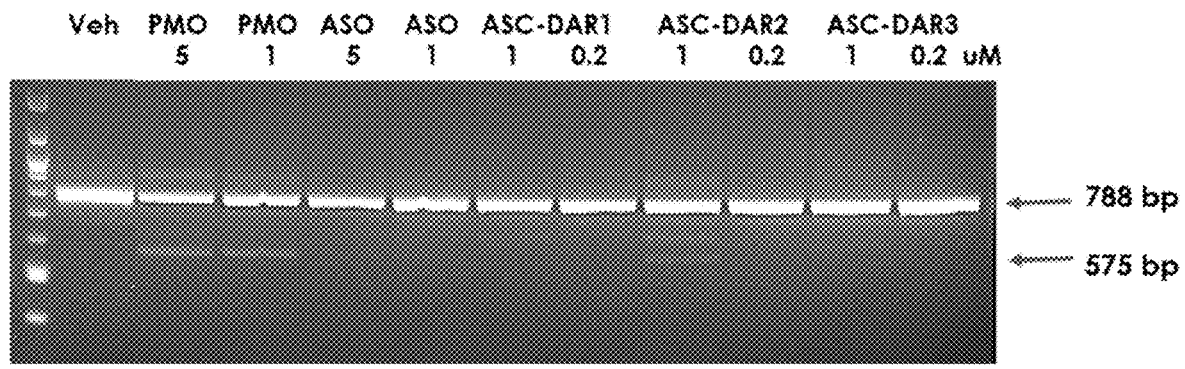
FIG. 11 depicts an agarose gel from nested PCR detecting exon 23 skipping in differentiated C2C12 cells PMO, ASO, conjugated anti-CD71 mAb-ASO of DAR1 ("ASC-DAR1"), conjugated anti-CD71 mAb-ASO of DAR2 ("ASC-DAR2"), and conjugated anti-CD71 mAb-ASO of DAR3 ("ASC-DAR3").

The anti-CD71 mAb-PS ASO conjugate was made and characterized as described in Example 3. The conjugate was assessed for its ability to mediate exon skipping in vitro in differentiated C2C12 cells using nested PCR using similar methods as described in Example 2. Briefly, the potency of "naked" phosphorothioate ASO (PS ASO) was compared to an anti-CD71 mAb-PS ASO conjugate at multiple concentrations, with the relevant vehicle control. Two rounds of of PCR amplification (primary and nested PCR) were performed following cDNA synthesis to detect exon-skipping. PCR reactions were analyzed in a 4% TAE agarose gel (FIG. 11). FIG. 11 shows an agarose gel of PMO, ASO, conjugated anti-CD71 mAb-ASO of DAR1 ("ASC-DAR1"), conjugated anti-CD71 mAb-ASO of DAR2 ("ASC-DAR2"), and conjugated anti-CD71 mAb-ASO of DAR3 ("ASC-DAR3"). "PMO" and "ASO" refers to free PMO and ASO, unconjugated to antibody. "Veh" refers to vehicle only. The concentrations tested included 0.2, 1, and 5 micromolar (μM).

Referring to FIG. 11, the anti-CD71 mAb-PS ASO conjugate produced measurable exon 23 skipping in differentiated C2C12 cells and lower concentrations than the "naked" PS ASO control. The wild-type product had an expected size of 788 base pairs and the skipped DMD A23 of 575 base pairs.

Example 6: In Vivo Activity of Anti-CD71 mAb-PMO Conjugate

The anti-CD71 mAb-PMO conjugate was made and characterized as described in Example 3. The conjugate anti-CD71 mAb-PMO DAR1,2 anti-CD71 and mAb-PMO DAR>2 were assessed for its ability to mediate exon skipping in vivo in wild-type CD-1 mice using similar methods as described in Example 2. "DAR" refers to drug-to-antibody ratio.

Mice were dosed via intravenous (iv) injection with the mAb, vehicle control, and antisense conjugates (ASCs) at the doses as provided in Table 12. "DAR" refers to drug-to-antibody ratio. The "naked" PMO was dosed via intramuscular injection into the gastrocnemius muscle at the doses provided in Table 12. After 4, 7, or 14 days, heart and gastrocnemius muscle tissues were harvested and snap-frozen in liquid nitrogen. RNAs were isolated, reversed transcribed and a nested PCR reactions were performed. PCR reactions were analyzed in 4% TAE agarose gels which were then quantitated by densitometry.

TABLE 12

In vivo study design

| Group | Test Article | N | mAb dose (mg/kg) | PMO Dose (mg/kg) | PMO:mAb Ratio (mol/mol) | Harvest Time (h) |
|---|---|---|---|---|---|---|
| 1 | anti-CD71 mAb-PMO, DAR1,2 | 3 | 50 | 4.8 | 1.6 | 96 |
| 2 | anti-CD71 mAb-PMO, DAR1,2 | 3 | 50 | 4.8 | 1.6 | 168 |
| 3 | anti-CD71 mAb-PMO, DAR1,2 | 3 | 50 | 4.8 | 1.6 | 336 |
| 4 | anti-CD71 mAb-PMO, DAR>2 | 3 | 50 | 10.5 | 3.7 | 96 |
| 5 | anti-CD71 mAb-PMO, DAR>2 | 3 | 50 | 10.5 | 3.7 | 168 |
| 6 | anti-CD71 mAb-PMO, DAR>2 | 3 | 50 | 10.5 | 3.7 | 336 |
| 7 | anti-CD71 mAb | 3 | 50 | | | 96 |
| 8 | anti-CD71 mAb | 3 | 50 | | | 168 |
| 9 | anti-CD71 mAb | 3 | 50 | | | 336 |
| 10 | PMO | 3 | | 40 ug/inj. | | 96 |
| 11 | PMO | 3 | | 40 ug/inj. | | 168 |
| 12 | PMO | 3 | | 40 ug/inj. | | 336 |
| 13 | Vehicle | 3 | | | | 96 |
| 14 | Vehicle | 3 | | | | 168 |
| 15 | Vehicle | 3 | | | | 336 |

Figure 12A:
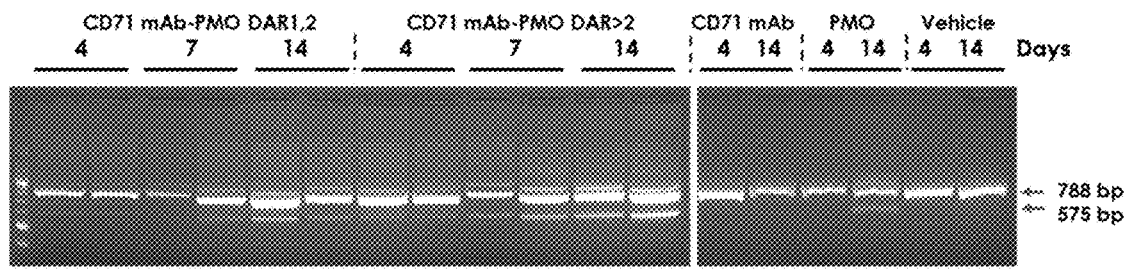
FIG. 12A depicts an agarose gel from nested PCR detecting exon 23 skipping in gastrocnemius muscle of wild-type mice administered a single intravenous injection of anti-CD71 mAb-PMO conjugate.
Figure 12B:
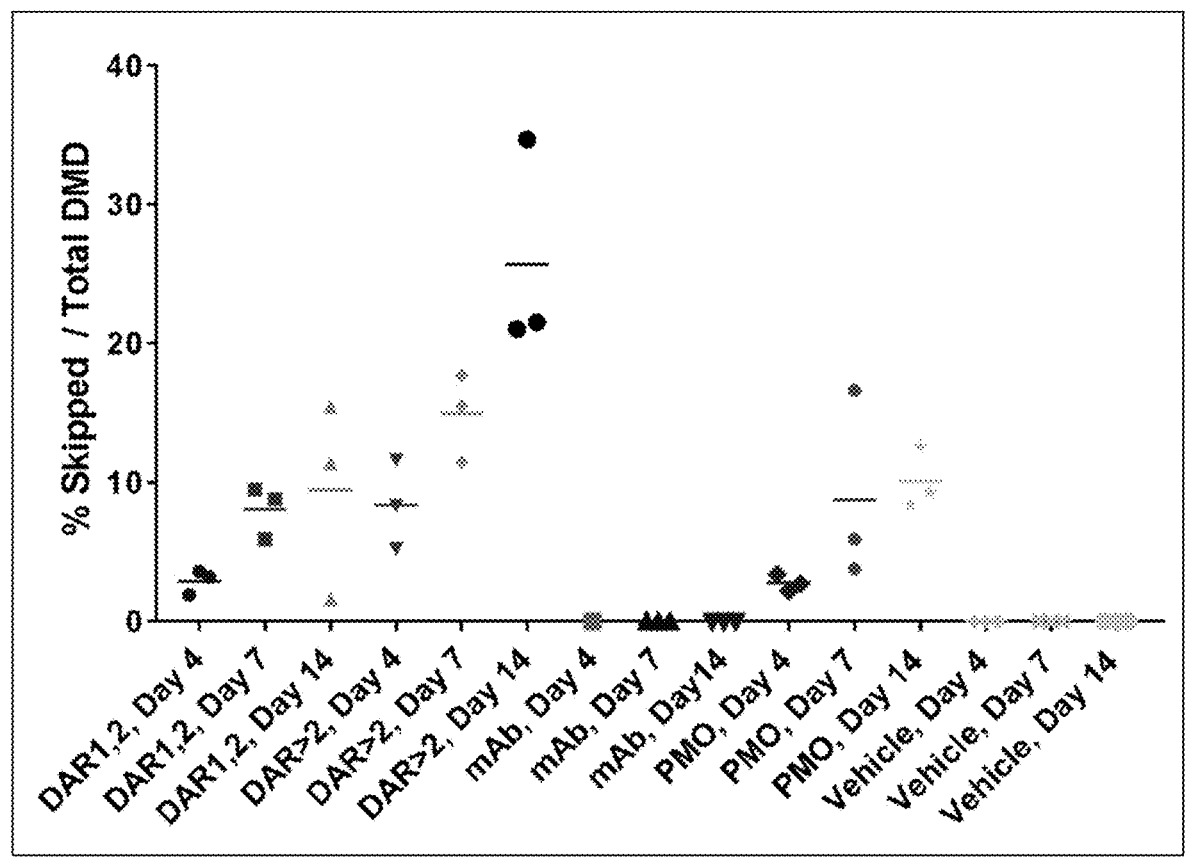
FIG. 12B is a graph of quantification of PCR products from gastrocnemius muscle.
Figure 12C:
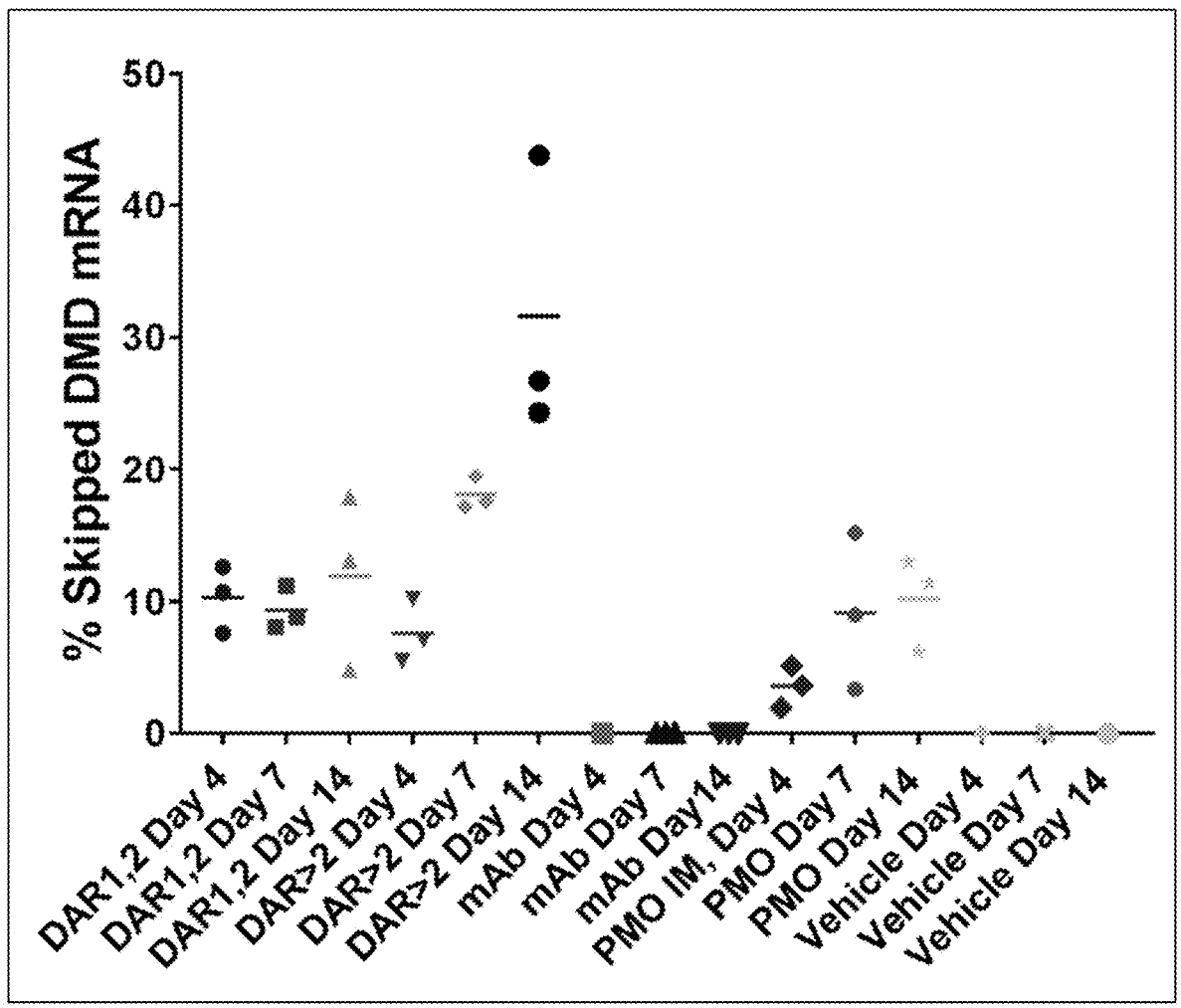
FIG. 12C is a graph of quantification of in vivo exon skipping using Taqman qPCR from gastrocnemius muscle from wild-type mice.

FIG. 12A shows a gel electrophoresis of gastrocnemius muscle samples from mice administered anti-CD71 mAb-PMO DAR 1,2, anti-CD71 mAb-PMO DAR>2, anti-CD71 mAb, PMO, and vehicle for 4, 7, or 14 days. The wild-type product had an expected size of 788 base pairs and the skipped DMD A23 of 575 base pairs. Anti-CD71 mAb-PMO DAR 1,2 and anti-CD71 mAb-PMO DAR>2 produced measurable exon 23 skipping in gastrocnemius muscle and lower concentrations than the "naked" PMO control. The intensity of the bands on the gel (FIG. 12A) was quantitated by densitometry as seen in FIG. 12B. FIG. 12C shows the quantification of in vivo exon skipping in wild-type mice gastrocnemius muscle using Taqman qPCR.

Figure 13A:
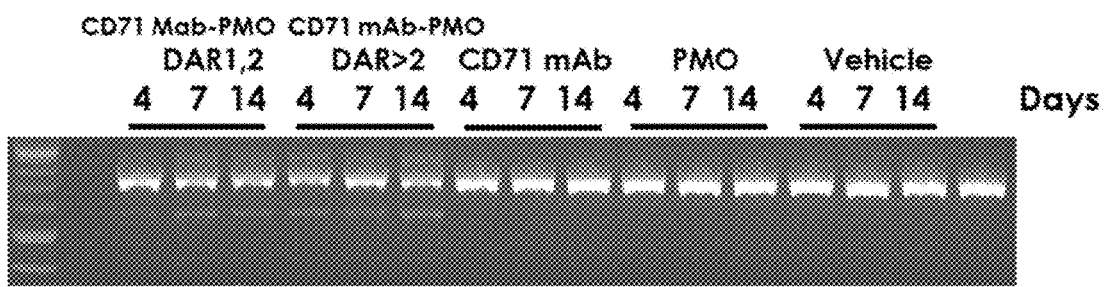
FIG. 13A depicts an agarose gel from nested PCR detecting exon 23 skipping in heart muscle from wild-type mice after a single intravenous injection.
Figure 13B:
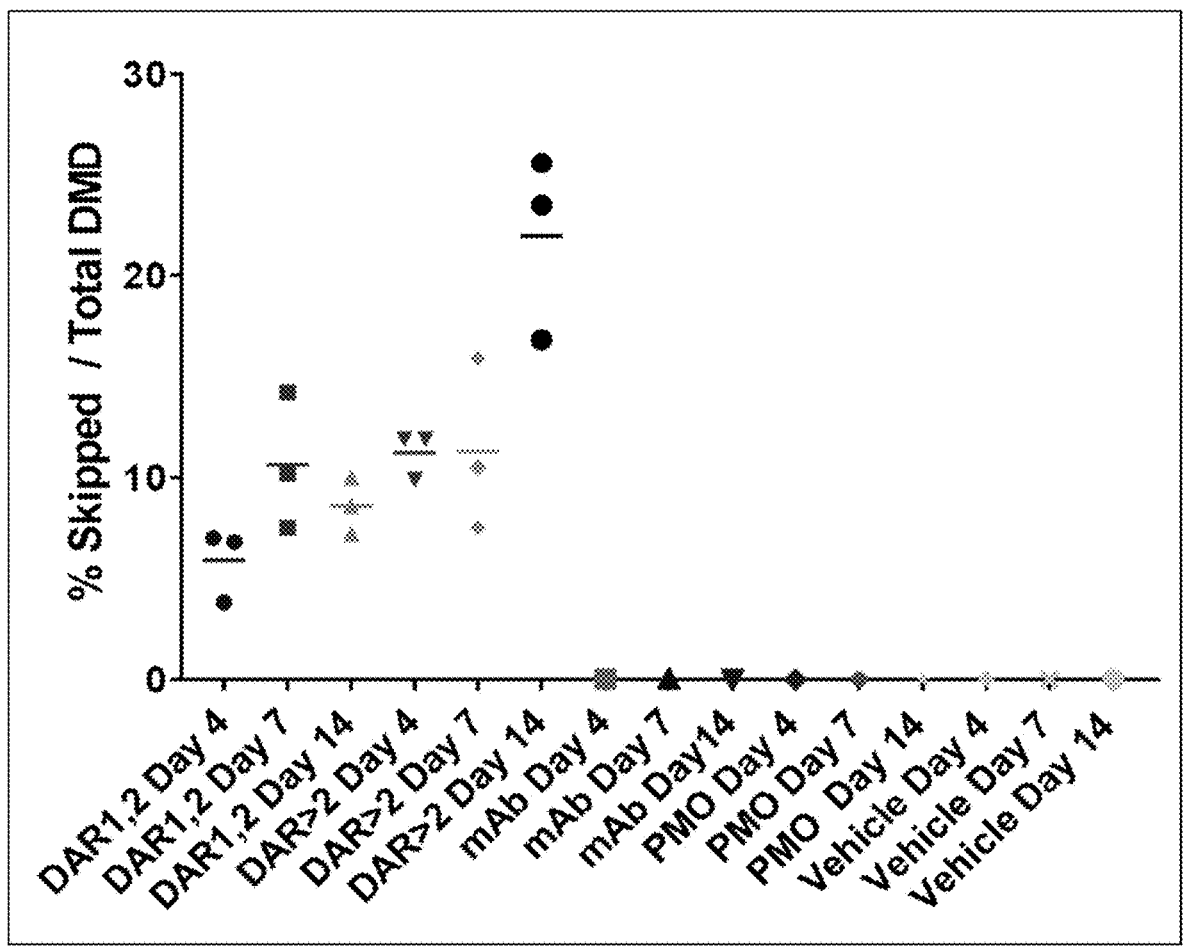
FIG. 13B is a graph of quantification of PCR products from heart muscle.

FIG. 13A shows a gel electrophoresis of heart samples from mice administered anti-CD71 mAb-PMO DAR 1,2, anti-CD71 mAb-PMO DAR>2, anti-CD71 mAb, PMO, and vehicle for 4, 7, or 14 days. The wild-type product had an expected size of 788 base pairs and the skipped DMD A23 of 575 base pairs. The intensity of the bands on the gel (FIG. 13A) was quantitated by densitometry as seen in FIG. 13B. Similar results as with the gastrocnemius muscle samples were obtained. Anti-CD71 mAb-PMO DAR 1,2 and anti-CD71 mAb-PMO DAR>2 produced measurable exon 23 skipping in gastrocnemius muscle and lower concentrations than the "naked" PMO control.

Figure 14:
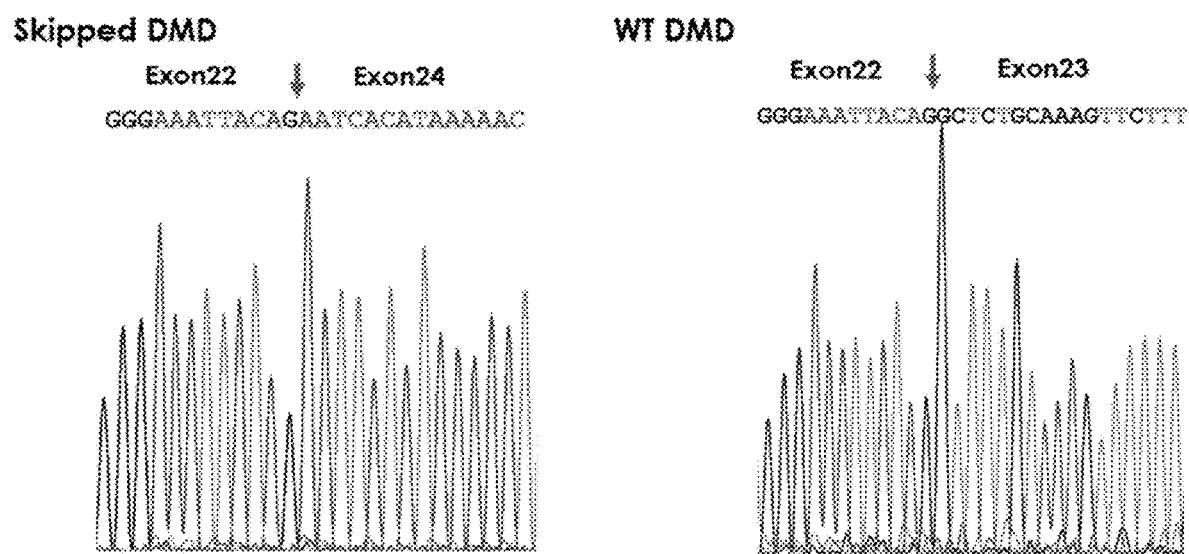
FIG. 14 depicts sequencing data of DNA fragments from skipped and wild-type PCR products (SEQ ID NOS 976-977, respectively).

DNA fragments were then isolated from the 4% agarose gels and sequenced. The sequencing data confirmed the correct sequence in the skipped and wild-type products as seen in FIG. 14.

Example 7. Antisense Oligonucleotide Sequences and Synthesis

The sequences in Table 13 were made targeting different exons in different genes.

TABLE 13

Sequences

| SEQ ID NO. | Target | PMO sequence (5'to 3') |
|---|---|---|
| 45 | Exon 23 in mouse dystrophin | GGCCAAACCTCGGCTTACCTGAAAT |
| 46 | Exon 2 in mouse myostatin (MSTN) | AGCCCATCTTCTCCTGGTCCTGGGAAGG |
| 47 | Exon 11 in mouse phenylalanine hydroxylase (PAH) | ATCCTCTTTGGTAACCTCACCTCAC |
| 48 | KRAS-011 (human cancer) | TCGTCCACAAAATGATTCTGAATTA |
| 49 | Scramble | CGGTGTGTGTATCATTCTCTAGTGT |

Example 8. In Vivo Activity of CD71 mAb-PMO Conjugate in Multiple Tissues

The CD71 mAb-PMO conjugates were made and characterized as described in Example 3. The conjugate (DAR3+) was assessed for its ability to mediate exon skipping in vivo in wild type CD-1 mice, see example 2 for full experimental details. In brief, mice were dosed via intravenous (iv) injection with vehicle control and indicated ASCs at the doses indicated, see FIG. 7A. After 7, 14 or 28 days, diaphragm, heart and gastrocnemius muscle tissues were harvested and snap-frozen in liquid nitrogen. RNAs were isolated, reversed transcribed, real-time qPCR and nested PCR reactions were performed as described in Example 2 using the appropriate primer/probe sets. PCR reactions were analyzed in 1% TAE agarose gels.

In vivo study design to assess the ability of the CD71 mAb-PMO conjugate to mediate exon 23 skipping in wild type mice is seen in Table 14.

TABLE 14

In vivo study design

| Group | Test Article | N | mAb-PMO mAb dose (mg/kg) | PMO Dose (mg/kg) | PMO:mAb Ratio (mol/mol) | Harvest Time (WEEKS) |
|---|---|---|---|---|---|---|
| 1 | Vehicle | 3 | | | | 1 |
| 2 | Vehicle | 3 | | | | 4 |
| 3 | CD71-scr, DAR3+ | 3 | 50 | 10 | 3.0 | 2 |
| 4 | CD71-DMD PMO, DAR3+ | 3 | 50 | 10 | 3.0 | 1 |
| 5 | CD71-DMD PMO, DAR3+ | 3 | 50 | 10 | 3.0 | 2 |
| 6 | CD71-DMD PMO, DAR3+ | 3 | 50 | 10 | 3.0 | 4 |

Figure 15A:
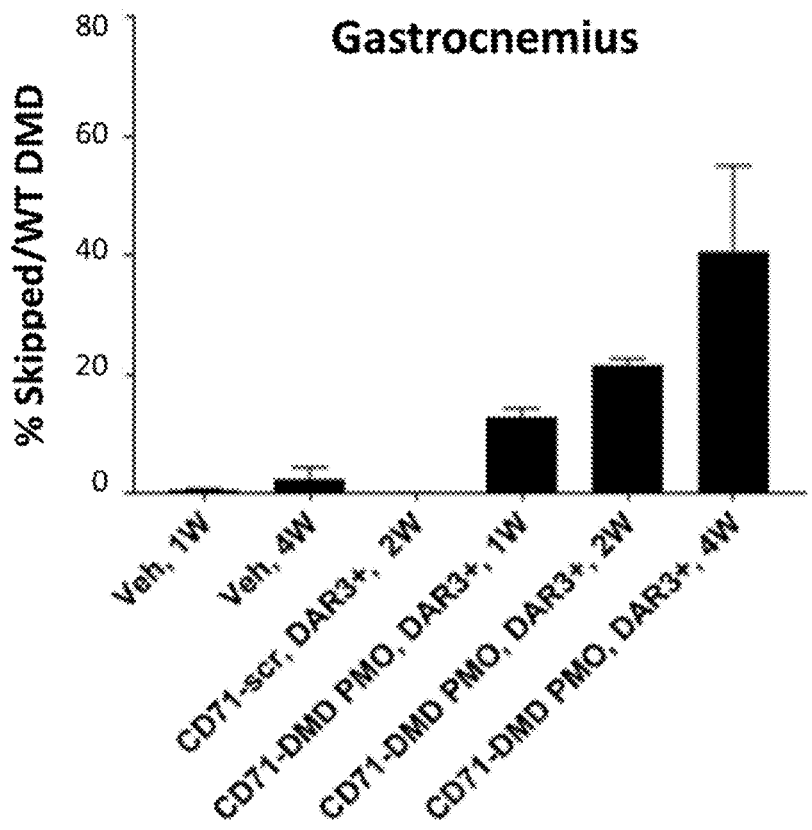
FIG. 15A is a graph of quantification of in vivo exon skipping in wild type mice in gastrocnemius muscle using Taqman qPCR.
Figure 15B:
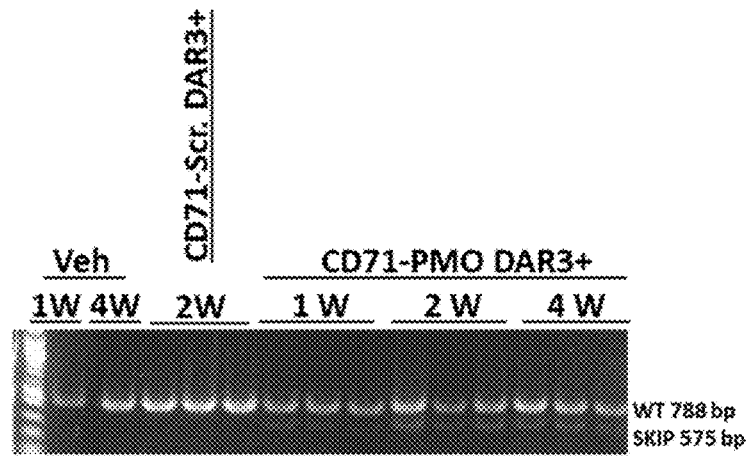
FIG. 15B is a graph of quantification of in vivo exon skipping in wild type mice in gastrocnemius muscle using nested PCR.
Figure 15C:
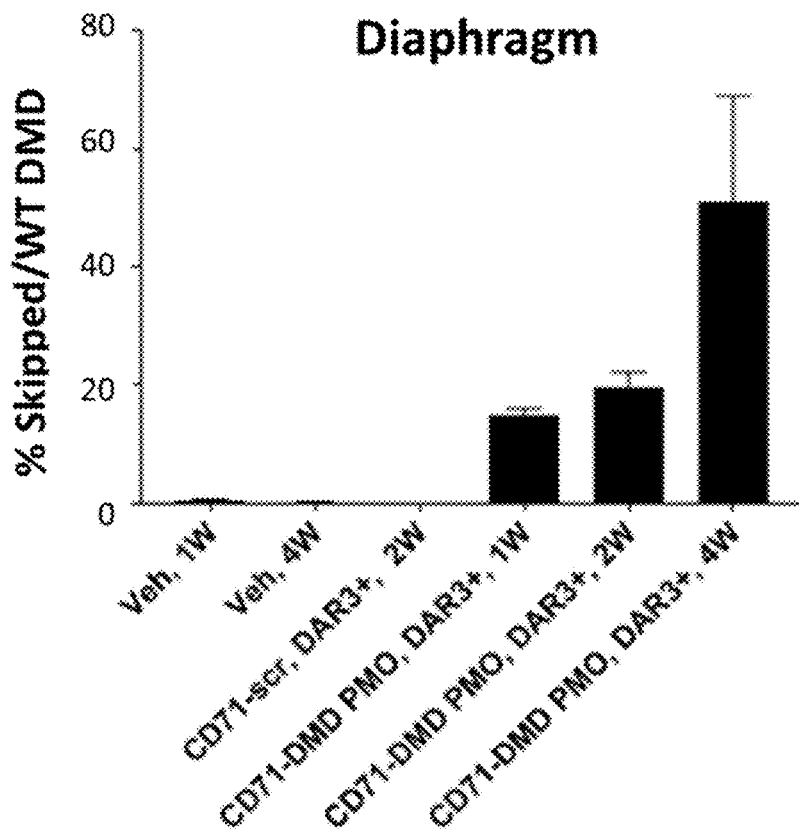
FIG. 15C is a graph of quantification of in vivo exon skipping in wild type mice in diaphragm muscle using Taqman qPCR.
Figure 15D:
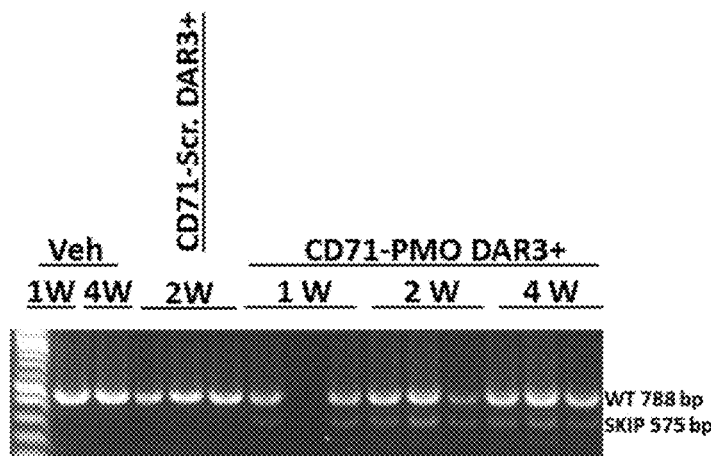
FIG. 15D is a graph of quantification of in vivo exon skipping in wild type mice in diaphragm muscle using nested PCR.
Figure 15E:
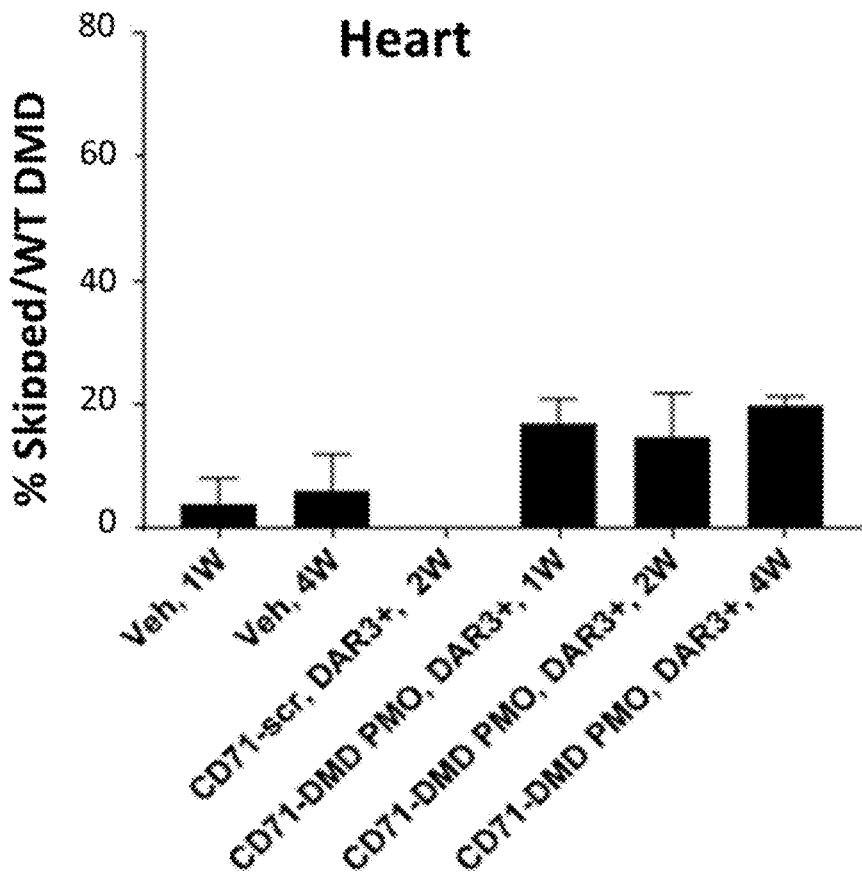
FIG. 15E is a graph of quantification of in vivo exon skipping in wild type mice in heart muscle using Taqman qPCR.
Figure 15F:
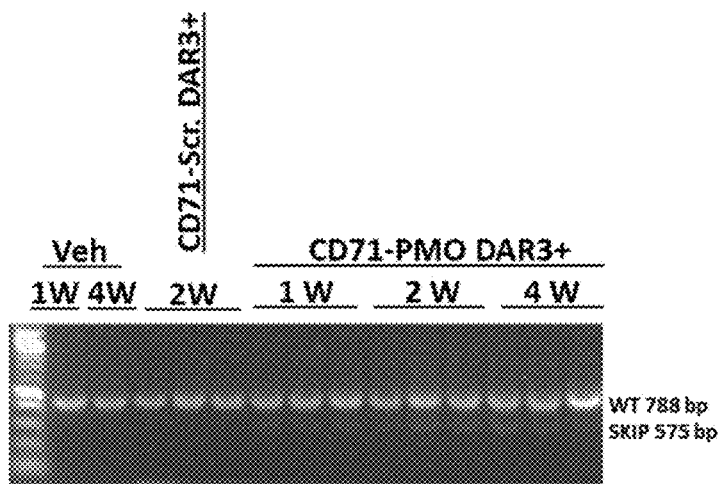
FIG. 15F is a graph of quantification of in vivo exon skipping in wild type mice in heart muscle using nested PCR.

Referring to FIG. 15A, FIG. 15C, and FIG. 15E, in vivo exon skipping was measured in wild type mice in the gastrocnemius (FIG. 15A), diaphragm (FIG. 15C) and heart muscle (FIG. 15E) using Taqman qPCR. Referring to FIG. 15B, FIG. 15D, and FIG. 15F, the CD71 mAb-PMO conjugates produced measurable exon23 skipping in gastrocnemius (FIG. 15B), diaphragm (FIG. 15D), and heart muscle (FIG. 15F) using nested PCR. The wild type product had an expected size of 788 bp, and the skipped DMD A23 had a size of 575 bp. The intensity of the bands on the gel was quantitated by densitometry, and the data are presented as the % of skipped product compared to wild-type dystrophin.

Example 9. In Vivo Activity of CD71 mAb-PMO Conjugates Against Mouse MSTN

The CD71 mAb-PMO conjugate targeting exon 2 of mouse myostatin (5'AGCCCATCTTCTCCTGGTCCTGG-GAAGG) (SEQ ID NO: 46) was made and characterized as described in Example 3. The conjugates (DAR1/2 and DAR3+) were assessed for its ability to mediate exon skipping in vivo in wild type CD-1 mice using similar methods as described in Example 2. In brief, mice were dosed via intravenous (iv) injection with the mAb, vehicle control and indicated ASCs at the doses indicated as seen in Table 15.

TABLE 15

In vivo study design

| Group | Test Article | N | mAb-PMO mAb dose (mg/kg) | PMO Dose (mg/kg) | PMO:mAb Ratio (mol/mol) | Harvest Time (WEEKS) |
|---|---|---|---|---|---|---|
| 1 | CD71 mAb-PMO, DAR1/2 | 3 | 50 | 5 | 1.5 | 1 |
| 2 | CD71 mAb-PMO, DAR1/2 | 3 | 50 | 5 | 1.5 | 2 |
| 3 | CD71 mAb-PMO, DAR1/2 | 3 | 50 | 5 | 1.5 | 4 |
| 4 | CD71 mAb-PMO, DAR3+ | 3 | 50 | 10 | 3.0 | 1 |
| 5 | CD71 mAb-PMO, DAR3+ | 3 | 50 | 10 | 3.0 | 2 |
| 6 | CD71 mAb-PMO. DAR3+ | 3 | 50 | 10 | 3.0 | 4 |
| 7 | CD71-scr, DAR1/2 | 3 | 50 | 5 | 1.5 | 2 |
| 8 | CD71-scr, DAR3+ | 3 | 50 | 10 | 3.0 | 2 |
| 9 | Vehicle | 3 | | | | 1 |
| 10 | Vehicle | 3 | | | | 2 |
| 11 | Vehicle | 3 | | | | 4 |

Figure 16A:
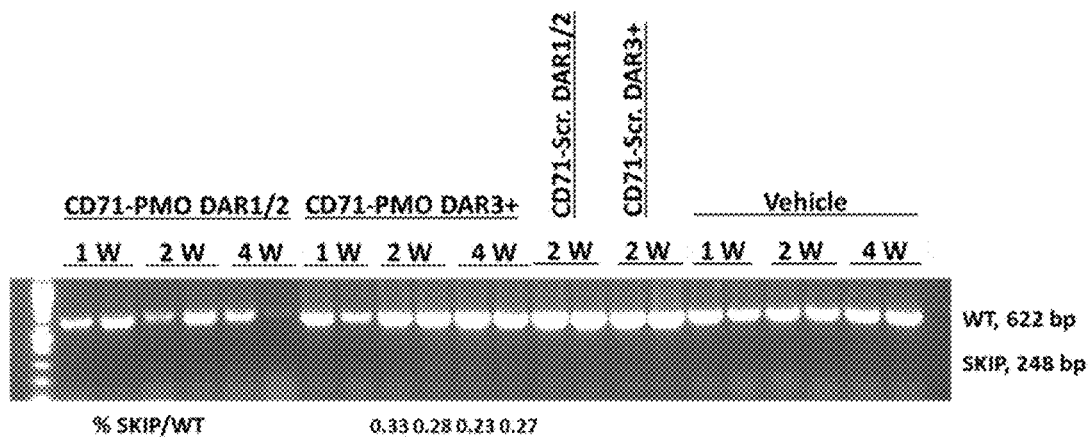
FIG. 16A depicts an agarose gel from PCR detecting CD71 mAb-PMO conjugate induction of MSTN exon 2 skipping in diaphragm muscle tissues in wild type mice after a single intravenous (i.v.) injection.
Figure 16B:
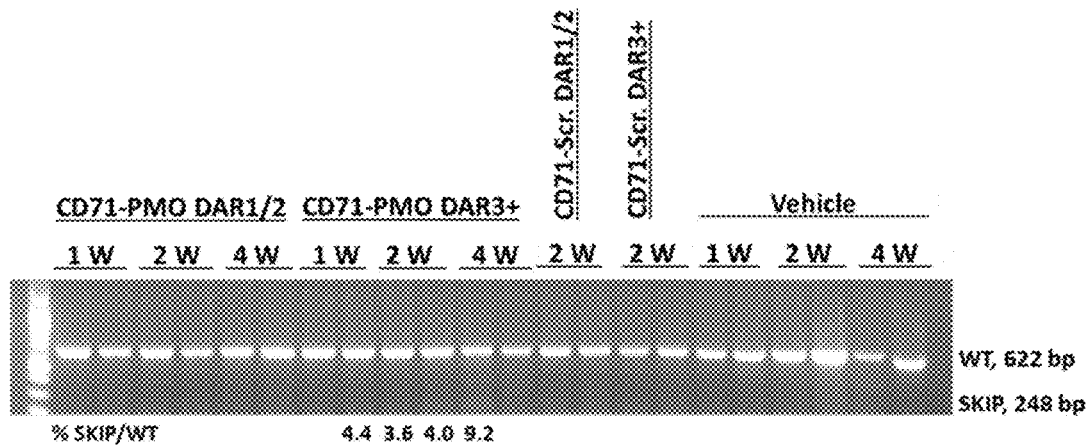
FIG. 16B depicts an agarose gel from PCR detecting CD71 mAb-PMO conjugate induction of MSTN exon 2 skipping in heart muscle tissues in wild type mice after a single intravenous (i.v.) injection.
Figure 16C:
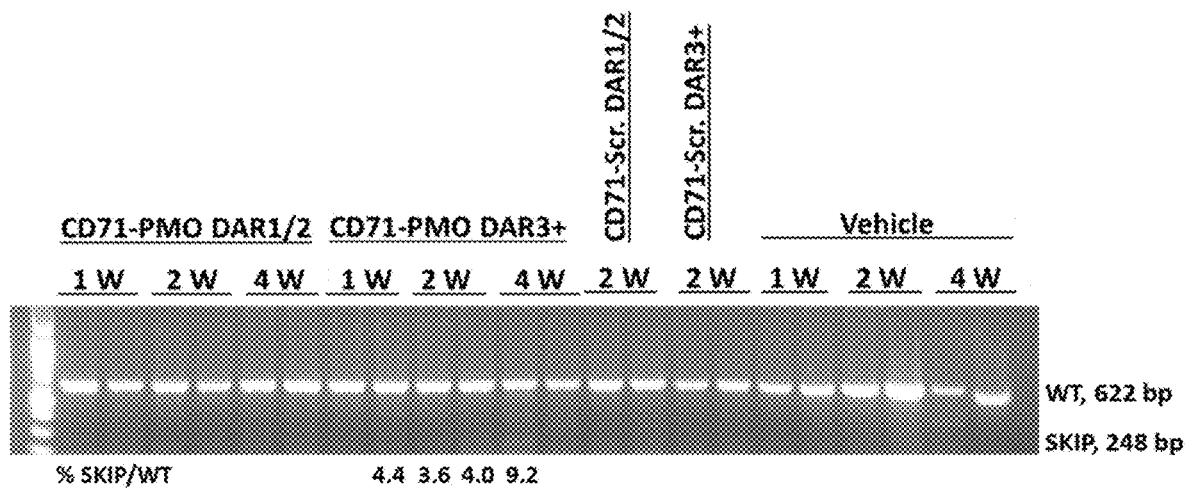
FIG. 16C depicts an agarose gel from PCR detecting CD71 mAb-PMO conjugate induction of MSTN exon 2 skipping in gastrocnemius muscle tissues in wild type mice after a single intravenous (i.v.) injection.

After 7, 14 or 28 days, diaphragm, heart and gastrocnemius muscle tissues were harvested and snap-frozen in liquid nitrogen. RNAs were isolated and reversed transcribed. PCR reactions were performed with forward primer (mMSTN-F1: 5'CCTGGAAACAGCTCCTAACATC (SEQ ID NO: 50) and reverse primer (mMSTN-R1: 5'CAGT-CAAGCCCAAAGTCTCTC (SEQ ID NO: 51) (hot start: 95° C. for 2 minutes, Denaturation at 95° C. for 45 seconds, Annealing of primers at 56° C. for 30 seconds, primer extension at 72° C. for 40 seconds for 35 cycles). PCR reactions were analyzed in a 100 TAE agarose gel as seen in FIGS. 16A-16C. The CD71 mAb-PMO conjugates produced measurable exon2 skipping in mouse diaphragm (FIG. 16A), heart (FIG. 16B) and gastrocnemius (FIG. 16C) muscle tissues. The wild type product had an expected size of 622 bp and the skipped MSTN Δ2 of 248 bp.

Example 10. In Vitro Activity of ASGPR mAb-PMO Conjugates Against the PAH Gene

Figure 17:
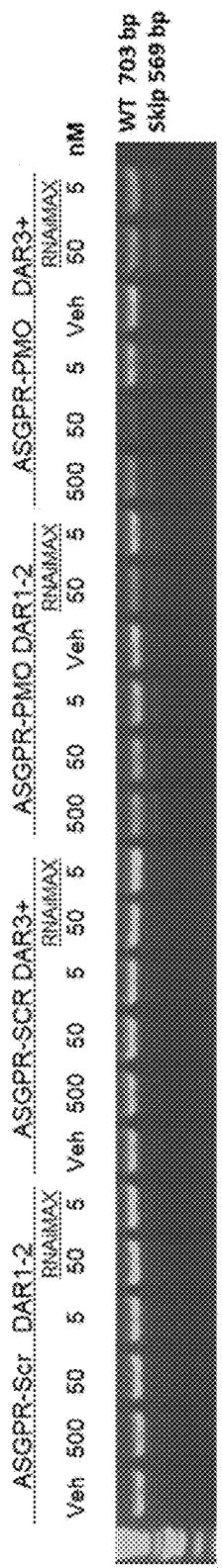
FIG. 17 depicts an agarose gel from PCR detecting ASGPR mAb-PMO conjugate induction of PAH exon 11 skipping in primary mouse hepatocytes.

The ASGPR mAb-PMO (5'ATCCTCTTTGGTAACCT-CACCTCAC (SEQ ID NO: 47) conjugate targeting exon 11 of mouse PAH was made and characterized as described in Example 3. The conjugate was assessed for its ability to mediate exon 11 skipping in the mouse PAH gene in vitro in primary mouse hepatocytes using PCR (forward primer 5'-CTAGTGCCCTTGTTTTCAGA-3' (SEQ ID NO: 52) and reverse primer 5'-AGGATCTACCACTGATGGGT-3') (SEQ ID NO: 53). In brief, the potency of ASGPR mAb-PAH PMO conjugate was compared to ASGPR mAb-scramble PMO at multiple concentrations, with the relevant vehicle control. RNAiMAX was also used to transfect the conjugates as positive controls. PCR reactions were analyzed in a 1% TAE agarose gel as seen in FIG. 17. As seen from the gel in FIG. 17, the ASGPR mAb-PMO conjugate produced measurable exon11 skipping comparable to the RNAiMAX transfected controls. The wild type product had an expected size of 703 bp and the skipped PAH Δ11 of 569 bp.

Example 11. In Vivo Activity of ASGPR mAb-PMO Conjugates

The ASGPR mAb-PMO (5'ATCCTCTTTGGTAACCT-CACCTCAC) (SEQ ID NO: 47) conjugate targeting exon 11 of mouse PAH was made and characterized as described in Example 3. The conjugate (DAR1/2 and DAR3+) was assessed for its ability to mediate exon skipping in vivo in wild type CD-1 mice using methods as described in Example 2. In brief, mice were dosed via intravenous (iv) injection with the mAb, vehicle control and indicated ASCs at the doses indicated as seen in Table 16.

TABLE 16

In vivo study design

| Group | Test Article | N | mAb-ASO mAb dose (mg/kg) | PMO Dose (mg/kg) | PMO:mAb Ratio (mol/mol) | Harvest Time (Weeks) |
|---|---|---|---|---|---|---|
| 1 | ASGPR mAb-PMO, DAR1/2 | 3 | 50 | 5 | 1.5 | 1 |
| 2 | ASGPR mAb-PMO, DAR1/2 | 3 | 50 | 5 | 1.5 | 2 |
| 3 | ASGPR mAb-PMO, DAR1/2 | 3 | 50 | 5 | 1.5 | 4 |
| 4 | ASGPR mAb-PMO, DAR3+ | 2 | 50 | 10 | 3.0 | 1 |
| 5 | ASGPR mAb-PMO, DAR3+ | 2 | 50 | 10 | 3.0 | 2 |
| 6 | ASGPR mAb-PMO, DAR3+ | 2 | 50 | 10 | 3.0 | 4 |
| 7 | ASGPR-Scr, DAR1/2 | 3 | 50 | | 1.5 | 2 |
| 8 | ASGPR-Scr, DAR3+ | 3 | 50 | | 3.0 | 2 |
| 9 | Vehicle | 3 | | | | 1 |
| 10 | Vehicle | 3 | | | | 2 |
| 11 | Vehicle | 3 | | | | 4 |

Figure 18:
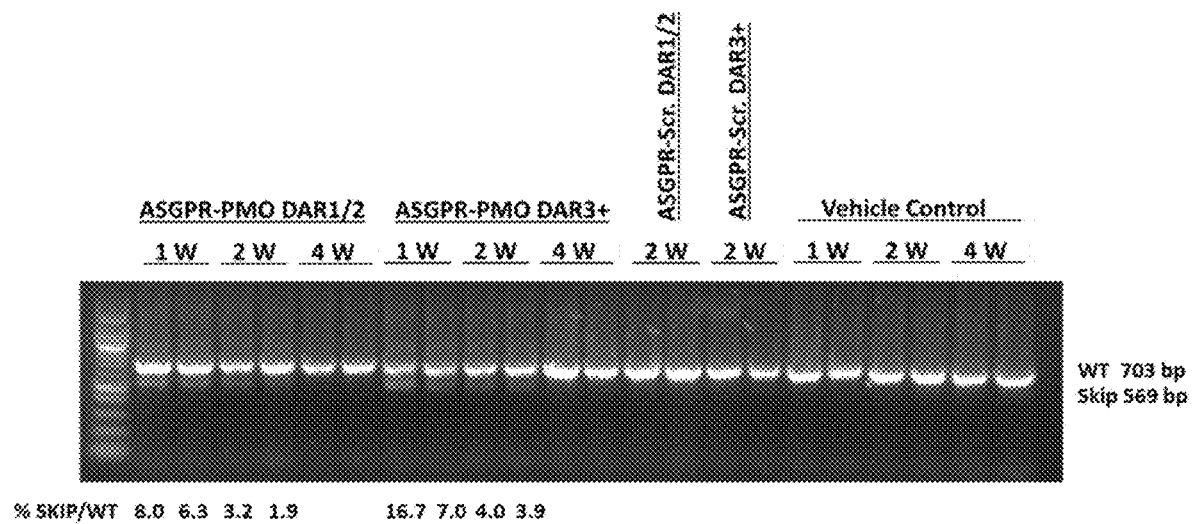
FIG. 18 depicts an agarose gel from PCR detecting ASGPR mAb-PMO conjugate induction of PAH exon 11 skipping in livers from wild type mice after a single intravenous (i.v.) injection.

RNAs were isolated from harvested liver tissues and reverse transcribed. PCR reactions using forward primer 5'-CTAGTGCCCTTGTTTTCAGA-3' (SEQ ID NO: 52) and reverse primer 5'-AGGATCTACCACTGATGGGT-3' (SEQ ID NO: 53) were analyzed in a 1% TAE agarose gel as seen in FIG. 18. As can be seen from the gel in FIG. 18, the ASGPR mAb-PMO conjugates produced measurable exon11 skipping in mouse livers up to two weeks. The wild type product had an expected size of 703 bp and the skipped PAH Δ11 of 569 bp.

Example 12. Sequences

Table 17 illustrates exemplary target sequences to induce insertion, deletion, duplications, or alteration in the DMD gene using compositions and methods as described herein. Table 18 illustrates exemplary nucleotide sequences to induce an insertion, deletion, duplication, or alteration in the DMD gene using compositions and methods as described herein. Table 19 and Table 20 illustrate exemplary target sequences in several genes for inducing an insertion, deletion, duplications, or alteration in the gene. Table 21 illustrates exemplary sequences, including sequences in the DMD gene to induce an insertion, deletion, duplication, or alteration in the gene using compositions and methods as described herein.

TABLE 17

| Target Exon | Antisense Sequence | SEQ ID NO. |
|---|---|---|
| 19 | 5'GCCUGAGCUGAUCUGCUGGCAUCUUGCAGUU 3' | 54 |
| 19 or 20 | 5'GCAGAAUUCGAUCCACCGGCUGUUCAAGCCUGAGCUGAUCUGCUCGCAUCUUGCAGU 3' | 55 |
| 20 | 5'CAGCAGUAGUUGUCAUCUGCUC 3' | 56 |
| 21 | 5'CACAAAGUCUGCAUCCAGGAACAUGGGUC 3' | 57 |
| 22 | 5'CUGCAAUUCCCCGAGUCUCUGC 3' | 58 |
| 51 | 5'CUCAUACCUUCUGCUUGAUGAUC 3' | 59 |
| 52 | 5'UCCAACUGGGGACGCCUCUGUUCCAAAUCC 3' | 60 |

TABLE 18

| Gene | Target Location | Nucleotide Sequence (5'-3') | SEQ ID NO. |
|---|---|---|---|
| DMD | H8A(-06+18) | GAUAGGUGGUAUCAACAUCUGUAA | 61 |
| DMD | H8A(-03+18) | GAUAGGUGGUAUCAACAUCUG | 62 |
| DMD | H8A(-07+18) | GAUAGGUGGUAUCAACAUCUGUAAG | 63 |
| DMD | H8A(-06+14) | GGUGGUAUCAACAUCUGUAA | 64 |
| DMD | H8A(-10+10) | GUAUCAACAUCUGUAAGCAC | 65 |
| DMD | H7A(+45+67) | UGCAUGUUCCAGUCGUUGUGUGG | 66 |
| DMD | H7A(+02+26) | CACUAUUCCAGUCAAAUAGGUCUGG | 67 |
| DMD | H7D(+15-10) | AUUUACCAACCUUCAGGAUCGAGUA | 68 |
| DMD | H7A(-18+03) | GGCCUAAAACACAUACACAUA | 69 |
| DMD | C6A(-10+10) | CAUUUUUGACCUACAUGUGG | 70 |
| DMD | C6A(-14+06) | UUUGACCUACAUGUGGAAAG | 71 |
| DMD | C6A(-14+12) | UACAUUUUUGACCUACAUGUGGAAAG | 72 |
| DMD | C6A(-13+09) | AUUUUUGACCUACAUGGGAAAG | 73 |
| DMD | CH6A(+69+91) | UACGAGUUGAUUGUCGGACCCAG | 74 |
| DMD | C6D(+12-13) | GUGGUCUCCUUACCUAUGACUGUGG | 75 |
| DMD | C6D(+06-11) | GGUCUCCUUACCUAUGA | 76 |
| DMD | H6D(+04-21) | UGUCUCAGUAAUCUUCUUACCUAU | 77 |
| DMD | H6D(+18-04) | UCUUACCUAUGACUAUGGAUGAGA | 78 |
| DMD | H4A(+13+32) | GCAUGAACUCUUGUGGAUCC | 79 |
| DMD | H4D(+04-16) | CCAGGGUACUACUUACAUUA | 80 |
| DMD | H4D(-24-44) | AUCGUGUGUCACAGCAUCCAG | 81 |
| DMD | H4A(+11+40) | UGUUCAGGGCAUGAACUCUUGUGGAUCCUU | 82 |
| DMD | H3A(+30+60) | UAGGAGGCGCCUCCCAUCCUGUAGGUCACUG | 83 |
| DMD | H3A(+35+65) | AGGUCUAGGAGGCGCCUCCCAUCCUGUAGGU | 84 |
| DMD | H3A(+30+54) | GCGCCUCCCAUCCUGUAGGUCACUG | 85 |
| DMD | H3D(+46-21) | CUUCGAGGAGGUCUAGGAGGCGCCUC | 86 |
| DMD | H3A(+30+50) | CUCCCAUCCUGUAGGUCACUG | 87 |
| DMD | H3D(+19-03) | UACCAGUUUUUGCCCUGUCAGG | 88 |
| DMD | H3A(-06+20) | UCAAUAUGCUGCUUCCCAAACUGAAA | 89 |
| DMD | H3A(+37+61) | CUAGGAGGCGCCUCCCAUCCUGUAG | 90 |
| DMD | H5A(+20+50) | UUAUGAUUUCCAUCUACGAUGUCAGUACUUC | 91 |
| DMD | H5D(+25-05) | CUUACCUGCCAGUGGAGGAUUAUAUUCCAAA | 92 |

TABLE 18-continued

| Gene | Target Location | Nucleotide Sequence (5'-3') | SEQ ID NO. |
|---|---|---|---|
| DMD | H5D(+10-15) | CAUCAGGAUUCUUACCUGCCAGUGG | 93 |
| DMD | H5A(+10+34) | CGAUGUCAGUACUUCCAAUAUUCAC | 94 |
| DMD | H5D(-04-21) | ACCAUUCAUCAGGAUUCU | 95 |
| DMD | H5D(+16-02) | ACCUGCCAGUGGAGGAUU | 96 |
| DMD | H5A(-07+20) | CCAAUAUUCACUAAAUCAACCUGUUAA | 97 |
| DMD | H5D(+18-12) | CAGGAUUGUUACCUGCCAGUGGAGGAUUAU | 98 |
| DMD | H5A(+05+35) | ACGAUGUCAGUACUUCCAAUAUUCACUAAAU | 99 |
| DMD | H5A(+15+45) | AUUUCCAUCUACGAUGUCAGUACUUCCAAUA | 100 |
| DMD | H10A(-05+16) | CAGGAGCUUCCAAAUGCUGCA | 101 |
| DMD | H10A(-05+24) | CUUGUCUUCAGGAGCUUCCAAAUGCUGCA | 102 |
| DMD | H10A(+98+119) | UCCUCAGCAGAAAGAAGCCACG | 103 |
| DMD | H10A(+130+149) | UUAGAAAUCUCUCCUUGUGC | 104 |
| DMD | H10A(-33-14) | UAAAUUGGGUGUUACACAAU | 105 |
| DMD | H11D(+26+49) | CCCUGAGGCAUUCCCAUCUUGAAU | 106 |
| DMD | H11D(+11-09) | AGGACUUACUUGCUUUGUUU | 107 |
| DMD | H11A(+118+140) | CUUGAAUUUAGGAGAUUCAUCUG | 108 |
| DMD | H11A(+75+97) | CAUCUUCUGAUAAUUUUCCUGUU | 109 |
| DMD | H12A(+52+75) | UCUUCUGUUUUUGUUAGCCAGUCA | 110 |
| DMD | H12A(-10+10) | UCUAUGUAAACUGAAAAUUU | 111 |
| DMD | H12A(+11+30) | UUCUGGAGAUCCAUUAAAAC | 112 |
| DMD | H13A(+77+100) | CAGCAGUUGCGUGAUCUCCACUAG | 113 |
| DMD | H13A(+55+75) | UUCAUCAACUACCACCACCAU | 114 |
| DMD | H13D(+06-19) | CUAAGCAAAAUAAUCUGACCUUAAG | 115 |
| DMD | H14A(+37+64) | CUUGUAAAAGAACCCAGCGGUCUUCUGU | 116 |
| DMD | H14A(+14+35) | CAUCUACAGAUGUUUGCCCAUC | 117 |
| DMD | H14A(+51+73) | GAAGGAUGUCUUGUAAAAGAACC | 118 |
| DMD | H14D(-02+18) | ACCUGUUCUUCAGUAAGACG | 119 |
| DMD | H14D(+14-10) | CAUGACACACCUGUUCUUCAGUAA | 120 |
| DMD | H14A(+61+80) | CAUUUGAGAAGGAUGUCUUG | 121 |
| DMD | H14A(-12+12) | AUCUCCCAAUACCUGGAGAAGAGA | 122 |
| DMD | H15A(-12+19) | GCCAUGCACUAAAAAGGCACUGCAAGACAUU | 123 |
| DMD | H15A(+48+71) | UCUUUAAAGCCAGUUGUGUGAAUC | 124 |
| DMD | H15A(+08+28) | UUUCUGAAAGCCAUGCACUAA | 125 |
| DMD | H15D(+17-08) | GUACAUACGGCCAGUUUUUGAAGAC | 126 |
| DMD | H16A(-12+19) | CUAGAUCCGCUUUUAAAACCUGUUAAAACAA | 127 |
| DMD | H16A(-06+25) | UCUUUUCUAGAUCCGCUUUUAAAACCUGUUA | 128 |
| DMD | H16A(-06+19) | CUAGAUCCGCUUUUAAAACCUGUUA | 129 |
| DMD | H16A(+87+109) | CCGUCUUCUGGGUCACUGACUUA | 130 |
| DMD | H16A(-07+19) | CUAGAUCCGCUUUUAAAACCUGUUAA | 131 |
| DMD | H16A(-07+13) | CCGCUUUUAAAACCUGUUAA | 132 |
| DMD | H16A(+12+37) | UGGAUUGCUUUUUCUUUUCUAGAUCC | 133 |
| DMD | H16A(+92+116) | CAUGCUUCCGUCUUCUGGGUCACUG | 134 |
| DMD | H16A(+45+67) | GAUCUUGUUUGAGUGAAUACAGU | 135 |
| DMD | H16A(+105+126) | GUUAUCCAGCCAUGCUUCCGUC | 136 |
| DMD | H16D(+05-20) | UGAUAAUUGGUAUCACUAACCUGUG | 137 |
| DMD | H16D(+12-11) | GUAUCACUAACCUGUGCUGUAC | 138 |
| DMD | H19A(+35+53) | CUGCUGGCAUCUUGCAGUU | 139 |
| DMD | H19A(+35+65) | GCCUGAGCUGAUCUGCUGGCAUCUUGCAGUU | 140 |
| DMD | H20A(+44+71) | CUGGCAGAAUUCGAUCCACCGGCUGUUC | 141 |
| DMD | H20A(+147+168) | CAGCAGUAGUUGUCAUCUGCUC | 142 |
| DMD | H20A(+185+203) | UGAUGGGGUGGUGGGUUGG | 143 |
| DMD | H20A(-08+17) | AUCUGCAUUAACACCCUCUAGAAAG | 144 |
| DMD | H20A(+30+53) | CCGGCUGUUCAGUUGUUCUGAGGC | 145 |
| DMD | H20A(-11+17) | AUCUGCAUUAACACCCUCUAGAAAGAAA | 146 |
| DMD | H20D(+08-20) | GAAGGAGAAGAGAUUCUUACCUUACAAA | 147 |
| DMD | H20A(+44+63) | AUUCGAUCCACCGGCUGUUC | 148 |
| DMD | H20A(+149+168) | CAGCAGUAGUUGUCAUCUGC | 149 |
| DMD | H21A(-06+16) | GCCGGUUGACUUCAUCCUGUGC | 150 |
| DMD | H21A(+85+106) | CUGCAUCCAGGAACAUGGGUCC | 151 |
| DMD | H21A(+85+108) | GUCUGCAUCCAGGAACAUGGGUC | 152 |
| DMD | H21A(+08+31) | GUUGAAGAUCUGAUAGCCGGUUGA | 153 |
| DMD | H21D(+18-07) | UACUUACUGUCUGUAGCUCUUUCU | 154 |
| DMD | H22A(+22+45) | CACUCAUGGUCUCCUGAUAGCGCA | 155 |
| DMD | H22A(+125+106) | CUGCAAUUCCCGAGUCUCUGC | 156 |
| DMD | H22A(+47+69) | ACUGCUGGACCCAUGUCCUGAUG | 157 |
| DMD | H22A(+80+101) | CUAAGUUGAGGUAUGGAGAGU | 158 |
| DMD | H22D(+13-11) | UAUUCACAGACCUGCAAUUCCCC | 159 |
| DMD | H23A(+34+59) | ACAGUGGUGCUGAGAUAGUAUAGGCC | 160 |
| DMD | H23A(+18+39) | UAGGCCACUUUGUUGCUCUUGC | 161 |
| DMD | H23A(+72+90) | UUCAGAGGGCGCUUUCUUC | 162 |
| DMD | H24A(+48+70) | GGGCAGGCCAUUCCUCCUUCAGA | 163 |
| DMD | H24A(-02+22) | UCUUCAGGGUUUGUAUGUGAUUCU | 164 |
| DMD | H25A(+9+36) | CUGGGCUGAAUUGUCUGAAUAUCACUG | 165 |
| DMD | H25A(+131+156) | CUGUUGGCACAUGUGAUCCCACUGAG | 166 |
| DMD | H25D(+16-08) | GUCUAUACCUGUUGGCACAUGUGA | 167 |
| DMD | H26A(+132+156) | UGCUUUCUGUAAUUCAUCUGGAGUU | 168 |
| DMD | H26A(-07+19) | CCUCCUUUCUGGCAUAGACCUUCCAC | 169 |

TABLE 18-continued

| Gene | Target Location | Nucleotide Sequence (5'-3') | SEQ ID NO. |
|---|---|---|---|
| DMD | H26A(+68+92) | UGUGUCAUCCAUUCGUGCAUCUCUG | 170 |
| DMD | H27A(+82+106) | UUAAGGCCUCUUGUGCUACAGGUGG | 171 |
| DMD | H27A(-4+19) | GGGGCUCUUCUUUAGCUCUCUGA | 172 |
| DMD | H27D(+19-03) | GACUUCCAAAGUCUUGCAUUUC | 173 |
| DMD | H28A(-05+19) | GCCAACAUGCCCAAACUUCCUAAG | 174 |
| DMD | H28A(+99+124) | CAGAGAUUUCCUCAGCUCCGCCAGGA | 175 |
| DMD | H28D(+16-05) | CUUACAUCUAGCACCUCAGAG | 176 |
| DMD | H29A(+57+81) | UCCGCCAUCUGUUAGGGUCUGUGCC | 177 |
| DMD | H29A(+18+42) | AUUUGGGUUAUCCUCUGAAUGUCGC | 178 |
| DMD | H29A(+17-05) | CAUACCUCUUCAUGUAGUUCCC | 179 |
| DMD | H30A(+122+147) | CAUUUGAGCUGCGUCCACCUUGUCUG | 180 |
| DMD | H30A(+25+50) | UCCUGGGCAGACUGGAUGCUCUGUUC | 181 |
| DMD | H30D(+19-04) | UUGCCUGGGCUUCCUGAGGCAUU | 182 |
| DMD | H31D(+06-18) | UUCUGAAAUAACAUAUACCUGUGC | 183 |
| DMD | H31D(+03-22) | UAGUUUCUGAAAUAACAUAUACCUG | 184 |
| DMD | H31A(+05+25) | GACUUGUCAAAUCAGAUUGGA | 185 |
| DMD | H31D(+04-20) | GUUUCUGAAAUAACAUAUACCUGU | 186 |
| DMD | H32D(+04-16) | CACCAGAAAUACAUACCACA | 187 |
| DMD | H32A(+151+170) | CAAUGAUUUAGCUGUGACUG | 188 |
| DMD | H32A(+10+32) | CGAAACUUCAUGGAGACAUCUUG | 189 |
| DMD | H32A(+49+73) | CUUGUAGACGCUGCUCAAAAUUGGC | 190 |
| DMD | H33D(+09-11) | CAUGCACACACCUUUGCUCC | 191 |
| DMD | H33A(+53+76) | UCUGUACAAUCGACGUCCAGUCU | 192 |
| DMD | H33A(+30+56) | GUCUUUAUCACCAUUUCCACUUCAGAC | 193 |
| DMD | H33A(+64+88) | CCGUCUGCUUUUUCUGUACAAUCUG | 194 |
| DMD | H34A(+83+104) | UCCAUAUCUGUAGCUGCCAGCC | 195 |
| DMD | H34A(+143+165) | CCAGGCAACUUCAGAAUCCAAAU | 196 |
| DMD | H34A(-20+10) | UUUCUGUUACCUGAAAAGAAUUAUAAUGAA | 197 |
| DMD | H34A(+46+70) | CAUUCAUUCCUUUCGCAUCUUACG | 198 |
| DMD | H34A(+95+120) | UGAUCUCUUUGUCAAUUCCAUAUCUG | 199 |
| DMD | H34D(+10-20) | UUCAGUGAUAUAGGUUUUACCUUUCCCAG | 200 |
| DMD | H34A(+72+96) | CUG UAG CUG CCA GCC AUU CUG UCA AG | 201 |
| DMD | H35A(+141+161) | UCU UCU GCU CGG GAG GUG ACA | 202 |
| DMD | H35A(+116+135) | CCA GUU ACU AUU CAG AAG AC | 203 |
| DMD | H35A(+24+43) | UCU UCA GGU GCA CCU UCU GU | 204 |
| DMD | H36A(+26+50) | UGUGAUGUGGUCCACAUUCUGGUCA | 205 |
| DMD | H36A(-02+18) | CCAUGUGUUUCUGGUAUUCC | 206 |
| DMD | H37A(+26+50) | CGUGUAGAGUCCACCUUUGGGCGUA | 207 |
| DMD | H37A(+82+105) | UACUAAUUUCCUGCAGUGGUCACC | 208 |
| DMD | H37A(+134+157) | UUCUGUGUGAAAUGGCUGCAAAUC | 209 |
| DMD | H38A(-01+19) | CCUUCAAAGGAAUGGAGGCC | 210 |
| DMD | H38A(+59+83) | UGCUGAAUUUCAGCCUCCAGUGGUU | 211 |
| DMD | H38A(+88+112) | UGAAGUCUUCCUCUUUCAGAUUCAC | 212 |
| DMD | H39A(+62+85) | CUGGCUUUCUCUCAUCUGUGAUUC | 213 |
| DMD | H39A(+39+58) | GUUGUAAGUUGUCUCCUCUU | 214 |
| DMD | H39A(+102+121) | UUGUCUGUAACAGCUGCUGU | 215 |
| DMD | H39D(+10-10) | GCUCUAAUACCUUGAGAGCA | 216 |
| DMD | H40A(-05+17) | CUUUGAGACCUCAAAUCCUGUU | 217 |
| DMD | H40A(+129+153) | CUUUAUUUUCCUUUCAUCUCUGGGC | 218 |
| DMD | H42A(-04+23) | AUCGUUUCUUCACGGACAGUGUGCUGG | 219 |
| DMD | H42A(+86+109) | GGGCUUGUGAGACAUGAGUGAUUU | 220 |
| DMD | H42D(+19-02) | ACCUUCAGAGGACUCCUCUUGC | 221 |
| DMD | H43D(+10-15) | UAUGUGUUACCUACCCUUGUCGGUC | 222 |
| DMD | H43A(+101+120) | GGAGAGAGCUUCCUGUAGCU | 223 |
| DMD | H43A(+78+100) | UCACCCUUUCCACAGGCGUUGCA | 224 |
| DMD | H44A(+85+104) | UUUGUGUCUUUCUGAGAAAC | 225 |
| DMD | H44D(+10-10) | AAAGACUUACCUUAAGAUAC | 226 |
| DMD | H44A(-06+14) | AUCUGUCAAAUCGCCUGCAG | 227 |
| DMD | H46D(+16-04) | UUACCUUGACUUGCUCAAGC | 228 |
| DMD | H46A(+90+109) | UCCAGGUUCAAGUGGGAUAC | 229 |
| DMD | H47A(+76+100) | GCUCUUCGGGCUUAUGGGAGCACU | 230 |
| DMD | H47D(+25-02) | ACCUUUAUCCACUGGAGAUUUGUCUGC | 231 |
| DMD | H47A(-9+12) | UUCCACCAGUAACUGAAACAG | 232 |
| DMD | H50A(+02+30) | CCACUCAGAGCUCAGAUCUUCUAACUUCC | 233 |
| DMD | H50A(+07+33) | CUUCCACUCAGAGCUCAGAUCUUCUAA | 234 |
| DMD | H50D(+07-18) | GGGAUCCAGUAUACUUACAGGCUCC | 235 |
| DMD | H51A(-01+25) | ACCAGAGUAACAGUCUGAGUAGGAGC | 236 |
| DMD | H51D(+16-07) | CUCAUACCUUCUGCUUGAUGAUC | 237 |
| DMD | H51A(+111+134) | UUCUGUCCAAGCCCGGUUGAAAUC | 238 |
| DMD | H51A(+61+90) | ACAUCAAGGAAGAUGGCAUUUCUAGUUUGG | 239 |
| DMD | H51A(+66+90) | ACAUCAAGGAAGAUGGCAUUUCUAG | 240 |
| DMD | H51A(+66+95) | CUCCAACAUCAAGGAAGAUGGCAUUUCUAG | 241 |
| DMD | H51D(+08-17) | AUCAUUUUUCUCAUACCUUCUGCU | 242 |
| DMD | H51A/D(+08-17) &(-15+) | AUCAUUUUUCUCAUACCUUCUGCUAG GAGCUAAAA | 243 |
| DMD | H51A(+175+195) | CACCCACCAUCACCCUCUGUG | 245 |
| DMD | H51A(+199+220) | AUCAUCUCGUUGAUAUCCUCAA | 246 |

TABLE 18-continued

| Gene | Target Location | Nucleotide Sequence (5'-3') | SEQ ID NO. |
|---|---|---|---|
| DMD | H52A(-07+14) | UCCUGCAUUGUUGCCUGUAAG | 247 |
| DMD | H52A(+12+41) | UCCAACUGGGGACGCCUCUGUUCCAAAUCC | 248 |
| DMD | H52A(+17+37) | ACUGGGGACGCCUCUGUUCCA | 249 |
| DMD | H52A(+93+112) | CCGUAAUGAUUGUUCUAGCC | 250 |
| DMD | H52D(+05-15) | UGUUAAAAAACUUACUUCGA | 251 |
| DMD | H53A(+45+69) | CAUUCAACUGUUGCCUCCGGUUCUG | 252 |
| DMD | H53A(+39+62) | CUGUUGCCUCCGGUUCUGAAGGUG | 253 |
| DMD | H53A(+39+69) | CAUUCAACUGUUGCCUCCGGUUCUGAAGGUG | 254 |
| DMD | H53D(+14-07) | UACUAACCUUGGUUUCUGUGA | 255 |
| DMD | H53A(+23+47) | CUGAAGGUGUUCUUGUACUUCAUCC | 256 |
| DMD | H53A(+150+176) | UGUAUAGGGACCCUCCUUCCAUGACUC | 257 |
| DMD | H53D(+20-05) | CUAACCUUGGUUUCUGUGAUUUUCU | 258 |
| DMD | H53D(+09-18) | GGUAUCUUUGAUACUAACCUUGGUUUC | 259 |
| DMD | H53A(-12+10) | AUUCUUUCAACUAGAAUAAAAG | 260 |
| DMD | H53A(-07+18) | GAUUCUGAAUUCUUUCAACUAGAAU | 261 |
| DMD | H53A(+07+26) | AUCCCACUGAUUCUGAAUUC | 262 |
| DMD | H53A(+124+145) | UUGGCUCUGGCCUGUCCUAAGA | 263 |
| DMD | H46A(+86+115) | CUCUUUUCCAGGUUCAAGUGGGAUACUAGC | 264 |
| DMD | H46A(+107+137) | CAAGCUUUUCUUUUAGUUGCUGCUCUUUUCC | 265 |
| DMD | H46A(-10+20) | UAUUCUUUUGUUCUUCUAGCCUGGAGAAAG | 266 |
| DMD | H46A(+50+77) | CUGCUUCCUCCAACCAUAAAACAAAUUC | 267 |
| DMD | H45A(-06+20) | CCAAUGCCAUCCUGGAGUUCCUGUAA | 268 |
| DMD | H45A(+91+110) | UCCUGUAGAAUACUGGCAUC | 269 |
| DMD | H45A(+125+151) | UGCAGACCUCCUGCCACCGCAGAUUCA | 270 |
| DMD | H45D(+16-04) | CUACCUCUUUUUUCUGUCUG | 271 |
| DMD | H45A(+71+90) | UGUUUUUGAGGAUUGCUGAA | 272 |

* The first letter designates the species (e.g. H: human, M: murine, C: canine).
"#"designates target DMD exon number.
"A/D"indicates acceptor or donor splice site at the beginning and end of the exon, respectively.
(x y) represents the annealing coordinates where "-"or "+"indicate intronic or exonic sequences respectively.

TABLE 19

| Gene | Nucleotide Sequence (5'-3') | SEQ ID NO. |
|---|---|---|
| Bcl-x | TGGTTCTTACCCAGCCGCCG | 273 |
| β-globin 623 | GTTATTCTTTAGAATGGTGC | 274 |
| β-globin 654 | TGCTATTACCTTAACCCAGA | 275 |
| c-myc | CTGTGCTTACCGGGTTTTCCACCTCCC | 276 |
| c-myc | ATCGTCGTGACTGTCTGTTGGAGGG | 277 |
| c-myc | GCTCACGTTGAGGGGCATCG | 278 |
| c-myc | ACGTTGAGGGGCATCGTCGC | 279 |
| c-myc | GGGGCAUCGUCGCGGGAGGCUG | 280 |
| c-myc | CGUCGUGACUGUCUGUUGGAGG | 281 |
| c-myc | CGTCGTGACTGTCTGTTGGAGG | 282 |
| c-myc | GGCAUCGUCGCGGGAGGCUGCUGGAGCG | 283 |
| c-myc | CCGCGACAUAGGACGGAGAGCAGAGCCC | 284 |
| c-myc | ACTGTGAGGGCGATCGCTGC | 285 |
| c-myc | ACGATGAGTGGCATAGTCGC | 286 |
| c-myc | GGCATCGTCGCGGGAGGCTG | 287 |
| c-myc | GGGCATCGTCGCGGGAGGCT | 288 |
| c-myc | GGGGCATCGTCGCGGGAGGC | 289 |
| c-myc | AGGGGCATCGTCGCGGGAGG | 290 |
| c-myc | GAGGGGCATCGTCGCGGGAG | 291 |
| c-myc | TGAGGGGCATCGTCGCGGGA | 292 |
| c-myc | TTGAGGGGCATCGTCGCGGG | 293 |
| c-myc | GTTGAGGGGCATCGTCGCGG | 294 |
| c-myc | CGTTGAGGGGCATCGTCGCG | 295 |
| c-myc | ACGTTGAGGGGCATCGTCGC | 296 |
| c-myc | AACGTTGAGGGGCATCGTCG | 297 |
| c-myc | TAACGTTGAGGGGCATCGTC | 298 |
| c-myc | CTAACGTTGAGGGGCATCGT | 299 |
| c-myc | GCTAACGTTGAGGGGCATCG | 300 |
| c-myc | AGCTAACGTTGAGGGGCATC | 301 |
| c-myc | AAGCTAACGTTGAGGGGCAT | 302 |
| c-myc | GAAGCTAACGTTGAGGGGCA | 303 |
| BCL-2 (rat) | CTCCGCAATGCTGAAAGGTG | 304 |
| PCNA-1 (rat) | GGCGUGCCUCAAACAUGGUGGCGG | 305 |

TABLE 20

| Gene | Target Location | Nucleotide Sequence (5'-3') | SEQ ID NO. |
|---|---|---|---|
| Rat c-myc | 2553-79 | CTGTGCTTACCGGGTTTTCCACCTCCC | 306 |
| Rat c-myc | 4140-64 | ATCGTCGTGACTGTCTGTTGGAGGG | 307 |
| Rat c-myc | 4161-80 | GCTCACGTTGAGGGGCATCG | 308 |
| Rat CYP3A2 | 1155-74 | GGTCACTCACCGGTAGAGAA | 309 |
| Rat CYP3A2 | 1526-45 | GGGTTCCAAGTCTATAAAGG | 310 |
| Human androgen receptor exon 2 | 31-44 | TGTGTCTTTTCCAG | 311 |

TABLE 20-continued

| Gene | Target Location | Nucleotide Sequence (5'-3') | SEQ ID NO. |
|---|---|---|---|
| Human androgen receptor exon 2 | 45-67 | TTTGGAGACTGCCAGGGACCATG | 312 |
| Human androgen receptor exon 2 | 48-67 | CATGGTCCCTGGCAGTCTCC | 313 |
| Human androgen receptor exon 2 | 45-80 | TCAATGGGCAAAACATGGTCCCTGGCAGTCTCCAAA | 314 |
| Human androgen receptor exon 3 | 28-43 | TTTGTGTTCTCCCAG | 315 |
| Human androgen receptor exon 3 | 44-66 | GGAAACAGAAGTACCTGTGCGCC | 316 |
| Human androgen receptor exon 3 | 49-66 | GGCGCACAGGTACTTCTG | 317 |
| Human androgen receptor exon 3 | 44-79 | AATCATTTCTGCTGGCGCACAGGTACTTCTGTTTCC | 318 |
| Human HCG-β subunit | 1321-38 | CCCCTGCAGCACGCGGGT | 319 |
| Human HCG-β subunit | 1321-57 | GAGGCAGGGCCGGCAGGACCCCCTGCAGCACGCGGGT | 320 |
| Human c-myc | 4506-25 | GGCATCGTCGCGGGAGGCTG | 321 |
| Human c-myc | 4507-26 | GGGCATCGTCGCGGGAGGCT | 322 |
| Human c-myc | 4508-27 | GGGGCATCGTCGCGGGAGGC | 323 |
| Human c-myc | 4509-28 | AGGGGCATCGTCGCGGGAGG | 324 |
| Human c-myc | 4510-29 | GAGGGGCATCGTCGCGGGAG | 325 |
| Human c-myc | 4511-30 | TGAGGGGCATCGTCGCGGGA | 326 |
| Human c-myc | 4512-31 | TTGAGGGGCATCGTCGCGGG | 327 |
| Human c-myc | 4513-32 | GTTGAGGGGCATCGTCGCGG | 328 |
| Human c-myc | 4514-33 | CGTTGAGGGGCATCGTCGCG | 329 |
| Human c-myc | 4515-34 | ACGTTGAGGGGCATCGTCGC | 330 |
| Human c-myc | 4516-35 | AACGTTGAGGGGCATCGTCG | 331 |
| Human c-myc | 4517-36 | TAACGTTGAGGGGCATCGTC | 332 |
| Human c-myc | 4518-37 | CTAACGTTGAGGGGCATCGT | 333 |
| Human c-myc | 4519-38 | GCTAACGTTGAGGGGCATCG | 334 |
| Human c-myc | 4520-39 | AGCTAACGTTGAGGGGCATC | 335 |
| Human c-myc | 4521-40 | AAGCTAACGTTGAGGGGCAT | 336 |
| Human c-myc | 4522-41 | GAAGCTAACGTTGAGGGGCA | 337 |
| Human c-myc | 6656-75 | TCCTCATCTTCTTGTTCCTC | 338 |
| Human c-myc | 6656-91 | AACAACATCGATTTCTTCCTCATCTTCTTGTTCCTC | 339 |
| Human p53 | 11691-708 | CCCGGAAGGCAGTCTGGC | 340 |
| Human p53 | 11689-724 | TCCTCCATGGCAGTGACCCGGAAGGCAGTCTGGCTG | 341 |
| Human abl (ds of bcr-abl fusion point) | 376-94 | CTACTGGCCGCTGAAGGGC | 342 |
| Human abl (ds of bcr-abl fusion point) | 374-409 | GCTCAAAGTCAGATGCTACTGGCCGCTGAAGGGCTT | 343 |
| HW-1 rev | 5517-43 | TCGTCGGTCTCTCCGCTTCTTCTTGCC | 344 |
| HW-1 rev | 7885-7904 | CTCTGGTGGTGGGTAAGGGT | 345 |
| HW-1 rev | 7885-7921 | CGGGTCTGTCGGGTTCCCTCTGGTGGTGGGTAAGGGT | 346 |
| Rat c-myc | 4140-69 | GGGGCAUCGUCGUGACUGUCUGUUGGAGGG | 347 |
| Rat c-myc | 4141-62 | CGUCGUGACUGUCUGUUGGAGG | 348 |
| Rat c-myc | 4141-62 | CGTCGTGACTGTCTGTTGGAGG | 349 |
| Human c-myc | 4498-4505 | GGCAUCGUCGCGGGAGGCUG/CUGGAGCG | 350 |
| Rat c-myc | 4364-91 | CCGCGACAUAGGACGGAGAGCAGAGCCC | 351 |

TABLE 21

| Target | Nucleotide Sequence (5'-3') | SEQ ID NO. |
|---|---|---|
| Hu.DMD.Exon44.25.001 | CTGCAGGTAAAAGCATATGGATCAA | 352 |
| Hu.DMD.Exon44.25.002 | ATCGCCTGCAGGTAAAAGCATATGG | 353 |
| Hu.DMD.Exon44.25.003 | GTCAAATCGCCTGCAGGTAAAAGCA | 354 |
| Hu.DMD.Exon44.25.004 | GATCTGTCAAATCGCCTGCAGGTAA | 355 |
| Hu.DMD.Exon44.25.005 | CAACAGATCTGTCAAATCGCCTGCA | 356 |
| Hu.DMD.Exon44.25.006 | TTTCTCAACAGATCTGTCAAATCGC | 357 |
| Hu.DMD.Exon44.25.007 | CCATTTCTCAACAGATCTGTCAAAT | 358 |
| Hu.DMD.Exon44.25.008 | ATAATGAAAACGCCGCCATTTCTCA | 359 |

TABLE 21-continued

| Target | Nucleotide Sequence (5'-3') | SEQ ID NO. |
| --- | --- | --- |
| Hu.DMD.Exon44.25.009 | AAATATCTTTATATCATAATGAAAA | 360 |
| Hu.DMD.Exon44.25.010 | TGTTAGCCACTGATTAAATATCTTT | 361 |
| Hu.DMD.Exon44.25.011 | AAACTGTTCAGCTTCTGTTAGCCAC | 362 |
| Hu.DMD.Exon44.25.012 | TTGTGTCTTTCTGAGAAACTGTTCA | 363 |
| Hu.DMD.Exon44.25.013 | CCAATTCTCAGGAATTTGTGTCTTT | 364 |
| Hu.DMD.Exon44.25.014 | GTATTTAGCATGTTCCCAATTCTCA | 365 |
| Hu.DMD.Exon44.25.015 | CTTAAGATACCATTTGTATTTAGCA | 366 |
| Hu.DMD.Exon44.25.016 | CTTACCTTAAGATACCATTTGTATT | 367 |
| Hu.DMD.Exon44.25.017 | AAAGACTTACCTTAAGATACCATTT | 368 |
| Hu.DMD.Exon44.25.018 | AAATCAAAGACTTACCTTAAGATAC | 369 |
| Hu.DMD.Exon44.25.019 | AAAACAAATCAAAGACTTACCTTAA | 370 |
| Hu.DMD.Exon44.25.020 | TCGAAAAAACAAATCAAAGACTTAC | 371 |
| Hu.DMD.Exon45.25.001 | CTGTAAGATACCAAAAAGGCAAAAC | 372 |
| Hu.DMD.Exon45.25.002 | CCTGTAAGATACCAAAAAGGCAAAA | 373 |
| Hu.DMD.Exon45.25.002.2 | AGTTCCTGTAAGATACCAAAAAGGC | 374 |
| Hu.DMD.Exon45.25.003 | GAGTTCCTGTAAGATACCAAAAAGG | 375 |
| Hu.DMD.Exon45.25.003.2 | CCTGGAGTTCCTGTAAGATACCAAA | 376 |
| Hu.DMD.Exon45.25.004 | TCCTGGAGTTCCTGTAAGATACCAA | 377 |
| Hu.DMD.Exon45.25.004.2 | GCCATCCTGGAGTTCCTGTAAGATA | 378 |
| Hu.DMD.Exon45.25.005 | TGCCATCCTGGAGTTCCTGTAAGAT | 379 |
| Hu.DMD.Exon45.25.005.2 | CCAATGCCATCCTGGAGTTCCTGTA | 380 |
| Hu.DMD.Exon45.25.006 | CCCAATGCCATCCTGGAGTTCCTGT | 381 |
| Hu.DMD.Exon45.25.006.2 | GCTGCCCAATGCCATCCTGGAGTTC | 382 |
| Hu.DMD.Exon45.25.007 | CGCTGCCCAATGCCATCCTGGAGTT | 383 |
| Hu.DMD.Exon45.25.008 | AACAGTTTGCCGCTGCCCAATGCCA | 384 |
| Hu.DMD.Exon45.25.008.2 | CTGACAACAGTTTGCCGCTGCCCAA | 385 |
| Hu.DMD.Exon45.25.009 | GTTGCATTCAATGTTCTGACAACAG | 386 |
| Hu.DMD.Exon45.25.010 | GCTGAATTATTCTTCCCCAGTTGC | 387 |
| Hu.DMD.Exon45.25.010.2 | ATTATTTCTTCCCCAGTTGCATTCA | 388 |
| Hu.DMD.Exon45.25.011 | GGCATCTGTTTTTGAGGATTGCTGA | 389 |
| Hu.DMD.Exon45.25.011.2 | TTTGAGGATTGCTGAATTATTTCTT | 390 |
| Hu.DMD.Exon45.25.012 | AATTTTTCCTGTAGAATACTGGCAT | 391 |
| Hu.DMD.Exon45.25.012.2 | ATACTGGCATCTGTTTTTGAGGATT | 392 |
| Hu.DMD.Exon45.25.013 | ACCGCAGATTCAGGCTTCCCAATTT | 393 |
| Hu.DMD.Exon45.25.013.2 | AATTTTTCCTGTAGAATACTGGCAT | 394 |
| Hu.DMD.Exon45.25.014 | CTGTTTGCAGACCTCCTGCCACCGC | 395 |
| Hu.DMD.Exon45.25.014.2 | AGATTCAGGCTTCCCAATTTTTCCT | 396 |
| Hu.DMD.Exon45.25.015 | CTCTTTTTTCTGTCTGACAGCTGTT | 397 |
| Hu.DMD.Exon45.25.015.2 | ACCTCCTGCCACCGCAGATTCAGGC | 398 |
| Hu.DMD.Exon45.25.016 | CCTACCTCTTTTTTCTGTCTGACAG | 399 |
| Hu.DMD.Exon45.25.016.2 | GACAGCTGTTTGCAGACCTCCTGCC | 400 |
| Hu.DMD.Exon45.25.017 | GTCGCCCTACCTCTTTTTTCTGTCT | 401 |
| Hu.DMD.Exon45.25.018 | GATCTGTCGCCCTACCTCTTTTTTC | 402 |
| Hu.DMD.Exon45.25.019 | TATTAGATCTGTCGCCCTACCTCTT | 403 |
| Hu.DMD.Exon45.25.020 | ATTCCTATTAGATCTGTCGCCCTAC | 404 |
| Hu.DMD.Exon45.20.001 | AGATACCAAAAAGGCAAAAC | 405 |
| Hu.DMD.Exon45.20.002 | AAGATACCAAAAAGGCAAAA | 406 |
| Hu.DMD.Exon45.20.003 | CCTGTAAGATACCAAAAAGG | 407 |
| Hu.DMD.Exon45.20.004 | GAGTTCCTGTAAGATACCAA | 408 |
| Hu.DMD.Exon45.20.005 | TCCTGGAGTTCCTGTAAGAT | 409 |
| Hu.DMD.Exon45.20.006 | TGCCATCCTGGAGTTCCTGT | 410 |
| Hu.DMD.Exon45.20.007 | CCCAATGCCATCCTGGAGTT | 411 |
| Hu.DMD.Exon45.20.008 | CGCTGCCCAATGCCATCCTG | 412 |
| Hu.DMD.Exon45.20.009 | CTGACAACAGTTTGCCGCTG | 413 |
| Hu.DMD.Exon45.20.010 | GTTGCATTCAATGTTCTGAC | 414 |
| Hu.DMD.Exon45.20.011 | ATTATTTCTTCCCCAGTTGC | 415 |
| Hu.DMD.Exon45.20.012 | TTTGAGGATTGCTGAATTAT | 416 |
| Hu.DMD.Exon45.20.013 | ATACTGGCATCTGTTTTTGA | 417 |
| Hu.DMD.Exon45.20.014 | AATTTTTCCTGTAGAATACT | 418 |
| Hu.DMD.Exon45.20.015 | AGATTCAGGCTTCCCAATTT | 419 |
| Hu.DMD.Exon45.20.016 | ACCTCCTGCCACCGCAGATT | 420 |
| Hu.DMD.Exon45.20.017 | GACAGCTGTTTGCAGACCTC | 421 |
| Hu.DMD.Exon45.20.018 | CTCTTTTTTCTGTCTGACAG | 422 |
| Hu.DMD.Exon45.20.019 | CCTACCTCTTTTTTCTGTCT | 423 |
| Hu.DMD.Exon45.20.020 | GTCGCCCTACCTCTTTTTTC | 424 |
| Hu.DMD.Exon45.20.021 | GATCTGTCGCCCTACCTCTT | 425 |
| Hu.DMD.Exon45.20.022 | TATTAGATCTGTCGCCCTAC | 426 |
| Hu.DMD.Exon45.20.023 | ATTCCTATTAGATCTGTCGC | 427 |
| Hu.DMD.Exon46.25.001 | GGGGGATTTGAGAAAATAAAATTAC | 428 |
| Hu.DMD.Exon46.25.002 | ATTTGAGAAAATAAAATTACCTTGA | 429 |
| Hu.DMD.Exon46.25.002.2 | CTAGCCTGGAGAAAGAAGAATAAAA | 430 |
| Hu.DMD.Exon46.25.003 | AGAAAATAAAATTACCTTGACTTGC | 431 |
| Hu.DMD.Exon46.25.003.2 | TTCTTCTAGCCTGGAGAAAGAAGAA | 432 |
| Hu.DMD.Exon46.25.004 | ATAAAATTACCTTGACTTGCTCAAG | 433 |
| Hu.DMD.Exon46.25.004.2 | TTTTGTTCTTCTAGCCTGGAGAAAG | 434 |
| Hu.DMD.Exon46.25.005 | ATTACCTTGACTTGCTCAAGCTTTT | 435 |
| Hu.DMD.Exon46.25.005.2 | TATTCTTTTGTTCTTCTAGCCTGGA | 436 |

TABLE 21-continued

| Target | Nucleotide Sequence (5'-3') | SEQ ID NO. |
|---|---|---|
| Hu.DMD.Exon46.25.006 | CTTGACTTGCTCAAGCTTTTCTTTT | 437 |
| Hu.DMD.Exon46.25.006.2 | CAAGATATTCTTTTGTTCTTCTAGC | 438 |
| Hu.DMD.Exon46.25.007 | CTTTTAGTTGCTGCTCTTTTCCAGG | 439 |
| Hu.DMD.Exon46.25.008 | CCAGGTTCAAGTGGGATACTAGCAA | 440 |
| Hu.DMD.Exon46.25.008.2 | ATCTCTTTGAAATTCTGACAAGATA | 441 |
| Hu.DMD.Exon46.25.009 | AGCAATGTTATCTGCTTCCTCCAAC | 442 |
| Hu.DMD.Exon46.25.009.2 | AACAAATTCATTTAAATCTCTTTGA | 443 |
| Hu.DMD.Exon46.25.010 | CCAACCATAAAACAAATTCATTTAA | 444 |
| Hu.DMD.Exon46.25.010.2 | TTCCTCCAACCATAAAACAAATTCA | 445 |
| Hu.DMD.Exon46.25.011 | TTTAAATCTCTTTGAAATTCTGACA | 446 |
| Hu.DMD.Exon46.25.012 | TGACAAGATATTCTTTTGTTCTTCT | 447 |
| Hu.DMD.Exon46.25.012.2 | TTCAAGTGGGATACTAGCAATGTTA | 448 |
| Hu.DMD.Exon46.25.013 | AGATATTCTTTTGTTCTTCTAGCCT | 449 |
| Hu.DMD.Exon46.25.013.2 | CTGCTCTTTTCCAGGTTCAAGTGGG | 450 |
| Hu.DMD.Exon46.25.014 | TTCTTTTGTTCTTCTAGCCTGGAGA | 451 |
| Hu.DMD.Exon46.25.014.2 | CTTTTCTTTTAGTTGCTGCTCTTTT | 452 |
| Hu.DMD.Exon46.25.015 | TTGTTCTTCTAGCCTGGAGAAAGAA | 453 |
| Hu.DMD.Exon46.25.016 | CTTCTAGCCTGGAGAAAGAAGAATA | 454 |
| Hu.DMD.Exon46.25.017 | AGCCTGGAGAAAGAAGAATAAAATT | 455 |
| Hu.DMD.Exon46.25.018 | CTGGAGAAAGAAGAATAAAATTGTT | 456 |
| Hu.DMD.Exon46.20.001 | GAAAGAAGAATAAAATTGTT | 457 |
| Hu.DMD.Exon46.20.002 | GGAGAAAGAAGAATAAAATT | 458 |
| Hu.DMD.Exon46.20.003 | AGCCTGGAGAAAGAAGAATA | 459 |
| Hu.DMD.Exon46.20.004 | CTTCTAGCCTGGAGAAAGAA | 460 |
| Hu.DMD.Exon46.20.005 | TTGTTCTTCTAGCCTGGAGA | 461 |
| Hu.DMD.Exon46.20.006 | TTCTTTTGTTCTTCTAGCCT | 462 |
| Hu.DMD.Exon46.20.007 | TGACAAGATATTCTTTTGTT | 463 |
| Hu.DMD.Exon46.20.008 | ATCTCTTTGAAATTCTGACA | 464 |
| Hu.DMD.Exon46.20.009 | AACAAATTCATTTAAATCTC | 465 |
| Hu.DMD.Exon46.20.010 | TTCCTCCAACCATAAAACAA | 466 |
| Hu.DMD.Exon46.20.011 | AGCAATGTTATCTGCTTCCT | 467 |
| Hu.DMD.Exon46.20.012 | TTCAAGTGGGATACTAGCAA | 468 |
| Hu.DMD.Exon46.20.013 | CTGCTCTTTTCCAGGTTCAA | 469 |
| Hu.DMD.Exon46.20.014 | CTTTTCTTTTAGTTGCTGCT | 470 |
| Hu.DMD.Exon46.20.015 | CTTGACTTGCTCAAGCTTTT | 471 |
| Hu.DMD.Exon46.20.016 | ATTACCTTGACTTGCTCAAG | 472 |
| Hu.DMD.Exon46.20.017 | ATAAAATTACCTTGACTTGC | 473 |
| Hu.DMD.Exon46.20.018 | AGAAAATAAAATTACCTTGA | 474 |
| Hu.DMD.Exon46.20.019 | ATTTGAGAAAATAAAATTAC | 475 |
| Hu.DMD.Exon46.20.020 | GGGGGATTTGAGAAAATAAA | 476 |
| Hu.DMD.Exon47.25.001 | CTGAAACAGACAAATGCAACAACGT | 477 |
| Hu.DMD.Exon47.25.002 | AGTAACTGAAACAGACAAATGCAAC | 478 |
| Hu.DMD.Exon47.25.003 | CCACCAGTAACTGAAACAGACAAAT | 479 |
| Hu.DMD.Exon47.25.004 | CTCTTCCACCAGTAACTGAAACAGA | 480 |
| Hu.DMD.Exon47.25.005 | GGCAACTCTTCCACCAGTAACTGAA | 481 |
| Hu.DMD.Exon47.25.006 | GCAGGGGCAACTCTTCCACCAGTAA | 482 |
| Hu.DMD.Exon47.25.007 | CTGGCGCAGGGGCAACTCTTCCACC | 483 |
| Hu.DMD.Exon47.25.008 | TTTAATTGTTTGAGAATTCCCTGGC | 484 |
| Hu.DMD.Exon47.25.008.2 | TTGTTTGAGAATTCCCTGGCGCAGG | 485 |
| Hu.DMD.Exon47.25.009 | GCACGGGTCCTCCAGTTTCATTTAA | 486 |
| Hu.DMD.Exon47.25.009.2 | TCCAGTTTCATTTAATTGTTTGAGA | 487 |
| Hu.DMD.Exon47.25.010 | GCTTATGGGAGCACTTACAAGCACG | 488 |
| Hu.DMD.Exon47.25.010.2 | TACAAGCACGGGTCCTCCAGTTTCA | 489 |
| Hu.DMD.Exon47.25.011 | AGTTTATCTTGCTCTTCTGGGCTTA | 490 |
| Hu.DMD.Exon47.25.012 | TCTGCTTGAGCTTATTTTCAAGTTT | 491 |
| Hu.DMD.Exon47.25.012.2 | ATCTTGCTCTTCTGGGCTTATGGGA | 492 |
| Hu.DMD.Exon47.25.013 | CTTTATCCACTGGAGATTTGTCTGC | 493 |
| Hu.DMD.Exon47.25.013.2 | CTTATTTTCAAGTTTATCTTGCTCT | 494 |
| Hu.DMD.Exon47.25.014 | CTAACCTTTATCCACTGGAGATTTG | 495 |
| Hu.DMD.Exon47.25.014.2 | ATTTGTCTGCTTGAGCTTATTTTCA | 496 |
| Hu.DMD.Exon47.25.015 | AATGTCTAACCTTTATCCACTGGAG | 497 |
| Hu.DMD.Exon47.25.016 | TGGTTAATGTCTAACCTTTATCCAC | 498 |
| Hu.DMD.Exon47.25.017 | AGAGATGGTTAATGTCTAACCTTTA | 499 |
| Hu.DMD.Exon47.25.018 | ACGGAAGAGATGGTTAATGTCTAAC | 500 |
| Hu.DMD.Exon47.20.001 | ACAGACAAATGCAACAACGT | 501 |
| Hu.DMD.Exon47.20.002 | CTGAAACAGACAAATGCAAC | 502 |
| Hu.DMD.Exon47.20.003 | AGTAACTGAAACAGACAAAT | 503 |
| Hu.DMD.Exon47.20.004 | CCACCAGTAACTGAAACAGA | 504 |
| Hu.DMD.Exon47.20.005 | CTCTTCCACCAGTAACTGAA | 505 |
| Hu.DMD.Exon47.20.006 | GGCAACTCTTCCACCAGTAA | 506 |
| Hu.DMD.Exon47.20.007 | CTGGCGCAGGGGCAACTCTT | 507 |
| Hu.DMD.Exon47.20.008 | TTGTTTGAGAATTCCCTGGC | 508 |
| Hu.DMD.Exon47.20.009 | TCCAGTTTCATTTAATTGTT | 509 |
| Hu.DMD.Exon47.20.010 | TACAAGCACGGGTCCTCCAG | 510 |
| Hu.DMD.Exon47.20.011 | GCTTATGGGAGCACTTACAA | 511 |
| Hu.DMD.Exon47.20.012 | ATCTTGCTCTTCTGGGCTTA | 512 |
| Hu.DMD.Exon47.20.013 | CTTATTTTCAAGTTTATCTT | 513 |

TABLE 21-continued

| Target | Nucleotide Sequence (5'-3') | SEQ ID NO. |
|---|---|---|
| Hu.DMD.Exon47.20.014 | ATTTGTCTGCTTGAGCTTAT | 514 |
| Hu.DMD.Exon47.20.015 | CTTTATCCACTGGAGATTTG | 515 |
| Hu.DMD.Exon47.20.016 | CTAACCTTTATCCACTGGAG | 516 |
| Hu.DMD.Exon47.20.017 | AATGTCTAACCTTTATCCAC | 517 |
| Hu.DMD.Exon47.20.018 | TGGTTAATGTCTAACCTTTA | 518 |
| Hu.DMD.Exon47.20.019 | AGAGATGGTTAATGTCTAAC | 519 |
| Hu.DMD.Exon47.20.020 | ACGGAAGAGATGGTTAATGT | 520 |
| Hu.DMD.Exon48.25.001 | CTGAAAGGAAAATACATTTTAAAAA | 521 |
| Hu.DMD.Exon48.25.002 | CCTGAAAGGAAAATACATTTTAAAA | 522 |
| Hu.DMD.Exon48.25.002.2 | GAAACCTGAAAGGAAAATACATTTT | 523 |
| Hu.DMD.Exon48.25.003 | GGAAACCTGAAAGGAAAATACATTT | 524 |
| Hu.DMD.Exon48.25.003.2 | CTCTGGAAACCTGAAAGGAAAATAC | 525 |
| Hu.DMD.Exon48.25.004 | GCTCTGGAAACCTGAAAGGAAAATA | 526 |
| Hu.DMD.Exon48.25.004.2 | TAAAGCTCTGGAAACCTGAAAGGAA | 527 |
| Hu.DMD.Exon48.25.005 | GTAAAGCTCTGGAAACCTGAAAGGA | 528 |
| Hu.DMD.Exon48.25.005.2 | TCAGGTAAAGCTCTGGAAACCTGAA | 529 |
| Hu.DMD.Exon48.25.006 | CTCAGGTAAAGCTCTGGAAACCTGA | 530 |
| Hu.DMD.Exon48.25.006.2 | GTTTCTCAGGTAAAGCTCTGGAAAC | 531 |
| Hu.DMD.Exon48.25.007 | TGTTTCTCAGGTAAAGCTCTGGAAA | 532 |
| Hu.DMD.Exon48.25.007.2 | AATTTCTCCTTGTTTCTCAGGTAAA | 533 |
| Hu.DMD.Exon48.25.008 | TTTGAGCTTCAATTTCTCCTTGTTT | 534 |
| Hu.DMD.Exon48.25.008 | TTTTATTTGAGCTTCAATTTCTCCT | 535 |
| Hu.DMD.Exon48.25.009 | AAGCTGCCCAAGGTCTTTTATTTGA | 536 |
| Hu.DMD.Exon48.25.010 | AGGTCTTCAAGCTTTTTTTCAAGCT | 537 |
| Hu.DMD.Exon48.25.010.2 | TTCAAGCTTTTTTTCAAGCTGCCCA | 538 |
| Hu.DMD.Exon48.25.011 | GATGATTTAACTGCTCTTCAAGGTC | 539 |
| Hu.DMD.Exon48.25.011.2 | CTGCTCTTCAAGGTCTTCAAGCTTT | 540 |
| Hu.DMD.Exon48.25.012 | AGGAGATAACCACAGCAGCAGATGA | 541 |
| Hu.DMD.Exon48.25.012.2 | CAGCAGATGATTTAACTGCTCTTCA | 542 |
| Hu.DMD.Exon48.25.013 | ATTTCCAACTGATTCCTAATAGGAG | 543 |
| Hu.DMD.Exon48.25.014 | CTTGGTTTGGTTGGTTATAAATTTC | 544 |
| Hu.DMD.Exon48.25.014.2 | CAACTGATTCCTAATAGGAGATAAC | 545 |
| Hu.DMD.Exon48.25.015 | CTTAACGTCAAATGGTCCTTCTTGG | 546 |
| Hu.DMD.Exon48.25.015.2 | TTGGTTATAAATTTCCAACTGATTC | 547 |
| Hu.DMD.Exon48.25.016 | CCTACCTTAACGTCAAATGGTCCTT | 548 |
| Hu.DMD.Exon48.25.016.2 | TCCTTCTTGGTTTGGTTGGTTATAA | 549 |
| Hu.DMD.Exon48.25.017 | AGTTCCCTACCTTAACGTCAAATGG | 550 |
| Hu.DMD.Exon48.25.018 | CAAAAAGTTCCCTACCTTAACGTCA | 551 |
| Hu.DMD.Exon48.25.019 | TAAAGCAAAAAGTTCCCTACCTTAA | 552 |
| Hu.DMD.Exon48.25.020 | ATATTTAAAGCAAAAAGTTCCCTAC | 553 |
| Hu.DMD.Exon48.20.001 | AGGAAAATACATTTTAAAAA | 554 |
| Hu.DMD.Exon48.20.002 | AAGGAAAATACATTTTAAAA | 555 |
| Hu.DMD.Exon48.20.003 | CCTGAAAGGAAAATACATTT | 556 |
| Hu.DMD.Exon48.20.004 | GGAAACCTGAAAGGAAAATA | 557 |
| Hu.DMD.Exon48.20.005 | GCTCTGGAAACCTGAAAGGA | 558 |
| Hu.DMD.Exon48.20.006 | GTAAAGCTCTGGAAACCTGA | 559 |
| Hu.DMD.Exon48.20.007 | CTCAGGTAAAGCTCTGGAAA | 560 |
| Hu.DMD.Exon48.20.008 | AATTTCTCCTTGTTTCTCAG | 561 |
| Hu.DMD.Exon48.20.009 | TTTTATTTGAGCTTCAATTT | 562 |
| Hu.DMD.Exon48.20.010 | AAGCTGCCCAAGGTCTTTTA | 563 |
| Hu.DMD.Exon48.20.011 | TTCAAGCTTTTTTTCAAGCT | 564 |
| Hu.DMD.Exon48.20.012 | CTGCTCTTCAAGGTCTTCAA | 565 |
| Hu.DMD.Exon48.20.013 | CAGCAGATGATTTAACTGCT | 566 |
| Hu.DMD.Exon48.20.014 | AGGAGATAACCACAGCAGCA | 567 |
| Hu.DMD.Exon48.20.015 | CAACTGATTCCTAATAGGAG | 568 |
| Hu.DMD.Exon48.20.016 | TTGGTTATAAATTTCCAACT | 569 |
| Hu.DMD.Exon48.20.017 | TCCTTCTTGGTTTGGTTGGT | 570 |
| Hu.DMD.Exon48.20.018 | CTTAACGTCAAATGGTCCTT | 571 |
| Hu.DMD.Exon48.20.019 | CCTACCTTAACGTCAAATGG | 572 |
| Hu.DMD.Exon48.20.020 | AGTTCCCTACCTTAACGTCA | 573 |
| Hu.DMD.Exon48.20.021 | CAAAAAGTTCCCTACCTTAA | 574 |
| Hu.DMD.Exon48.20.022 | TAAAGCAAAAAGTTCCCTAC | 575 |
| Hu.DMD.Exon48.20.023 | ATATTTAAAGCAAAAAGTTC | 576 |
| Hu.DMD.Exon49.25.001 | CTGGGGAAAAGAACCCATATAGTGC | 577 |
| Hu.DMD.Exon49.25.002 | TCCTGGGGAAAAGAACCCATATAGT | 578 |
| Hu.DMD.Exon49.25.002.2 | GTTTCCTGGGGAAAAGAACCCATAT | 579 |
| Hu.DMD.Exon49.25.003 | CAGTTTCCTGGGGAAAAGAACCCAT | 580 |
| Hu.DMD.Exon49.25.003.2 | TTTCAGTTTCCTGGGGAAAAGAACC | 581 |
| Hu.DMD.Exon49.25.004 | TATTTCAGTTTCCTGGGGAAAAGAA | 582 |
| Hu.DMD.Exon49.25.004.2 | TGCTATTTCAGTTTCCTGGGGAAAA | 583 |
| Hu.DMD.Exon49.25.005 | ACTGCTATTTCAGTTTCCTGGGGAA | 584 |
| Hu.DMD.Exon49.25.005.2 | TGAACTGCTATTTCAGTTTCCTGGG | 585 |
| Hu.DMD.Exon49.25.006 | CTTGAACTGCTATTTCAGTTTCCTG | 586 |
| Hu.DMD.Exon49.25.006.2 | TAGCTTGAACTGCTATTTCAGTTTC | 587 |
| Hu.DMD.Exon49.25.007 | TTTAGCTTGAACTGCTATTTCAGTT | 588 |
| Hu.DMD.Exon49.25.008 | TTCCACATCCGGTTGTTTAGCTTGA | 589 |
| Hu.DMD.Exon49.25.009 | TGCCCTTTAGACAAAATCTCTTCCA | 590 |

TABLE 21-continued

| Target | Nucleotide Sequence (5'-3') | SEQ ID NO. |
|---|---|---|
| Hu.DMD.Exon49.25.009.2 | TTTAGACAAAATCTCTTCCACATCC | 591 |
| Hu.DMD.Exon49.25.010 | GTTTTTCCTTGTACAAATGCTGCCC | 592 |
| Hu.DMD.Exon49.25.010.2 | GTACAAATGCTGCCCTTTAGACAAA | 593 |
| Hu.DMD.Exon49.25.011 | CTTCACTGGCTGAGTGGCTGGTTTT | 594 |
| Hu.DMD.Exon49.25.011.2 | GGCTGGTTTTTCCTTGTACAAATGC | 595 |
| Hu.DMD.Exon49.25.012 | ATTACCTTCACTGGCTGAGTGGCTG | 596 |
| Hu.DMD.Exon49.25.013 | GCTTCATTACCTTCACTGGCTGAGT | 597 |
| Hu.DMD.Exon49.25.014 | AGGTTGCTTCATTACCTTCACTGGC | 598 |
| Hu.DMD.Exon49.25.015 | GCTAGAGGTTGCTTCATTACCTTCA | 599 |
| Hu.DMD.Exon49.25.016 | ATATTGCTAGAGGTTGCTTCATTAC | 600 |
| Hu.DMD.Exon49.20.001 | GAAAAGAACCCATATAGTGC | 601 |
| Hu.DMD.Exon49.20.002 | GGGAAAAGAACCCATATAGT | 602 |
| Hu.DMD.Exon49.20.003 | TCCTGGGGAAAAGAACCCAT | 603 |
| Hu.DMD.Exon49.20.004 | CAGTTTCCTGGGGAAAAGAA | 604 |
| Hu.DMD.Exon49.20.005 | TATTTCAGTTTCCTGGGGAA | 605 |
| Hu.DMD.Exon49.20.006 | ACTGCTATTTCAGTTTCCTG | 606 |
| Hu.DMD.Exon49.20.007 | CTTGAACTGCTATTTCAGTT | 607 |
| Hu.DMD.Exon49.20.008 | TTTAGCTTGAACTGCTATTT | 608 |
| Hu.DMD.Exon49.20.009 | TTCCACATCCGGTTGTTTAG | 609 |
| Hu.DMD.Exon49.20.010 | TTTAGACAAAATCTCTTCCA | 610 |
| Hu.DMD.Exon49.20.011 | GTACAAATGCTGCCCTTTAG | 611 |
| Hu.DMD.Exon49.20.012 | GGCTGGTTTTTCCTTGTACA | 612 |
| Hu.DMD.Exon49.20.013 | CTTCACTGGCTGAGTGGCTG | 613 |
| Hu.DMD.Exon49.20.014 | ATTACCTTCACTGGCTGAGT | 614 |
| Hu.DMD.Exon49.20.015 | GCTTCATTACCTTCACTGGC | 615 |
| Hu.DMD.Exon49.20.016 | AGGTTGCTTCATTACCTTCA | 616 |
| Hu.DMD.Exon49.20.017 | GCTAGAGGTTGCTTCATTAC | 617 |
| Hu.DMD.Exon49.20.018 | ATATTGCTAGAGGTTGCTTC | 618 |
| Hu.DMD.Exon50.25.001 | CTTTAACAGAAAAGCATACACATTA | 619 |
| Hu.DMD.Exon50.25.002 | TCCTCTTTAACAGAAAAGCATACAC | 620 |
| Hu.DMD.Exon50.25.002.2 | TTCCTCTTTAACAGAAAAGCATACA | 621 |
| Hu.DMD.Exon50.25.003 | TAACTTCCTCTTTAACAGAAAAGCA | 622 |
| Hu.DMD.Exon50.25.003.2 | CTAACTTCCTCTTTAACAGAAAAGC | 623 |
| Hu.DMD.Exon50.25.004 | TCTTCTAACTTCCTCTTTAACAGAA | 624 |
| Hu.DMD.Exon50.25.004.2 | ATCTTCTAACTTCCTCTTTAACAGA | 625 |
| Hu.DMD.Exon50.25.005 | TCAGATCTTCTAACTTCCTCTTTAA | 626 |
| Hu.DMD.Exon50.25.005.2 | CTCAGATCTTCTAACTTCCTCTTTA | 627 |
| Hu.DMD.Exon50.25.006 | AGAGCTCAGATCTTCTAACTTCCTC | 628 |
| Hu.DMD.Exon50.25.006.2 NG-08-0731 | CAGAGCTCAGATCTTCTAACTTCCT | 629 |
| Hu.DMD.Exon50.25.007 | CACTCAGAGCTCAGATCTTCTACT | 630 |
| Hu.DMD.Exon50.25.007.2 | CCTTCCACTCAGAGCTCAGATCTTC | 631 |
| Hu.DMD.Exon50.25.008 | GTAAACGGTTTACCGCCTTCCACTC | 632 |
| Hu.DMD.Exon50.25.009 | CTTTGCCCTCAGCTCTTGAAGTAAA | 633 |
| Hu.DMD.Exon50.25.009.2 | CCCTCAGCTCTTGAAGTAAACGGTT | 634 |
| Hu.DMD.Exon50.25.010 | CCAGGAGCTAGGTCAGGCTGCTTTG | 635 |
| Hu.DMD.Exon50.25.010.2 | GGTCAGGCTGCTTTGCCCTCAGCTC | 636 |
| Hu.DMD.Exon50.25.011 | AGGCTCCAATAGTGGTCAGTCCAGG | 637 |
| Hu.DMD.Exon50.25.011.2 | TCAGTCCAGGAGCTAGGTCAGGCTG | 638 |
| Hu.DMD.Exon50.25.012 AVI-5038 | CTTACAGGCTCCAATAGTGGTCAGT | 639 |
| Hu.DMD.Exon50.25.013 | GTATACTTACAGGCTCCAATAGTGG | 640 |
| Hu.DMD.Exon50.25.014 | ATCCAGTATACTTACAGGCTCCAAT | 641 |
| Hu.DMD.Exon50.25.015 NG-08-0741 | ATGGGATCCAGTATACTTACAGGCT | 642 |
| Hu.DMD.Exon50.25.016 NG-08-0742 | AGAGAATGGGATCCAGTATACTTAC | 643 |
| Hu.DMD.Exon50.20.001 | ACAGAAAAGCATACACATTA | 644 |
| Hu.DMD.Exon50.20.002 | TTTAACAGAAAAGCATACAC | 645 |
| Hu.DMD.Exon50.20.003 | TCCTCTTTAACAGAAAAGCA | 646 |
| Hu.DMD.Exon50.20.004 | TAACTTCCTCTTTAACAGAA | 647 |
| Hu.DMD.Exon50.20.005 | TCTTCTAACTTCCTCTTTAA | 648 |
| Hu.DMD.Exon50.20.006 | TCAGATCTTCTAACTTCCTC | 649 |
| Hu.DMD.Exon50.20.007 | CCTTCCACTCAGAGCTCAGA | 650 |
| Hu.DMD.Exon50.20.008 | GTAAACGGTTTACCGCCTTC | 651 |
| Hu.DMD.Exon50.20.009 | CCCTCAGCTCTTGAAGTAAA | 652 |
| Hu.DMD.Exon50.20.010 | GGTCAGGCTGCTTTGCCCTC | 653 |
| Hu.DMD.Exon50.20.011 | TCAGTCCAGGAGCTAGGTCA | 654 |
| Hu.DMD.Exon50.20.012 | AGGCTCCAATAGTGGTCAGT | 655 |
| Hu.DMD.Exon50.20.013 | CTTACAGGCTCCAATAGTGG | 656 |
| Hu.DMD.Exon50.20.014 | GTATACTTACAGGCTCCAAT | 657 |
| Hu.DMD.Exon50.20.015 | ATCCAGTATACTTACAGGCT | 658 |
| Hu.DMD.Exon50.20.016 | ATGGGATCCAGTATACTTAC | 659 |
| Hu.DMD.Exon50.20.017 | AGAGAATGGGATCCAGTATA | 660 |
| Hu.DMD.Exon51.25.001-44 | CTAAAATATTTTGGGTTTTTGCAAAA | 661 |
| Hu.DMD.Exon51.25.002-45 | GCTAAAATATTTTGGGTTTTTGCAAA | 662 |
| Hu.DMD.Exon51.25.002.2-46 | TAGGAGCTAAAATATTTTGGGTTTTT | 663 |

TABLE 21-continued

| Target | Nucleotide Sequence (5'-3') | SEQ ID NO. |
|---|---|---|
| Hu.DMD.Exon51.25.003 | AGTAGGAGCTAAAATATTTTGGGTT | 664 |
| Hu.DMD.Exon51.25.003.2 | TGAGTAGGAGCTAAAATATTTTGGG | 665 |
| Hu.DMD.Exon51.25.004 | CTGAGTAGGAGCTAAAATATTTTGGG | 666 |
| Hu.DMD.Exon51.25.004.2 | CAGTCTGAGTAGGAGCTAAAATATT | 667 |
| Hu.DMD.Exon51.25.005 | ACAGTCTGAGTAGGAGCTAAAATATT | 668 |
| Hu.DMD.Exon51.25.005.2 | GAGTAACAGTCTGAGTAGGAGCTAAA | 669 |
| Hu.DMD.Exon51.25.006 | CAGAGTAACAGTCTGAGTAGGAGCT | 670 |
| Hu.DMD.Exon51.25.006.2 | CACCAGAGTAACAGTCTGAGTAGGAG | 671 |
| Hu.DMD.Exon51.25.007 | GTCACCAGAGTAACAGTCTGAGTAG | 672 |
| Hu.DMD.Exon51.25.007.2 | AACCACAGGTTGTGTCACCAGAGTAA | 673 |
| Hu.DMD.Exon51.25.008 | GTTGTGTCACCAGAGTAACAGTCTG | 674 |
| Hu.DMD.Exon51.25.009 | TGGCAGTTTCCTTAGTAACCACAGGT | 675 |
| Hu.DMD.Exon51.25.010 | ATTTCTAGTTTGGAGATGGCAGTTTC | 676 |
| Hu.DMD.Exon51.25.010.2 | GGAAGATGGCATTTCTAGTTTGGAG | 677 |
| Hu.DMD.Exon51.25.011 | CATCAAGGAAGATGGCATTTCTAGTT | 678 |
| Hu.DMD.Exon51.25.011.2 | GAGCAGGTACCTCCAACATCAAGGAA | 679 |
| Hu.DMD.Exon51.25.012 | ATCTGCCAGAGCAGGTACCTCCAAC | 680 |
| Hu.DMD.Exon51.25.013 | AAGTTCTGTCCAAGCCCGGTTGAAAT | 681 |
| Hu.DMD.Exon51.25.013.2 | CGGTTGAAATCTGCCAGAGCAGGTAC | 682 |
| Hu.DMD.Exon51.25.014 | GAGAAAGCCAGTCGGTAAGTTCTGTC | 683 |
| Hu.DMD.Exon51.25.014.2 | GTCGGTAAGTTCTGTCCAAGCCCGG | 684 |
| Hu.DMD.Exon51.25.015 | ATAACTTGATCAAGCAGAGAAAGCCA | 685 |
| Hu.DMD.Exon51.25.015.2 | AAGCAGAGAAAGCCAGTCGGTAAGT | 686 |
| Hu.DMD.Exon51.25.016 | CACCCTCTGTGATTTTATAACTTGAT | 687 |
| Hu.DMD.Exon51.25.017 | CAAGGTCACCCACCATCACCCTCTGT | 688 |
| Hu.DMD.Exon51.25.017.2 | CATCACCCTCTGTGATTTTATAACT | 689 |
| Hu.DMD.Exon51.25.018 | CTTCTGCTTGATGATCATCTCGTTGA | 690 |
| Hu.DMD.Exon51.25.019 | CCTTCTGCTTGATGATCATCTCGTTG | 691 |
| Hu.DMD.Exon51.25.019.2 | ATCTCGTTGATATCCTCAAGGTCACC | 692 |
| Hu.DMD.Exon51.25.020 | TCATACCTTCTGCTTGATGATCATCT | 693 |
| Hu.DMD.Exon51.25.020.2 | TCATTTTTTCTCATACCTTCTGCTTG | 694 |
| Hu.DMD.Exon51.25.021 | TTTTCTCATACCTTCTGCTTGATGAT | 695 |
| Hu.DMD.Exon51.25.022 | TTTTATCATTTTTTCTCATACCTTCT | 696 |
| Hu.DMD.Exon51.25.023 | CCAACTTTTATCATTTTTTCTCATAC | 697 |
| Hu.DMD.Exon51.20.001 | ATATTTTGGGTTTTTGCAAA | 698 |
| Hu.DMD.Exon51.20.002 | AAAATATTTTGGGTTTTTGC | 699 |
| Hu.DMD.Exon51.20.003 | GAGCTAAAATATTTTGGGTT | 700 |
| Hu.DMD.Exon51.20.004 | AGTAGGAGCTAAAATATTTT | 701 |
| Hu.DMD.Exon51.20.005 | GTCTGAGTAGGAGCTAAAAT | 702 |
| Hu.DMD.Exon51.20.006 | TAACAGTCTGAGTAGGAGCT | 703 |
| Hu.DMD.Exon51.20.007 | CAGAGTAACAGTCTGAGTAG | 704 |
| Hu.DMD.Exon51.20.008 | CACAGGTTGTGTCACCAGAG | 705 |
| Hu.DMD.Exon51.20.009 | AGTTTCCTTAGTAACCACAG | 706 |
| Hu.DMD.Exon51.20.010 | TAGTTTGGAGATGGCAGTTT | 707 |
| Hu.DMD.Exon51.20.011 | GGAAGATGGCATTTCTAGTT | 708 |
| Hu.DMD.Exon51.20.012 | TACCTCCAACATCAAGGAAG | 709 |
| Hu.DMD.Exon51.20.013 | ATCTGCCAGAGCAGGTACCT | 710 |
| Hu.DMD.Exon51.20.014 | CCAAGCCCGGTTGAAATCTG | 711 |
| Hu.DMD.Exon51.20.015 | GTCGGTAAGTTCTGTCCAAG | 712 |
| Hu.DMD.Exon51.20.016 | AAGCAGAGAAAGCCAGTCGG | 713 |
| Hu.DMD.Exon51.20.017 | TTTTATAACTTGATCAAGCA | 714 |
| Hu.DMD.Exon51.20.018 | CATCACCCTCTGTGATTTTA | 715 |
| Hu.DMD.Exon51.20.019 | CTCAAGGTCACCCACCATCA | 716 |
| Hu.DMD.Exon51.20.020 | CATCTCGTTGATATCCTCAA | 717 |
| Hu.DMD.Exon51.20.021 | CTTCTGCTTGATGATCATCT | 718 |
| Hu.DMD.Exon51.20.022 | CATACCTTCTGCTTGATGAT | 719 |
| Hu.DMD.Exon51.20.023 | TTTCTCATACCTTCTGCTTG | 720 |
| Hu.DMD.Exon51.20.024 | CATTTTTTCTCATACCTTCT | 721 |
| Hu.DMD.Exon51.20.025 | TTTATCATTTTTTCTCATAC | 722 |
| Hu.DMD.Exon51.20.026 | CAACTTTTATCATTTTTTCT | 723 |
| Hu.DMD.Exon52.25.001 | CTGTAAGAACAAATATCCCTTAGTA | 724 |
| Hu.DMD.Exon52.25.002 | TGCCTGTAAGAACAAATATCCCTTA | 725 |
| Hu.DMD.Exon52.25.002.2 | GTTGCCTGTAAGAACAAATATCCCT | 726 |
| Hu.DMD.Exon52.25.003 | ATTGTTGCCTGTAAGAACAAATATC | 727 |
| Hu.DMD.Exon52.25.003.2 | GCATTGTTGCCTGTAAGAACAAATA | 728 |
| Hu.DMD.Exon52.25.004 | CCTGCATTGTTGCCTGTAAGAACAA | 729 |
| Hu.DMD.Exon52.25.004.2 | ATCCTGCATTGTTGCCTGTAAGAAC | 730 |
| Hu.DMD.Exon52.25.005 | CAAATCCTGCATTGTTGCCTGTAAG | 731 |
| Hu.DMD.Exon52.25.005.2 | TCCAAATCCTGCATTGTTGCCTGTA | 732 |
| Hu.DMD.Exon52.25.006 | TGTTCCAAATCCTGCATTGTTGCCT | 733 |
| Hu.DMD.Exon52.25.006.2 | TCTGTTCCAAATCCTGCATTGTTGC | 734 |
| Hu.DMD.Exon52.25.007 | AACTGGGGACGCCTCTGTTCCAAAT | 735 |
| Hu.DMD.Exon52.25.007.2 | GCCTCTGTTCCAAATCCTGCATTGT | 736 |
| Hu.DMD.Exon52.25.008 | CAGCGGTAATGAGTTCTTCCAACTG | 737 |
| Hu.DMD.Exon52.25.008.2 | CTTCCAACTGGGGACGCCTCTGTTC | 738 |
| Hu.DMD.Exon52.25.009 | CTTGTTTTTCAAATTTTGGGCAGCG | 739 |
| Hu.DMD.Exon52.25.010 | CTAGCCTCTTGATTGCTGGTCTTGT | 740 |

TABLE 21-continued

| Target | Nucleotide Sequence (5'-3') | SEQ ID NO. |
|---|---|---|
| Hu.DMD.Exon52.25.010.2 | TTTTCAAATTTTGGGCAGCGGTAAT | 741 |
| Hu.DMD.Exon52.25.011 | TTCGATCCGTAATGATTGTTCTAGC | 742 |
| Hu.DMD.Exon52.25.011.2 | GATTGCTGGTCTTGTTTTTCAAATT | 743 |
| Hu.DMD.Exon52.25.012 | CTTACTTCGATCCGTAATGATTGTT | 744 |
| Hu.DMD.Exon52.25.012.2 | TTGTTCTAGCCTCTTGATTGCTGGT | 745 |
| Hu.DMD.Exon52.25.013 | AAAAACTTACTTCGATCCGTAATGA | 746 |
| Hu.DMD.Exon52.25.014 | TGTTAAAAAACTTACTTCGATCCGT | 747 |
| Hu.DMD.Exon52.25.015 | ATGCTTGTTAAAAAACTTACTTCGA | 748 |
| Hu.DMD.Exon52.25.016 | GTCCCATGCTTGTTAAAAAACTTAC | 749 |
| Hu.DMD.Exon52.20.001 | AGAACAAATATCCCTTAGTA | 750 |
| Hu.DMD.Exon52.20.002 | GTAAGAACAAATATCCCTTA | 751 |
| Hu.DMD.Exon52.20.003 | TGCCTGTAAGAACAAATATC | 752 |
| Hu.DMD.Exon52.20.004 | ATTGTTGCCTGTAAGAACAA | 753 |
| Hu.DMD.Exon52.20.005 | CCTGCATTGTTGCCTGTAAG | 754 |
| Hu.DMD.Exon52.20.006 | CAAATCCTGCATTGTTGCCT | 755 |
| Hu.DMD.Exon52.20.007 | GCCTCTGTTCCAAATCCTGC | 756 |
| Hu.DMD.Exon52.20.008 | CTTCCAACTGGGGACGCCTC | 757 |
| Hu.DMD.Exon52.20.009 | CAGCGGTAATGAGTTCTTCC | 758 |
| Hu.DMD.Exon52.20.010 | TTTTCAAATTTTGGGCAGCG | 759 |
| Hu.DMD.Exon52.20.011 | GATTGCTGGTCTTGTTTTTC | 760 |
| Hu.DMD.Exon52.20.012 | TTGTTCTAGCCTCTTGATTG | 761 |
| Hu.DMD.Exon52.20.013 | TTCGATCCGTAATGATTGTT | 762 |
| Hu.DMD.Exon52.20.014 | CTTACTTCGATCCGTAATGA | 763 |
| Hu.DMD.Exon52.20.015 | AAAAACTTACTTCGATCCGT | 764 |
| Hu.DMD.Exon52.20.016 | TGTTAAAAAACTTACTTCGA | 765 |
| Hu.DMD.Exon52.20.017 | ATGCTTGTTAAAAAACTTAC | 766 |
| Hu.DMD.Exon52.20.018 | GTCCCATGCTTGTTAAAAAA | 767 |
| Hu.DMD.Exon53.25.001 | CTAGAATAAAAGGAAAAATAAATAT | 768 |
| Hu.DMD.Exon53.25.002 | AACTAGAATAAAAGGAAAAATAAAT | 769 |
| Hu.DMD.Exon53.25.002.2 | TTCAACTAGAATAAAAGGAAAAATA | 770 |
| Hu.DMD.Exon53.25.003 | CTTTCAACTAGAATAAAAGGAAAAA | 771 |
| Hu.DMD.Exon53.25.003.2 | ATTCTTTCAACTAGAATAAAAGGAA | 772 |
| Hu.DMD.Exon53.25.004 | GAATTCTTTCAACTAGAATAAAAGG | 773 |
| Hu.DMD.Exon53.25.004.2 | TCTGAATTCTTTCAACTAGAATAAA | 774 |
| Hu.DMD.Exon53.25.005 | ATTCTGAATTCTTTCAACTAGAATA | 775 |
| Hu.DMD.Exon53.25.005.2 | CTGATTCTGAATTCTTTCAACTAGA | 776 |
| Hu.DMD.Exon53.25.006 | CACTGATTCTGAATTCTTTCAACTA | 777 |
| Hu.DMD.Exon53.25.006.2 | TCCCACTGATTCTGAATTCTTTCAA | 778 |
| Hu.DMD.Exon53.25.007 | CATCCCACTGATTCTGAATTCTTTC | 779 |
| Hu.DMD.Exon53.25.008 | TACTTCATCCCACTGATTCTGAATT | 780 |
| Hu.DMD.Exon53.25.008.2 | CTGAAGGTGTTCTTGTACTTCATCC | 781 |
| Hu.DMD.Exon53.25.009 | CGGTTCTGAAGGTGTTCTTGTACT | 782 |
| Hu.DMD.Exon53.25.009.2 | CTGTTGCCTCCGGTTCTGAAGGTGT | 783 |
| Hu.DMD.Exon53.25.010 | TTTCATTCAACTGTTGCCTCCGGTT | 784 |
| Hu.DMD.Exon53.25.010.2 | TAACATTTCATTCAACTGTTGCCTC | 785 |
| Hu.DMD.Exon53.25.011 | TTGTGTTGAATCCTTTAACATTTCA | 786 |
| Hu.DMD.Exon53.25.012 | TCTTCCTTAGCTTCCAGCCATTGTG | 787 |
| Hu.DMD.Exon53.25.012.2 | CTTAGCTTCCAGCCATTGTGTTGAA | 788 |
| Hu.DMD.Exon53.25.013 | GTCCTAAGACCTGCTCAGCTTCTTC | 789 |
| Hu.DMD.Exon53.25.013.2 | CTGCTCAGCTTCTTCCTTAGCTTCC | 790 |
| Hu.DMD.Exon53.25.014 | CTCAAGCTTGGCTCTGGCCTGTCCT | 791 |
| Hu.DMD.Exon53.25.014.2 | GGCCTGTCCTAAGACCTGCTCAGCT | 792 |
| Hu.DMD.Exon53.25.015 | TAGGGACCCTCCTTCCATGACTCAA | 793 |
| Hu.DMD.Exon53.25.016 | TTTGGATTGCATCTACTGTATAGGG | 794 |
| Hu.DMD.Exon53.25.016.2 | ACCCTCCTTCCATGACTCAAGCTTG | 795 |
| Hu.DMD.Exon53.25.017 | CTTGGTTTCTGTGATTTTCTTTTGG | 796 |
| Hu.DMD.Exon53.25.017.2 | ATCTACTGTATAGGGACCCTCCTTC | 797 |
| Hu.DMD.Exon53.25.018 | CTAACCTTGGTTTCTGTGATTTTCT | 798 |
| Hu.DMD.Exon53.25.018.2 | TTTCTTTTGGATTGCATCTACTGTA | 799 |
| Hu.DMD.Exon53.25.019 | TGATACTAACCTTGGTTTCTGTGAT | 800 |
| Hu.DMD.Exon53.25.020 | ATCTTTGATACTAACCTTGGTTTCT | 801 |
| Hu.DMD.Exon53.25.021 | AAGGTATCTTTGATACTAACCTTGG | 802 |
| Hu.DMD.Exon53.25.022 | TTAAAAAGGTATCTTTGATACTAAC | 803 |
| Hu.DMD.Exon53.20.001 | ATAAAAGGAAAAATAAATAT | 804 |
| Hu.DMD.Exon53.20.002 | GAATAAAAGGAAAAATAAAT | 805 |
| Hu.DMD.Exon53.20.003 | AACTAGAATAAAAGGAAAAA | 806 |
| Hu.DMD.Exon53.20.004 | CTTTCAACTAGAATAAAAGG | 807 |
| Hu.DMD.Exon53.20.005 | GAATTCTTTCAACTAGAATA | 808 |
| Hu.DMD.Exon53.20.006 | ATTCTGAATTCTTTCAACTA | 809 |
| Hu.DMD.Exon53.20.007 | TACTTCATCCCACTGATTCT | 810 |
| Hu.DMD.Exon53.20.008 | CTGAAGGTGTTCTTGTACT | 811 |
| Hu.DMD.Exon53.20.009 | CTGTTGCCTCCGGTTCTGAA | 812 |
| Hu.DMD.Exon53.20.010 | TAACATTTCATTCAACTGTT | 813 |
| Hu.DMD.Exon53.20.011 | TTGTGTTGAATCCTTTAACA | 814 |
| Hu.DMD.Exon53.20.012 | CTTAGCTTCCAGCCATTGTG | 815 |
| Hu.DMD.Exon53.20.013 | CTGCTCAGCTTCTTCCTTAG | 816 |
| Hu.DMD.Exon53.20.014 | GGCCTGTCCTAAGACCTGCT | 817 |

TABLE 21-continued

| Target | Nucleotide Sequence (5'-3') | SEQ ID NO. |
|---|---|---|
| Hu.DMD.Exon53.20.015 | CTCAAGCTTGGCTCTGGCCT | 818 |
| Hu.DMD.Exon53.20.016 | ACCCTCCTTCCATGACTCAA | 819 |
| Hu.DMD.Exon53.20.017 | ATCTACTGTATAGGGACCCT | 820 |
| Hu.DMD.Exon53.20.018 | TTTCTTTTGGATTGCATCTA | 821 |
| Hu.DMD.Exon53.20.019 | CTTGGTTTCTGTGATTTTCT | 822 |
| Hu.DMD.Exon53.20.020 | CTAACCTTGGTTTCTGTGAT | 823 |
| Hu.DMD.Exon53.20.021 | TGATACTAACCTTGGTTTCT | 824 |
| Hu.DMD.Exon53.20.022 | ATCTTTGATACTAACCTTGG | 825 |
| Hu.DMD.Exon53.20.023 | AAGGTATCTTTGATACTAAC | 826 |
| Hu.DMD.Exon53.20.024 | TTAAAAAGGTATCTTTGATA | 827 |
| Hu.DMD.Exon54.25.001 | CTATAGATTTTTATGAGAAAGAGA | 828 |
| Hu.DMD.Exon54.25.002 | AACTGCTATAGATTTTTATGAGAAA | 829 |
| Hu.DMD.Exon54.25.003 | TGGCCAACTGCTATAGATTTTTATG | 830 |
| Hu.DMD.Exon54.25.004 | GTCTTTGGCCAACTGCTATAGATTT | 831 |
| Hu.DMD.Exon54.25.005 | CGGAGGTCTTTGGCCAACTGCTATA | 832 |
| Hu.DMD.Exon54.25.006 | ACTGGCGGAGGTCTTTGGCCAACTG | 833 |
| Hu.DMD.Exon54.25.007 | TTTGTCTGCCACTGGCGGAGGTCTT | 834 |
| Hu.DMD.Exon54.25.008 | AGTCATTTGCCACATCTACATTTGT | 835 |
| Hu.DMD.Exon54.25.008.2 | TTTGCCACATCTACATTTGTCTGCC | 836 |
| Hu.DMD.Exon54.25.009 | CCGGAGAAGTTTCAGGGCCAAGTCA | 837 |
| Hu.DMD.Exon54.25.010 | GTATCATCTGCAGAATAATCCCGGA | 838 |
| Hu.DMD.Exon54.25.010.2 | TAATCCCGGAGAAGTTTCAGGGCCA | 839 |
| Hu.DMD.Exon54.25.011 | TTATCATGTGGACTTTTCTGGTATC | 840 |
| Hu.DMD.Exon54.25.012 | AGAGGCATTGATATTCTCTGTTATC | 841 |
| Hu.DMD.Exon54.25.012.2 | ATGTGGACTTTTCTGGTATCATCTG | 842 |
| Hu.DMD.Exon54.25.013 | CTTTTATGAATGCTTCTCCAAGAGG | 843 |
| Hu.DMD.Exon54.25.013.2 | ATATTCTCTGTTATCATGTGGACTT | 844 |
| Hu.DMD.Exon54.25.014 | CATACCTTTTATGAATGCTTCTCCA | 845 |
| Hu.DMD.Exon54.25.014.2 | CTCCAAGAGGCATTGATATTCTCTG | 846 |
| Hu.DMD.Exon54.25.015 | TAATTCATACCTTTTATGAATGCTT | 847 |
| Hu.DMD.Exon54.25.015.2 | CTTTTATGAATGCTTCTCCAAGAGG | 848 |
| Hu.DMD.Exon54.25.016 | TAATGTAATTCATACCTTTTATGAA | 849 |
| Hu.DMD.Exon54.25.017 | AGAAATAATGTAATTCATACCTTTT | 850 |
| Hu.DMD.Exon54.25.018 | GTTTTAGAAATAATGTAATTCATAC | 851 |
| Hu.DMD.Exon54.20.001 | GATTTTTATGAGAAAGAGA | 852 |
| Hu.DMD.Exon54.20.002 | CTATAGATTTTTATGAGAAA | 853 |
| Hu.DMD.Exon54.20.003 | AACTGCTATAGATTTTTATG | 854 |
| Hu.DMD.Exon54.20.004 | TGGCCAACTGCTATAGATTT | 855 |
| Hu.DMD.Exon54.20.005 | GTCTTTGGCCAACTGCTATA | 856 |
| Hu.DMD.Exon54.20.006 | CGGAGGTCTTTGGCCAACTG | 857 |
| Hu.DMD.Exon54.20.007 | TTTGTCTGCCACTGGCGGAG | 858 |
| Hu.DMD.Exon54.20.008 | TTTGCCACATCTACATTTGT | 859 |
| Hu.DMD.Exon54.20.009 | TTCAGGGCCAAGTCATTTGC | 860 |
| Hu.DMD.Exon54.20.010 | TAATCCCGGAGAAGTTTCAG | 861 |
| Hu.DMD.Exon54.20.011 | GTATCATCTGCAGAATAATC | 862 |
| Hu.DMD.Exon54.20.012 | ATGTGGACTTTTCTGGTATC | 863 |
| Hu.DMD.Exon54.20.013 | ATATTCTCTGTTATCATGTG | 864 |
| Hu.DMD.Exon54.20.014 | CTCCAAGAGGCATTGATATT | 865 |
| Hu.DMD.Exon54.20.015 | CTTTTATGAATGCTTCTCCA | 866 |
| Hu.DMD.Exon54.20.016 | CATACCTTTTATGAATGCTT | 867 |
| Hu.DMD.Exon54.20.017 | TAATTCATACCTTTTATGAA | 868 |
| Hu.DMD.Exon54.20.018 | TAATGTAATTCATACCTTTT | 869 |
| Hu.DMD.Exon54.20.019 | AGAAATAATGTAATTCATAC | 870 |
| Hu.DMD.Exon54.20.020 | GTTTTAGAAATAATGTAATT | 871 |
| Hu.DMD.Exon55.25.001 | CTGCAAAGGACCAAATGTTCAGATG | 872 |
| Hu.DMD.Exon55.25.002 | TCACCCTGCAAAGGACCAAATGTTC | 873 |
| Hu.DMD.Exon55.25.003 | CTCACTCACCCTGCAAAGGACCAAA | 874 |
| Hu.DMD.Exon55.25.004 | TCTCGCTCACTCACCCTGCAAAGGA | 875 |
| Hu.DMD.Exon55.25.005 | CAGCCTCTCGCTCACTCACCCTGCA | 876 |
| Hu.DMD.Exon55.25.006 | CAAAGCAGCCTCTCGCTCACTCACC | 877 |
| Hu.DMD.Exon55.25.007 | TCTTCCAAAGCAGCCTCTCGCTCAC | 878 |
| Hu.DMD.Exon55.25.007.2 | TCTATGAGTTTCTTCCAAAGCAGCC | 879 |
| Hu.DMD.Exon55.25.008 | GTTGCAGTAATCTATGAGTTTCTTC | 880 |
| Hu.DMD.Exon55.25.008.2 | GAACTGTTGCAGTAATCTATGAGTT | 881 |
| Hu.DMD.Exon55.25.009 | TTCCAGGTCCAGGGGAACTGTTGC | 882 |
| Hu.DMD.Exon55.25.010 | GTAAGCCAGGCAAGAAACTTTTCCA | 883 |
| Hu.DMD.Exon55.25.010.2 | CCAGGCAAGAAACTTTTCCAGGTCC | 884 |
| Hu.DMD.Exon55.25.011 | TGGCAGTTGTTTCAGCTTCTGTAAG | 885 |
| Hu.DMD.Exon55.25.011.2 | TTCAGCTTCTGTAAGCCAGGCAAGA | 886 |
| Hu.DMD.Exon55.25.012 | GGTAGCATCCTGTAGGACATTGGCA | 887 |
| Hu.DMD.Exon55.25.012.2 | GACATTGGCAGTTGTTTCAGCTTCT | 888 |
| Hu.DMD.Exon55.25.013 | TCTAGGAGCCTTTCCTTACGGGTAG | 889 |
| Hu.DMD.Exon55.25.014 | CTTTTACTCCCTTGGAGTCTTCTAG | 890 |
| Hu.DMD.Exon55.25.014.2 | GAGCCTTTCCTTACGGGTAGCATCC | 891 |
| Hu.DMD.Exon55.25.015 | TTGCCATTGTTTCATCAGCTCTTTT | 892 |
| Hu.DMD.Exon55.25.015.2 | CTTGGAGTCTTCTAGGAGCCTTTCC | 893 |
| Hu.DMD.Exon55.25.016 | CTTACTTGCCATTGTTTCATCAGCT | 894 |

TABLE 21-continued

| Target | Nucleotide Sequence (5'-3') | SEQ ID NO. |
|---|---|---|
| Hu.DMD.Exon55.25.016.2 | CAGCTCTTTTACTCCCTTGGAGTCT | 895 |
| Hu.DMD.Exon55.25.017 | CCTGACTTACTTGCCATTGTTTCAT | 896 |
| Hu.DMD.Exon55.25.018 | AAATGCCTGACTTACTTGCCATTGT | 897 |
| Hu.DMD.Exon55.25.019 | AGCGGAAATGCCTGACTTACTTGCC | 898 |
| Hu.DMD.Exon55.25.020 | GCTAAAGCGGAAATGCCTGACTTAC | 899 |
| Hu.DMD.Exon55.20.001 | AAGGACCAAATGTTCAGATG | 900 |
| Hu.DMD.Exon55.20.002 | CTGCAAAGGACCAAATGTTC | 901 |
| Hu.DMD.Exon55.20.003 | TCACCCTGCAAAGGACCAAA | 902 |
| Hu.DMD.Exon55.20.004 | CTCACTCACCCTGCAAAGGA | 903 |
| Hu.DMD.Exon55.20.005 | TCTCGCTCACTCACCCTGCA | 904 |
| Hu.DMD.Exon55.20.006 | CAGCCTCTCGCTCACTCACC | 905 |
| Hu.DMD.Exon55.20.007 | CAAAGCAGCCTCTCGCTCAC | 906 |
| Hu.DMD.Exon55.20.008 | TCTATGAGTTTCTTCCAAAG | 907 |
| Hu.DMD.Exon55.20.009 | GAACTGTTGCAGTAATCTAT | 908 |
| Hu.DMD.Exon55.20.010 | TTCCAGGTCCAGGGGGAACT | 909 |
| Hu.DMD.Exon55.20.011 | CCAGGCAAGAAACTTTTCCA | 910 |
| Hu.DMD.Exon55.20.012 | TTCAGCTTCTGTAAGCCAGG | 911 |
| Hu.DMD.Exon55.20.013 | GACATTGGCAGTTGTTTCAG | 912 |
| Hu.DMD.Exon55.20.014 | GGTAGCATCCTGTAGGACAT | 913 |
| Hu.DMD.Exon55.20.015 | GAGCCTTTCCTTACGGGTAG | 914 |
| Hu.DMD.Exon55.20.016 | CTTGGAGTCTTCTAGGAGCC | 915 |
| Hu.DMD.Exon55.20.017 | CAGCTCTTTTACTCCCTTGG | 916 |
| Hu.DMD.Exon55.20.018 | TTGCCATTGTTTCATCAGCT | 917 |
| Hu.DMD.Exon55.20.019 | CTTACTTGCCATTGTTTCAT | 918 |
| Hu.DMD.Exon55.20.020 | CCTGACTTACTTGCCATTGT | 919 |
| Hu.DMD.Exon55.20.021 | AAATGCCTGACTTACTTGCC | 920 |
| Hu.DMD.Exon55.20.022 | AGCGGAAATGCCTGACTTAC | 921 |
| Hu.DMD.Exon55.20.023 | GCTAAAGCGGAAATGCCTGA | 922 |
| H50A(+02+30)-AVI-5656 | CCACTCAGAGCTCAGATCTTCTAACTTCC | 923 |
| H5OD(+07-18)-AVI-5915 | GGGATCCAGTATACTTACAGGCTCC | 924 |
| H50A(+07+33) | CTTCCACTCAGAGCTCAGATCTTCTAA | 925 |
| H51A(+61+90)-AVI-4657 | ACATCAAGGAAGATGGCATTTCTAGTTTGG | 926 |
| H51A(+66+95)-AVI-4658 | CTCCAACATCAAGGAAGATGGCATTTCTAG | 927 |
| H51A(+111+134) | TTCTGTCCAAGCCCGGTTGAAATC | 928 |
| H51A(+175+195) | CACCCACCATCACCCTCYGTG | 929 |
| H51A(+199+220) | ATCATCTCGTTGATATCCTCAA | 930 |
| H51A(+66+90) | ACATCAAGGAAGATGGCATTTCTAG | 931 |
| H51A(-01+25) | ACCAGAGTAACAGTCTGAGTAGGAGC | 932 |
| h51AON1 | TCAAGGAAGATGGCATTTCT | 933 |
| h51AON2 | CCTCTGTGATTTTATAACTTGAT | 934 |
| H51D(+08-17) | ATCATTTTTCTCATACCTTCTGCT | 935 |
| H51D(+16-07) | CTCATACCTTCTGCTTGATGATC | 936 |
| hAON#23 | TGGCATTTCTAGTTTGG | 937 |
| hAON#24 | CCAGAGCAGGTACCTCCAACATC | 938 |
| H44A(+61+84) | TGTTCAGCTTCTGTTAGCCACTGA | 939 |
| H44A(+85+104) | TTTTGTGTCTTTCTGAGAAAC | 940 |
| h44AON1 | CGCCGCCATTTCTCAACAG | 941 |
| H44A(-06+14) | ATCTGTCAAATCGCCTGCAG | 942 |
| H45A(+71+90) | TGTTTTTGAGGATTGCTGAA | 943 |
| h45AON1 | GCTGAATTATTTCTTCCCC | 944 |
| h45AON5 | GCCCAATGCCATCCTGG | 945 |
| H45A(-06+20) | CCAATGCCATCCTGGAGTTCCTGTAA | 946 |
| H53A(+39+69) | CATTCAACTGTTGCCTCCGGTTCTGAAGGTG | 947 |
| H53A(+23+47) | CTGAAGGTGTTCTTGTACTTCATCC | 948 |
| h53AON1 | CTGTTGCCTCCGGTTCTG | 949 |
| H53A(-12+10) | ATTCTTTCAACTAGAATAAAAG | 950 |
| huEx45.30.66 | GCCATCCTGGAGTTCCTGTAAGATACCAAA | 951 |
| huEx45.30.71 | CCAATGCCATCCTGGAGTTCCTGTAAGATA | 952 |
| huEx45.30.79 | GCCGCTGCCCAATGCCATCCTGGAGTTCCT | 953 |
| huEx45.30.83 | GTTTGCCGCTGCCCAATGCCATCCTGGAGT | 954 |
| huEx45.30.88 | CAACAGTTTGCCGCTGCCCAATGCCATCCT | 955 |
| huEx45.30.92 | CTGACAACAGTTTGCCGCTGCCCAATGCCA | 956 |
| huEx45.30.96 | TGTTCTGACAACAGTTTGCCGCTGCCCAAT | 957 |
| huEx45.30.99 | CAATGTTCTGACAACAGTTTGCCGCTGCCC | 958 |
| huEx45.30.103 | CATTCAATGTTCTGACAACAGTTTGCCGCT | 959 |
| huEx45.30.120 | TATTTCTTCCCCAGTTGCATTCAATGTTCT | 960 |
| huEx45.30.127 | GCTGAATTATTTCTTCCCCAGTTGCATTCA | 961 |
| huEx45.30.132 | GGATTGCTGAATTATTTCTTCCCCAGTTGC | 962 |
| huEx45.30.137 | TTTGAGGATTGCTGAATTATTTCTTCCCCA | 963 |
| huEx53.30.84 | GTACTTCATCCCACTGATTCTGAATTCTTT | 964 |
| huEx53.30.88 | TCTTGTACTTCATCCCACTGATTCTGAATT | 965 |
| huEx53.30.91 | TGTTCTTGTACTTCATCCCACTGATTCTGA | 966 |
| huEx53.30.103 | CGGTTCTGAAGGTGTTCTTGTACTTCATCC | 967 |
| huEx53.30.106 | CTCCGGTTCTGAAGGTGTTCTTGTACTTCA | 968 |
| huEx53.30.109 | TGCCTCCGGTTCTGAAGGTGTTCTTGTACT | 969 |
| huEx53.30.112 | TGTTGCCTCCGGTTCTGAAGGTGTTCTTGT | 970 |

TABLE 21-continued

| Target | Nucleotide Sequence (5'-3') | SEQ ID NO. |
| --- | --- | --- |
| huEx53.30.115 | AACTGTTGCCTCCGGTTCTGAAGGTGTTCT | 971 |
| huEx53.30.118 | TTCAACTGTTGCCTCCGGTTCTGAAGGTGT | 972 |

Step 1: Antibody Conjugation with Maleimide-PEG-NHS Followed by siRNA-DMD Conjugates Anti-dystrophin antibody is exchanged with 1× Phosphate buffer (pH 7.4) and made up to 5 mg/mi concentration. To this solution, 2 equivalents of SMCC linker or maleimide-PEGxkDa-NHS (x=1, 5, 10, 20) is added and rotated for 4 hours at room temperature. Unreacted maleimide-PEG is removed by spin filtration using 50 kDa MWCO Amicon spin filters and PBS pH 7.4. The antibody-PEG-Mal conjugate is collected and transferred into a reaction vessel. Various siRNA conjugates are synthesized using sequences listed in Tables 13-17. siRNA-DMD conjugates (2 equivalents) is added at RT to the antibody-PEG-maleimide in PBS and rotated overnight. The reaction mixture is analyzed by analytical SAX column chromatography and conjugate along with Unreacted antibody and siRNA is seen.

Step 2: Purification

The crude reaction mixture is purified by AKTA explorer FPLC using anion exchange chromatography. Fractions containing the antibody-PEG-DMD conjugate are pooled, concentrated and buffer exchanged with PBS, pH 7.4. Antibody siRNA conjugates with SMCC linker, PEG1 kDa, PEG5 kDa and PEG10 kDa are separated based on the siRNA loading.

Step-3: Analysis of the Purified Conjugate

The isolated conjugate is characterized by either mass spec or SDS-PAGE. The purity of the conjugate is assessed by analytical HPLC using anion exchange chromatography.

The examples and embodiments described herein are for illustrative purposes only and various modifications or changes suggested to persons skilled in the art are to be included within the spirit and purview of this application and scope of the appended claims.

What is claimed is:

1. A single stranded oligonucleotide conjugate comprising an anti-transferrin receptor antibody or antigen binding fragment thereof conjugated to a single stranded oligonucleotide hybridizing to an acceptor splice site, a donor splice site, or an exonic splice enhancer element of a pre-mRNA transcript of the DMD gene; wherein the single stranded oligonucleotide induces exon skipping in said pre-mRNA transcript to generate a mRNA transcript encoding a truncated DMD protein.

2. The single stranded oligonucleotide conjugate of claim 1, wherein the single stranded oligonucleotide is a phosphorodiamidate morpholino oligonucleotide (PMO) or an antisense oligonucleotide (ASO).

3. The single stranded oligonucleotide conjugate of claim 1, wherein the single stranded oligonucleotide is delivered into a muscle cell.

4. The single stranded oligonucleotide conjugate of claim 1, wherein the single stranded oligonucleotide induces skipping of exon 8 of the DMD gene.

5. The single stranded oligonucleotide conjugate of claim 1, wherein the single stranded oligonucleotide induces skipping of exon 23 of the DMD gene.

6. The single stranded oligonucleotide conjugate of claim 1, wherein the single stranded oligonucleotide induces skipping of exon 35 of the DMD gene.

7. The single stranded oligonucleotide conjugate of claim 1, wherein the single stranded oligonucleotide induces skipping of exon 43 of the DMD gene.

8. The single stranded oligonucleotide conjugate of claim 1, wherein the single stranded oligonucleotide induces skipping of exon 44 of the DMD gene.

9. The single stranded oligonucleotide conjugate of claim 1, wherein the single stranded oligonucleotide induces skipping of exon 45 of the DMD gene.

10. The single stranded oligonucleotide conjugate of claim 1, wherein the single stranded oligonucleotide induces skipping of exon 50 of the DMD gene.

11. The single stranded oligonucleotide conjugate of claim 1, wherein the single stranded oligonucleotide induces skipping of exon 51 of the DMD gene.

12. The single stranded oligonucleotide conjugate of claim 1, wherein the single stranded oligonucleotide induces skipping of exon 52 of the DMD gene.

13. The single stranded oligonucleotide conjugate of claim 1, wherein the single stranded oligonucleotide induces skipping of exon 53 of the DMD gene.

14. The single stranded oligonucleotide conjugate of claim 1, wherein the single stranded oligonucleotide induces skipping of exon 55 of the DMD gene.

15. The single stranded oligonucleotide conjugate of claim 1, wherein the antibody or antigen binding fragment thereof comprises a humanized antibody or antigen binding fragment thereof, chimeric antibody or antigen binding fragment thereof, monoclonal antibody or antigen binding fragment thereof, monovalent Fab', divalent Fab2, single chain variable fragment (scFv), diabody, minibody, nanobody, single domain antibody (sdAb), or camelid antibody or antigen binding fragment thereof.

16. The single stranded oligonucleotide conjugate of claim 1, wherein the single stranded oligonucleotide comprises at least from about 10 to about 30 nucleotides in length.

17. The single stranded oligonucleotide conjugate of claim 1, wherein the single stranded oligonucleotide is conjugated to the antibody or antigen binding fragment thereof via a linker.

18. The single stranded oligonucleotide conjugate of claim 17, wherein the linker is a cleavable linker.

19. The single stranded oligonucleotide conjugate of claim 17, wherein the linker is a non-cleavable linker.

20. The single stranded oligonucleotide conjugate of claim 17, wherein the linker is selected from the group consisting of a heterobifunctional linker, a homobifunctional linker, a maleimide group, a dipeptide moiety, a benzoic acid group or derivatives thereof, a $C_1$-$C_6$ alkyl A group, and a combination thereof.

21. The single stranded oligonucleotide conjugate of claim 1, wherein the single stranded oligonucleotide conjugate has a single stranded oligonucleotide to antibody ratio of about 1:1, 2:1, 3:1, or 4:1.

22. The single stranded oligonucleotide conjugate of claim 1, wherein the single stranded oligonucleotide conjugate is formulated for parenteral administration.

23. The single stranded oligonucleotide conjugate of claim 1, wherein the truncated DMD protein modulates muscular dystrophy.

24. The single stranded oligonucleotide of claim 23, wherein the muscular dystrophy is Duchenne muscular dystrophy or Becker muscular dystrophy.

* * * * *